| 
US009598422B2

(12) United States Patent
Beck et al.

(10) Patent No.: US 9,598,422 B2
(45) Date of Patent: Mar. 21, 2017

(54) IMMUNOREGULATORY AGENTS

(71) Applicant: Flexus Biosciences, Inc., Princeton, NJ (US)

(72) Inventors: Hilary Plake Beck, Emerald Hills, CA (US); Juan Carlos Jaen, Burlingame, CA (US); Maksim Osipov, Belmont, CA (US); Jay Patrick Powers, Pacifica, CA (US); Maureen Kay Reilly, Belmont, CA (US); Hunter Paul Shunatona, San Francisco, CA (US); James Ross Walker, Menlo Park, CA (US); Mikhail Zibinsky, Lodi, CA (US); James Aaron Balog, Lambertville, NJ (US); David K. Williams, Delran, NJ (US); Jay A. Markwalder, Lahaska, PA (US); Steven P. Seitz, Swarthmore, PA (US); Emily Charlotte Cherney, Newtown, PA (US); Liping Zhang, East Windsor, NJ (US); Weifang Shan, Princeton, NJ (US); Weiwei Guo, Lawrenceville, NJ (US); Audris Huang, New Hope, PA (US)

(73) Assignee: Flexus Biosciences, Inc., Princeton, NJ (US)

( * ) Notice: Subject to any disclaimer, the term of this patent is extended or adjusted under 35 U.S.C. 154(b) by 0 days.

(21) Appl. No.: 14/933,879

(22) Filed: Nov. 5, 2015

(65) Prior Publication Data
US 2016/0137653 A1 May 19, 2016

Related U.S. Application Data

(60) Provisional application No. 62/075,678, filed on Nov. 5, 2014.

(51) Int. Cl.
| | |
|---|---|
| *C07C 255/50* | (2006.01) |
| *A61K 31/277* | (2006.01) |
| *C07C 233/65* | (2006.01) |
| *C07D 487/04* | (2006.01) |
| *A61K 31/166* | (2006.01) |
| *C07D 211/08* | (2006.01) |
| *A61K 31/445* | (2006.01) |
| *C07C 211/45* | (2006.01) |
| *A61K 31/136* | (2006.01) |
| *C07D 215/04* | (2006.01) |
| *A61K 31/47* | (2006.01) |
| *A61K 31/4709* | (2006.01) |
| *C07D 215/233* | (2006.01) |
| *C07D 213/68* | (2006.01) |
| *A61K 31/4412* | (2006.01) |
| *A61K 31/496* | (2006.01) |
| *A61K 31/519* | (2006.01) |
| *A61K 31/5377* | (2006.01) |
| *A61K 45/06* | (2006.01) |
| *A61K 31/00* | (2006.01) |

(52) U.S. Cl.
CPC ............ *C07D 487/04* (2013.01); *A61K 31/00* (2013.01); *A61K 31/136* (2013.01); *A61K 31/166* (2013.01); *A61K 31/277* (2013.01); *A61K 31/445* (2013.01); *A61K 31/4412* (2013.01); *A61K 31/47* (2013.01); *A61K 31/4709* (2013.01); *A61K 31/496* (2013.01); *A61K 31/519* (2013.01); *A61K 31/5377* (2013.01); *A61K 45/06* (2013.01); *C07C 211/45* (2013.01); *C07C 233/65* (2013.01); *C07C 255/50* (2013.01); *C07D 211/08* (2013.01); *C07D 213/68* (2013.01); *C07D 215/04* (2013.01); *C07D 215/233* (2013.01); *C07C 2101/14* (2013.01)

(58) Field of Classification Search
None
See application file for complete search history.

(56) References Cited

U.S. PATENT DOCUMENTS

| | | | |
|---|---|---|---|
| 5,455,273 | A | 10/1995 | Maier et al. |
| 5,723,464 | A | 3/1998 | Brightwell et al. |
| 7,645,771 | B2 | 1/2010 | Kazmierski et al. |
| 8,088,803 | B2 | 1/2012 | Combs et al. |
| 2002/0016463 | A1 | 2/2002 | Zablocki et al. |
| 2003/0190298 | A1 | 10/2003 | Bradley et al. |
| 2004/0029887 | A1 | 2/2004 | Bhatia et al. |
| 2004/0234623 | A1 | 11/2004 | Munn et al. |
| 2006/0258719 | A1 | 11/2006 | Combs et al. |
| 2007/0129347 | A1 | 6/2007 | Hinze et al. |
| 2007/0197584 | A1 | 8/2007 | Schwink et al. |
| 2008/0039453 | A1 | 2/2008 | Putman |
| 2008/0146569 | A1 | 6/2008 | Blake et al. |
| 2009/0275523 | A1 | 11/2009 | Schudok et al. |
| 2010/0008866 | A1 | 1/2010 | Blum et al. |
| 2010/0233166 | A1 | 9/2010 | Prendergast et al. |
| 2011/0218183 | A1* | 9/2011 | Chen .................. C07D 253/07 514/210.18 |
| 2011/0306644 | A1 | 12/2011 | Hoekstra et al. |
| 2013/0197095 | A1 | 8/2013 | Nolte et al. |
| 2013/0217706 | A1 | 8/2013 | Tran et al. |
| 2014/0212444 | A1 | 7/2014 | Holoshitz et al. |
| 2016/0137652 | A1 | 5/2016 | Beck et al. |
| 2016/0137653 | A1 | 5/2016 | Beck et al. |

FOREIGN PATENT DOCUMENTS

| | | |
|---|---|---|
| EP | 0596298 B1 | 1/2002 |
| EP | 1781656 B1 | 12/2007 |

(Continued)

OTHER PUBLICATIONS

Robinson et al. Tetrahedron (2003), 14(1): p. 1407-1446.*

(Continued)

*Primary Examiner* — Yong Chu
(74) *Attorney, Agent, or Firm* — Baker & Hostetler LLP

(57) ABSTRACT

Compounds that modulate the oxidoreductase enzyme indoleamine 2,3-dioxygenase, and compositions containing the compounds, are described herein. The use of such compounds and compositions for the treatment and/or prevention of a diverse array of diseases, disorders and conditions, including cancer- and immune-related disorders, that are mediated by indoleamine 2,3-dioxygenase is also provided.

34 Claims, 4 Drawing Sheets

(56) References Cited

FOREIGN PATENT DOCUMENTS

| | | |
|---|---|---|
| WO | WO 99/29310 | 6/1999 |
| WO | WO 00/56727 | 9/2000 |
| WO | WO 01/92204 | 12/2001 |
| WO | WO 2004/094409 | 11/2004 |
| WO | WO 2005/080317 | 9/2005 |
| WO | WO 2006/018279 | 2/2006 |
| WO | WO 2006/029879 | 3/2006 |
| WO | WO 2006/105021 | 10/2006 |
| WO | WO 2007/005874 | 1/2007 |
| WO | WO 2008/132601 | 11/2008 |
| WO | WO 2009/009116 | 1/2009 |
| WO | WO 2009/044273 | 4/2009 |
| WO | WO 2009/052320 | 4/2009 |
| WO | WO 2010/015655 | 2/2010 |
| WO | WO 2010/019570 | 2/2010 |
| WO | WO 2010/075376 | 7/2010 |
| WO | WO 2010/077634 | 7/2010 |
| WO | WO 2011/028683 | 3/2011 |
| WO | WO 2011/070024 | 6/2011 |
| WO | WO 2011/107553 | 9/2011 |
| WO | WO 2011/109400 | 9/2011 |
| WO | WO 2011/131407 | 10/2011 |
| WO | WO 2011/140249 | 11/2011 |
| WO | WO 2012/032433 | 3/2012 |
| WO | WO 2012/087699 | 6/2012 |
| WO | WO 2012/145493 | 10/2012 |
| WO | WO 2013/079174 | 6/2013 |
| WO | WO 2013/079425 | 6/2013 |
| WO | WO 2013/119716 | 8/2013 |
| WO | WO 2013/132044 | 9/2013 |
| WO | WO 2013/169264 | 11/2013 |
| WO | WO 2014/008218 | 1/2014 |
| WO | WO 2014/036357 | 3/2014 |
| WO | WO 2014/036412 | 3/2014 |
| WO | WO 2014/150677 | 9/2014 |
| WO | WO 2014/160967 | 10/2014 |
| WO | WO 2015/188085 | 12/2015 |
| WO | WO 2016/071283 | 5/2016 |
| WO | WO 2016/073738 | 5/2016 |
| WO | WO 2016/073770 | 5/2016 |
| WO | WO 2016/073774 | 5/2016 |

OTHER PUBLICATIONS

International Search Report dated Mar. 17, 2016 issued in PCT/US15/59311, 3 pages.
International Search Report dated May 17, 2016 issued in PCT/US15/59316, 2 pages.
International Search Report dated Dec. 10, 2015 issued in PCT/US15/34449, 1 page.
https://pubchem.ncbi.nlm.gov/compound/70339979#section=top; Pub Chem Open Chemistry Database; Compound Summary for CID 70339979; Dec. 20, 2015; 3 pages.
National Center for Biotechnology Information, Pubchem Compound Database; CID=24231423, https://pubchem.ncbi.nlm.nih.gov/compound/24231423 (accessed Jun. 23, 2016). 9 pages.
Pubchem SID=162741420, May 22, 2013, pp. 1-5 [online], [retrieved on Dec. 21, 2015], retrieved from the Internet <URL: https://pubchem.ncbi.nlm.nih.gov/substance/162741420>; p. 3. (accessed Jul. 11, 2016).
Serafini, P. et al., Myeloid suppressor cells in cancer: recruitment, phenotype, properties, and mechanisms of immune suppression. Seminars in Cancer Biology, 16(1):53-65 Feb. 2006.
Ball, H.J. et al., Characterization of an indoleamine 2, 3-dioxygenase-like protein found in humans and mice, Gene, 396(1):203-213 Jul. 2007.
Brandacher, G. et al., Prognostic value of indolemaine 2,3-dioxygenase expression in colorectal cancer: effect on tumor-infiltrasting T cells, Clin. Cancer Res., 12(4):1144-1151 Feb. 2006.
Berge, S. M. et al., Pharmaceutical Salts, J. Pharm. Sci., 66:1-19, Jan. 1977.
Munsen et al., Ligand a versatile computerized approach for characterization of ligand-binding systems, Analytical Biochemistry, 107(1), 220-239, Sep. 1980.
Platten, M. et al., Tryptophan catabolism in cancer: beyond IDO and tryptophan depletion, Cancer Research, 72(21):5435-5440, Nov. 2012.
Ishiyama, et al., Palladium (0)-catalyzed cross-coupling reaction of alkoxydiboron with halorenes: a direct procedure for arylboronic esters., J. Org. Chem., 60, 7508-7510, Nov. 1995.
El-Faham, et al., Peptide coupling reagents, more than a letter soup, Chemical Reviews, 111.11, 6557-6602, Aug. 2011.
Evans, et al., Asymmetric alkylation reactions of chiral imide enolates. A practical approach to the enantioselective synthesis of alpha-substituted carboxylic acid derivatives, Journal of the American Chemical Society, 104(6), pp. 1737-1739, Mar. 1982.
Chiang et al., An Fc Domain Protein-Small Molecule Conjugate as an Enhanced Immunomodular, Journal of the American Chemical Society, 136(9):3370-3373, Feb. 2014.
Li, W. et al., Current drug research on PEGylation with small molecular agents, Progress in Polymer Science, 38:421-444, Apr. 2013.
Ramirez-Montagut et al., Immunity to melanoma: unraveling the relation of tumor immunity and autoimmunity, Oncogene, 22(20):3180-3187, May 2003.
Sawaya et al., Risk of cervical cancer associated with extending the interval between cervical-cancer screenings, New England Journal of Medicine, 349(16): 1501-1509, Oct. 2003.
Pardoll, The blockade of immune checkpoints in cancer immunotherapy, Nature Reviews Cancer, 12(4):252-264, Apr. 2012.
Sarkar, et al., Induction of indoleamine 2, 3-dioxygenase by interferon-y in human islets, Diabetes, 56(1):72-79, Jan. 2007.
Littlejohn, et al., Expression and Purification of Recombinant Human Indoleamine 2,3-Dioxygenase, Protein Expression and Purification, 19(1):22-29, Jun. 2000.
Fox, et al., Discovery of 6-phenylpyrimido [4,5-b][1,4] oxazines as potent and selective acyl CoA: diacylglycerol acytransferase 1 (DGAT1) inhibitors with in vivo efficacy in rodents, Journal of Medical Chemistry, 57(8):3464-3483, Apr. 2014.
Yamamoto, et al., Additional reaction of arylboronic acid to aldehydes and α,β-unsaturated carbonyl compounds catalyzed by conventional palladium complexes in the presence of chloroform, J Organomet, Chem., 69(9)4:1325-1332, Apr. 2009.
Li, G. et al., Discovery of novel orally active ureido NPY Y5 receptor antagonists, Bioorganic & Medical Chemistry Letters, 18(3):1146-1150, Feb. 2008.
Kawamura et al., Iron-catalysed cross-coupling of halohydrins with aryl aluminum reagents: a protecting-group-free strategy attaining remarkable rate enhancement and diastereoinduction, Chemical Communications, 48(75):9376-9378, Aug. 2012.
Vilums, Design and synthesis of novel small molecule CCR2 antagonists: Evaluation of 4-aminopiperidine derivatives, Bioorganic Medical Chemistry Letters, 24(23):5377, Dec. 2014.
Qureshi et al., Indoleamine 2,3-dioxygenase; potential in cancer immunotherapy, Science Vision, 2013, vol. 19(1,2), pp. 33-40.
Kotha et al, Recent applications of Suzuki-Miyaura cross-coupling reaction in organic synthesis, Tetrahedron, Nov. 2002, 58:9633-9695.
Kinzel et al., A new palladium precatalyst allows for the fast Suzuki-Miyaura coupling reactions of unstable polyfluorophenyl and 2-heteroaryl boronic acids, Jouranl of the American Chemical Society, Sep. 2010, 132(40), 14073-14075.
Evans et al., Contrasteric carboximide hydrolysis with lithium hydroperoxide, Tetrahedron Letters, Dec. 1987, 28(49), 6141-6144.
Stocks et al., Evidence for a Common Non-Heme Chelatable-Iron-Dependent Activation Mechanism for Semisynthetic and Synthetic Endoperoxide Antimalarial Drugs, Angew. Chem. Int. Ed., Aug. 2007, 46(33), 6278-6283.
Barlind et al., Design and optimization of pyrazinecarboxamide-based inhibitors of diacylglycerol acyltransferase 1 (DGAT1) leading to a clinical candidate dimethylpyrazinecarboxamide phenylcyclohexylacetic acid (AZD7687), Journal of medicinal chemistry, Nov. 2012, 55(23), 10610-10629.

(56) References Cited

OTHER PUBLICATIONS

Corsello, et al. Endorine Side effects induced by immune checkpoint inhibitors, 98(4), Apr. 2013, 1361-1375.
Kohrt, et al., Anti-KIR antibody enhancement of anti-lymphoma activity of natural killer cells as monotherapy and in combinatin with anti-CD20 antibodies, Blood 123.5, Jan. 2014, 678-686.
Stucchi, et al., Multicomponent Synthesis and Biological Evaluation of a Piperazine-Based Dopamine Receptor Ligand Library, ACS medicinal chemistry letters 6(8), Jun. 2015, 882-887.
Pubchem CID 57911539, Aug. 19, 2012, pp. 1-11 [online], [retrieved on Dec. 17, 2015], Retrieved from the Internet <URL:https://pubchem.ncbi.nlm.nih.gov/compound/57911539#section=Top.>; p. 3.

* cited by examiner

IMMUNOREGULATORY AGENTS

CROSS-REFERENCE TO RELATED APPLICATIONS

This application claims priority to U.S. Provisional Application Ser. No. 62/075,678, filed Nov. 5, 2014, the entire content of which is incorporated herein by reference.

BACKGROUND OF THE INVENTION

Indoleamine 2,3-dioxygenase (IDO; also known as IDO1) is an IFN-γ target gene that plays a role in immunomodulation. IDO is an oxidoreductase and one of two enzymes that catalyze the first and rate-limiting step in the conversion of tryptophan to N-formyl-kynurenine. It exists as a 41 kD monomer that is found in several cell populations, including immune cells, endothelial cells, and fibroblasts. IDO is relatively well-conserved between species, with mouse and human sharing 63% sequence identity at the amino acid level. Data derived from its crystal structure and site-directed mutagenesis show that both substrate binding and the relationship between the substrate and iron-bound dioxygenase are necessary for activity. A homolog to IDO (IDO2) has been identified that shares 44% amino acid sequence homology with IDO, but its function is largely distinct from that of IDO. (See, e.g., Serafini, P. et al., *Semin. Cancer Biol.*, 16(1):53-65 (February 2006) and Ball, H. J. et al., *Gene*, 396(1):203-213 (Jul. 1, 2007)).

IDO plays a major role in immune regulation, and its immunosuppressive function manifests in several manners. Importantly, IDO regulates immunity at the T cell level, and a nexus exists between IDO and cytokine production. In addition, tumors frequently manipulate immune function by upregulation of IDO. Thus, modulation of IDO can have a therapeutic impact on a number of diseases, disorders and conditions.

A pathophysiological link exists between IDO and cancer. Disruption of immune homeostasis is intimately involved with tumor growth and progression, and the production of IDO in the tumor microenvironment appears to aid in tumor growth and metastasis. Moreover, increased levels of IDO activity are associated with a variety of different tumors (Brandacher, G. et al., *Clin. Cancer Res.*, 12(4):1144-1151 (Feb. 15, 2006)).

Treatment of cancer commonly entails surgical resection followed by chemotherapy and radiotherapy. The standard treatment regimens show highly variable degrees of long-term success because of the ability of tumor cells to essentially escape by regenerating primary tumor growth and, often more importantly, seeding distant metastasis. Recent advances in the treatment of cancer and cancer-related diseases, disorders and conditions comprise the use of combination therapy incorporating immunotherapy with more traditional chemotherapy and radiotherapy. Under most scenarios, immunotherapy is associated with less toxicity than traditional chemotherapy because it utilizes the patient's own immune system to identify and eliminate tumor cells.

In addition to cancer, IDO has been implicated in, among other conditions, immunosuppression, chronic infections, and autoimmune diseases or disorders (e.g., rheumatoid arthritis). Thus, suppression of tryptophan degradation by inhibition of IDO activity has tremendous therapeutic value. Moreover, inhibitors of IDO can be used to enhance T cell activation when the T cells are suppressed by pregnancy, malignancy, or a virus (e.g., HIV). Although their roles are not as well defined, IDO inhibitors may also find use in the treatment of patients with neurological or neuropsychiatric diseases or disorders (e.g., depression).

Small molecule inhibitors of IDO have been developed to treat or prevent IDO-related diseases. For example, the IDO inhibitors 1-methyl-DL-tryptophan; p-(3-benzofuranyl)-DL-alanine; p-[3-benzo(b)thienyl]-DL-alanine; and 6-nitro-L-tryptophan have been used to modulate T cell-mediated immunity by altering local extracellular concentrations of tryptophan and tryptophan metabolites (WO 99/29310). Compounds having IDO inhibitory activity are further reported in PCT Publication No. WO 2004/094409.

In view of the role played by indoleamine 2,3-dioxygenase in a diverse array of diseases, disorders and conditions, and the limitations (e.g., efficacy) of current IDO inhibitors, new IDO modulators, and compositions and methods associated therewith, are needed.

BRIEF SUMMARY OF THE INVENTION

The present invention relates to compounds that modulate the oxidoreductase enzyme indoleamine 2,3-dioxygenase (IDO), and compositions (e.g., pharmaceutical compositions) comprising the compounds. Such compounds, including methods of their synthesis, and compositions are described in detail below.

The present invention also relates to the use of such compounds and compositions for the treatment and/or prevention of a diverse array of diseases, disorders and conditions mediated, in whole or in part, by IDO. Such diseases, disorders and conditions are described in detail elsewhere herein. Unless otherwise indicated, when uses of the compounds of the present invention are described herein, it is to be understood that such compounds may be in the form of a composition (e.g., a pharmaceutical composition).

As discussed hereafter, although the compounds of the present invention are believed to effect their activity by inhibition of IDO, a precise understanding of the compounds' underlying mechanism of action is not required to practice the invention. It is envisaged that the compounds may alternatively effect their activity through inhibition of tryptophan-2,3-dioxygenase (TDO) activity. It is also envisaged that the compounds may effect their activity through inhibition of both IDO and TDO function. Although the compounds of the invention are generally referred to herein as IDO inhibitors, it is to be understood that the term "IDO inhibitors" encompasses compounds that act individually through inhibition of TDO or IDO, and/or compounds that act through inhibition of both IDO and TDO.

In one aspect, the present invention provides compounds represented by formula (I):

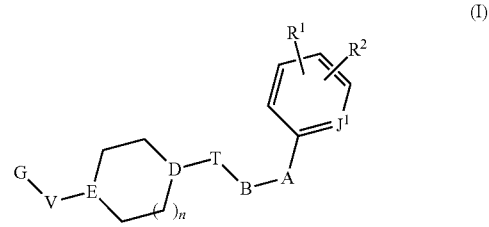

or a pharmaceutically acceptable salt, hydrate or solvate thereof, wherein,
the subscript n is 1 or 0;
A is —C(O)—, —NH—, —SO$_2$—, —CH$_2$—, or —CHR$^3$—;
B is a bond, —C(O)—, —NH—, —CH$_2$—, or —CHR$^3$—;

T is a bond, —CH$_2$—, —NH—, —O—, —OCH$_2$—, —C(O)CH$_2$—, or —CR$^3$R$^4$—;
  wherein when A is —NH— and B is —C(O)—, then T is other than —C(R$^3$)(R$^4$)—; D is N or C(R$^5$);
E is N or C(R$^6$);
V is a bond, —O—, or —C(R$^{5a}$)$_2$;
G is an optionally substituted aryl, optionally substituted heteroaryl, or an optionally substituted 9- or 10-membered fused bicyclic heteroaryl;
J$^1$ is CH, N or C(R$^2$), when R$^2$ is attached to the ring vertex identified as J$^1$;
R$^1$ and R$^2$ are independently hydrogen, halogen, optionally substituted C$_1$-C$_4$ haloalkyl, optionally substituted C$_3$-C$_6$ cycloalkyl, optionally substituted 3- to 6-membered cycloheteroalkyl, optionally substituted phenyl, optionally substituted heteroaryl, optionally substituted C$_1$-C$_4$ alkyl, optionally substituted C$_1$-C$_4$ alkoxy, CN, SO$_2$NH$_2$, NHSO$_2$CH$_3$, NHSO$_2$CF$_3$, OCF$_3$, SO$_2$CH$_3$, SO$_2$CF$_3$, or CONH$_2$, and when R$^1$ and R$^2$ are on adjacent vertices of a phenyl ring they may be joined together to form a 5- or 6-membered cycloheteroalkyl ring having one or two ring vertices independently selected from O, N and S, wherein said cycloheteroalkyl ring is optionally substituted with from one to three members selected from fluoro and C$_1$-C$_3$ alkyl;
R$^3$ and R$^4$ are independently hydrogen, optionally substituted C$_1$-C$_6$ alkyl, optionally substituted C$_1$-C$_6$ haloalkyl, fluorine, OH, CN, CO$_2$H, C(O)NH$_2$, N(R$^{5a}$)$_2$, optionally substituted —O—C$_1$-C$_6$ alkyl, —(CR$^5$R$^5$)$_m$—OH, —(CR$^5$R$^5$)$_m$—CO$_2$H, —(CR$^5$R$^5$)$_m$—C(O)NH$_2$, —(CR$^5$R$^5$)$_m$—C(O)NHR$^{5a}$, —(CR$^5$R$^5$)$_m$N(R$^{5a}$)$_2$, —NH(CR$^5$R$^5$)$_m$CO$_2$H or —NH(CR$^5$R$^5$)$_m$—C(O)NH$_2$;
each R$^5$ is independently H, F, OH, optionally substituted C$_1$-C$_6$ alkyl or optionally substituted —O—C$_1$-C$_6$ alkyl;
each R$^{5a}$ is independently H, or optionally substituted C$_1$-C$_6$ alkyl;
R$^6$ is H, OH, F, optionally substituted C$_1$-C$_6$ alkyl, optionally substituted —O—C$_1$-C$_6$ alkyl, or —N(R$^{5a}$)$_2$;
and each m is independently 1, 2, or 3.

In yet another aspect, the present invention provides compositions in which compounds of formula (I), are combined with one or more pharmaceutically acceptable excipients.

In some embodiments, the present invention contemplates methods for treating or preventing cancer in a subject (e.g., a human) comprising administering to the subject a therapeutically effective amount of at least one IDO inhibitor described herein. The present invention includes methods of treating or preventing a cancer in a subject by administering to the subject an IDO inhibitor in an amount effective to reverse or stop the progression of IDO-mediated immunosuppression. In some embodiments, the IDO-mediated immunosuppression is mediated by an antigen-presenting cell (APC).

Examples of the cancers that may be treated using the compounds and compositions described herein include, but are not limited to: cancers of the prostate, colorectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma. In some embodiments of the present invention, the cancer is melanoma, colon cancer, pancreatic cancer, breast cancer, prostate cancer, lung cancer, leukemia, a brain tumor, lymphoma, sarcoma, ovarian cancer, head and neck cancer, cervical cancer, or Kaposi's sarcoma. Cancers that are candidates for treatment with the compounds and compositions of the present invention are discussed further hereafter.

The present invention contemplates methods of treating a subject receiving a bone marrow transplant or peripheral blood stem cell transplant by administering a therapeutically effective amount of an IDO inhibitor sufficient to increase the delayed-type hypersensitivity reaction to tumor antigen, delay the time-to-relapse of post-transplant malignancy, increase relapse-free survival time post-transplant, and/or increase long-term post-transplant survival.

In certain embodiments, the present invention contemplates methods for treating or preventing an infective disorder (e.g., a viral infection) in a subject (e.g., a human) comprising administering to the subject a therapeutically effective amount of at least one IDO inhibitor (e.g., a novel inhibitor of the instant invention). In some embodiments, the infective disorder is a viral infection (e.g., a chronic viral infection), a bacterial infection, or a parasitic infection. In certain embodiments, the viral infection is human immunodeficiency virus or cytomegalovirus. In other embodiments, the bacterial infection is a *Mycobacterium* infection (e.g., *Mycobacterium leprae* or *Mycobacterium tuberculosis*). In still other embodiments, the parasitic infection is *Leishmania donovani, Leishmania tropica, Leishmania major, Leishmania aethiopica, Leishmania mexicana, Plasmodium falciparum, Plasmodium vivax, Plasmodium ovale,* or *Plasmodium malariae*. In further embodiments, the infective disorder is a fungal infection.

In still other embodiments, the present invention contemplates methods for treating or preventing an immune-related disease, disorder or condition in a subject (e.g., a human), comprising administering to the subject a therapeutically effective amount of at least one IDO inhibitor (e.g., preferably a novel inhibitor of the instant invention). Examples of immune-related diseases, disorders and conditions are described hereafter.

Other diseases, disorders and conditions that may be treated or prevented, in whole or in part, by modulation of IDO activity are candidate indications for the IDO inhibitor compounds that are described herein.

The present invention further contemplates the use of the IDO inhibitors described herein in combination with one or more additional agents. The one or more additional agents may have some IDO modulating activity and/or they may function through distinct mechanisms of action. In some embodiments, such agents comprise radiation (e.g., localized radiation therapy or total body radiation therapy) and/or other treatment modalities of a non-pharmacological nature. When combination therapy is utilized, the IDO inhibitor(s) and the one additional agent(s) may be in the form of a single composition or multiple compositions, and the treatment modalities may be administered concurrently, sequentially, or through some other regimen. By way of example, the present invention contemplates a treatment regimen wherein a radiation phase is followed by a chemotherapeutic phase. The combination therapy may have an additive or synergistic effect. Other benefits of combination therapy are described hereafter.

In some embodiments, the present invention further comprises the use of the IDO inhibitors described herein in combination with bone marrow transplantation, peripheral blood stem cell transplantation, or other types of transplantation therapy.

In particular embodiments, the present invention contemplates the use of the inhibitors of IDO function described herein in combination with immune checkpoint inhibitors. The blockade of immune checkpoints, which results in the amplification of antigen-specific T cell responses, has been shown to be a promising approach in human cancer therapeutics. Examples of immune checkpoints (ligands and receptors), some of which are selectively upregulated in various types of tumor cells, that are candidates for blockade include PD1 (programmed cell death protein 1); PDL1 (PD1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); A2aR (adenosine A2a receptor A2aR); and Killer Inhibitory Receptors. Immune checkpoint inhibitors, and combination therapy therewith, are discussed in detail elsewhere herein.

In other embodiments, the present invention provides methods for treating cancer in a subject, comprising administering to the subject a therapeutically effective amount of at least one IDO inhibitor and at least one chemotherapeutic agent, such agents including, but not limited to alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nucleoside analogs (e.g., gemcitabine); nitroso ureas such as carmustine, lomustine, and streptozocin; topoisomerase 1 inhibitors (e.g., irinotecan); platinum complexes such as cisplatin and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, estramustine, vinblastine, docetaxol, epothilone derivatives, and paclitaxel); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide). The present invention also contemplates the use of the IDO inhibitors in combination with other agents known in the art (e.g., arsenic trioxide) and other chemotherapeutic agents developed in the future.

In some embodiments drawn to methods of treating cancer, the administration of a therapeutically effective amount of an IDO inhibitor in combination with at least one chemotherapeutic agent results in a cancer survival rate greater than the cancer survival rate observed by administering either alone. In further embodiments drawn to methods of treating cancer, the administration of a therapeutically effective amount of an IDO inhibitor in combination with at least one chemotherapeutic agent results in a reduction of tumor size or a slowing of tumor growth greater than reduction of the tumor size or tumor growth observed by administration of one agent alone.

In further embodiments, the present invention contemplates methods for treating or preventing cancer in a subject, comprising administering to the subject a therapeutically effective amount of at least one IDO inhibitor and at least one signal transduction inhibitor (STI). In a particular embodiment, the at least one STI is selected from the group consisting of bcr/abl kinase inhibitors, epidermal growth factor (EGF) receptor inhibitors, her-2/neu receptor inhibitors, and farnesyl transferase inhibitors (FTIs). Other candidate STI agents are set forth elsewhere herein.

The present invention also contemplates methods of augmenting the rejection of tumor cells in a subject comprising administering an IDO inhibitor in conjunction with at least one chemotherapeutic agent and/or radiation therapy, wherein the resulting rejection of tumor cells is greater than that obtained by administering either the IDO inhibitor, the chemotherapeutic agent or the radiation therapy alone.

In further embodiments, the present invention provides methods for treating cancer in a subject, comprising administering to the subject a therapeutically effective amount of at least one IDO inhibitor and at least one immunomodulator other than an IDO inhibitor. In particular embodiments, the at least one immunomodulator is selected from the group consisting of CD40L, B7, B7RP1, ant-CD40, anti-CD38, anti-ICOS, 4-IBB ligand, dendritic cell cancer vaccine, IL2, IL12, ELC/CCL19, SLC/CCL21, MCP-1, IL-4, IL-18, TNF, IL-15, MDC, IFN-α/-β, M-CSF, IL-3, GM-CSF, IL-13, and anti-IL-10. Other candidate immunomodulator agents are set forth elsewhere herein.

The present invention contemplates embodiments comprising methods for treating or preventing an infective disorder (e.g., a viral infection) in a subject (e.g., a human) comprising administering to the subject a therapeutically effective amount of at least one IDO inhibitor and a therapeutically effective amount of an anti-infective agent(s)

In some embodiments of the present invention, the additional therapeutic agent is a cytokine, including, for example, granulocyte-macrophage colony stimulating factor (GM-CSF) or flt3-ligand. The present invention also contemplates methods for treating or preventing a viral infection (e.g., a chronic viral infection) including, but not limited to, hepatitis C virus (HCV), human papilloma virus (HPV), cytomegalovirus (CMV), Epstein-Barr virus (EBV), varicella zoster virus, coxsackie virus, and human immunodeficiency virus (HIV). The use of the IDO inhibitors described herein to treat (either alone or as a component of combination therapy) infection is discussed further hereafter.

In additional embodiments, treatment of an infective disorder is effected through the co-administration of a vaccine in combination with administration of a therapeutically effective amount of an IDO inhibitor of the present invention. In some embodiments, the vaccine is an anti-viral vaccine, including, for example, an anti-HIV vaccine. In other embodiments, the vaccine is effective against tuberculosis or malaria. In still other embodiments, the vaccine is a tumor vaccine (e.g., a vaccine effective against melanoma); the tumor vaccine may comprise genetically modified tumor cells or a genetically modified cell line, including genetically modified tumor cells or a genetically modified cell line that has been transfected to express granulocyte-macrophage stimulating factor (GM-CSF). In particular embodiments, the vaccine includes one or more immunogenic peptides and/or dendritic cells.

In some embodiments, the present invention contemplates methods of using the IDO inhibitors disclosed herein in combination with one or more antimicrobial agents.

In certain embodiments drawn to treatment of an infection by administering an IDO inhibitor and at least one additional therapeutic agent, a symptom of infection observed after administering both the IDO inhibitor and the additional therapeutic agent is improved over the same symptom of infection observed after administering either alone. In some embodiments, the symptom of infection observed may be reduction in viral load, increase in CD4+ T cell count, decrease in opportunistic infections, increased survival time, eradication of chronic infection, or a combination thereof.

DETAILED DESCRIPTION OF THE INVENTION

Figure 1A:
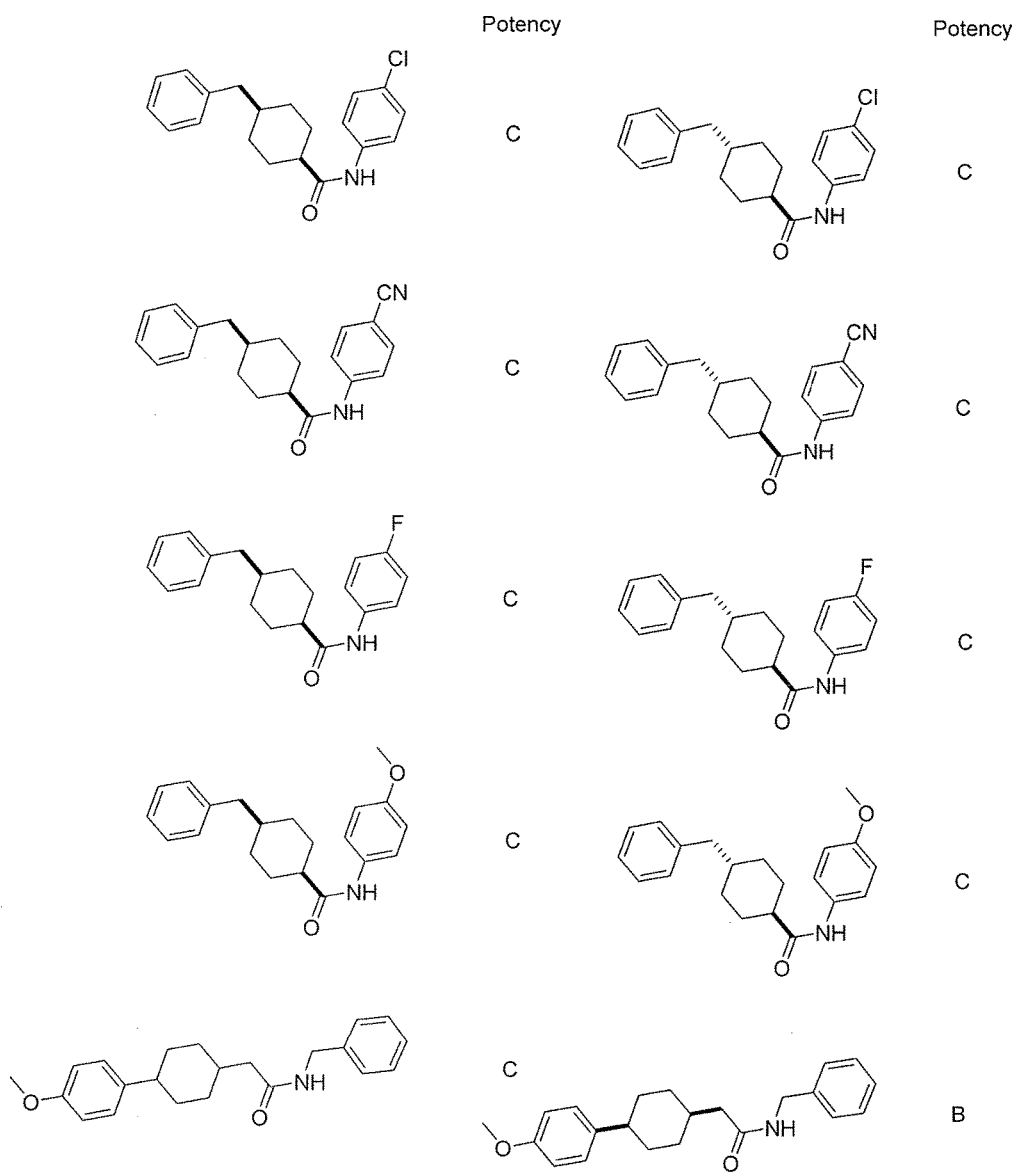
FIGS. 1A, 1B, 1C and 1D provide structures and biological activity for compounds described herein.

Before the present invention is further described, it is to be understood that the invention is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology such as "solely", "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

General

Immune dysregulation is intimately associated with tumor evasion of the host immune system, resulting in tumor growth and progression. Traditional treatment approaches comprising chemotherapy and radiotherapy are generally difficult for the patient to tolerate and become less effective as tumors evolve to survive such treatments. By utilizing the patient's own immune system to identify and eliminate tumor cells, immunotherapy has the benefit of reduced toxicity. As upregulation of the immunoregulatory enzyme indoleamine 2,3-dioxygenase comprises one mechanism manipulated by tumors to promote growth, agents (e.g., small molecule compounds) that inhibit enzyme activity present a promising avenue for prophylaxis and/or treatment.

In addition, a large body of experimental data indicates a role for IDO inhibition in immunosuppression, tumor resistance and/or rejection, chronic infections, HIV-infection, and autoimmune diseases or disorders. Inhibition of IDO may also be an important treatment strategy for patients with neurological or neuropsychiatric diseases or disorders such as depression. The compounds, compositions and methods herein address the need for new classes of IDO modulators.

Definitions

Unless otherwise indicated, the following terms are intended to have the meaning set forth below. Other terms are defined elsewhere throughout the specification.

The term "alkyl", by itself or as part of another substituent, means, unless otherwise stated, a straight or branched chain hydrocarbon radical, having the number of carbon atoms designated (i.e., $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like.

The term "cycloalkyl" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc.

The term "cycloheteroalkyl" refers to a cycloalkyl ring having the indicated number of ring vertices (or members) and having from one to five heteroatoms selected from N, O, and S, which replace one to five of the carbon vertices, and wherein the nitrogen and sulfur atoms are optionally oxidized, and the nitrogen atom(s) are optionally quaternized. The cycloheteroalkyl may be a monocyclic, a bicyclic or a polycyclic ring system. Non limiting examples of cycloheteroalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A cycloheteroalkyl group can be attached to the remainder of the molecule through a ring carbon or a heteroatom.

As used herein, a wavy line, "⌇", that intersects a single, double or triple bond in any chemical structure depicted herein, represent the point attachment of the single, double, or triple bond to the remainder of the molecule. Additionally, a bond extending to the center of a ring (e.g., a phenyl ring) is meant to indicate attachment at any of the available ring vertices. One of skill in the art will understand that multiple substituents shown as being attached to a ring will occupy ring vertices that provide stable compounds and are otherwise sterically compatible. For a divalent component, a representation is meant to include either orientation (forward or reverse). For example, the group "—C(O)NH—" is meant to include a linkage in either orientation: —C(O)NH— or —NHC(O)—, and similarly, "—O—CH$_2$CH$_2$—" is meant to include both —O—CH$_2$CH$_2$— and —CH$_2$CH$_2$—O—.

The terms "alkoxy", "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as dialkylamino or —NR$^a$R$^b$ is meant to include piperidinyl, pyrrolidinyl, morpholinyl, azetidinyl and the like.

The terms "halo" or "halogen", by themselves or as part of another substituent, mean, unless otherwise stated, a fluorine, chlorine, bromine, or iodine atom. Additionally, terms such as "haloalkyl", are meant to include monohaloalkyl and polyhaloalkyl. For example, the term "C$_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. Non-limiting examples of aryl groups include phenyl, naphthyl and biphenyl.

The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for a heteroaryl ring can be selected from the group of acceptable substituents described below.

The above terms (e.g., "alkyl", "aryl" and "heteroaryl"), in some embodiments, will be optionally substituted. Selected substituents for each type of radical are provided below.

Optional substituents for the alkyl radicals (including those groups often referred to as alkylene, alkenyl, alkynyl and cycloalkyl) can be a variety of groups selected from: halogen, —OR', —NR'R'', —SR', —SiR'R''R''', —OC(O)R', —C(O)R', —CO$_2$R', —CONR'R'', —OC(O)NR'R'', —NR''C(O)R', —NR'—C(O)NR''R''', —NR''C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R'', —NR'S(O)$_2$R'', —CN and —NO$_2$ in a number ranging from zero to (2m'+1), where m' is the total number of carbon atoms in such radical. R', R'' and R''' each independently refer to hydrogen, unsubstituted C$_{1-8}$ alkyl, unsubstituted aryl, aryl substituted with 1-3 halogens, unsubstituted C$_{1-8}$ alkyl, C$_{1-8}$ alkoxy or C$_{1-8}$ thioalkoxy groups, or unsubstituted aryl-C$_{1-4}$ alkyl groups. When R' and R'' are attached to the same nitrogen atom, they can be combined with the nitrogen atom to form a 3-, 4-, 5-, 6-, or 7-membered ring. For example, —NR'R'' is meant to include 1-pyrrolidinyl and 4-morpholinyl.

Similarly, optional substituents for the aryl and heteroaryl groups are varied and are generally selected from: -halogen, —OR', —OC(O)R', —NR'R'', —SR', —R', —CN, —NO$_2$, —CO$_2$R', —CONR'R'', —C(O)R', —OC(O)NR'R'', —NR''C(O)R', —NR''C(O)$_2$R', —NR'—C(O)NR''R''', —NH—C(NH$_2$)=NH, —NR'C(NH$_2$)=NH, —NH—C(NH$_2$)=NR', —S(O)R', —S(O)$_2$R', —S(O)$_2$NR'R'', —NR'S(O)$_2$R'', —N$_3$, perfluoro(C$_1$-C$_4$)alkoxy, and perfluoro(C$_1$-C$_4$)alkyl, in a number ranging from zero to the total number of open valences on the aromatic ring system; and where R', R'' and R''' are independently selected from hydrogen, C$_{1-8}$ alkyl, C$_{1-8}$ haloalkyl, C$_{3-6}$ cycloalkyl, C$_{2-8}$ alkenyl and C$_{2-8}$ alkynyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically acceptable inorganic bases include aluminum, ammonium, calcium, copper, ferric, ferrous, lithium, magnesium, manganic, manganous, potassium, sodium, zinc and the like. Salts derived from pharmaceutically acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M. et al., "Pharmaceutical Salts", J. Pharm. Sci., 66:1-19 (1977)). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer the compound in which one of the isomers is present and substantially free of the other isomer. "Substantially free of" another isomer indicates at least an 80/20 ratio of the two isomers, more preferably 90/10, or 95/5 or more. In some embodiments, one of the isomers will be present in an amount of at least 99%.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as, for example, tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, an inhibitor of IDO, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", "treatment" and the like refer to a course of action (such as administering an inhibitor of IDO or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering an IDO inhibitor or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of and IDO inhibitor (or, e.g., a metabolite thereof) at a particular time post-administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule may be more permeable to cells, less susceptible to degradation, and less likely to elicit an immune response than large molecules.

As used herein, the terms "IDO inhibitor", "IDO blocker" and terms similar thereto refer to agents capable of inhibiting the activity of IDO, thereby reversing IDO-mediated immunosuppression. An IDO inhibitor may be a competitive, noncompetitive, or irreversible IDO inhibitor. "A competitive IDO inhibitor" is a compound that reversibly inhibits IDO enzyme activity at the catalytic site; "a noncompetitive IDO Inhibitor" is a compound that reversibly inhibits IDO enzyme activity at a non-catalytic site; and "an irreversible IDO inhibitor" is a compound that irreversibly eliminates IDO enzyme activity by forming a covalent bond (or other stable means of inhibiting enzyme function) with the enzyme. A number of IDO inhibitors are commercially available (e.g., 5-Br-4-Cl-indoxyl 1,3-diacetate and 1-methyl-DL-tryptophan (1 MT); both available from Sigma-Aldrich, St. Louis, Mo.) and may be used as, for example, "tool" or "reference" compounds The term "ligand" refers to, for example, a peptide, a polypeptide, a membrane-associated or membrane-bound molecule, or a complex thereof, that can act as an agonist or antagonist of a receptor. A ligand encompasses natural and synthetic ligands, e.g., cytokines, cytokine variants, analogs, muteins, and binding compositions derived from antibodies, as well as small molecules. The term also encompasses an agent that is neither an agonist nor antagonist, but that can bind to a receptor without significantly influencing its biological properties, e.g., signaling or adhesion. Moreover, the term includes a membrane-bound ligand that has been changed by, e.g., chemical or recombinant methods, to a soluble version of the membrane-bound ligand. A ligand or receptor may be entirely intracellular, that is, it may reside in the cytosol, nucleus, or some other intracellular compartment. The complex of a ligand and receptor is termed a "ligand-receptor complex".

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of IDO, either directly or indirectly. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently (though not always) means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect may refer to efficacy, stability, solubility, or immunogenicity.

"Substantially pure" indicates that a component makes up greater than about 50% of the total content of the composition, and typically greater than about 60% of the total polypeptide content. More typically, "substantially pure"

refers to compositions in which at least 75%, at least 85%, at least 90% or more of the total composition is the component of interest. In some cases, the polypeptide will make up greater than about 90%, or greater than about 95% of the total content of the composition.

The terms "specifically binds" or "selectively binds", when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two-fold greater, at least ten times greater, at least 20-times greater, or at least 100-times greater than the affinity with any other antibody, or binding composition derived therefrom. In a particular embodiment, the antibody will have an affinity that is greater than about $10^9$ liters/mol, as determined by, e.g., Scatchard analysis (Munsen et al., *Analyt. Biochem.*, 107:220-239 (1980)).

The term "response", for example, of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects.

The terms "polypeptide", "peptide", and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence, fusion proteins with heterologous and homologous leader sequences, with or without N-terminus methionine residues; immunologically tagged proteins; and the like.

As used herein, the terms "variants" and "homologs" are used interchangeably to refer to amino acid or DNA sequences that are similar to reference amino acid or nucleic acid sequences, respectively. The term encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Thus, variants and homologs encompass naturally occurring DNA sequences and proteins encoded thereby and their isoforms, as well as splice variants of a protein or gene. The terms also encompass nucleic acid sequences that vary in one or more bases from a naturally-occurring DNA sequence but still translate into an amino acid sequence that corresponds to the naturally-occurring protein due to degeneracy of the genetic code. Non-naturally-occurring variants and homologs include polypeptides and nucleic acids that comprise a change in amino acid or nucleotide sequence, respectively, where the change in sequence is artificially introduced (e.g., muteins); for example, the change is generated in the laboratory by human intervention ("hand of man"). Therefore, non-naturally occurring variants and homologs may also refer to those that differ from the naturally-occurring sequences by one or more conservative substitutions and/or tags and/or conjugates.

The term "muteins" as used herein refers broadly to mutated recombinant proteins. These proteins usually carry single or multiple amino acid substitutions and are frequently derived from cloned genes that have been subjected to site-directed or random mutagenesis, or from completely synthetic genes.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

Indoleamine 2,3-Dioxygenase

As previously alluded to, IDO is an immune regulatory enzyme that is normally expressed in tumor cells and in activated immune cells. IDO is one of several immune response checkpoints that are involved in tumor immune escape; thus, IDO inhibitors disrupt mechanisms by which tumors evade the body's normal immune system.

IDO down-regulates the immune response mediated through oxidation of tryptophan. This results in inhibition of T-cell activation and induction of T-cell apoptosis, creating an environment in which tumor-specific cytotoxic T lymphocytes are rendered functionally inactive or are no longer able to attack a subject's cancer cells. Therefore, therapeutic agents aimed at suppression of tryptophan degradation by inhibiting IDO activity are desirable. Inhibitors of IDO can be used to activate T cells and therefore enhance T cell activation when the T cells are suppressed by pregnancy, malignancy or a virus such as HIV Inhibition of IDO may also be an important treatment strategy for patients with neurological or neuropsychiatric diseases or disorders such as depression. The compounds, compositions and methods herein help meet the current need for IDO modulators.

The expression of IDO is modulated by a complex array of signals, thus implicating a number of different mechanisms of actions. For example, IDO may be induced by inhibition of DNA methyl transferases or histone deacetylases. The NF-κB signaling pathway has also been implicated in IDO function. Inhibiting NF-κB activity blocks IDO expression and produces robust anti-tumor responses that are both T cell- and IDO-dependent; alternatively, NF-κB activation (which may be effected by various factors such as interferon-γR1/-γR2 signaling and toll-like-receptor activation) induces IDO gene expression.

Other mechanisms are involved with modulation of IDO function. By way of example, inhibitors of reactive oxidative species (ROS) may effect stabilization of IDO; IDO levels may be modulated by inhibition or activation of pathways that are both downstream and upstream of IDO; and activation of interferon-γ can activate an autocrine induction of IDO.

Studies indicate that the IDO pathway is active in many cancers, both within tumor cells as a direct defense against T cell attack, and also within antigen-presenting cells (APCs) in tumor-draining lymph nodes resulting in peripheral tolerance to tumor-associated antigens (TAAs). Cancers may use the IDO pathway to facilitate survival, growth, invasion, and metastasis of malignant cells expressing TAAs that might otherwise be recognized and attacked by the immune system.

As alluded to herein, tryptophan catabolism in tumor tissue by the rate-limiting enzyme IDO provides an opportunity for the use of IDO inhibitors as a therapeutic alternative to, or an additive with, conventional chemotherapy. However, certain cancers are capable of catabolizing tryptophan but are largely IDO-negative. Recent studies indicate that the alternative enzymatic pathway of tryptophan catabolism involving tryptophan-2,3-dioxygenase (TDO) is also relevant in cancer. TDO, which is considered responsible for regulating systemic tryptophan levels in the liver, is constitutively expressed in some cancers and is also capable of suppressing antitumor immune responses (See, e.g., Platten, M. et al., *Cancer Res.*, 72(21):5435-5440 (Nov. 1, 2012)).

IDO is expressed in a wide variety of human tumors and tumor cell lines as well as in host APCs, which correlates with a worse clinical prognosis. Therefore, inhibition of IDO may improve survival in cancer patients with IDO-mediated immunosuppression. In comparison, TDO is expressed in a wide variety of human tumors and tumor cell lines, and expression of TDO is evident in advanced human glioblastomas. The identification of tumors expressing high levels of IDO or TDO may allow more selective inhibition of the tryptophan-regulated immunosuppressive pathways. Alternatively, compounds inhibiting both IDO and TDO could provide the greatest coverage to prevent tumor escape by compensatory expression of the other tryptophan-degrading enzyme. Therefore, the use of dual IDO/TDO inhibitors or combinations of IDO- and TDO-specific inhibitors may prove to be a superior treatment alternative in immunotherapy of cancer to block immunosuppression mediated by tryptophan metabolism.

Although a precise understanding of the underlying mechanism of action by which the compounds of the present invention effect their activity is not required to practice the invention, the compounds (or a subset thereof) are believed to inhibit IDO function. Alternatively, the compounds (or a subset thereof) may inhibit TDO function. The compounds (or a subset thereof) may also have inhibitory activity on both IDO and TDO function. Although the compounds of the invention are generally referred to herein as IDO inhibitors, it is to be understood that the term "IDO inhibitors" encompasses compounds that act individually through inhibition of TDO or IDO, and/or compounds that act through inhibition of both IDO and TDO.

Identification of IDO Inhibitors Possessing Desirable Characteristics

The present invention is drawn, in part, to the identification of inhibitors of IDO with at least one property or characteristic that is of therapeutic relevance. Candidate inhibitors may be identified by using, for example, an art-accepted assay or model, examples of which are described herein.

After identification, candidate inhibitors can be further evaluated by using techniques that provide data regarding characteristics of the inhibitors (e.g., pharmacokinetic parameters, means of determining solubility or stability). Comparisons of the candidate inhibitors to a reference standard (which may the "best-of-class" of current inhibitors) are indicative of the potential viability of such candidates.

Compounds of the Invention

As noted above, the present invention provides compounds represented by formula (I):

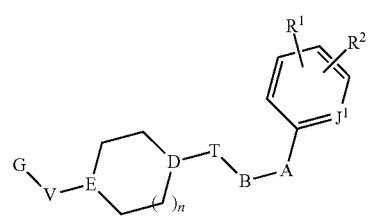

or a pharmaceutically acceptable salt, hydrate or solvate thereof, wherein, the subscript n is 1 or 0;

A is —C(O)—, —NH—, —SO$_2$—, —CH$_2$—, or —CHR$^3$—;

B is a bond, —C(O)—, —NH—, —CH$_2$—, or —CHR$^3$—;

T is a bond, —CH$_2$—, —NH—, —O—, —OCH$_2$—, —C(O)CH$_2$—, or —CR$^3$R$^4$—;
  wherein when A is —NH— and B is —C(O)—, then T is other than —C(R$^3$)(R$^4$)—;

D is N or C(R$^5$);

E is N or C(R$^6$);

V is a bond, —O—, or —C(R$^{5a}$)$_2$;

G is an optionally substituted aryl, optionally substituted heteroaryl, or an optionally substituted 9- or 10-membered fused bicyclic heteroaryl;

J$^1$ is CH, N or C(R$^2$), when R$^2$ is attached to the ring vertex identified as J$^1$;

R$^1$ and R$^2$ are independently hydrogen, halogen, optionally substituted C$_1$-C$_4$ haloalkyl, optionally substituted C$_3$-C$_6$ cycloalkyl, optionally substituted 3- to 6-membered cycloheteroalkyl, optionally substituted phenyl, optionally substituted heteroaryl, optionally substituted C$_1$-C$_4$ alkyl, optionally substituted C$_1$-C$_4$ alkoxy, CN, SO$_2$NH$_2$, NHSO$_2$CH$_3$, NHSO$_2$CF$_3$, OCF$_3$, SO$_2$CH$_3$, SO$_2$CF$_3$, or CONH$_2$, and when R$^1$ and R$^2$ are on adjacent vertices of a phenyl ring they may be joined together to form a 5- or 6-membered cycloheteroalkyl ring having one or two ring vertices independently selected from O, N and S, wherein said cycloheteroalkyl ring is optionally substituted with from one to three members selected from fluoro and C$_1$-C$_3$ alkyl;

R$^3$ and R$^4$ are independently hydrogen, optionally substituted C$_1$-C$_6$ alkyl, optionally substituted C$_1$-C$_6$ haloalkyl, fluorine, OH, CN, CO$_2$H, C(O)NH$_2$, N(R$^{5a}$)$_2$, optionally substituted —O—C$_1$-C$_6$ alkyl, —(CR$^5$R$^5$)$_m$—OH, —(CR$^5$R$^5$)$_m$—CO$_2$H, —(CR$^5$R$^5$)$_m$—C(O)NH$_2$, —(CR$^5$R$^5$)$_m$—C(O)NHR$^{5a}$, —(CR$^5$R$^5$)$_m$N(R$^{5a}$)$_2$, —NH(CR$^5$R$^5$)$_m$CO$_2$H or —NH(CR$^5$R$^5$)$_m$—C(O)NH$_2$;

each R$^5$ is independently H, F, OH, optionally substituted C$_1$-C$_6$ alkyl or optionally substituted —O—C$_1$-C$_6$ alkyl;

each R$^{5a}$ is independently H, or optionally substituted C$_1$-C$_6$ alkyl;

R$^6$ is H, OH, F, optionally substituted C$_1$-C$_6$ alkyl, optionally substituted —O—C$_1$-C$_6$ alkyl, or —N(R$^{5a}$)$_2$;

and each m is independently 1, 2, or 3.

In some embodiments, the compounds provided herein have the formula (Ia):

(Ia)

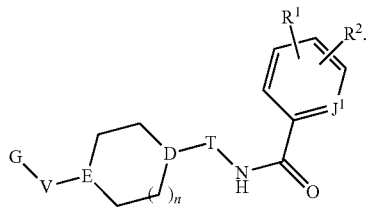

In some selected embodiments of formula (Ia), compounds are provided having formulae (Ia1), (Ia2) or (Ia3):

(Ia1)

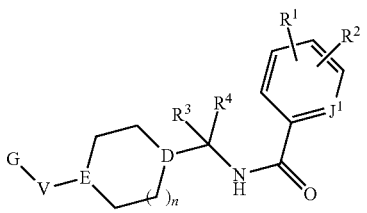

(Ia2)

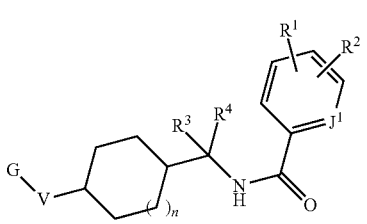

(Ia3)

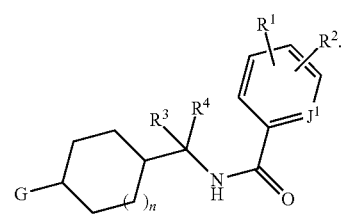

In some embodiments, the compounds provided herein have the formula (Ib), (Ic), or (Id):

(Ib)

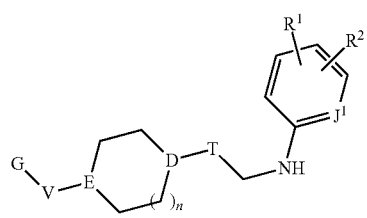

(Ic)

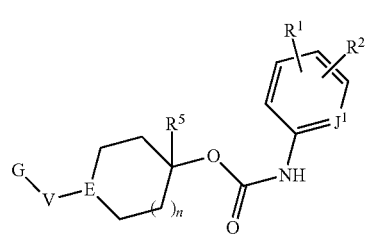

(Id)

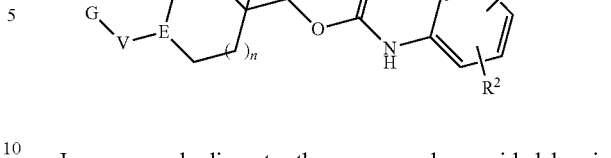

In some embodiments, the compounds provided herein have the formula (Ie):

(Ie)

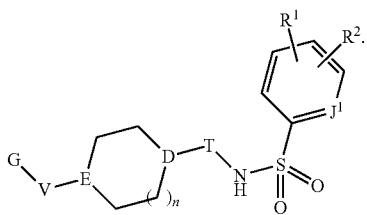

In some selected embodiments of formula (Ie), compounds are provided having formulae (Ie1):

(Ie1)

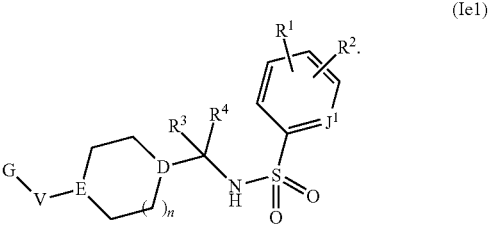

In some embodiments, the compounds provided herein have the formula (If), (Ig), or (Ih):

(If)

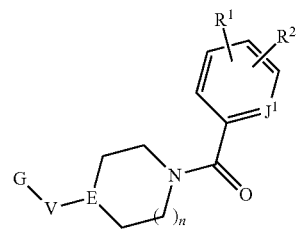

(Ig)

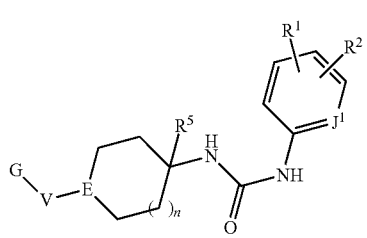

21

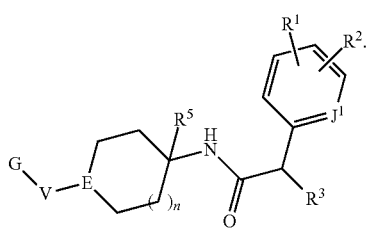

(Ih)

In some embodiments, the compounds provided herein have the formula (Ii) or (Ij):

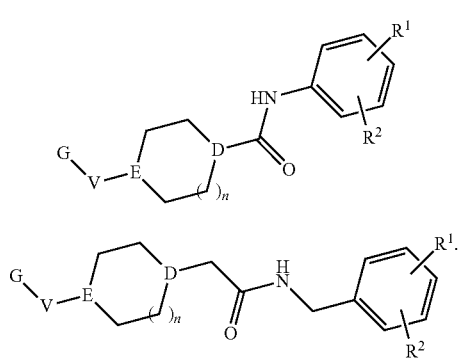

For each of the above formulae (Ia), (Ia1), (Ia2), (Ia3), (Ib), (Ic), (Id), (Ie), (Ie1), (If), (Ig), (Ih), (Ii) and (Ij), each of the subscript, letters, $J^1$, $R^1$, $R^2$, $R^3$, $R^4$ and $R^5$ have the meanings provided with reference to formula (I), unless noted otherwise.

Figure 1B:
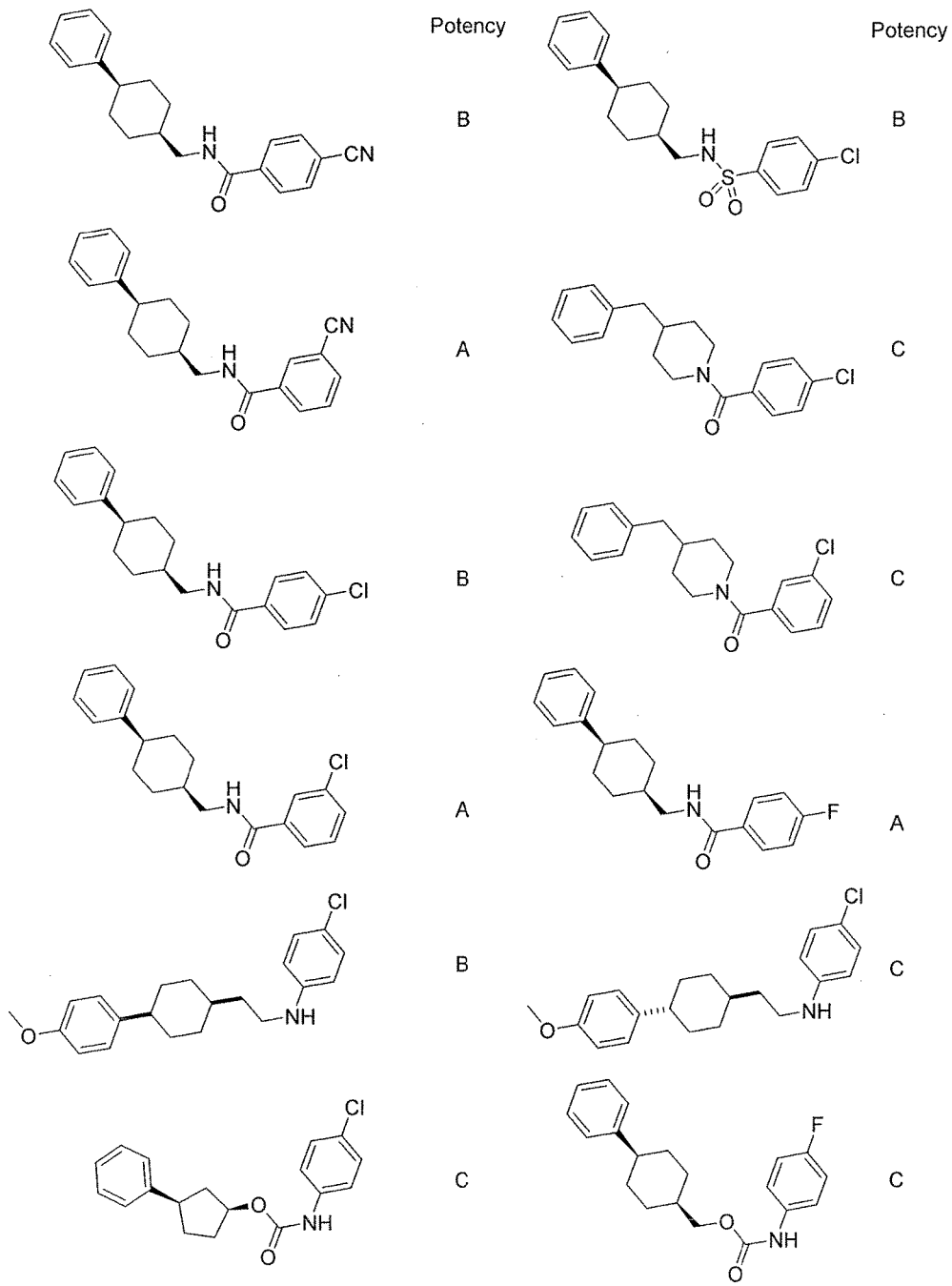
Figure 1C:
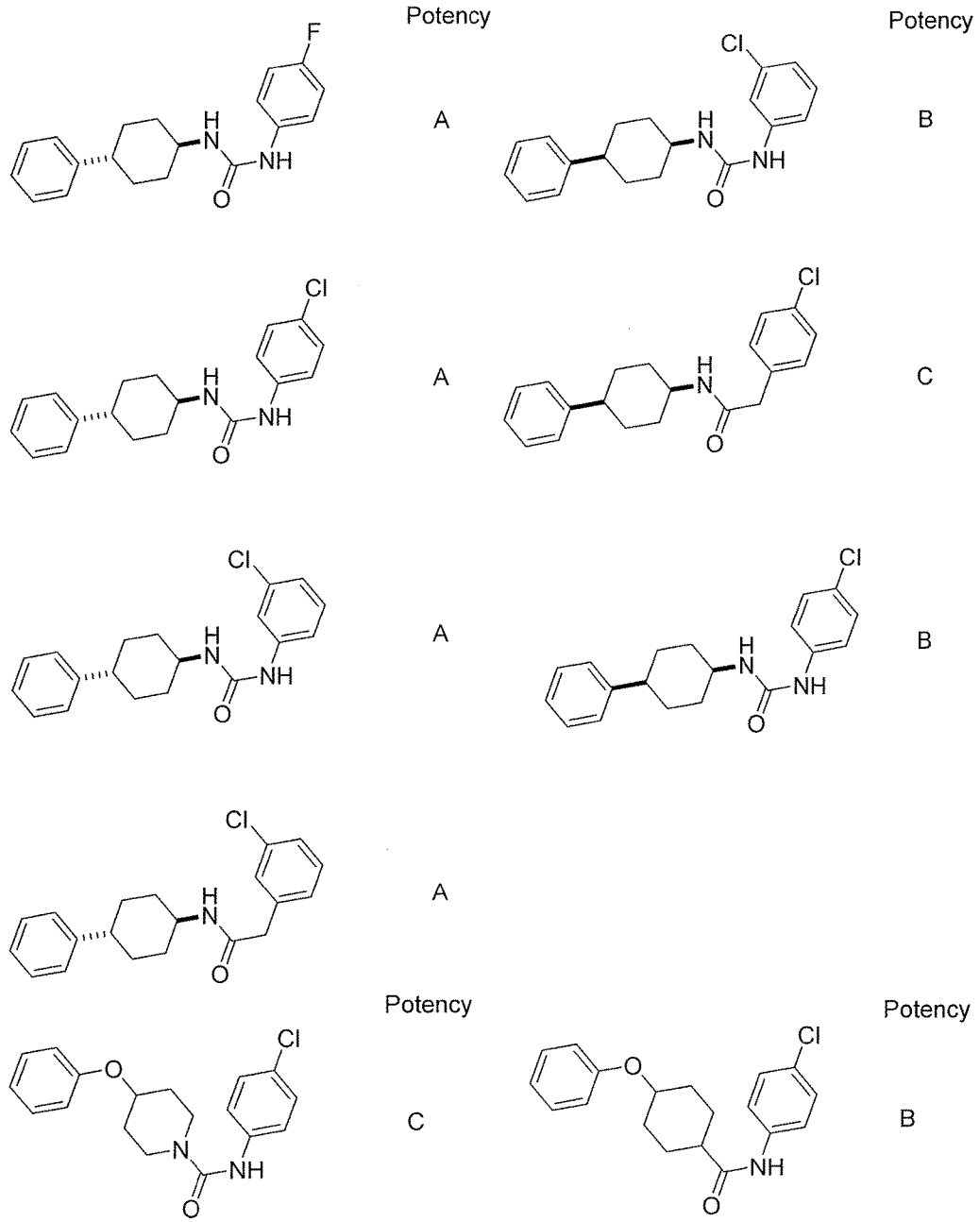
Figure 1D:
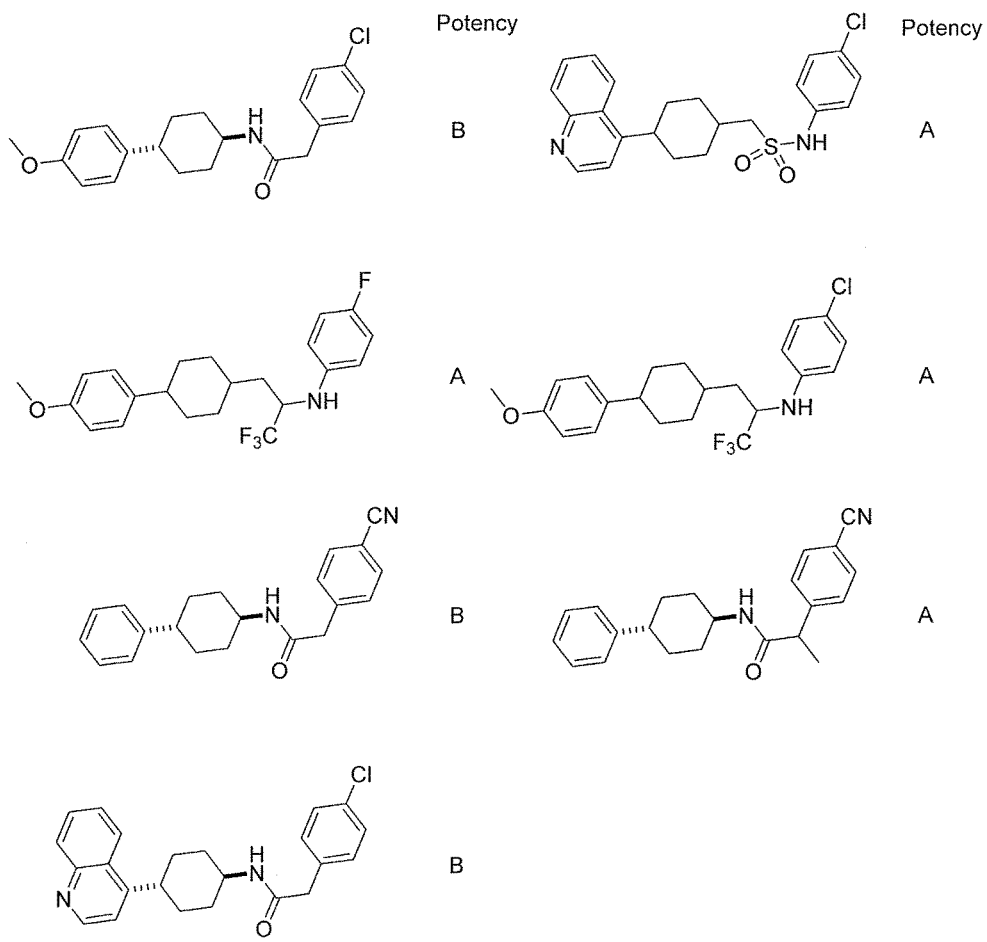

In one group of selected embodiments, any one compound of FIG. 1 is provided.

In another group of selected embodiments, any one compound of FIG. 1 is provided having an activity level identified as "A" or "B".

In another group of selected embodiments, any one compound of FIG. 1 is provided having an activity level identified as "A".

22

Methods of Synthesis

The compounds of the present invention may be prepared from starting materials which are known in the chemical literature or are commercially available by methods such as those illustrated in the following Schemes utilizing chemical transformations known to those skilled in the art of organic chemistry. Solvents, temperatures, pressures, and other reaction conditions may readily be selected by one of ordinary skill in the art. These Schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). Further, the representation of the reactions in these Schemes as discrete steps does not preclude their being performed in tandem, either by telescoping multiple steps in the same reaction vessel or by performing multiple steps without purifying or characterizing the intermediate(s). In addition, many of the compounds prepared by the methods below can be further modified using conventional chemistry well known to those skilled in the art. All documents cited herein are incorporated herein by reference in their entirety.

References to many of these chemical transformations employed herein can be found in Smith, M. B. et al., March's Advanced Organic Chemistry Reactions, Mechanisms, and Structure, Fifth Edition, Wiley-Interscience, New York (2001), or other standard texts on the topic of synthetic organic chemistry. Certain transformations may require that reactive functional groups be masked by protecting group(s). A convenient reference which provides conditions for introduction, removal, and relative susceptibility to reaction conditions of these groups is Greene, T. W. et al., Protective Groups in Organic Synthesis, Third Edition, Wiley-Interscience, New York (1999).

Scheme 1

Reverse Amides and Sulfonamides, Cycloalkyl Core, Direct or O-Linked G

Scheme 1

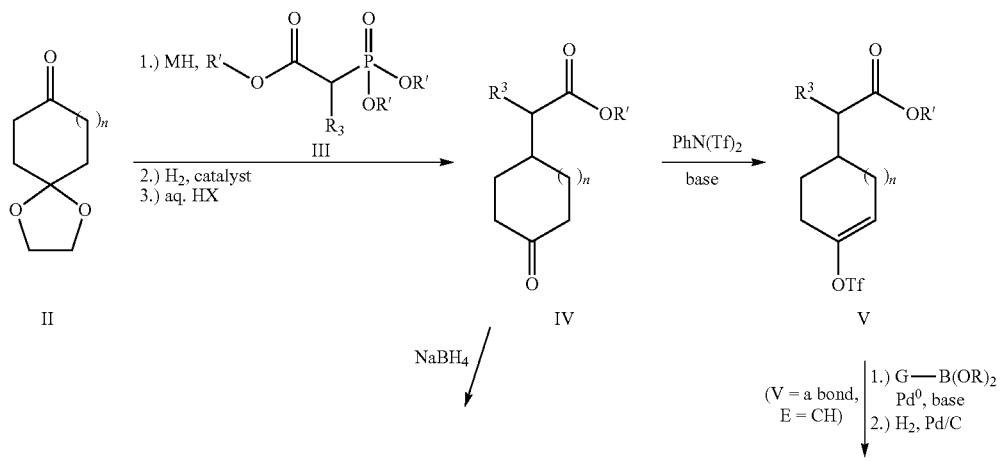

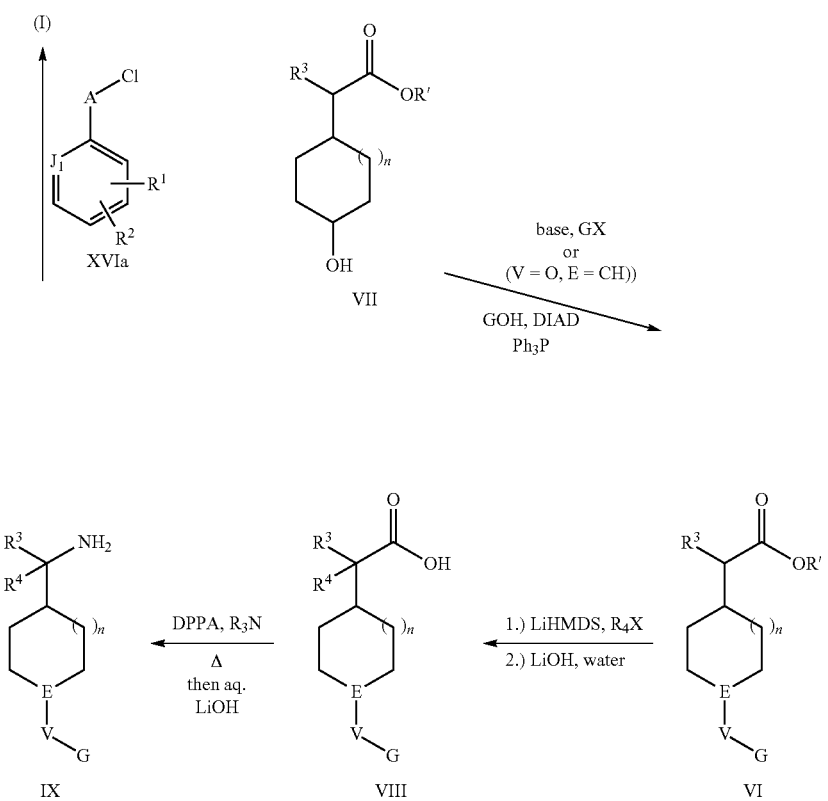

Treatment of a phosphonoacetate ester (III), with a base such as sodium hydride in a solvent such as THF (Scheme 1) followed by a ketone of the general structure II affords a trisubstituted olefin. Substituted analogs of III ($R^3$ is not H) afford tetrasubstituted olefins. This method and additional methods described below are transformations familiar to those skilled in the art of organic/medicinal chemistry. Alternative methods for olefination and the transformations described below are known and will be selected by one skilled in the art based on their applicability to the specific substrate under consideration. Reduction is accomplished by stirring or shaking a solution of the olefin in a suitable solvent under an atmosphere or more of $H_2$ in the presence of a catalyst, normally palladium on carbon. Hydrolysis of the ketal group affords a ketone of the general structure IV. Typically, this is accomplished by heating with an aqueous acid such as HCl in the presence of a co-solvent such as THF. In addition to the cyclic ethylene glycol-based ketal shown, other cyclic and acyclic ketal protecting groups could be used. Ketones are deprotonated with bases such as LiHMDS and react with N-phenyltrifluoromethanesulfonimide or similar reagents to afford triflates of the general structure V. These triflates participate in Suzuki couplings (T. Ishiyama, M. Murata, N. Miyaura, *J. Org. Chem.*, 1995, 60, 7508-7510) with boronic acids or esters $G-B(OR)_2$ to afford coupled products. Many variations on this reaction are known, but generally it involves heating the two substrates and a catalyst such as $(Ph_3P)_4Pd$ in a solvent such as DMF with a base such as aq. potassium carbonate. Reduction of the olefin provides intermediate VI (where V=a bond and E=CH). Ketones IV can be reduced by $NaBH_4$ or similar hydride reducing agents to afford alcohols of the general structure VII. These alcohols can be deprotonated with bases such as sodium hydride or KHMDS, and the resulting alkoxides can react with aryl or heteroaryl halides under SNAr conditions to afford additional intermediates VI (where V=O and E=CH). Alternatively, reaction can be accomplished by activation of alcohol VII with DIAD, DEAD, or a related azodicarboxylate and a trialkyl or triarylphosphine and coupling with a phenol or related heteroaryl GOH. (Mitsunobu reaction) Intermediates VI (and later intermediates) may be obtained as mixtures of cis and trans isomers. Methods for control of the stereochemical outcome of the above reactions are known to those familiar in the art of organic/medicinal chemistry. Additionally, methods for the separation of these isomers are known and described in detail in the synthetic examples. If required, the group $R^4$ can be appended by alkylation of intermediate VI. Methods for control of the absolute stereochemistry of the resulting asymmetric center are known to those familiar with the art, as are chiral separation methods. Saponification of the ester by heating with aq. LiOH or a similar base, generally in the presence of an organic co-solvent such as THF affords carboxylic acids VIII. Acids VIII can be rearranged, usually by heating with DPPA and triethylamine (Curtius and related rearrangements), and the intermediate isocyanates react with aq. base to afford primary amines IX. These can react with electrophiles including, but not limited to acid chlorides and sulfonyl chlorides XVIa to afford compounds of the invention I. Another means of preparing compounds I from IX where A is CO uses the carboxylic acid derivative of XVIa and peptide coupling reagents. For a recent review of peptide coupling methods see: Ayman El-Faham and Fernando Albericio. Chem. Rev. 2011, 111, 6557-6602.

Scheme 2

Reverse Amides and Sulfonamides, Piperidine Core, Direct or C-Linked G

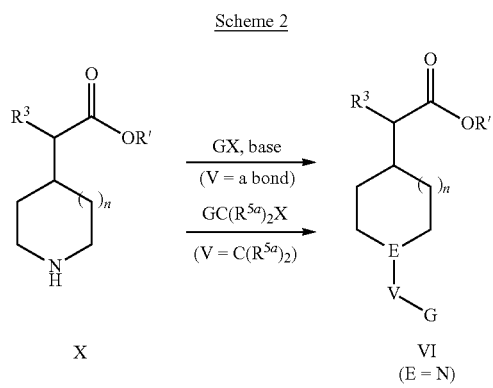

Piperidine and pyrrolidine esters X are known compounds and can undergo $S_NAr$ (V=a bond) and N-alklyation (V=C$(R^{5a})_2$) reactions to afford intermediates VI (E=N). These intermediates may be transformed to compounds of the invention I as shown in Scheme I.

Scheme 3

Reverse Amides and Sulfonamides, Cycloalkyl or Piperidine Core, Direct C, or O-Linked G, Alternate Method

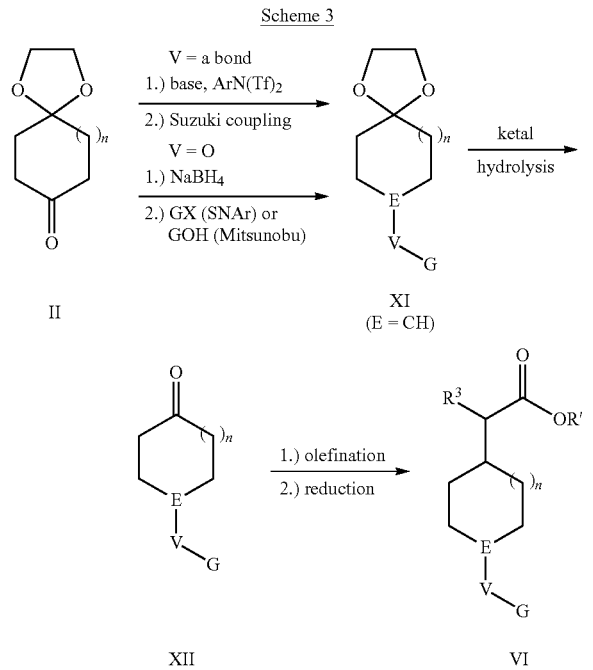

Scheme 3 illustrates a method of making intermediate VI by performing the steps of Scheme 1 in a different order. Intermediate II can be converted to a triflate as described above and coupled with a boronic acid or ester G-B(OR)$_2$ to give intermediate XI (V=a bond). Analogs where V=O can be prepared by reduction of ketone II and conversion to the ether XI as described above. Ketal hydrolysis affords ketone XII. Transformation to intermediate VI is accomplished by olefination and reduction as described above. Intermediates XII in which E=N can be prepared from ketones XIII using SNAr (V=a bond) or alkylation (V=C$(R^{5a})_2$) chemistry.

Scheme 4

Truncated Normal Amides, Cycloalkyl or Piperidine Core, Direct, C, or O-Linked G

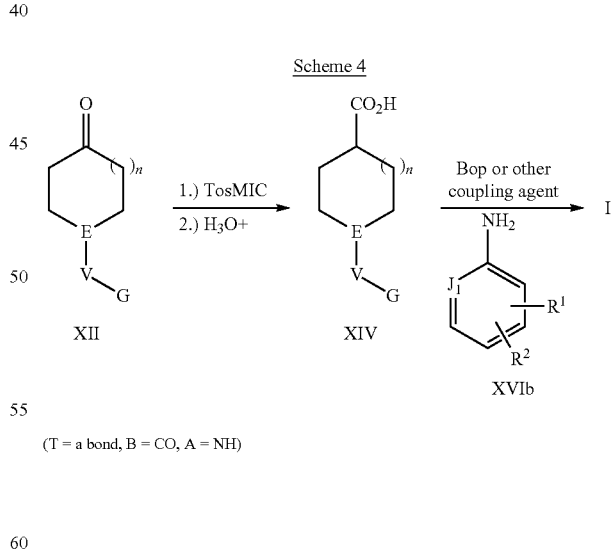

(T = a bond, B = CO, A = NH)

Scheme 4 illustrates a method of making additional compounds of the invention. Ketone XII can be transformed into a nitrile by the use of TosMIC (Van Leusen reaction). Hydrolysis of the nitrile affords acid XIV which can be converted into compounds of the invention I by treatment with amines under amide coupling conditions.

Scheme 5

Ureas and Phenylaceticamides of Cyclohexylamine or 4-aminopiperidine, Direct, C, or O-Linked G

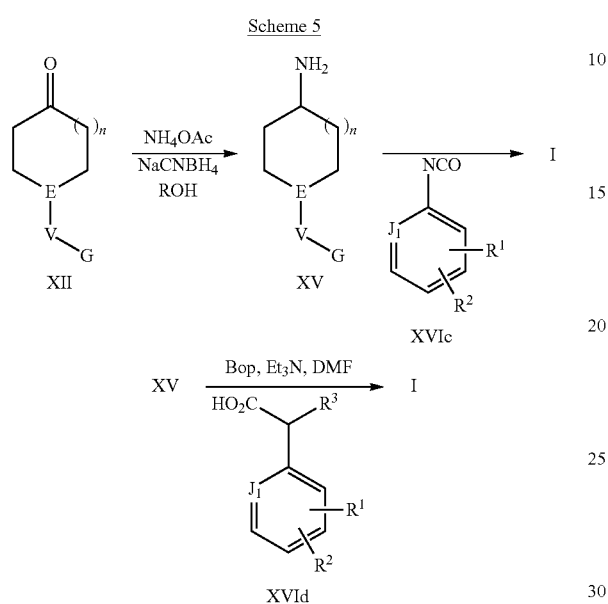

Scheme 5 illustrates a method of making additional compounds of the invention. Ketones XII can be transformed into primary amines XV by reductive amination with ammonia or an ammonium salt. This reaction is generally performed using sodium cyanoborohydride in an alcoholic solvent. Treatment with isocyanates XVIc affords ureas which are compounds of the invention I. Arylacetamides which are compounds of the invention I are obtained by coupling amine XV with arylacetic acids XVId using a reagent such as Bop and a tertiary amine base in a solvent such as DMF.

Scheme 6

Control of Absolute Stereochemistry in the Conversion of VI to VIII

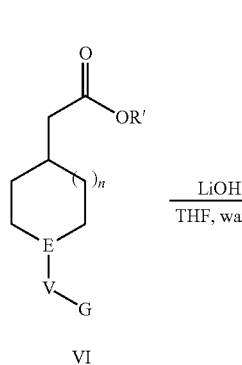

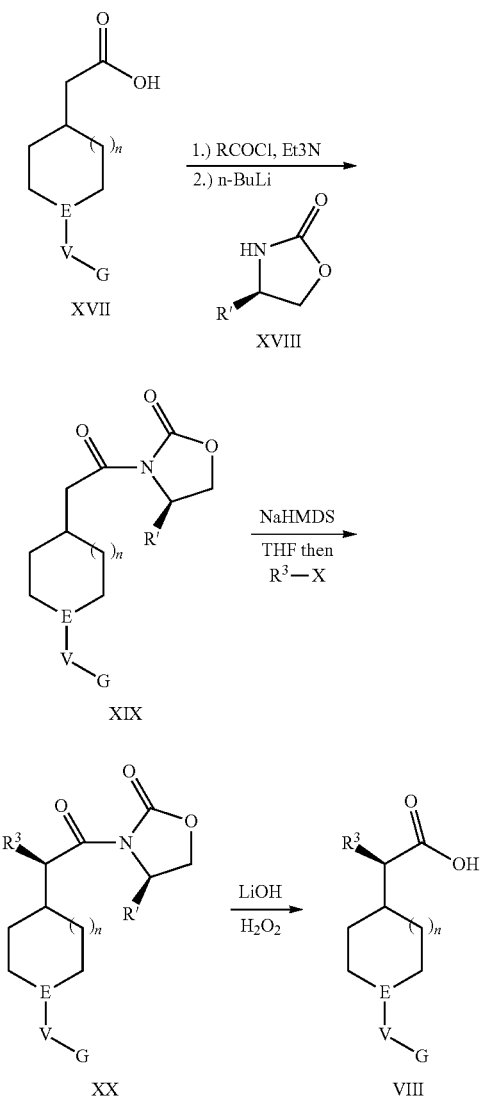

Scheme 6 illustrates a method for controlling the absolute stereochemistry of intermediate VIII and materials arising from it. Saponification of esters VI provides carboxylic acids XVII. Treatment of these acids with an acid chloride such as pivaloyl chloride provides a mixed anhydride intermediate. In a separate vessel, an optically pure oxazolidinone of known stereochemistry and general structure XVIII is deprotonated by treatment with a strong base such as n-BuLi. These activated species are combined to form the acyloxazolidinone XIX which is deprotonated by bases such as NaHMDS. Alkylation of the resulting enolate proceeds with predictable control of stereochemistry at the newly-formed center to provide materials XX. Removal of the chiral auxiliary to give optically-active carboxylic acids VIII is accomplished by treatment with a solution of basic hydrogen peroxide. For a review of the history and scope scope of this reaction see: D. A. Evans, M. D. Ennis, D. J. Mathre. J. Am. Chem. Soc., 1982, 104 (6), pp 1737-1739.

Scheme 7

Synthesis of Compounds of the Invention (I) where $R^6$=OH

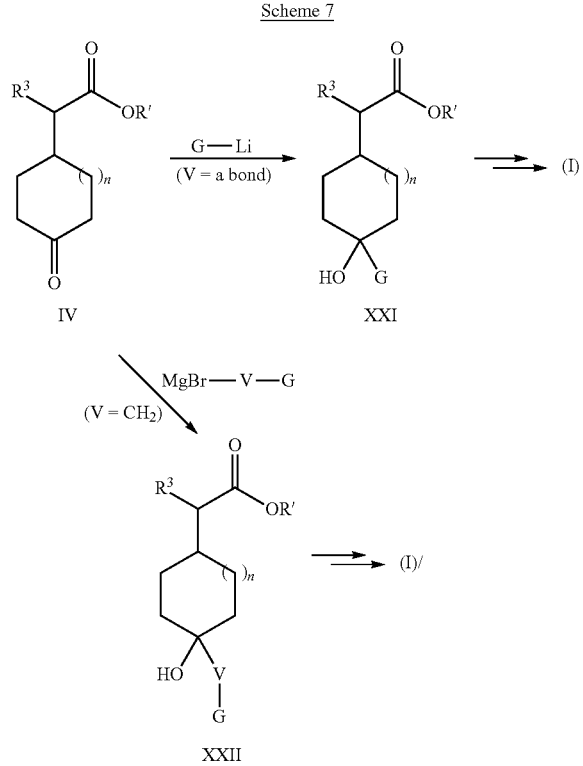

As shown in Scheme 7, a ketone of general structure IV can be treated with a the lithiate G-Li, which can be generated by several methods well-known to one skilled in the art, to produce a tertiary alcohol of general structure XXI. The ester of general structure XXXI can be converted to a compound of general structure I via methods already described herein. Alternatively, the ketone IV can be treated with the organometallic MgBr—V-G (Grignard reagent) to give a tertiary alcohol of general structure XXII.

Scheme 8

Synthesis of Compounds of the Invention (I) where $R^5$=OH

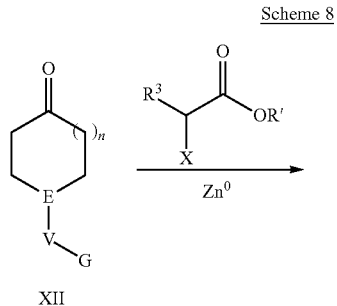

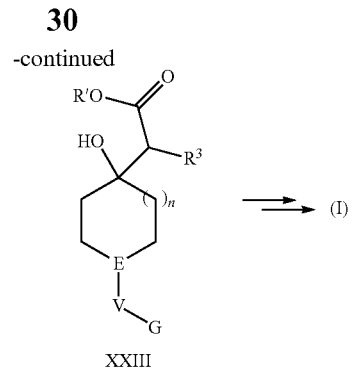

As shown in Scheme 8, a ketone of general structure XII can be treated with a halo acetate where X=Br in the presence of Zinc metal (Reformatsky reaction) to give the a tertiary alcohol of general structure XXIII. The ester XXIII can be converted to a compound of the Invention (I) by methods already described herein.

In addition to the above general schemes, the compounds described herein can be prepared by representative methods as provided in the Examples below.

Modifications to Enhance Inhibitor Characteristics

It is frequently beneficial, and sometimes imperative, to improve one of more physical properties of the treatment modalities disclosed herein and/or the manner in which they are administered. Improvements of physical properties include, for example, methods of increasing water solubility, bioavailability, serum half-life, and/or therapeutic half-life; and/or modulating biological activity.

Modifications known in the art include pegylation, Fc-fusion and albumin fusion. Although generally associated with large molecule agents (e.g., polypeptides), such modifications have recently been evaluated with particular small molecules. By way of example, Chiang, M. et al., (*J. Am. Chem. Soc.*, 136(9):3370-3373 (2014)) describe a small molecule agonist of the adenosine 2a receptor conjugated to the immunoglobulin Fc domain. The small molecule-Fc conjugate retained potent Fc receptor and adenosine 2a receptor interactions and showed superior properties compared to the unconjugated small molecule. Covalent attachment of PEG molecules to small molecule therapeutics has also been described (Li, W. et al., *Progress in Polymer Science*, 38:421-444 (2013)).

Therapeutic and Prophylactic Uses

The present invention contemplates the use of the TDO inhibitors described herein in the treatment or prevention of a broad range of diseases, disorders and/or conditions, and/or the symptoms thereof. While particular uses are described in detail hereafter, it is to be understood that the present invention is not so limited. Furthermore, although general categories of particular diseases, disorders and conditions are set forth hereafter, some of the diseases, disorders and conditions may be a member of more than one category, and others may not be a member of any of the disclosed categories.

Oncology-Related Disorders.

In accordance with the present invention, an IDO inhibitor can be used to treat or prevent a proliferative condition or disorder, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present invention also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. The invention contemplates reducing tolerance to a tumor cell or cancer cell antigen, e.g., by modulating activity of a regulatory T-cell and/or a CD8+ T-cell (see, e.g., Ramirez-Montagut et al., *Oncogene*, 22:3180-3187 (2003); and Sawaya et al., *New Engl. J. Med.*, 349:1501-1509 (2003)). In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia.

In some embodiments, the present invention provides methods for treating a proliferative condition, cancer, tumor, or precancerous condition with an IDO inhibitor and at least one additional therapeutic or diagnostic agent, examples of which are set forth elsewhere herein.

Immune- and Inflammatory-Related Disorders.

As used herein, terms such as "immune disease", "immune condition", "immune disorder", "inflammatory disease", "inflammatory condition", "inflammatory disorder" and the like are meant to broadly encompass any immune- or inflammatory-related condition (e.g., pathological inflammation and autoimmune diseases). Such conditions frequently are inextricably intertwined with other diseases, disorders and conditions. By way of example, an "immune condition" may refer to proliferative conditions, such as cancer, tumors, and angiogenesis; including infections (acute and chronic), tumors, and cancers that resist eradication by the immune system.

A non-limiting list of immune- and inflammatory-related diseases, disorders and conditions which may be treated or prevented with the compounds and compositions of the present invention include, arthritis (e.g., rheumatoid arthritis), kidney failure, lupus, asthma, psoriasis, colitis, pancreatitis, allergies, fibrosis, surgical complications (e.g., where inflammatory cytokines prevent healing), anemia, and fibromyalgia. Other diseases and disorders which may be associated with chronic inflammation include Alzheimer's disease, congestive heart failure, stroke, aortic valve stenosis, arteriosclerosis, osteoporosis, Parkinson's disease, infections, inflammatory bowel disease (e.g., Crohn's disease and ulcerative colitis), allergic contact dermatitis and other eczemas, systemic sclerosis, transplantation and multiple sclerosis.

Among other immune-related disorders, it is contemplated that inhibition of IDO function may also play a role in immunologic tolerance and prevention of fetal rejection in utero.

In some embodiments, an IDO inhibitor described herein can be combined with an immunosuppressive agent to reduce the number of immune effector cells.

Some of the aforementioned diseases, disorders and conditions for which an IDO inhibitor may be particularly efficacious (due to, for example, limitations of current therapies) are described in more detail hereafter.

Rheumatoid Arthritis (RA), which is generally characterized by chronic inflammation in the membrane lining (the synovium) of the joints, affects approximately 1% of the U.S. population (~2.1 million people). Further understanding of the role of cytokines, including TNF-α and IL-1, in the inflammatory process has enabled the development and introduction of a new class of disease-modifying antirheumatic drugs (DMARDs). Agents (some of which overlap with treatment modalities for RA) include ENBREL® (etanercept), REMICADE® (infliximab), HUMIRA® (adalimumab) and KINERET® (anakinra). Though some of these agents relieve symptoms, inhibit progression of structural damage, and improve physical function in particular patient populations, there is still a need for alternative agents with improved efficacy, complementary mechanisms of action, and fewer/less severe adverse effects.

Psoriasis, a constellation of common immune-mediated chronic skin diseases, affects more than 4.5 million people in the U.S., of which 1.5 million are considered to have a moderate-to severe form of the disease. Moreover, over 10% of patients with psoriasis develop psoriatic arthritis, which damages the bone and connective tissue around the joints. An improved understanding of the underlying physiology of psoriasis has resulted in the introduction of agents that, for example, target the activity of T lymphocytes and cytokines responsible for the inflammatory nature of the disease. Such agents include the TNF-α inhibitors (also used in the treatment of rheumatoid arthritis (RA)), including ENBREL® (etanercept), REMICADE® (infliximab) and HUMIRA® (adalimumab)), and T-cell inhibitors such as AMEVIVE® (alefacept) and RAPTIVA® (efalizumab). Though several of these agents are effective to some extent in certain patient populations, none have been shown to effectively treat all patients.

Subjects suffering from multiple sclerosis (MS), a seriously debilitating autoimmune disease comprising multiple areas of inflammation and scarring of the myelin in the brain and spinal cord, may be particularly helped by the IDO inhibitors described herein, as current treatments only alleviate symptoms or delay the progression of disability.

Similarly, the IDO inhibitors may be particularly advantageous for subjects afflicted with neurodegenerative disorders, such as Alzheimer's disease (AD), a brain disorder that seriously impairs patients' thought, memory, and language processes; and Parkinson's disease (PD), a progressive disorder of the CNS characterized by, for example, abnormal movement, rigidity and tremor. These disorders are progressive and debilitating, and no curative agents are available.

Viral-Related Disorders.

The present invention contemplates the use of the IDO inhibitors in the treatment and/or prevention of any viral disease, disorder or condition for which treatment with an IDO inhibitor may be beneficial. In particular embodiments, the viral disorder is a chronic viral disorder. Examples of viral diseases, disorders and conditions that are contemplated include, but are not limited to, hepatitis B virus (HBV), hepatitis C virus (HCV), human papilloma virus (HPV), HIV, AIDS (including its manifestations such as cachexia, dementia, and diarrhea), herpes simplex virus (HSV), Epstein-Barr virus (EBV), varicella zoster virus, coxsackie virus, and cytomegalovirus (CMV).

Bacterial- and Parasitic-Related Disorders.

Embodiments of the present invention contemplate the administration of the IDO inhibitors described herein to a subject for the treatment of a bacterial infection, for example, a *Mycobacterium* infection (e.g., *Mycobacterium leprae* or *Mycobacterium tuberculosis*) or an infection caused by *Listeria monocytogenes* or *Toxplasma gondii*. Other embodiments contemplate the treatment of a parasitic infection including, but not limited to, *Leishmania donovani, Leishmania tropica, Leishmania major, Leishmania aethiopica, Leishmania mexicana, Plasmodium falciparum, Plasmodium vivax, Plasmodium ovale,* or *Plasmodium malariae*. Frequently, anti-parasitic therapy is administered prophylactically (e.g., before a subject travels to an area with a high frequency of parasitic infection).

Pharmaceutical Compositions

The IDO inhibitors of the present invention may be in the form of compositions suitable for administration to a subject. In general, such compositions are "pharmaceutical compositions" comprising an IDO inhibitor(s) and one or more pharmaceutically acceptable or physiologically acceptable diluents, carriers or excipients. In certain embodiments, the IDO inhibitors are present in a therapeutically acceptable amount. The pharmaceutical compositions may be used in the methods of the present invention; thus, for example, the pharmaceutical compositions can be administered ex vivo or in vivo to a subject in order to practice the therapeutic and prophylactic methods and uses described herein.

The pharmaceutical compositions of the present invention can be formulated to be compatible with the intended method or route of administration; exemplary routes of administration are set forth herein. Furthermore, the pharmaceutical compositions may be used in combination with other therapeutically active agents or compounds as described herein in order to treat or prevent the diseases, disorders and conditions as contemplated by the present invention.

The pharmaceutical compositions containing the active ingredient (e.g., an inhibitor of IDO function) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example, starch, gelatin or acacia, and lubricating agents, for example, magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly(methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example, peanut oil, liquid paraffin, or olive oil.

Aqueous suspensions contain the active materials in admixture with excipients suitable for the manufacture thereof. Such excipients can be suspending agents, for example, sodium carboxymethylcellulose, methylcellulose, hydroxy-propylmethylcellulose, sodium alginate, polyvinyl-pyrrolidone, gum tragacanth and gum acacia; dispersing or wetting agents, for example, a naturally-occurring phosphatide (e.g., lecithin), or condensation products of an alkylene oxide with fatty acids (e.g., polyoxyethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present invention may also be in the form of oil-in-water emulsions. The oily phase may be a vegetable oil, for example, olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

Formulations can also include carriers to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, may be employed.

The pharmaceutical compositions typically comprise a therapeutically effective amount of an IDO inhibitor contemplated by the present invention and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-hydroxyethyl)piperazine-N'-(2-ethanesulfonic acid) (HEPES), 2-(N-morpholino)ethanesulfonic acid (MES), 2-(N-morpholino)ethanesulfonic acid sodium salt (MES), 3-(N-morpholino)propanesulfonic acid (MOPS), and N-tris[hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EPIPEN®)), whereas a multi-use container (e.g., a multi-use vial) is provided in other embodiments. Any drug delivery apparatus may be used to deliver and IDO inhibitor, including implants (e.g., implantable pumps) and catheter systems, slow injection pumps and devices, all of which are well known to the skilled artisan. Depot injections, which are generally administered subcutaneously or intramuscularly, may also be utilized to release the polypeptides disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, CREMOPHOR® EL (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The present invention contemplates the administration of the IDO inhibitors in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The IDO inhibitors contemplated by the present invention may be in the form of any other suitable pharmaceutical composition (e.g., sprays for nasal or inhalation use) currently known or developed in the future.

The concentration of a polypeptide or fragment thereof in a formulation can vary widely (e.g., from less than about 0.1%, usually at or at least about 2% to as much as 20% to 50% or more by weight) and will usually be selected primarily based on fluid volumes, viscosities, and subject-based factors in accordance with, for example, the particular mode of administration selected.

Routes of Administration

The present invention contemplates the administration of IDO inhibitors, and compositions thereof, in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), sublingual and inhalation. Depot injections, which are generally administered subcutaneously or intramuscularly, may also be utilized to release the IDO inhibitors disclosed herein over a defined period of time.

Particular embodiments of the present invention contemplate oral administration.

Combination Therapy

The present invention contemplates the use of IDO inhibitors in combination with one or more active therapeutic agents (e.g., chemotherapeutic agents) or other prophylactic or therapeutic modalities (e.g., radiation). In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the IDO inhibitors are administered or applied sequentially, e.g., where one agent is administered prior to one or more other agents. In other embodiments, the IDO inhibitors are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present invention.

The IDO inhibitors of the present invention may be used in combination with at least one other (active) agent in any manner appropriate under the circumstances. In one embodiment, treatment with the at least one active agent and at least one IDO inhibitor of the present invention is maintained over a period of time. In another embodiment, treatment with the at least one active agent is reduced or discontinued (e.g., when the subject is stable), while treatment with an IDO inhibitor of the present invention is maintained at a constant dosing regimen. In a further embodiment, treatment with the at least one active agent is reduced or discontinued (e.g., when the subject is stable), while treatment with an IDO inhibitor of the present invention is reduced (e.g., lower dose, less frequent dosing or shorter treatment regimen). In yet another embodiment, treatment with the at least one active agent is reduced or discontinued (e.g., when the subject is stable), and treatment with the IDO inhibitor of the present invention is increased (e.g., higher dose, more frequent dosing or longer treatment regimen). In yet another embodiment, treatment with the at least one active agent is maintained and treatment with the IDO inhibitor of the present invention is reduced or discontinued (e.g., lower dose, less frequent dosing or shorter treatment regimen). In yet another embodiment, treatment with the at least one active agent and treatment with the IDO inhibitor of the present invention are reduced or discontinued (e.g., lower dose, less frequent dosing or shorter treatment regimen).

Oncology-Related Disorders.

The present invention provides methods for treating and/or preventing a proliferative condition, cancer, tumor, or precancerous disease, disorder or condition with an IDO inhibitor and at least one additional therapeutic agent, such as radiation, an immunomodulatory agent or chemotherapeutic agent, or diagnostic agent. Suitable immunomodulatory agents that may be used in the present invention include CD40L, B7, and B7RP1; activating monoclonal antibodies (mAbs) to stimulatory receptors, such as, ant-CD40, anti-CD38, anti-ICOS, and 4-IBB ligand; dendritic cell antigen loading (in vitro or in vivo); anti-cancer vaccines such as dendritic cell cancer vaccines; cytokines/chemokines, such as, IL1, IL2, IL12, IL18, ELC/CCL19, SLC/CCL21, MCP-1, IL-4, IL-18, TNF, IL-15, MDC, IFNa/b, M-CSF, IL-3, GM-CSF, IL-13, and anti-IL-10; bacterial lipopolysaccharides (LPS); and immune-stimulatory oligonucleotides.

Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; and pharmaceutically acceptable salts, acids or derivatives of any of the above.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above. In certain embodiments, combination therapy comprises administration of a hormone or related hormonal agent.

Chemotherapeutic agents also include signal transduction inhibitors (STI). The term "signal transduction inhibitor" refers to an agent that selectively inhibits one or more steps in a signaling pathway. Signal transduction inhibitors (STIs) of the present invention include: (i) bcr/abl kinase inhibitors (e.g., GLEEVEC); (ii) epidermal growth factor (EGF) receptor inhibitors, including kinase inhibitors and antibodies; (iii) her-2/neu receptor inhibitors (e.g., HERCEPTIN); (iv) inhibitors of Akt family kinases or the Akt pathway (e.g., rapamycin); (v) cell cycle kinase inhibitors (e.g., flavopiridol); and (vi) phosphatidyl inositol kinase inhibitors.

Additional treatment modalities that may be used in combination with an IDO inhibitor include a cytokine or cytokine antagonist, such as IL-12, IFN, or anti-epidermal growth factor receptor, radiotherapy, a monoclonal antibody against another tumor antigen, a complex of a monoclonal antibody and toxin, a T-cell adjuvant, bone marrow transplant, or antigen presenting cells (e.g., dendritic cell therapy). Vaccines (e.g., as a soluble protein or as a nucleic acid encoding the protein) are also provided herein.

Cardiovascular Diseases.

The present invention provides methods for treating and/or preventing certain cardiovascular- and/or metabolic-related diseases, disorders and conditions, as well as disorders associated therewith, with an IDO inhibitor and at least one additional therapeutic or diagnostic agent.

Examples of therapeutic agents useful in combination therapy for the treatment of hypercholesterolemia (and atherosclerosis as well) include statins (e.g., CRESTOR, LESCOL, LIPITOR, MEVACOR, PRAVACOL, and ZOCOR), which inhibit the enzymatic synthesis of cholesterol; bile acid resins (e.g., COLESTID, LO-CHOLEST, PREVALITE, QUESTRAN, and WELCHOL), which sequester cholesterol and prevent its absorption; ezetimibe (ZETIA), which blocks cholesterol absorption; fibric acid (e.g., TRICOR), which reduces triglycerides and may modestly increase HDL; niacin (e.g., NIACOR), which modestly lowers LDL cholesterol and triglycerides; and/or a combination of the aforementioned (e.g., VYTORIN (ezetimibe with simvastatin). Alternative cholesterol treatments that may be candidates for use in combination with the IDO inhibitors described herein include various supplements and herbs (e.g., garlic, policosanol, and guggul). The present invention encompasses pharmaceutically acceptable salts, acids or derivatives of any of the above.

Immune- and Inflammatory-Related Disorders.

The present invention provides methods for treating and/or preventing immune- and/or inflammatory-related diseases, disorders and conditions, as well as disorders associated therewith, with an IDO inhibitor and at least one additional therapeutic or diagnostic agent.

Examples of therapeutic agents useful in combination therapy include, but are not limited to, the following: non-steroidal anti-inflammatory drug (NSAID) such as aspirin, ibuprofen, and other propionic acid derivatives (alminoprofen, benoxaprofen, bucloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone). Other combinations include cyclooxygenase-2 (COX-2) inhibitors.

Other active agents for combination include steroids such as prednisolone, prednisone, methylprednisolone, betamethasone, dexamethasone, or hydrocortisone. Such a combination may be especially advantageous since one or more adverse effects of the steroid can be reduced or even eliminated by tapering the steroid dose required.

Additional examples of active agents that may be used in combinations for treating, for example, rheumatoid arthritis, include cytokine suppressive anti-inflammatory drug(s) (CSAIDs); antibodies to, or antagonists of, other human cytokines or growth factors, for example, TNF, LT, IL-1β, IL-2, IL-6, IL-7, IL-8, IL-15, IL-16, IL-18, EMAP-II, GM-CSF, FGF, or PDGF.

Particular combinations of active agents may interfere at different points in the autoimmune and subsequent inflammatory cascade, and include TNF antagonists such as chimeric, humanized or human TNF antibodies, REMICADE, anti-TNF antibody fragments (e.g., CDP870), and soluble p55 or p75 TNF receptors, derivatives thereof, p75TNFRIgG (ENBREL.) or p55TNFR1gG (LENERCEPT), soluble IL-13 receptor (sIL-13), and also TNFα-converting enzyme (TACE) inhibitors; similarly, IL-1 inhibitors (e.g., Interleukin-1-converting enzyme inhibitors) may be effective. Other combinations include Interleukin 11, anti-P7s and p-selectin glycoprotein ligand (PSGL). Other examples of agents useful in combination with the IDO inhibitors described herein include interferon-β1a (AVONEX); interferon-β1b (BETASERON); copaxone; hyperbaric oxygen; intravenous immunoglobulin; clabribine; and antibodies to, or antagonists of, other human cytokines or growth factors (e.g., antibodies to CD40 ligand and CD80).

Immune Checkpoint Inhibitors.

The present invention contemplates the use of the inhibitors of IDO function described herein in combination with additional immune checkpoint inhibitors.

The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism.

T cells have been the major focus of efforts to therapeutically manipulate endogenous antitumor immunity because of i) their capacity for the selective recognition of peptides derived from proteins in all cellular compartments; ii) their capacity to directly recognize and kill antigen-expressing cells (by CD8+ effector T cells; also known as cytotoxic T lymphocytes (CTLs)); and iii) their ability to orchestrate diverse immune responses by CD4+ helper T cells, which integrate adaptive and innate effector mechanisms. In the clinical setting, the blockade of immune checkpoints—which results in the amplification of antigen-specific T cell responses—has shown to be a promising approach in human cancer therapeutics.

T cell-mediated immunity includes multiple sequential steps, each of which is regulated by counterbalancing stimulatory and inhibitory signals in order to optimize the response. While nearly all inhibitory signals in the immune response ultimately modulate intracellular signaling pathways, many are initiated through membrane receptors, the ligands of which are either membrane-bound or soluble (cytokines). While co-stimulatory and inhibitory receptors and ligands that regulate T-cell activation are frequently not over-expressed in cancers relative to normal tissues, inhibitory ligands and receptors that regulate T cell effector functions in tissues are commonly overexpressed on tumor cells or on non-transformed cells associated with the tumor microenvironment. The functions of the soluble and membrane-bound receptor-ligand immune checkpoints can be modulated using agonist antibodies (for co-stimulatory pathways) or antagonist antibodies (for inhibitory pathways). Thus, in contrast to most antibodies currently approved for cancer therapy, antibodies that block immune checkpoints do not target tumor cells directly, but rather target lymphocyte receptors or their ligands in order to enhance endogenous antitumor activity. [See Pardoll, (April 2012) Nature Rev. Cancer 12:252-64].

Examples of immune checkpoints (ligands and receptors), some of which are selectively upregulated in various types of tumor cells, that are candidates for blockade include PD1 (programmed cell death protein 1); PDL1 (PD1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); A2aR (adenosine A2a receptor A2aR); and Killer Inhibitory Receptors, which can be divided into two classes based on their structural features: i) killer cell immunoglobulin-like receptors (KIRs), and ii) C-type lectin receptors (members of the type II transmembrane receptor family). Other less well-defined immune checkpoints have been described in the literature, including both receptors (e.g., the 2B4 (also known as CD244) receptor) and ligands (e.g., certain B7 family inhibitory ligands such B7-H3 (also known as CD276) and B7-H4 (also known as B7-S1, B7x and VCTN1)). [See PardoII, (April 2012) Nature Rev. Cancer 12:252-64].

The present invention contemplates the use of the inhibitors of IDO function described herein in combination with inhibitors of the aforementioned immune-checkpoint receptors and ligands, as well as yet-to-be-described immune-checkpoint receptors and ligands. Certain modulators of immune checkpoints are currently available, whereas others are in late-stage development. To illustrate, when it was approved for the treatment of melanoma in 2011, the fully humanized CTLA4 monoclonal antibody ipilimumab (YERVOY; Bristol-Myers Squibb) became the first immune checkpoint inhibitor to receive regulatory approval in the US. Fusion proteins comprising CTLA4 and an antibody (CTLA4-Ig; abatcept (ORENCIA; Bristol-Myers Squibb)) have been used for the treatment of rheumatoid arthritis, and other fusion proteins have been shown to be effective in renal transplantation patients that are sensitized to Epstein Barr Virus. PD1 antibodies are also available for the treatment of cancer, including for example nivolumab (Bristol-Myers Squibb) and pembroluzimab (Merck), and anti-PDL1 antibodies are also being evaluated (e.g., MPDL3280A (Roche)). Nivolumab (Opdivo®) has shown promise in patients with melanoma, lung and kidney cancer, as well as multiple other malignancies.

In one aspect of the present invention, the claimed IDO inhibitors are combined with an immuno-oncology agent that is (i) an agonist of a stimulatory (including a co-stimulatory) receptor or (ii) an antagonist of an inhibitory (including a co-inhibitory) signal on T cells, both of which result in amplifying antigen-specific T cell responses. Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In another aspect, the immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In one aspect, T cell responses can be stimulated by a combination of the claimed IDO inhibitors and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and/or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD2. Other agents that can be combined with the IDO inhibitors of the present invention for the treatment of cancer include antagonists of inhibitory receptors on NK cells or agonists of activating receptors on NK cells. For example, compounds herein can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, the claimed IDO inhibitors can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab/lambrolizumab), or MEDI-0680 (AMP-514; WO2012/145493). The immuno-oncology agent may also include pidilizumab (CT- 011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. Suitable PD-L1 antibodies include, for example, MPDL3280A (RG7446; WO2010/077634), durvalumab (MEDI4736), BMS-936559 (WO2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-IBB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The present invention encompasses pharmaceutically acceptable salts, acids or derivatives of any of the above.

Viral Diseases.

The present invention provides methods for treating and/or preventing viral diseases, disorders and conditions, as well as disorders associated therewith, with an IDO inhibitor and at least one additional therapeutic or diagnostic agent (e.g., one or more other antiviral agents and/or one or more agents not associated with viral therapy).

Such combination therapy includes anti-viral agents targeting various viral life-cycle stages and having different mechanisms of action, including, but not limiting to, the following: inhibitors of viral uncoating (e.g., amantadine and rimantidine); reverse transcriptase inhibitors (e.g., acyclovir, zidovudine, and lamivudine); agents that target integrase; agents that block attachment of transcription factors to viral DNA; agents (e.g., antisense molecules) that impact translation (e.g., fomivirsen); agents that modulate translation/ribozyme function; protease inhibitors; viral assembly modulators (e.g., rifampicin); antiretrovirals such as, for example, nucleoside analogue reverse transcriptase inhibitors (e.g., azidothymidine (AZT), ddl, ddC, 3TC, d4T); non-nucleoside reverse transcriptase inhibitors (e.g., efavirenz, nevirapine); nucleotide analogue reverse transcriptase inhibitors; and agents that prevent release of viral particles (e.g., zanamivir and oseltamivir). Treatment and/or prevention of certain viral infections (e.g., HIV) frequently entail a group ("cocktail") of antiviral agents.

Other antiviral agents contemplated for use in combination with an IDO inhibitor include, but are not limited to, the following: abacavir, adefovir, amantadine, amprenavir, ampligen, arbidol, atazanavir, atripla, boceprevirertet, cidofovir, combivir, darunavir, delavirdine, didanosine, docosanol, edoxudine, emtricitabine, enfuvirtide, entecavir, famciclovir, fosamprenavir, foscarnet, fosfonet, ganciclovir, ibacitabine, imunovir, idoxuridine, imiquimod, indinavir, inosine, various interferons (e.g., peginterferon alfa-2a), lopinavir, loviride, maraviroc, moroxydine, methisazone, nelfinavir, nexavir, penciclovir, peramivir, pleconaril, podophyllotoxin, raltegravir, ribavirin, ritonavir, pyramidine, saquinavir, stavudine, telaprevir, tenofovir, tipranavir, trifluridine, trizivir, tromantadine, truvada, valaciclovir, valganciclovir, vicriviroc, vidarabine, viramidine, and zalcitabine.

The present invention encompasses pharmaceutically acceptable salts, acids or derivatives of any of the above.

Parasitic Disorders.

The present invention contemplates the use of the inhibitors of IDO function described herein in combination with antiparasitic agents. Such agents include, but are not limited to, thiabendazole, pyrantel pamoate, mebendazole, praziquantel, niclosamide, bithionol, oxamniquine, metrifonate, ivermectin, albendazole, eflornithine, melarsoprol, pentamidine, benznidazole, nifurtimox, and nitroimidazole. The skilled artisan is aware of other agents that may find utility for the treatment of parasitic disorders.

The present invention encompasses pharmaceutically acceptable salts, acids or derivatives of any of the above.

Bacterial Infections.

Embodiments of the present invention contemplate the use of the IDO inhibitors described herein in combination with agents useful in the treatment or prevention of bacterial disorders. Antibacterial agents can be classified in various manners, including based on mechanism of action, based on chemical structure, and based on spectrum of activity. Examples of antibacterial agents include those that target the bacterial cell wall (e.g., cephalosporins and penicillins) or the cell membrane (e.g., polymyxins), or interfere with essential bacterial enzymes (e.g., sulfonamides, rifamycins, and quinolines). Most antibacterial agents that target protein synthesis (e.g., tetracyclines and macrolides) are bacteriostatic, whereas agents such as the aminoglycoside are bactericidal. Another means of categorizing antibacterial agents is based on their target specificity; "narrow-spectrum" agents target specific types of bacteria (e.g., Gram-positive bacteria such as *Streptococcus*), while "broad-spectrum" agents have activity against a broader range of bacteria. The skilled artisan is aware of types of anti-bacterial agents that are appropriate for use in specific bacterial infections.

The present invention encompasses pharmaceutically acceptable salts, acids or derivatives of the agents (and members of the classes of agents) set forth above.

Dosing

The IDO inhibitors of the present invention may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the IDO inhibitors of the present invention may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In certain embodiments, the dosage of the desired IDO inhibitor is contained in a "unit dosage form". The phrase "unit dosage form" refers to physically discrete units, each unit containing a predetermined amount of the IDO inhibitor, either alone or in combination with one or more additional agents, sufficient to produce the desired effect. It will be appreciated that the parameters of a unit dosage form will depend on the particular agent and the effect to be achieved.

Kits

The present invention also contemplates kits comprising an IDO inhibitor, and pharmaceutical compositions thereof. The kits are generally in the form of a physical structure housing various components, as described below, and may be utilized, for example, in practicing the methods described above.

A kit can include one or more of the IDO inhibitors disclosed herein (provided in, e.g., a sterile container), which may be in the form of a pharmaceutical composition suitable for administration to a subject. The IDO inhibitors can be provided in a form that is ready for use (e.g., a tablet or capsule) or in a form requiring, for example, reconstitution or dilution (e.g., a powder) prior to administration. When the IDO inhibitors are in a form that needs to be reconstituted or diluted by a user, the kit may also include diluents (e.g., sterile water), buffers, pharmaceutically acceptable excipients, and the like, packaged with or separately from the IDO inhibitors. When combination therapy is contemplated, the kit may contain the several agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

Experimental

The following Examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: wt=wildtype; bp=base pair(s); kb=kilobase(s); nt=nucleotides(s); aa=amino acid(s); s or sec=second(s); min=minute(s); h or hr=hour(s); ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar; kDa=kilodalton; i.m.=intramuscular(ly); i.p.=intraperitoneal(ly); SC or SQ=subcutaneous(ly); QD=daily; BID=twice daily;

QW=weekly; QM=monthly; HPLC=high performance liquid chromatography; BW=body weight; U=unit; ns=not statistically significant; PBS=phosphate-buffered saline; IHC=immunohistochemistry; DMEM=Dulbecco's Modification of Eagle's Medium; EDTA=ethylenediaminetetraacetic acid.

Materials and Methods

The following general materials and methods were used, where indicated, or may be used in the Examples below:

Standard methods in molecular biology are described in the scientific literature (see, e.g., Sambrook et al., *Molecular Cloning*, Third Edition, Cold Spring Harbor Laboratory Press, Cold Spring Harbor, N.Y. (2001); and Ausubel et al., *Current Protocols in Molecular Biology*, Vols. 1-4, John Wiley and Sons, Inc. New York, N.Y. (2001), which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan et al., *Current Protocols in Protein Science*, Vols. 1-2, John Wiley and Sons, Inc., NY (2000)).

Software packages and databases for determining, e.g., antigenic fragments, leader sequences, protein folding, functional domains, glycosylation sites, and sequence alignments, are available (see, e.g., GCG® Wisconsin Package (Accelrys, Inc., San Diego, Calif.); and DECYPHER® (TimeLogic Corp., Crystal Bay, Nev.).

The literature is replete with assays and other experimental techniques that can serve as a basis for evaluation of the compounds described herein.

An IDO enzyme assay and cellular production of kynurenine (KYN) is described in Sarkar, S. A. et al., *Diabetes*, 56:72-79 (2007). Briefly, all chemicals can be purchased from Sigma-Aldrich (St. Louis, Mo.) unless specified otherwise. Groups of 1,000 human islets can be cultured for 24 h in 1 mL medium with cytokines, recovered by centrifugation for 5 min at 800×g and sonicated in 150 µL PBS containing a protease inhibitor cocktail (Set 2; Calbiochem, EMD Biosciences, San Diego, Calif.). The sonicate can be centrifuged for 10 min at 10,000×g, and the supernatant can be assayed in triplicate by incubating a 40 µl sample with an equal volume of 100 mmol/L potassium phosphate buffer, pH 6.5, containing 40 mmol/L ascorbic acid (neutralized to pH 7.0), 100 µmol/L methylene blue, 200 µg/mL catalase, and 400 µmol/l L-Trp for 30 min at 37° C. The assay can be terminated by the addition of 16 µL 30% (w/v) trichloroacetic acid (TCA) and further incubated at 60° C. for 15 min to hydrolyze N-formylkynurenine to KYN. The mixture can then be centrifuged at 12,000 rpm for 15 min, and KYN can be quantified by mixing equal volume of supernatant with 2% (w/v) Ehrlich's reagent in glacial acetic acid in 96-well microtiter plate and reading the absorbance at 480 nm using L-KYN as standard. Protein in the islet samples can be quantified by Bio-Rad Protein assay at 595 nm. For the detection of L-KYN in the islet culture supernatants, proteins can be precipitated with 5% (w/v) TCA and centrifuged at 12,000 rpm for 15 min, and determination of KYN in the supernatant with Ehrlich's reagent can be determined as described above. IL-4 (10 µg/mL; 500-2,000 units/mL) and 1-α-methyl Trp (1-MT; 40 µmol/L) can be added to the incubation media as indicated. This assay can also form the basis of a cell-based assay, and may be quantified via LCMS/MS as an alternative to UV/Vis detection.

Western Blot Analyses.

Groups of 1,000-1,200 islets incubated for 24 h in Miami medium in the presence of cytokines can be harvested and sonicated in PBS as above, and 50 µg protein samples can be electrophoresed on 10% SDS-PAGE gels. COS7 cells ($0.6 \times 10^6$ cells/60 mm3 petri dish) transfected with human-IDO plasmid (3 µg) or empty vector cells can be used as positive and negative controls, respectively. Proteins can be transferred electrophoretically onto polyvinylidine fluoride membranes by semidry method and blocked for 1 h with 5% (w/v) nonfat dry milk in Tris-buffered saline and 0.1% Tween and then incubated overnight with anti-human mouse IDO antibody (1:500; Chemicon, Temecula, Calif.), phospho-$STAT_{1\alpha}$ p91, and $STAT_{1\alpha}$ p91 (1:500; Zymed, San Francisco, Calif.). Immunoreactive proteins can be visualized with ECL PLUS® Western blotting detection reagent (Amersham BioSciences, Buckinghamshire, U.K.) after incubation for 1 h with anti-mouse horseradish peroxidase-conjugated secondary antibody (Jackson Immunolabs, West Grove, Pa.).

Immunohistochemical Detection of IDO.

Islets can be fixed in 4% paraformaldehyde in PBS (Invitrogen) for 1 h, immobilized in molten 10% porcine skin gelatin blocks (37° C.), and embedded in optimal cutting temperature compound. Immunofluorescent staining on islet tissue can be performed on 7 µm sections that were stained with antibodies raised against pancreatic duodenal homeobox 1 (PDX1) and IDO. Antigen retrieval can be performed in a water bath for 30 min in a buffer containing 10 mmol/l Tris and 1 mmol/l EDTA (pH 9.0) at 97° C. The sections can be blocked for 1 h with 5% normal goat serum in PBS. The tissues can then be reacted with mouse monoclonal anti-human IDO antibody (1:20; Chemicon) and goat polyclonal anti-human PDX1 antibody (1:2,000; which may be requested from Dr. Chris Wright, School of Medicine, Vanderbilt, Tenn.) overnight at room temperature in a humid chamber. Secondary antibodies anti-goat (labeled with Cy3) and anti-mouse (labeled with Cy2) can be purchased from Jackson Immunolabs and can be used at a concentration of 1:200. The nuclei can be stained with Hoechst 33258 (Molecular Probes, Eugene, Oreg.). Images can be acquired by Intelligent Imaging System software from an Olympus 1X81 inverted motorized microscope equipped with Olympus DSU (spinning disk confocal) and Hamamatsu ORCA IIER monochromatic CCD camera.

Alternative means for evaluating the IDO inhibitors of the present invention are described in WO 2010/0233166 and are summarized hereafter.

Biochemical Assay.

cDNA clones for both human and mouse IDO have been isolated and verified by sequencing and are commercially available. In order to prepare IDO for biochemical studies, C-terminal His-tagged IDO protein can be produced in *E. coli* using the IPTG-inducible pET5a vector system and isolated over a nickel column. The yield of the partially purified protein can be verified by gel electrophoresis and the concentration estimated by comparison to protein standards. To assay IDO enzymatic activity, a 96-well plate spectrophotometric assay for kynurenine production can be run following published procedures (see, e.g., Littlejohn, T. K. et al., *Prot. Exp. Purif.*, 19:22-29 (2000)). To screen for IDO inhibitory activity, compounds can be evaluated at a single concentration of, for example, 200 µM against 50 ng of IDO enzyme in 100 µL reaction volumes with tryptophan added at increasing concentrations at, for example, 0, 2, 20, and 200 μM. Kynurenine production can be measured at 1 hour.

Cell-Based Assay.

COS-1 cells can be transiently transfected with a CMV promoter-driven plasmid expressing IDO cDNA using Lipofectamine 2000 (Invitrogen) as recommended by the manufacturer. A companion set of cells can be transiently transfected with TDO-expressing plasmid. Forty-eight hours post-transfection, the cells can be apportioned into a 96-well format at $6 \times 10^4$ cells per well. The following day, the wells can be washed and new media (phenol red free) containing 20 μg/mL tryptophan can be added together with inhibitor. The reaction can be stopped at 5 hours and the supernatant removed and spectrophotometrically-assayed for kynurenine as previously described for the enzyme assay. To obtain initial confirmation of IDO activity, compounds can be evaluated at a single concentration of, for example, 100 μM. More extensive dose-escalation profiles can be collected for select compounds.

Pharmacodynamic and Pharmacokinetic Evaluation.

A pharmacodynamic assay can be based on measuring serum levels of both kynurenine and tryptophan, and calculating the kynurenine/tryptophan ratio provides an estimate of IDO activity that is independent of baseline tryptophan levels. Serum tryptophan and kynurenine levels can be determined by HPLC analysis, and serum compound levels can optionally also be determined in the same HPLC run.

Compounds can be initially evaluated by challenging mice with LPS and then subsequently administering a bolus dose of compound at the time that the serum kynurenine level plateaus. As the kynurenine pool is rapidly turned over with a half-life in serum of less than 10 minutes, pre-existing kynurenine is not expected to unduly mask the impact that an IDO inhibitor has on kynurenine production. Each experiment can include non-LPS-exposed mice (to determine baseline kynurenine levels against which to compare the other mice) and a set of LPS-exposed mice dosed with vehicle alone (to provide a positive control for IDO activation). Each compound can initially be evaluated in mice at a single high i.p. bolus dose in the range of at least 100 mg/kg. Blood can be collected at defined time intervals (for example, 50 μL sample at 5, 15, 30 min., 1, 2, 4, 6, 8, and 24 hr. following compound administration) for HPLC analysis of kynurenine and tryptophan levels (pharmacodynamic analysis) as well as for the level of compound (pharmacokinetic analysis). From the pharmacokinetic data the peak serum concentration of compound achieved can be determined as well as the estimated rate of clearance. By comparing the level of compound in serum relative to the kynurenine/tryptophan ratio at various time points, the effective $IC_{50}$ for IDO inhibition in vivo can be roughly estimated. Compounds exhibiting efficacy can be evaluated to determine a maximum dose that achieves 100% IDO inhibition at the peak concentration.

HPLC/MS and Preparatory/Analytical HPLC Methods Employed in Characterization or Purification of Examples Analytical HPLC/MS was performed using the following methods:

Method A: Waters Acquity SDS using the following method: Linear Gradient of 2% to 98% Solvent B over 1.7 min; UV visualization at 220 nm; Column: BEH C18 2.1 mm×50 mm; 1.7 μm particle (Heated to Temp. 50° C.); Flow rate: 0.8 ml/min; Mobile Phase A: 100% Water, 0.05% TFA; Mobile Phase B: 100% Acetonitrile, 0.05% TFA.

Method B: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.00 mL/min; Detection: UV at 220 nm.

Method C: Waters SFC-100 MS, Column: Chiral OJ-H 25×3 cm ID, 5 μm Flow rate: 100.0 mL/min, Mobile Phase: 80/20 $CO_2$/MeOH, Detector Wavelength: 220 nm.

Method D: Aurora analytical SFC, Column: Chiral OJ-H 250×4.6 mm ID, 5 μm, Flow rate: 2.0 mL/min, Mobile Phase: 80/20 $CO_2$/MeOH.

Method E: Berger Prep SFC, Column: Chiral AS 25×3 cm ID, 5 μm Flow rate: 85.0 mL/min, Mobile Phase: 82/18 $CO_2$/MeOH w/ 0.1% DEA, Detector Wavelength: 220 nm.

Method F: Aurora analytical SFC, Column: Chiral AS 250×4.6 mm ID, 5 μm, Flow rate: 2.0 mL/min, Mobile Phase: 80/20 $CO_2$/MeOH w/ 0.1% DEA.

Method G: Berger Prep SFC, Column: Chiral AS 25×3 cm ID, 5 μm Flow rate: 85.0 mL/min, Mobile Phase: 86/14 $CO_2$/MeOH, Detector Wavelength: 220 nm.

Method H: Aurora analytical SFC, Column: Chiral AS 250×4.6 mm ID, 5 μm, Flow rate: 2.0 mL/min, Mobile Phase: 85/15 $CO_2$/MeOH.

Method I: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Method J: Preparative Chromatographic Conditions: Instrument: Berger Prep SFC MGII (LVL-L4021 Lab) Column: Chiral IC 25×3 cm ID, 5 μm; Flow rate: 85.0 mL/min; Mobile Phase: 74/26 $CO_2$/MeOH; Detector Wavelength: 220 nm.

Method K: Preparative Chromatographic Conditions: Instrument: Berger Prep SFC MGII (LVL-L4021 Lab) Column: Chiral IC 25×3 cm ID, 5 μm; Flow rate: 85.0 mL/min; Mobile Phase: 75/25 $CO_2$/MeOH hold for 18 minutes, 60/40 $CO_2$/MeOH hold for 11 minutes, 75/25 $CO_2$/MeOH hold for 3 minutes; Detector Wavelength: 220 nm.

Method L: Preparative Conditions: Berger SFC MGII; Stage-1: Column: Chiral OD-H 25×3 cm ID, 5-μm particles; Mobile Phase: 82/18 $CO_2$/MeOH; Detector Wavelength: 220 nm; Flow: 85 mL/min. Stage-2: Chiral IF 25×3 cm ID, 5-μm particles; Mobile Phase: 80/20 $CO_2$/MeOH; Detector Wavelength: 220 nm; Flow: 85 mL/min. Analytical Conditions: Aurora analytical SFC; Stage-1: Column: Chiral OD-H 250×4.6 mm ID, 5 μm; Mobile Phase: 80/20 $CO_2$/MeOH; Flow: 2.0 mL/min; Stage-2: Column: Chiral IF 250×4.6 mm ID, 5 μm; Mobile Phase: 80/20 $CO_2$/MeOH; Flow: 2.0 mL/min. Tr corresponds to the analytical condition.

Method M: Preparative Conditions: Berger SFC MGII; Stage-1: Column: Chiral OD-H 25×3 cm ID, 5-μm particles; Mobile Phase: 80/20 $CO_2$/MeOH; Detector Wavelength: 220 nm; Flow: 85 mL/min. Stage-2: Chiral IF 25×3 cm ID, 5-μm particles; Mobile Phase: 80/20 $CO_2$/MeOH; Detector Wavelength: 220 nm; Flow: 85 mL/min. Analytical Conditions: Aurora analytical SFC; Stage-1: Column: Chiral OD-H 250×4.6 mm ID, 5 μm; Mobile Phase: 80/20 $CO_2$/MeOH; Flow: 2.0 mL/min; Stage-2: Column: Chiral IF 250×4.6 mm ID, 5 µm; Mobile Phase: 80/20 $CO_2$/MeOH; Flow: 2.0 mL/min. Tr corresponds to the analytical condition.

Method N: Preparative Conditions: Berger SFC MGII; Column: WHELK-O® 1 KROMASIL® 25×3 cm ID, 5-µm particles; Mobile Phase: 80/20 $CO_2$/MeOH; Detector Wavelength: 220 nm; Flow: 85 mL/min. Analytical Conditions: Aurora analytical SFC; Column: WHELK-O® 1 KROMASIL® 250×4.6 mm ID, 5 µm; Mobile Phase: 80/20 $CO_2$/MeOH; Flow: 2.0 mL/min; Tr corresponds to the analytical condition.

Method O: Preparative Conditions: Berger SFC MGII; Column: Chiral OJ 25×3 cm ID, 5-µm; Mobile Phase: 90/10 $CO_2$/MeOH; Detector Wavelength: 220 nm; Flow: 85 mL/min. Analytical Conditions: Aurora analytical SFC; Column: Chiral OJ 250×4.6 mm ID, 5 µm; Mobile Phase: 90/10 $CO_2$/MeOH; Flow: 2.0 mL/min; Tr corresponds to the analytical condition.

Method P: Preparative Conditions: Waters SFC-100 MS; Column: PHENOMENEX® LUX Cellulose-2 25×3 cm ID, 5 µm; Mobile Phase: 75/25 $CO_2$/MeOH; Detector Wavelength: 220 nm; Flow: 100 mL/min. Analytical Conditions: Aurora analytical SFC; Column: PHENOMENEX® LUX Cellulose-2 250×4.6 mm ID, 5 µm; Mobile Phase: 75/25 $CO_2$/MeOH; Flow: 2.0 mL/min; Tr corresponds to the analytical condition.

Method Q: Preparative Conditions: Berger SFC MGII; Column: Chiral AD 25×3 cm ID, 5-µm; Mobile Phase: 80/20 $CO_2$/MeOH; Detector Wavelength: 220 nm; Flow: 85 mL/min. Analytical Conditions: Aurora analytical SFC; Column: Chiral AD 250×4.6 mm ID, 5 µm; Mobile Phase: 80/20 $CO_2$/MeOH; Flow: 2.0 mL/min; Tr corresponds to the analytical condition.

Method R: Preparative Conditions: Berger SFC MGII; Column: Chiral AD 25×3 cm ID, 5-µm; Mobile Phase: 87/13 $CO_2$/MeOH; Detector Wavelength: 220 nm; Flow: 85 mL/min. Analytical Conditions: Aurora analytical SFC; Column: Chiral AD 250×4.6 mm ID, 5 µm; Mobile Phase: 85/15 $CO_2$/MeOH; Flow: 2.0 mL/min; Tr corresponds to the analytical condition.

Method S: Preparative Conditions: Berger SFC MGII; Column: Chiral IF 25×3 cm ID, 5-µm; Mobile Phase: 75/25 $CO_2$/MeOH; Detector Wavelength: 220 nm; Flow: 85 mL/min. Analytical Conditions: Aurora analytical SFC; Column: Chiral IF 250×4.6 mm ID, 5 µm; Mobile Phase: 70/30 $CO_2$/MeOH; Flow: 2.0 mL/min; Tr corresponds to the analytical condition.

Method T: Preparative Conditions: Waters SFC100-MS; Column: Chiral IC 25×3 cm ID, 5-µm coupled to WHELK-O® R,R KROMASIL® 25×3 cm ID 5-µm; Mobile Phase: 70/30 $CO_2$/MeOH; Detector Wavelength: 220 nm; Flow: 100 mL/min. Analytical Conditions: Aurora analytical SFC; Column: Chiral IC 250×4.6 mm ID, 5 µm coupled to WHELK-O® R,R KROMASIL® 25×3 cm ID 5-µm; Mobile Phase: 70/30 $CO_2$/MeOH; Flow: 2.0 mL/min; Tr corresponds to the analytical condition.

Method U: Preparative Conditions: Waters SFC100-MS; Column: Chiral OJ-H 25×3 cm ID, 5-µm; Mobile Phase: 70/30 $CO_2$/MeOH; Detector Wavelength: 220 nm; Flow: 100 mL/min. Analytical Conditions: Aurora analytical SFC; Column: Chiral OJ-H 250×4.6 mm ID, 5 µm; Mobile Phase: 70/30 $CO_2$/MeOH; Flow: 2.0 mL/min; Tr corresponds to the analytical condition.

Method V: Preparative Conditions: Berger SFC MGII; Column: Chiral WHELK-O® 25×3 cm ID, 5-µm; Mobile Phase: 80/20 $CO_2$/MeOH; Detector Wavelength: 220 nm; Flow: 85 mL/min. Analytical Conditions: Aurora analytical SFC; Column: Chiral WHELK-O® 250×4.6 mm ID, 5 µm; Mobile Phase: 80/20 $CO_2$/MeOH; Flow: 2.0 mL/min; Tr corresponds to the analytical condition.

Method W: Preparative Conditions: Berger SFC MGH; Column: Chiral IC 25×3 cm ID, 5-µm; Mobile Phase: 85/15 $CO_2$/MeOH; Detector Wavelength: 220 nm; Flow: 85 mL/min. Analytical Conditions: Aurora analytical SFC; Column: Chiral IC 250×4.6 mm ID, 5 µm; Mobile Phase: 85/15 $CO_2$/MeOH; Flow: 2.0 mL/min; Tr corresponds to the analytical condition.

Method X: Preparative Conditions: Berger SFC MGII; Column: Chiral IC 25×3 cm ID, 5-µm; Mobile Phase: 75/25 $CO_2$/MeOH w/0.1% diethylamine; Detector Wavelength: 220 nm; Flow: 85 mL/min. Analytical Conditions: Aurora analytical SFC; Column: Chiral IC 250×4.6 mm ID, 5 µm; Mobile Phase: 75/25 $CO_2$/MeOH w/0.1% diethylamine; Flow: 2.0 mL/min; Tr corresponds to the analytical condition.

Method Y: Mobile Phase: 80/20 $CO_2$/MeOH/CAN 50/50; Flow: 2.0 mL/min; Tr corresponds: Preparative Conditions: Berger SFC MGII; Column: Chiral AD 25×3 cm, 5-µm; Mobile Phase: 80/20 $CO_2$/MeOH/CAN 50/50; Detector Wavelength: 220 nm; Flow: 85 mL/min. Analytical Conditions: Aurora analytical SFC; Column: Chiral AD 250×4.6 mm ID, 5 µm; to the analytical condition.

Method Z: Preparative Conditions: Berger SFC MGII; Column: Chiral IC 25×3 cm, 5-µm; Mobile Phase: 83/17 $CO_2$/MeOH; Detector Wavelength: 220 nm; Flow: 85 mL/min. Analytical Conditions: Aurora analytical SFC; Column: Chiral IC 250×4.6 mm ID, 5 µm; Mobile Phase: 80/20 $CO_2$/MeOH; Flow: 2.0 mL/min; Tr corresponds to the analytical condition.

Method AA: Preparative Conditions: Waters SFC100-MS; Column: Chiral AS-H coupled Chiral OJ-H 25×3 cm, 5-µm; Mobile Phase: 70/30 $CO_2$/MeOH; Detector Wavelength: 220 nm; Flow: 100 mL/min. Analytical Conditions: AGILENT® analytical SFC; Column: Chiral AS-H coupled to Chiral OJ-H 250×4.6 mm ID, 5 µm; Mobile Phase: 70/30 $CO_2$/MeOH; Flow: 2.0 mL/min; Tr corresponds to the analytical condition.

Method AB: Waters Acquity SDS using the following method: Linear Gradient of 2% to 98% Solvent B over 1.6 min; UV visualization at 220 nm; Column: BEH C18 2.1 mm×50 mm; 1.7 µm particle (Heated to Temp. 50° C.); Flow rate: 1 ml/min; Mobile Phase A: 100% Water, 0.05% TFA; Mobile Phase B: 100% Acetonitrile, 0.05% TFA.

Method AC: Preparative Conditions: Berger SFC MGII; Column: Chiral AD 25×3 cm ID, 5-µm; Mobile Phase: 90/10 $CO_2$/MeOH; Detector Wavelength: 220 nm; Flow: 85 mL/min. Analytical Conditions: Aurora analytical SFC; Column: Chiral AD 250×4.6 mm ID, 5 µm; Mobile Phase: 90/20 $CO_2$/MeOH; Flow: 2.0 mL/min; Tr corresponds to the analytical condition.

Method AD: Preparative Conditions: Berger SFC MGII; Column: Whelk-O1 Kromasil 25×3 cm ID, 5-µm particles; Mobile Phase: 85/15 $CO_2$/MeOH; Detector Wavelength: 220 nm; Flow: 85 mL/min. Analytical Conditions: Aurora analytical SFC; Column: Whelk-O1 Kromasil 250×4.6 mm ID, 5 µm; Mobile Phase: 85/15 $CO_2$/MeOH; Flow: 2.0 mL/min; Tr corresponds to the analytical condition.

Method AE: Preparative Conditions: Berger SFC MGII; Column: Whelk-O1 Kromasil 25×3 cm ID, 5-µm particles; Mobile Phase: 75/25 $CO_2$/MeOH; Detector Wavelength: 220 nm; Flow: 85 mL/min. Analytical Conditions: Aurora analytical SFC; Column: Whelk-O1 Kromasil 250×4.6 mm ID, 5 µm; Mobile Phase: 75/25 $CO_2$/MeOH; Flow: 2.0 mL/min; Tr corresponds to the analytical condition.

NMR Employed in Characterization of Examples $^1$H NMR spectra (unless otherwise noted) were obtained with JEOL® or Bruker FOURIER® transform spectrometers operating at 400 MHz or 500 MHz.

Spectral data are reported as chemical shift (multiplicity, number of hydrogens, coupling constants in Hz) and are reported in ppm (δ units) relative to either an internal standard (tetramethyl silane=0 ppm) for $^1$H NMR spectra, or are referenced to the residual solvent peak (2.49 ppm for $CD_3SOCD_2H$, 3.30 ppm for $CD_2HOD$, 1.94 for $CHD_2CN$, 7.26 ppm for $CHCl_3$, 5.32 ppm for $CDHCl_2$). Abbreviations used in the description of NMR peaks: "a"=apparent, "br. s."=broad singlet.

EXAMPLES

General Procedures

General Procedure A. Amide Bond Formation from Acid.

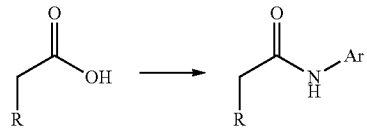

To a stirred solution of carboxylic acid (4.4 mmol) in dimethylformamide (DMF, 15 mL) was added aniline (6.6 mmol), diisopropylethylamine (1.53 mL, 8.8 mmol) and 1-[bis(dimethylamino)methylene]-1H-1,2,3-triazolo[4,5-b]pyridinium 3-oxid hexafluorophosphate (HATU) (2.00 g, 5.28 mmol). The resulting reaction mixture was stirred at rt for 3 h, at which point 3 M HCl (30 mL) and $CH_2Cl_2$ (30 mL) were added. The layers were separated, and the aqueous layer was extracted with $CH_2Cl_2$ (2×30 mL). The combined organic extracts were dried over anhydrous sodium sulfate and concentrated under reduced pressure. The resulting crude residue was purified by silica gel chromatography to afford the desired product(s).

General Procedure B. Reaction Between Amines and Acyl Chlorides.

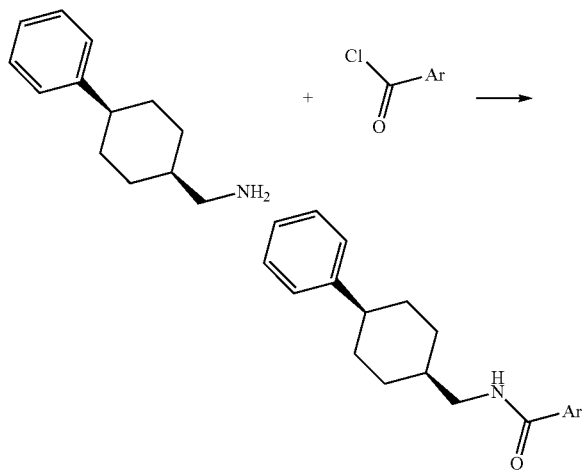

To a solution of the amine (1.1 equiv) and $NEt_3$ (5.0 equiv) in $CH_2Cl_2$ (0.1 M) was added the acyl chloride (1.0 equiv). The resulting reaction mixture was stirred at rt for 15 min and then concentrated under reduced pressure. The crude reaction mixture was purified using silica gel chromatography (0% to 100% EtOAc in hexanes) to afford the desired product.

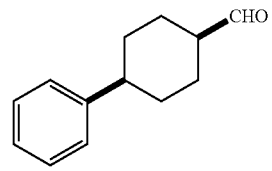

Cis-4-phenylcyclohexane-1-carbaldehyde: Prepared according the literature procedure (Fox, B. M. et al., *J. Med. Chem.*, 57:3464-3483 (2014)). The crude mixture was purified using silica gel chromatography (0% to 10% EtOAc in hexane) to afford the desired product as the first eluting isomer.

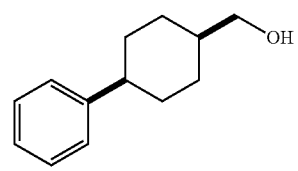

Cis-(4-phenylcyclohexyl)methanol: To a solution of cis-4-phenylcyclohexane-1-carbaldehyde (825 mg, 4.4 mmol) in THF (25 mL) and MeOH (7 mL) at rt was added $NaBH_4$ portionwise over 5 min. The resulting mixture was stirred at rt for 45 min. Then HCl (1 M) was added dropwise. The mixture was extracted with EtOAc (3×). The combined organic layers were washed with brine, dried over $Na_2SO_4$ and concentrated under reduced pressure. The resulting crude mixture was purified employing silica gel chromatography (0% to 25% EtOAc in hexanes) to afford the desired product.

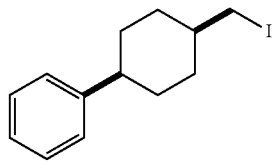

Cis-(4-(iodomethyl)cyclohexyl)benzene: To a solution of cis-(4-phenylcyclohexyl)methanol (2 g, 10.5 mmol), triphenylphosphine (3.3 g, 12.6 mmol) and imidazole (1.1 g, 15.8 mmol) in $CH_2Cl_2$ (70 mL) at 0° C. was added iodine (3.5 g, 13.7 mmol). The mixture was warmed to rt and stirred at rt for 2 h. The mixture was diluted with $CH_2Cl_2$ and washed with sodium thiosulfate (2 M). The organic layer was dried over anhydrous $MgSO_4$, filtered, and concentrated under reduced pressure. The crude reaction mixture was purified employing silica gel chromatography (0% to 25% EtOAc in hexanes) to afford the desired product as an oil (3 g, 95%).

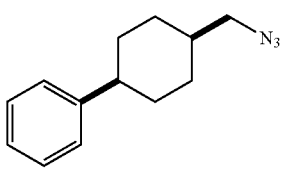

Cis-(4-(azidomethyl)cyclohexyl)benzene: To a solution of cis-(4-(iodomethyl)cyclohexyl)benzene (2.6 g, 8.8 mmol) in DMF (44 mL) was added sodium azide (2.8 g, 43.8 mmol). The mixture was stirred at rt for 2 h. Then more sodium azide (1.14 g, 17.5 mmol) was added and the mixture was stirred at rt for 18 h. The mixture was diluted with Et$_2$O and washed with water, 1 M LiCl (2×) and brine. The organic layers were dried over Na$_2$SO$_4$ and concentrated under reduced pressure to give the desired product (1.5 g, 80%).

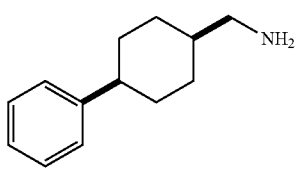

Cis-(4-phenylcyclohexyl)methanamine: To a solution of cis-(4-(azidomethyl)cyclohexyl)benzene (1.5 g, 7.0 mmol) in THF (35 mL) was added triphenylphosphine (2.56 g, 9.8 mmol). The mixture was stirred at rt for 30 min and then water (0.83 mL) was added. The mixture was stirred at rt for 24 h. The mixture was preabsorbed onto silica gel and purified employing silica gel chromatography [0% to 5% (2 M NH$_3$ in MeOH) in CH$_2$Cl$_2$] to afford the desired product as an oil (1.2 g, 94%).

Example 1

Cis-4-cyano-N-((4-phenylcyclohexyl)methyl)benzamide

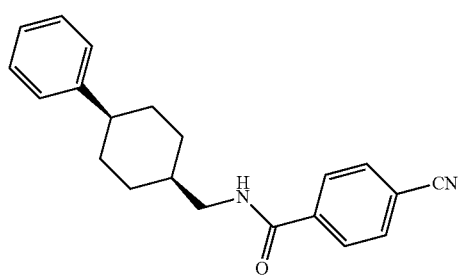 [SMILES: N#Cc1ccc(C(=O)NC[C@H]2CC[C@@H](c3ccccc3)CC2)cc1]

Prepared with General Procedure B employing cis-(4-phenylcyclohexyl)methanamine (19 mg, 0.1 mmol), 4-cyanobenzoyl chloride (17 mg, 0.1 mmol), and NEt$_3$ (51 mg, 0.5 mmol) in CH$_2$Cl$_2$ (1 mL). Purified using silica gel chromatography (10% to 30% EtOAc in hexanes) to afford the desired product as a white solid. $^1$H NMR (400 MHz; CDCl$_3$): δ 7.89-7.86 (m, 2H), 7.74-7.71 (m, 2H), 7.32-7.17 (m, 5H), 6.32-6.30 (m, 1H), 3.58 (dd, J=7.7, 6.0 Hz, 2H), 2.66-2.59 (m, 1H), 2.06-2.00 (m, 1H), 1.80-1.69 (m, 8H). m/z 319.3 (M+H$^+$).

Example 2

Cis-3-cyano-N-((4-phenylcyclohexyl)methyl)benzamide

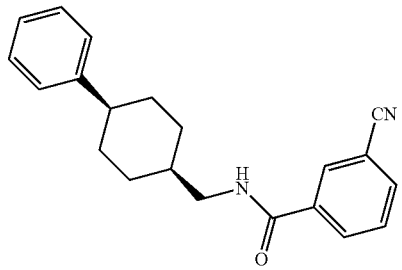 [SMILES: N#Cc1cccc(C(=O)NC[C@H]2CC[C@@H](c3ccccc3)CC2)c1]

Prepared with General Procedure B employing cis-(4-phenylcyclohexyl)methanamine (19 mg, 0.1 mmol), 3-cyanobenzoyl chloride (17 mg, 0.1 mmol), and NEt$_3$ (51 mg, 0.5 mmol) in CH$_2$Cl$_2$ (1 mL). Purified using silica gel chromatography (10% to 30% EtOAc in hexanes) to afford the desired product as a white solid. $^1$H NMR (400 MHz; CDCl$_3$): δ 8.09-8.08 (m, 1H), 8.04 (dt, J=7.9, 1.5 Hz, 1H), 7.76 (dt, J=7.7, 1.3 Hz, 1H), 7.56 (t, J=7.8 Hz, 1H), 7.32-7.17 (m, 5H), 6.49-6.46 (m, 1H), 3.58 (dd, J=7.7, 6.0 Hz, 2H), 2.66-2.59 (m, 1H), 2.07-2.01 (m, 1H), 1.80-1.68 (m, 8H). m/z 319.2 (M+H$^+$).

Example 3

Cis-4-chloro-N-((4-phenylcyclohexyl)methyl)benzamide

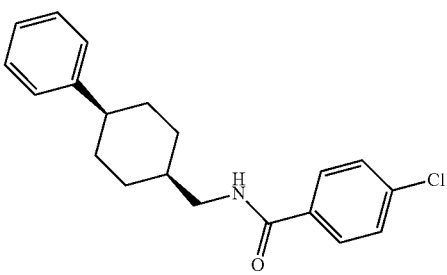 [SMILES: O=C(NC[C@H]1CC[C@@H](c2ccccc2)CC1)c1ccc(Cl)cc1]

Prepared with General Procedure B employing cis-(4-phenylcyclohexyl)methanamine (19 mg, 0.1 mmol), 4-chlorobenzoyl chloride (19 mg, 0.1 mmol), and NEt$_3$ (51 mg, 0.5 mmol) in CH$_2$Cl$_2$ (1 mL). Purified using silica gel chromatography (0% to 20% EtOAc in hexanes) to afford the desired product as a white solid. $^1$H NMR (400 MHz; CDCl$_3$): δ 7.73-7.69 (m, 2H), 7.41-7.38 (m, 2H), 7.31-7.23 (m, 4H), 7.20-7.16 (m, 1H), 3.55 (dd, J=7.7, 5.9 Hz, 2H), 2.63-2.59 (m, 1H), 2.04-1.98 (m, 1H), 1.79-1.67 (m, 8H). m/z 328.2 (M+H$^+$).

Example 4

Cis-3-chloro-N-((4-phenylcyclohexyl)methyl)benzamide

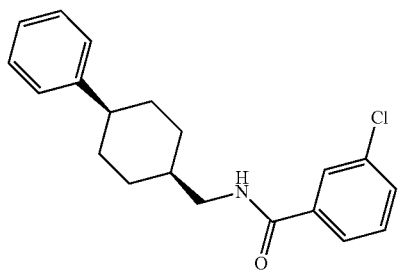 [SMILES: O=C(NC[C@H]1CC[C@@H](c2ccccc2)CC1)c1cccc(Cl)c1]

Prepared with General Procedure B employing cis-(4-phenylcyclohexyl)methanamine (19 mg, 0.1 mmol), 3-chlorobenzoyl chloride (19 mg, 0.1 mmol), and NEt$_3$ (51 mg, 0.5 mmol) in CH$_2$Cl$_2$ (1 mL). Purified using silica gel chromatography (0% to 20% EtOAc in hexanes) to afford the desired product as a white solid. $^1$H NMR (400 MHz; CDCl$_3$): δ 7.76 (t, J=1.8 Hz, 1H), 7.64 (dt, J=7.7, 1.4 Hz, 1H), 7.47-7.44 (m, 1H), 7.38-7.34 (m, 1H), 7.31-7.23 (m, 4H), 7.20-7.16 (m, 1H), 6.30-6.27 (m, 1H), 3.56 (dd, J=7.7, 6.0 Hz, 2H), 2.64-2.58 (m, 1H), 2.04-1.99 (m, 1H), 1.79-1.66 (m, 8H). m/z 328.2 (M+H$^+$).

Example 5

Cis-4-fluoro-N-((4-phenylcyclohexyl)methyl)benzamide

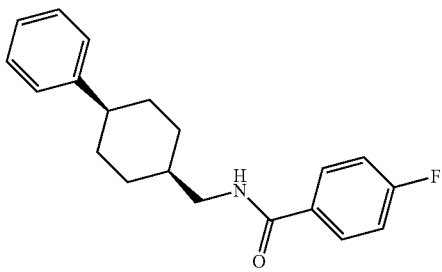 [SMILES: O=C(NC[C@H]1CC[C@@H](c2ccccc2)CC1)c1ccc(F)cc1]

Prepared with General Procedure B employing cis-(4-phenylcyclohexyl)methanamine (16 mg, 0.1 mmol), 4-fluorobenzoyl chloride (19 mg, 0.1 mmol), and NEt$_3$ (51 mg, 0.5 mmol) in CH$_2$Cl$_2$ (1 mL). Purified using silica gel chromatography (0% to 20% EtOAc in hexanes) to afford the desired product as a white solid.

Example 6

Cis-4-chloro-N-((4-phenylcyclohexyl)methyl)benzenesulfonamide

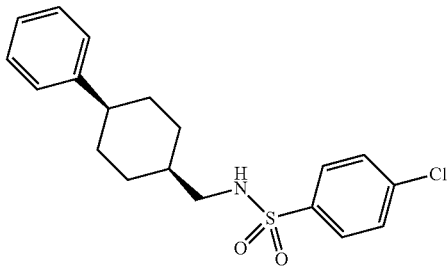 [SMILES: O=S(=O)(NC[C@H]1CC[C@@H](c2ccccc2)CC1)c1ccc(Cl)cc1]

Prepared in the manner of General Procedure B employing cis-(4-phenylcyclohexyl)methanamine (38 mg, 0.2 mmol), 4-chlorobenzenesulfonyl chloride (42 mg, 0.2 mmol), and NEt$_3$ (101 mg, 0.5 mmol) in CH$_2$Cl$_2$ (1 mL). Purified using silica gel chromatography (0% to 25% EtOAc in hexanes) to afford the desired product as a white solid. $^1$H NMR (400 MHz; CDCl$_3$): δ 7.87-7.83 (m, 2H), 7.52-7.48 (m, 2H), 7.31-7.27 (m, 2H), 7.20-7.16 (m, 3H), 5.10 (t, J=6.2 Hz, 1H), 3.01 (dd, J=7.7, 6.3 Hz, 2H), 2.56 (dt, J=9.8, 5.0 Hz, 1H), 1.87-1.81 (m, 1H), 1.68-1.52 (m, 8H). m/z 364.1 (M+H$^+$).

Example 7

(4-Benzylpiperidin-1-yl)(4-chlorophenyl)methanone

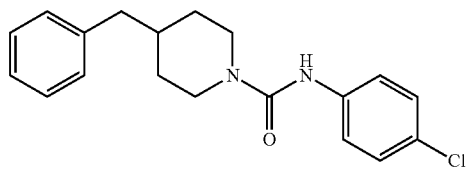 [SMILES: O=C(Nc1ccc(Cl)cc1)N1CCC(Cc2ccccc2)CC1]

To 4-chlorophenyl isocyanate (154 mg, 1.0 mmol) in Et$_2$O (5 mL) was added 4-benzyl piperidine (193 mg, 1.1 mmol) The homogenous reaction mixture produced a precipitate over 15 min. The reaction mixture was cooled to 0° C. and the solids were collected by filtration washing with additional Et$_2$O (25 mL) to provide the desired product as a white solid. $^1$H NMR (400 MHz; CDCl$_3$): δ 7.31-7.28 (m, 4H), 7.25-7.21 (m, 3H), 7.16-7.14 (m, 2H), 6.32 (s, 1H), 4.05-4.01 (m, 2H), 2.83 (td, J=12.9, 2.1 Hz, 2H), 2.57 (d, J=6.9 Hz, 2H), 1.77-1.70 (m, 3H), 1.31-1.20 (m, 2H). m/z 329.2 (M+H$^+$).

Example 8

(4-Benzylpiperidin-1-yl)(3-chlorophenyl)methanone

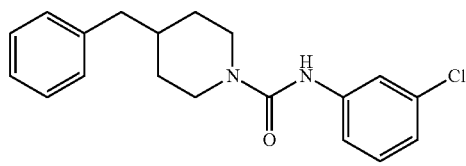 [SMILES: O=C(Nc1cccc(Cl)c1)N1CCC(Cc2ccccc2)CC1]

To 3-chlorophenyl isocyanate (154 mg, 1.0 mmol) in Et$_2$O (5 mL) was added 4-benzyl piperidine (193 mg, 1.1 mmol) The homogenous reaction mixture produced a precipitate over 15 min. The reaction mixture was cooled to 0° C. and the solids were collected by filtration washing with additional Et$_2$O (25 mL) to provide the desired product as a white solid. $^1$H NMR (400 MHz; CDCl$_3$): δ 7.47 (t, J=1.2 Hz, 1H), 7.29 (q, J=6.4 Hz, 2H), 7.23-7.14 (m, 5H), 7.01-6.96 (m, 1H), 6.33 (s, 1H), 4.05-4.01 (m, 2H), 2.83 (td, J=12.9, 2.1 Hz, 2H), 2.59-2.52 (m, 2H), 1.78-1.71 (m, 3H), 1.31-1.21 (m, 2H). m/z 329.2 (M+H$^+$).

Example 9

Cis-N-4-chloro-(2-(4-(4-methoxyphenyl)cyclohexyl)ethyl)aniline

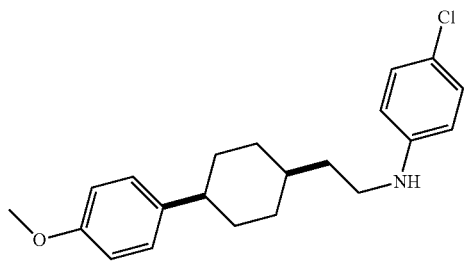

9A. Ethyl 2-(4-(4-hydroxyphenyl)cyclohexylidene)acetate

Triethylphosphonoacetate (46.9 mL, 236 mmol) in THF (250 mL) was added dropwise over 1 hour at 0° C. to a solution of NaH (60% dispersion in oil, 11.8 g, 295 mmol) in THF (120 mL). The mixture was warmed to rt and stirred at rt for 1 h. In a separate flask, a solution of 4-(4-hydroxyphenyl)cyclohexanone (37.5 g, 197 mmol) in THF (250 mL) was added carefully to a mixture of NaH (60% dispersion in oil, 8.67 g, 216 mmol) in THF (100 mL) at 0° C. The mixture was stirred at rt for 2 hours. The mixture of the cyclohexanone was added to the phosphonate mixture at 0° C. via cannulation. The mixture was warmed to rt and stirred at rt for 2 h. The mixture was quenched by careful addition of ice and water (1 L) and subsequently extracted with ethyl acetate (3×500 mL) and the combined organics were then washed with brine (1 L), dried over sodium sulfate, filtered, and concentrated to provide ethyl 2-(4-(4-hydroxyphenyl)cyclohexylidene)acetate in 97% yield as a white solid.

9B. Ethyl 2-(4-(4-hydroxyphenyl)cyclohexyl)acetate

To a solution ethyl 2-(4-(4-hydroxyphenyl)cyclohexylidene)acetate (9.74 g, 35.8 mmol) in ethyl acetate was added Pd/C (0.974 g, 10 wt. %). The reaction solution was sparged with a balloon of H$_2$ gas and stirred overnight under an atmosphere of hydrogen for 2 days. The reaction mixture was filtered through CELITE®, washing generously with ethyl acetate, and concentrated under reduced pressure to afford the desired product as a white crystalline solid in quantitative yield as a mixture of diastereomers.

9C. Ethyl 2-(4-(4-methoxyphenyl)cyclohexyl)acetate

A solution of the product of Example 9B (20.0 g, 76.2 mmol, 1.0 equiv.) was dissolved in 770 mL of DMF. To this solution was added 6 mL (95 mmol, 1.25 equiv.) of iodomethane followed by cesium carbonate (43.3 g, 133 mmol, 1.75 equiv.). This mixture was then stirred for 16 hours until starting material was consumed as monitored by LCMS. The reaction was then quenched by cooling to 0° C. and subsequent addition of 1.35 L of water. The mixture was then extracted with ethyl acetate (3×500 mL) and the combined organics were washed with brine (1 L) and dried over sodium sulfate before filtration and concentration. The crude residue was purified via column chromatography (5% ethyl acetate in hexanes) to afford the final compound as a clear oil in 69% yield. (R$_f$=0.5 in 10% ethyl acetate in hexanes).

9D. 2-(4-(4-Methoxyphenyl)cyclohexyl)acetic acid

Lithium hydroxide (1.58 g, 66.2 mmol) was added to water (8 mL). The slurry was allowed to stand at rt for 30 min before filtering. The filtrate was added to a solution of the product of Example 9C (2.95 g, 10.67 mmol) in EtOH (9 mL). The slurry was stirred at rt for 2 d and diluted with water. The mixture was filtered and the solid was diluted with EtOAc and 1 M HCl. The layers were separated and the organic layer was dried over sodium sulfate and concentrated under reduced pressure to provide 2-(4-(4-methoxyphenyl)cyclohexyl)acetic acid.

9E and 9F. cis-N-(4-Chlorophenyl)-2-(4-(4-methoxyphenyl)cyclohexyl)acetamide and trans-N-(4-Chlorophenyl)-2-(4-(4-methoxyphenyl)cyclohexyl)acetamide Prepared with General Procedure A employing 2-(4-(4-methoxyphenyl)cyclohexyl)acetic acid (product of Example 9D, 124 mg, 0.5 mmol), 4-chloroaniline (97 mg, 0.75 mmol), HATU (435 mg, 0.75 mmol), and $^i$Pr$_2$NEt (323 mg, 2.5 mmol) in DMF (1.0 mL). Purification using silica gel chromatography (0% to 25% EtOAc in hexanes) afforded cis-N-(4-chlorophenyl)-2-(4-(4-methoxyphenyl)cyclohexyl)acetamide (Example 9E), a white solid, as the first eluting isomer and trans-N-(4-chlorophenyl)-2-(4-(4-methoxyphenyl)cyclohexyl)acetamide (Example 9F) as the second eluting isomer.

cis-N-(4-Chlorophenyl)-2-(4-(4-methoxyphenyl)cyclohexyl)acetamide $^1$H NMR (400 MHz; CDCl$_3$): δ 7.49-7.45 (m, 2H), 7.29-7.26 (m, 2H), 7.17-7.15 (m, 3H), 6.87-6.83 (m, 2H), 3.79 (s, 3H), 2.63-2.55 (m, 1H), 2.45-2.37 (m, 3H), 1.77-1.64 (m, 8H). m/z 358.2 (M+H$^+$).

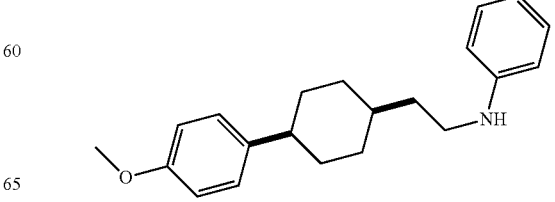

Example 9

Cis-N-4-chloro-(2-(4-(4-methoxyphenyl)cyclohexyl)ethyl)aniline

To a solution of cis-N-(4-chlorophenyl)-2-(4-(4-methoxyphenyl)cyclohexyl)acetamide (33 mg, 0.092 mmol) in THF (0.5 mL) at rt was added Borane tetrahydrofuran complex solution (0.5 mL, 0.5 mmol, 1 M in THF). The resulting mixture was stirred for 2.5 h at rt at which point aqueous HCl (1 M) was added and the mixture was stirred at rt for 30 min. Evolution of gas was observed. The mixture was basified with sat. $Na_2CO_3$ and extracted with $CH_2Cl_2$ (2×). The combined organic layers were dried over anhydrous $Na_2SO_4$, filtered, and concentrated under reduced pressure. The resulting crude mixture was purified employing silica gel chromatography (0% to 10% EtOAc in hexanes) to afford the desired product. $^1$H NMR (400 MHz, $CDCl_3$) δ 7.19-7.09 (m, 4H), 6.90-6.81 (m, 2H), 6.56 (d, J=8.7 Hz, 2H), 3.80 (s, 3H), 3.17-3.07 (m, 2H), 2.55 (s, 1H), 1.85 (s, 1H), 1.80-1.63 (m, 10H). m/z 344.2 (M+H$^+$).

Example 10

Trans-N-4-chloro-(2-(4-(4-methoxyphenyl)cyclohexyl)ethyl)aniline

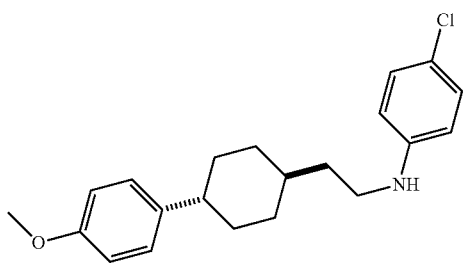

Prepared using the procedure from the previous example employing 73 mg of trans-N-(4-chlorophenyl)-2-(4-(4-methoxyphenyl)cyclohexyl)acetamide. Purified using silica gel chromatography (0% to 10% EtOAc in hexanes) to afford the desired product. $^1$H NMR (400 MHz, $CDCl_3$) δ 7.17-7.09 (m, 4H), 6.89-6.81 (m, 2H), 6.58-6.51 (m, 2H), 3.80 (s, 3H), 3.18-3.09 (m, 2H), 2.45 (t, J=12.3 Hz, 1H), 1.90 (d, J=12.3 Hz, 4H), 1.67-1.47 (m, 4H), 1.44 (dd, J=17.5, 7.8 Hz, 2H), 1.14 (dd, J=22.1, 12.0 Hz, 2H). m/z 344.2 (M+H$^+$).

Example 11

(+/−)-Cis-3-phenylcyclopentyl(4-chlorophenyl)carbamate

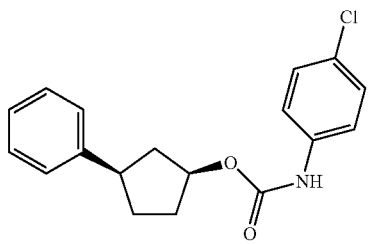 [SMILES: O=C(Nc1ccc(Cl)cc1)O[C@H]1CC[C@@H](c2ccccc2)C1]

11A. (+/−)-Cis-3-phenylcyclopentan-1-ol

3-Phenylcyclopentan-1-one was prepared as previously described (Yamamoto, T. et al., *J. Organomet. Chem.*, 694: 1325-1332 (2009)). To a solution of 3-phenylcyclopentan-1-one (1.0 g, 6.2 mmol) in 30 mL of methanol cooled to 0° C. was added $NaBH_4$ (0.27 g, 7.2 mmol). The ice bath was removed, and the reaction was allowed to warm to rt and stirred for 3 h. The reaction was quenched with 1 M HCl and diluted with EtOAc (30 mL), and the layers were separated. The organic extracts were dried over anhydrous $MgSO_4$, filtered, and concentrated under reduced pressure. The resulting crude mixture of ~1.6:1 cis: trans alcohols was purified using silica gel chromatography (15% EtOAc in pentane) to afford the desired cis-3-phenylcyclopentan-1-ol as a colorless oil (118 mg, 12%). $^1$H NMR (400 MHz; $CDCl_3$): δ 7.16-7.09 (m, 5H), 4.43-4.40 (m, 1H), 3.06-3.00 (m, 1H), 2.70 (br s, 1H), 2.53-2.43 (m, 1H), 2.06-1.63 (m, 5H).

Example 11

(+/−)-Cis-3-phenylcyclopentyl(4-chlorophenyl)carbamate

To a solution of cis-3-phenylcyclopentan-1-ol (150 mg, 0.95 mmol) in $CH_2CH_2$ was added 4-chlorophenyl isocyanate (150 mg, 0.95 mmol). After 5 min, the reaction mixture was concentrated under reduced pressure and triturated with diethyl ether (10 mL). The mixture was filtered, rinsing with diethyl ether, to afford the desired product as a white solid. $^1$H NMR (400 MHz; DMSO-$d_6$): δ 9.79 (br s, 1H), 7.49 (d, J=7.5 Hz, 2H), 7.33-7.14 (m, 7H), 5.09-5.04 (m, 1H), 3.13-3.02 (m, 1H), 2.60-2.48 (m, 1H), 2.08-1.61 (m, 6H).

Example 12

Cis-(4-phenylcyclohexyl)methyl(4-fluorophenyl)carbamate

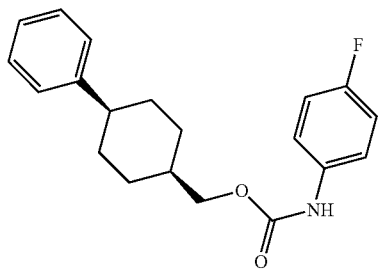 [SMILES: O=C(Nc1ccc(F)cc1)OC[C@H]1CC[C@@H](c2ccccc2)CC1]

To a solution of cis-(4-phenylcyclohexyl)methanol (200 mg, 1.05 mmol) in diethyl ether (5 mL) was added 4-fluorophenyl isocyanate (144 mg, 1.05 mmol). Upon consumption of the starting materials, the resulting solution was concentrated to provide a white solid, which was triturated in diethyl ether (3 mL) and filtered to afford the desired product as a white solid. $^1$H NMR (400 MHz; DMSO-$d_6$): δ 9.65 (br s, 1H), 7.48-7.42 (m, 2H), 7.18-7.06 (m, 7H), 4.20 (d, J=9.5 Hz, 2H), 2.61-2.51 (m, 1H), 2.07-2.01 (m, 1H), 1.77-1.57 (m, 8H).

Example 13

Trans-1-(4-fluorophenyl)-3-(4-phenylcyclohexyl) urea

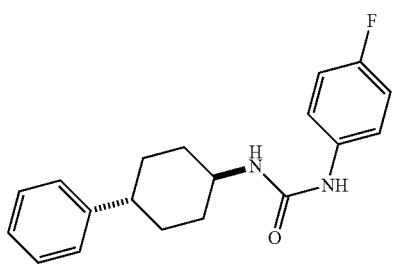

To a stirred solution of trans-4-phenylcyclohexylamine (Combi-Blocks, San Diego, Calif.) (50 mg, 0.3 mmol) in diethyl ether was added 4-fluorophenyl isocyanate (0.032 mL, 0.3 mmol) at rt. After stirring for 30 min the voluminous white precipitate was isolated by vacuum filtration to yield the desired product. $^1$H NMR (400 MHz, CDCl$_3$) δ 7.35-7.14 (m, 7H), 7.07-6.97 (m, 2H), 6.00 (s, 1H), 4.41-4.30 (m, 1H), 3.83-3.65 (m, 1H), 2.56-2.39 (m, 1H), 2.21-2.10 (m, 2H), 1.99-1.88 (m, 2H), 1.72-1.46 (m, 2H), 1.37-1.07 (m, 2H).

Example 14

Trans-1-(4-chlorophenyl)-3-(4-phenylcyclohexyl) urea

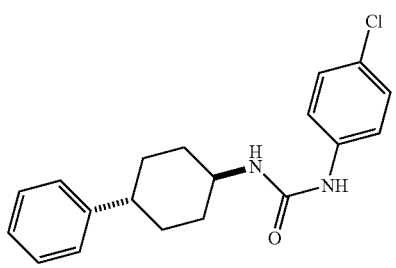

To a stirred solution of trans-4-phenylcyclohexylamine (50 mg, 0.3 mmol) in diethyl ether was added 4-chlorophenyl isocyanate (44 mg, 0.3 mmol) at rt. After stirring for 30 min the voluminous white precipitate was isolated by vacuum filtration to yield the desired product. $^1$H NMR (400 MHz, CDCl$_3$) δ 7.38-7.12 (m, 9H), 6.05 (s, 1H), 4.39 (d, J=7.4 Hz, 1H), 3.88-3.61 (m, 1H), 2.56-2.40 (m, 1H), 2.28-2.12 (m, 2H), 2.00-1.89 (m, 2H), 1.71-1.59 (m, 2H), 1.36-1.16 (m, 2H).

Example 15

Trans-1-(3-chlorophenyl)-3-(4-phenylcyclohexyl) urea

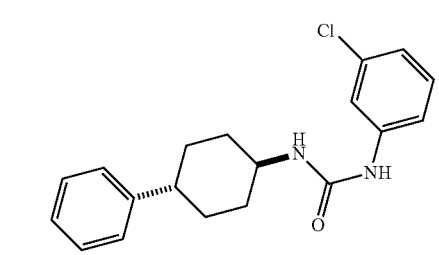

To a stirred solution of trans-4-phenylcyclohexylamine (50 mg, 0.3 mmol) in diethyl ether (1.4 mL) was added 3-chlorophenyl isocyanate (0.035 mL, 0.3 mmol) at rt. After stirring for 30 min the voluminous white precipitate was isolated by vacuum filtration and concentrated under reduced pressure to yield the desired product. $^1$H NMR (400 MHz, CDCl$_3$) δ 7.42 (t, J=2.0 Hz, 1H), 7.34-7.11 (m, 7H), 7.08-7.02 (m, 1H), 6.14 (s, 1H), 4.47 (s, 1H), 3.85-3.62 (m, 1H), 2.61-2.39 (m, 1H), 2.27-2.12 (m, 2H), 2.02-1.89 (m, 2H), 1.74-1.57 (m, 2H), 1.39-1.19 (m, 2H).

Example 16

Trans-2-(3-chlorophenyl)-N-(4-phenylcyclohexyl) acetamide

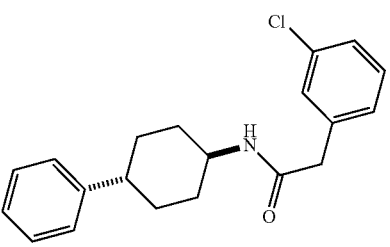

Prepared according to General Procedure A using trans-4-phenylcyclohexylamine and 3-chlorophenylacetic acid. Purified by silica gel chromatography (0% to 50% ethyl acetate in hexanes) which afforded the desired product as white solid. $^1$H NMR (400 MHz, CDCl$_3$) δ 7.36-7.12 (m, 9H), 5.21 (d, J=7.9 Hz, 1H), 3.84 (tdt, J=12.0, 8.1, 4.0 Hz, 1H), 3.53 (s, 2H), 2.51-2.37 (m, 1H), 2.13-1.99 (m, 2H), 1.99-1.85 (m, 2H), 1.67-1.49 (m, 2H), 1.29-1.09 (m, 2H). m/z 328.2 (M+H$^+$).

Example 17

Cis-1-(4-chlorophenyl)-3-(4-phenylcyclohexyl)urea

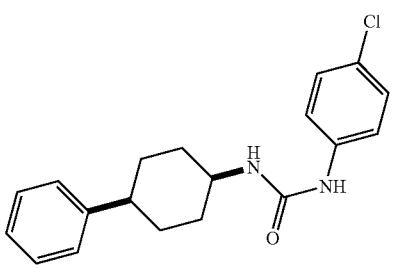

To a stirred solution of cis-4-phenylcyclohexylamine (Li, G. et al., *Bioorg. Med. Chem. Lett.,* 18:1146-1150 (2008)) (60 mg, 0.34 mmol) in diethyl ether (1.4 mL) was added 4-chlorophenyl isocyanate (53 mg, 0.34 mmol) at rt. After stirring for 30 min the voluminous white precipitate was isolated by vacuum filtration and concentrated under reduced pressure to yield the desired product. $^1$H NMR (400 MHz, CDCl$_3$) δ 7.37-7.09 (m, 9H), 6.28 (s, 1H), 4.88 (d, J=7.2 Hz, 1H), 4.17-4.03 (m, 1H), 2.68-2.49 (m, 1H), 1.98-1.87 (m, 2H), 1.87-1.69 (m, 4H), 1.65-1.50 (m, 2H).

Example 18

Cis-1-(3-chlorophenyl)-3-(4-phenylcyclohexyl)urea

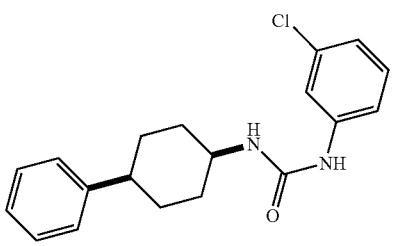

To a stirred solution of cis-4-phenylcyclohexylamine (60 mg, 0.36 mmol) in diethyl ether (1.4 mL) was added 3-chlorophenyl isocyanate (0.042 mL, 0.34 mmol) at rt. After stirring for 30 min the voluminous white precipitate was isolated by vacuum filtration and concentrated under reduced pressure to yield the desired product. $^1$H NMR (400 MHz, CDCl$_3$) δ 7.47-7.42 (m, 1H), 7.35-7.14 (m, 7H), 7.04 (dt, J=7.5, 1.7 Hz, 1H), 6.37 (s, 1H), 4.98 (d, J=6.6 Hz, 1H), 4.21-4.02 (m, 1H), 2.68-2.50 (m, 1H), 2.00-1.87 (m, 2H), 1.88-1.67 (m, 4H), 1.67-1.49 (m, 2H).

Example 19

Cis-2-(4-chlorophenyl)-N-(4-phenylcyclohexyl)acetamide

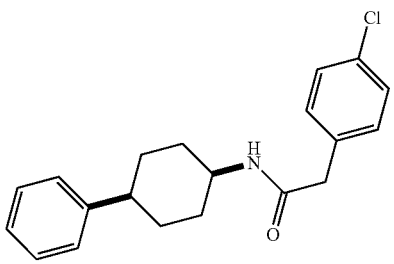

Prepared according to General Procedure A using cis-4-phenylcyclohexylamine and 4-chlorophenylacetic acid (Li, G. et al., *Bioorg. Med. Chem. Lett.,* 18:1146-1150 (2008)). Purified by silica gel chromatography (0% to 50% ethyl acetate in hexanes) which afforded the desired product as white solid. $^1$H NMR (400 MHz, CDCl$_3$) δ 7.43-7.17 (m, 7H), 7.07 (dd, J=7.5, 0.8 Hz, 2H), 5.86 (s, 1H), 4.25-4.05 (m, 1H), 3.60 (s, 2H), 2.60-2.46 (m, 1H), 1.89-1.55 (m, 6H), 1.42-1.22 (m, 2H). m/z 328.2 (M+H$^+$).

General Procedure C: Reaction Between Esters and Anilines.

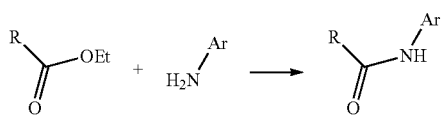

To a solution of the aniline (2.0 equiv) in THF (0.25 M) at 0° C. was added a solution of $^i$PrMgCl (2.0 equiv, 2 M in THF). The resulting solution was warmed to rt and stirred for 5 min at which point the ester (1.0 equiv) was added dropwise. The resulting reaction mixture was stirred at rt for 8 h and was poured into water. EtOAc was added, and the layers were separated. The aqueous layer was extracted with EtOAc (3×). The combined organic extracts were dried over anhydrous MgSO$_4$, filtered, and concentrated under reduced pressure. The crude reaction mixture was purified using silica gel chromatography (0% to 100% EtOAc in hexanes) to afford the desired product(s).

Example 20

Cis-4-benzyl-N-(4-chlorophenyl)cyclohexane-1-carboxamide

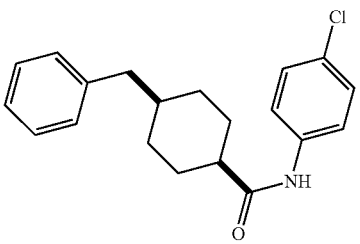

Prepared using General Procedure C employing ethyl 4-benzylcyclohexane-1-carboxylate (250 mg, 1.0 mmol), which can be prepared by methods shown in WO2005080317A2, and 4-chloroaniline (191 mg, 1.5 mmol). Purification using silica gel chromatography (0% to 50% EtOAc in hexanes) afforded the desired product. $^1$H NMR (400 MHz; CDCl$_3$): δ 7.49 (d, J=8.8 Hz, 2H), 7.28 (d, J=8.7 Hz, 2H), 7.23-7.10 (m, 5H), 2.62 (d, J=7.7 Hz, 2H), 2.48-2.37 (m, 1H), 2.04-1.93 (m, 2H), 1.88-1.82 (m, 2H), 1.74-1.43 (m, 4H), 1.10-0.93 (m, 1H); m/z 328.1 (M+H$^+$).

Example 21

Trans-4-benzyl-N-(4-chlorophenyl)cyclohexane-1-carboxamide

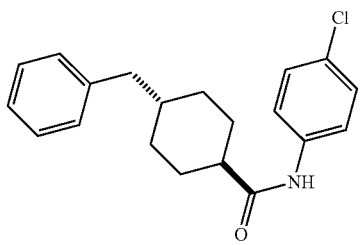

Further elution from the column in the previous example afforded the desired product as the second eluting isomer. $^1$H NMR (400 MHz; CDCl$_3$): δ 7.46 (d, J=8.8 Hz, 2H), 7.31-7.26 (m, 3H), 7.26-7.24 (m, 1H), 7.22-7.11 (m, 4H), 2.52 (d, J=7.1 Hz, 2H), 2.20-2.10 (m, 1H), 1.97 (d, J=11.4 Hz, 2H), 1.86-1.73 (m, 2H), 1.57-1.45 (m, 3H), 1.38-1.24 (m, 2H); m/z 328.1 (M+H$^+$).

Example 22

Cis-4-benzyl-N-(4-cyanophenyl)cyclohexane-1-carboxamide

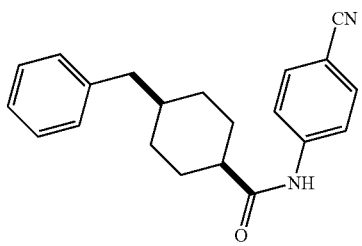

Prepared using General Procedure C employing ethyl 4-benzylcyclohexane-1-carboxylate (250 mg, 1.0 mmol) and 4-aminobenzonitrile (177 mg, 1.5 mmol). Purification using silica gel chromatography (0% to 50% EtOAc in hexanes) afforded the desired product. $^1$H NMR (400 MHz; CDCl$_3$): δ 7.73-7.63 (m, 2H), 7.63-7.55 (m, 2H), 7.51 (s, 1H), 7.32-7.24 (m, 2H), 7.23-7.10 (m, 3H), 2.61 (d, J=7.6 Hz, 2H), 2.49-2.45 (m, 1H), 2.04-1.91 (m, 1H), 1.89-1.77 (m, 1H), 1.74-1.46 (m, 7H); m/z 319.2 (M+H$^+$).

Example 23

Trans-4-benzyl-N-(4-cyanophenyl)cyclohexane-1-carboxamide

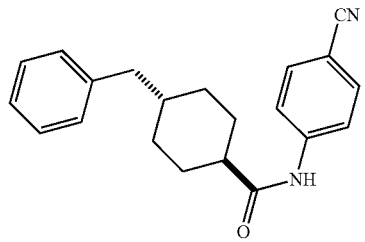

Further elution from the column in the previous example afforded the desired product as the second eluting isomer. $^1$H NMR (400 MHz; CDCl$_3$): δ 7.73-7.63 (m, 2H), 7.63-7.55 (m, 2H)), 7.46 (s, 1H), 7.32-7.24 (m, 2H), 7.23-7.10 (m, 3H), 2.52 (d, J=7.1 Hz, 2H), 2.21 (tt, J=12.1, 3.4 Hz, 1H), 2.04-1.91 (m, 2H), 1.89-1.77 (m, 2H), 1.74-1.46 (m, 3H), 1.03 (qd, J=13.2, 3.5 Hz, 2H).; m/z 319.2 (M+H$^+$).

Example 24

Cis-4-benzyl-N-(4-fluorophenyl)cyclohexane-1-carboxamide

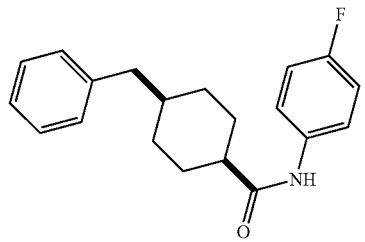

Prepared using General Procedure C employing ethyl 4-benzylcyclohexane-1-carboxylate (250 mg, 1.0 mmol) and 4-fluoroaniline (0.15 mL, 1.5 mmol). Purification using silica gel chromatography (0% to 50% EtOAc in hexanes) afforded the desired product. $^1$H NMR (400 MHz; CDCl$_3$): δ 7.48 (ddd, J=10.5, 6.9, 4.8 Hz, 2H), 7.34-7.11 (m, 5H), 7.09-6.94 (m, 3H), 2.62 (d, J=7.6 Hz, 2H), 2.48-2.36 (m, 1H), 2.04-1.92 (m, 2H), 1.88-1.76 (m, 1H), 1.74-1.40 (m, 5H), 1.12-0.94 (m, 1H); m/z 312.2 (M+H$^+$).

Example 25

Trans-4-benzyl-N-(4-fluorophenyl)cyclohexane-1-carboxamide

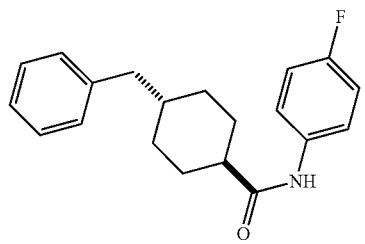

Further elution from the column in the previous example afforded the desired product as the second eluting isomer. $^1$H NMR (400 MHz; CDCl$_3$): δ 7.46 (dd, J=9.0, 4.8 Hz, 2H), 7.33-7.11 (m, 5H), 7.10-6.95 (m, 3H), 2.52 (d, J=7.0 Hz, 2H), 2.20-2.11 (m, 1H), 1.97 (d, J=10.4 Hz, 2H), 1.84 (d, J=13.0 Hz, 2H), 1.61-1.44 (m, 3H), 1.00 (dd, J=29.4, 10.9 Hz, 2H); m/z 312.2 (M+H$^+$).

Example 26

Cis-4-benzyl-N-(4-methoxyphenyl)cyclohexane-1-carboxamide

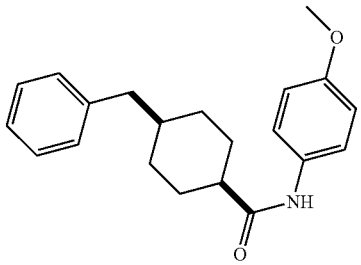

Prepared using General Procedure C employing ethyl 4-benzylcyclohexane-1-carboxylate (250 mg, 1.0 mmol) and 4-methoxyaniline (185 mg, 1.5 mmol). Purification using silica gel chromatography (0% to 50% EtOAc in hexanes) afforded the desired product. $^1$H NMR (400 MHz; CDCl$_3$): δ 7.46-7.38 (m, 2H), 7.33-7.23 (m, 2H), 7.22-7.09 (m, 4H), 6.92-6.80 (m, 2H), 3.79 (s, 3H), 2.62 (d, J=7.6 Hz, 2H), 2.48-2.35 (m, 1H), 2.05-1.95 (m, 2H), 1.86-1.75 (m, 1H), 1.70-1.63 (m, 2H), 1.65-1.48 (m, 4H); m/z 324.2 (M+H$^+$).

Example 27

Trans-4-benzyl-N-(4-methoxyphenyl)cyclohexane-1-carboxamide

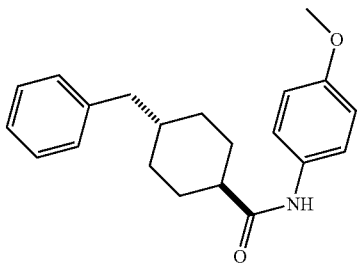

Further elution from the column in the previous example afforded the desired product as the second eluting isomer. $^1$H NMR (400 MHz; CDCl$_3$): δ 7.40 (d, J=9.0 Hz, 2H), 7.29 (d, J=7.0 Hz, 2H), 7.23-7.09 (m, 3H), 7.01 (s, 1H), 6.84 (d, J=8.9 Hz, 2H), 3.78 (s, 3H), 2.52 (d, J=6.9 Hz, 2H), 2.15 (tt, J=12.2, 3.5 Hz, 1H), 1.98 (d, J=11.2 Hz, 2H), 1.83 (d, J=13.6 Hz, 2H), 1.55-1.49 (m, 3H), 1.04 (qd, J=13.3, 3.3 Hz, 2H); m/z 324.2 (M+H$^+$).

Example 29

N-Benzyl-2-(4-(4-methoxyphenyl)cyclohexyl)acetamide

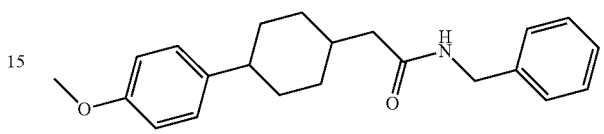

To solution of 2-(4-(4-methoxyphenyl)cyclohexyl)acetic acid (product of 9D, 152 mg, 0.61 mmol) in CH$_2$Cl$_2$ (1.2 mL) at rt was added oxalyl chloride (63 μL, 0.73 mmol) and one drop of DMF. Evolution of gas was observed and the mixture turned yellow in color. The mixture was stirred at rt for 1 h and then concentrated under reduced pressure. The residue was dissolved in CH$_2$Cl$_2$ (1.2 mL) and benzyl amine (67 μL, 0.61 mmol) and triethylamine (85 μL, 0.61 mmol) were added at rt. A white precipitate formed and more triethylamine (170 μL, 1.22 mmol) and CH$_2$Cl$_2$ (1.2 mL) were added. The homogenous mixture was stirred at rt for 3 h. The mixture was concentrated under reduced pressure. The residue was dissolved in EtOAc and washed with sat. NaHCO$_3$ and brine. The organic layer was dried over sodium sulfate and concentrated under reduced pressure. The residue was purified using silica gel chromatography (35% EtOAc in hexanes) to afford a mixture of isomers. The residue was recrystallized from heptane/IPA to afford the desired product as white solid as a 2:1 mixture of trans:cis isomers. m/z 338.3 (M+H$^+$).

Example 30

Cis-N-benzyl-2-(4-(4-methoxyphenyl)cyclohexyl)acetamide

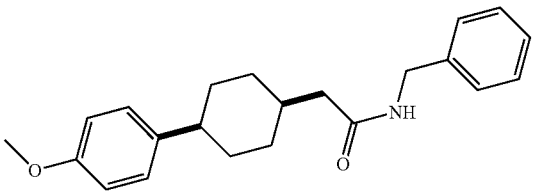

The mother liquors from the previous example were concentrated under reduced pressure to give the desired product. $^1$H NMR (400 MHz, CDCl$_3$) δ 7.45-7.23 (m, 5H), 7.20-7.07 (m, 2H), 6.92-6.71 (m, 2H), 5.80 (s, 1H), 4.46 (d, J=5.7 Hz, 2H), 3.79 (s, 3H), 2.66-2.48 (m, 1H), 2.38-2.28 (m, 3H), 1.79-1.58 (m, 8H); m/z 338.2 (M+H$^+$).

Example 31

N-(4-Chlorophenyl)-4-phenoxypiperidine-1-carboxamide

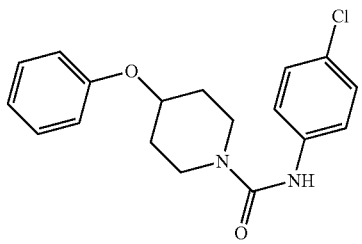

31A. N-(4-Chlorophenyl)-4-oxopiperidine-1-carboxamide

Piperidin-4-one hydrochloride (1.37 g, 10.1 mmol) was dissolved in $CH_2Cl_2$, washed with 1 M NaOH (60 mL), dried over anhydrous $MgSO_4$, filtered, and concentrated under reduced pressure to provide the free base as a clear, colorless oil. The piperidin-4-one was diluted with $CH_2Cl_2$ (6 mL), and the solution was cooled to 0° C. 4-Chlorophenyl isocyanate (1.59 g, 10.1 mmol) was added to the solution, and the ice bath was immediately removed. After 3 h, the reaction mixture was diluted with brine (10 mL) and 1 M NaOH (2 mL) and extracted with $CH_2Cl_2$ (2×30 mL). The combined organic layers were dried over anhydrous $MgSO_4$, filtered, and concentrated under reduced pressure to afford the desired intermediate as a white solid. $^1H$ NMR (400 MHz; $CDCl_3$): 8.80 (s, 1H), 7.50 (d, J=9.0 Hz, 2H), 7.27 (d, J=8.8 Hz, 2H), 3.72 (t, J=6.2 Hz, 4H), 2.38 (t, J=6.2 Hz, 4H); m/z 253.1 (M+H$^+$).

31B. N-(4-Chlorophenyl)-4-hydroxypiperidine-1-carboxamide

To a solution of N-(4-chlorophenyl)-4-oxopiperidine-1-carboxamide (401 mg, 1.58 mmol) in methanol (20 mL) was added $NaBH_4$ (89 mg, 2.36 mmol) at rt. The reaction was allowed to stir for 14 h before adding 1 M HCl (20 mL). The solution was extracted with $CH_2Cl_2$ (60 mL), dried over anhydrous $MgSO_4$, filtered, and concentrated under reduced pressure to afford the desired product as an oil. $^1H$ NMR (400 MHz; $CDCl_3$): 8.57 (s, 1H), 7.46 (d, J=9.0 Hz, 2H), 7.24 (d, J=9.0 Hz, 2H), 4.70 (d, J=4.3 Hz, 1H), 3.79 (td, J=4.3, 13.6 Hz, 2H), 3.68-3.58 (m, 1H), 3.02 (ddd, J=3.2, 10.0, 13.3 Hz, 2H), 1.75-1.67 (m, 2H), 1.34-1.21 (m, 2H).

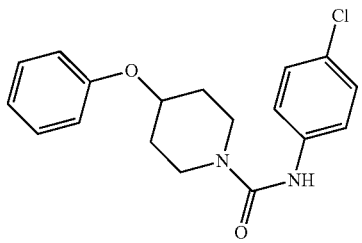 [SMILES: O=C(Nc1ccc(Cl)cc1)N1CCC(Oc2ccccc2)CC1]

Example 31

N-(4-Chlorophenyl)-4-phenoxypiperidine-1-carboxamide

To a solution of N-(4-chlorophenyl)-4-hydroxypiperidine-1-carboxamide (100 mg, 0.39 mmol) and $PPh_3$ (430 mg, 1.6 mmol) in THF (2 mL) at rt was added diethyl azodicarboxylate (DEAD) (0.068 mL, 0.43 mmol) and phenol (41 mg, 0.43 mmol). The solution was allowed to stir at rt for 16 h before concentrating under reduced pressure. The crude residue was purified using silica gel chromatography (30% EtOAc in hexanes) to afford the desired product as a clear, colorless film. $^1H$ NMR (400 MHz; $CDCl_3$): δ 7.34-7.22 (m, 6H), 6.99-6.90 (m, 3H), 6.48 (br s, 1H), 4.59-4.54 (m, 1H), 3.75-3.67 (m, 2H), 3.52-3.46 (m, 2H), 2.4-1.97 (m, 2H), 1.94-1.86 (m, 2H); m/z 331.2 (M+H$^+$).

Example 32

N-(4-Chlorophenyl)-4-phenoxycyclohexane-1-carboxamide

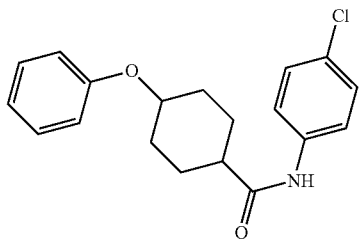 [SMILES: O=C(Nc1ccc(Cl)cc1)N1CCC(Oc2ccccc2)CC1]

32A. N-(4-Chlorophenyl)-4-hydroxycyclohexane-1-carboxamide

4-Hydroxycyclohexane-1-carboxylic acid (2.0 g, 14 mmol), 4-chloroaniline (1.8 g, 14 mmol), and 1-[bis(dimethylamino)methylene]-1H-1,2,3-triazolo[4,5-b]pyridinium 3-oxid hexafluorophosphate (HATU) (6.3, 17 mmol) were added to a 100 mL round bottom flask followed by DMF (46 mL) and diisopropylethylamine (2.5 mL, 28 mmol). The solution was stirred under argon for 16 h. The reaction solution was diluted with EtOAc (60 mL), washed with 1 N NaOH (50 mL), dried over anhydrous $MgSO_4$, filtered, and concentrated under reduced pressure. The crude residue was purified using silica gel chromatography (0% to 100% EtOAc in hexanes) to afford the desired product as a white solid. m/z 254.2 (M+H$^+$).

Example 32

N-(4-Chlorophenyl)-4-phenoxycyclohexane-1-carboxamide

To a 50 mL round bottom flask was added N-(4-chlorophenyl)-4-hydroxycyclohexane-1-carboxamide (1.6 g, 6.3 mmol), polymer-bound $PPh_3$ (3.0 mmol/g $PPh_3$, 8.4 g, 25 mmol), and phenol (0.894 g, 9.5 mmol). The flask was evacuated and backfilled with argon. To the flask was added THF (30 mL), and the mixture was cooled to 0° C. DEAD (1.49 mL, 9.5 mmol) was added dropwise by syringe, and the ice bath was removed. The mixture was allowed to warm to rt and stirred for 16 h. The reaction mixture was diluted with EtOAc (50 mL), filtered through a pad of 1:1 CELITE®:silica gel, and concentrated under reduced pressure. The crude residue was purified using silica gel chromatography (0% to 18%, then 18% to 30% EtOAc in hexanes) to afford the desired product as a white solid. $^1$H NMR (400 MHz; CDCl$_3$): δ 7.48 (d, J=8.7 Hz, 2H), 7.32-7.27 (m, 4H), 7.15 (br s, 1H), 6.99-6.84 (m, 3H), 4.34-4.14 (m, 1H), 2.36-2.19 (m, 3H), 2.08 (d, J=11.7 Hz, 2H), 1.81-1.68 (m, 2H), 1.55-1.43 (m, 2H); m/z 330.2 (M+H$^+$).

Example 33

2-(4-Chlorophenyl)-N-((trans)-4-(4-methoxyphenyl) cyclohexyl)acetamide

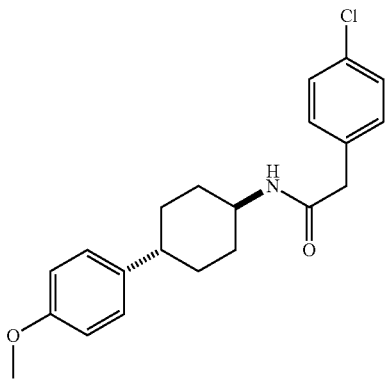

33A. cis-4-(4-Methoxyphenyl)cyclohexyl methanesulfonate

To a solution of cis-4-(4-methoxyphenyl)-cyclohexanol (*Chem. Commun.*, 48:9376 (2012)) (366 mg, 1.77 mmol) and triethylamine (0.49 mL, 3.55 mmol) in tetrahydrofuran (9 mL), at 0° C., was added methanesulfonyl chloride (0.21 mL, 2.66 mmol). The mixture was stirred for 1.5 h before being quenched with water, diluted with EtOAc, then washed sequentially with dilute HCl, saturated aqueous solution of sodium bicarbonate, and brine. The organic phases were dried over sodium sulfate then concentrated under reduced pressure before the resultant residue was purified using silica gel chromatography (20% to 50% EtOAc in hexanes) to afford cis-4-(4-methoxyphenyl)cyclohexyl methanesulfonate, as a white solid.

33B. (trans)-4-(4-Methoxyphenyl)cyclohexan-1-amine

To a mixture of cis-4-(4-methoxyphenyl)cyclohexyl methanesulfonate (430 mg, 1.51 mmol) in DMF (7.5 mL) was added sodium azide (108 mg, 1.66 mmol). The mixture was then heated at 70° C. for 4 h. The mixture was cooled to rt, quenched with water, then diluted with EtOAc. The organic phase was washed several times with water, then brine, before being concentrated under reduced pressure to ~10 mL. To this mixture was added wet 10% Pd/C (70 mg, 10% w/w) and the reaction vessel was placed under a hydrogen atmosphere, at rt, for 16 h. The mixture was filtered and the filtrate was concentrated under reduced pressure to afford a residue which was purified using silica gel chromatography (10% to 20% methanol in dichloromethane) to furnish the desired product, (trans)-4-(4-methoxyphenyl)cyclohexan-1-amine, as an off-white solid.

Example 33

2-(4-Chlorophenyl)-N-((trans)-4-(4-methoxyphenyl) cyclohexyl)acetamide

A solution containing 4-chlorophenylacetic acid (109 mg, 0.64 mmol) and 1-[bis(dimethylamino)methylene]-1H-1,2,3-triazolo[4,5-b]pyridinium 3-oxid hexafluorophosphate (266 mg, 0.70 mmol) in DMF (6 mL) was stirred at rt for 10 minutes before (trans)-4-(4-methoxyphenyl)cyclohexan-1-amine (131 mg, 0.64 mmol) was added. After stirring for 20 minutes, N,N-diisopropylethylamine (0.33 mL, 1.92 mmol) was added, and the mixture stirred for an additional 1 h. The flask contents were then poured into brine (30 mL) and filtered. The filtrate was concentrated under reduced pressure to afford a residue which was purified using silica gel chromatography (5% MeOH in CH$_2$Cl$_2$) to yield the desired 2-(4-chlorophenyl)-N-((trans)-4-(4-methoxyphenyl)cyclohexyl)acetamide as a white solid. $^1$H NMR (400 MHz; CDCl$_3$): δ 7.33 (d, J=8.4 Hz, 2H), 7.21 (d, J=8.1 Hz, 2H), 7.09 (d, J=8.7 Hz, 2H), 6.83 (d, J=9 Hz, 2H), 5.18 (d, J=8.4 Hz, 1H), 3.85-3.78 (m, 4H), 3.52 (s, 2H), 2.43-2.34 (m, 1H), 2.05-2.00 (m, 2H), 1.90-1.85 (m, 2H), 1.51-1.04 (m, 4H) ppm. m/z 358.2 (M+H)$^+$.

Example 34

4-Fluoro-N-(1,1,1-trifluoro-3-(4-(4-methoxyphenyl) cyclohexyl)propan-2-yl)aniline, HCl

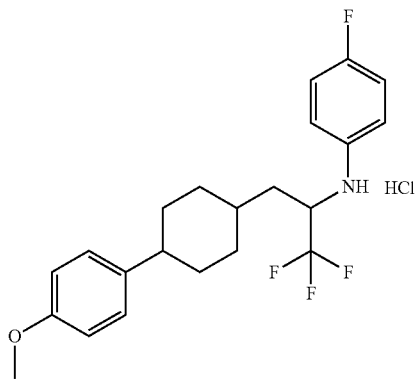 [SMILES: COc1ccc(C2CCC(CC(Nc3ccc(F)cc3)C(F)(F)F)CC2)cc1 ; Cl]

34A. Ethyl 2-(4-(4-hydroxyphenyl)cyclohexylidene)acetate

To an oven-dried flask (Flask #1) was added NaH (60% dispersion in oil, 11.8 g, 295 mmol) and 120 mL of THF, before the mixture was cooled to 0° C. To this mixture was added dropwise, over 1 hour, a mixture of triethylphosphonoacetate (46.9 mL, 236 mmol) in 250 mL of THF. After the addition was complete, the mixture was stirred for 1 h at rt.

To a separate flask (Flask #2), containing a 0° C. mixture of NaH (60% dispersion in oil, 8.67 g, 216 mmol) in 100 mL THF was carefully added, over 45 minutes, a solution of 37.47 g (196.9 mmol) of 4-(4-hydroxyphenyl)cyclohexanone in 250 mL THF. After addition was complete, the mixture was stirred at rt for 2 h until the mixture became a clear solution. Once this solution was clear, Flask #1 was cooled to 0° C. and the contents of Flask #2 are added via cannulation. After this addition was complete, the mixture was warmed to rt and stirred for 2 h. The mixture was then quenched by careful addition of ice and water (1 L) and subsequently extracted with EtOAc (3×500 mL). The combined organic layers were then washed with brine (1 L), dried over sodium sulfate, filtered, and concentrated under reduced pressure to provide ethyl 2-(4-(4-hydroxyphenyl) cyclohexylidene)acetate in 97% yield as a white solid.

34B. Ethyl 2-(4-(4-hydroxyphenyl)cyclohexyl)acetate

To a solution ethyl 2-(4-(4-hydroxyphenyl)cyclohexylidene)acetate (9.74 g, 35.8 mmol) in EtOAc was added Pd/C (0.974 g, 10 wt. %). The solution was sparged with a balloon of $H_2$ (g) and stirred under an atmosphere of hydrogen for 2 days. The mixture was then filtered through a pad of CELITE®, which was thoroughly rinsed with EtOAc. The combined filtrate was then concentrated under reduced pressure to afford ethyl 2-(4-(4-hydroxyphenyl) cyclohexyl)acetate as a white crystalline solid in quantitative yield as a mixture of diastereomers.

34C. Ethyl 2-(4-(4-methoxyphenyl)cyclohexyl)acetate

To a solution of ethyl 2-(4-(4-hydroxyphenyl)cyclohexyl) acetate (34B, 34.1 g, 130 mmol) in DMF (300 mL) was added $Cs_2CO_3$ (65.0 g, 200 mmol) followed by iodomethane (21.3 g, 150 mmol). The resulting suspension was stirred at rt for 16 h. The mixture was concentrated under reduced pressure and the residue was partitioned between EtOAc (150 ml) and water (200 mL). The layers were separated and the aqueous layer was extracted with EtOAc (3×150 mL). These combined organic extracts were combined with the original organic layer and were dried over anhydrous $MgSO_4$, filtered, and concentrated under reduced pressure. The residue was purified employing silica gel chromatography (0% to 30% EtOAc in hexanes) to afford ethyl 2-(4-(4-methoxyphenyl)cyclohexyl)acetate as a clear oil.

34D. 2-(4-(4-Methoxyphenyl)cyclohexyl)ethan-1-ol

Ethyl 2-(4-(4-methoxyphenyl)cyclohexyl)acetate (34C, 1.45 g, 5.25 mmol) was dissolved in THF (26 mL) and cooled to 0° C. $LiAlH_4$ (596 mg, 15.7 mmol) was then added portionwise, and the mixture was warmed to rt over 2 h. The mixture was quenched with water, then 2N aqueous HCl, before being extracted with EtOAc. The combined organic phases were washed with brine, dried over sodium sulfate, and concentrated under reduced pressure to furnish 2-(4-(4-methoxyphenyl)cyclohexyl)ethan-1-ol (1.17 g, 95%).

34E. 2-(4-(4-Methoxyphenyl)cyclohexyl)acetaldehyde

To a mixture of 2-(4-(4-methoxyphenyl)cyclohexyl) ethan-1-ol (34D, 1.17 g, 5.00 mmol) in dichloromethane (50 mL) was added sodium bicarbonate (1.26 g, 15.0 mmol), followed by Dess-Martin periodinane (3.19 g, 7.5 mmol) at 0° C. The resultant mixture was stirred at rt for 16 h, before being diluted with dichloromethane then washed with water. The organic layer was concentrated under reduced pressure to afford a residue which was adsorbed onto silica gel and purified using silica gel chromatography (20% EtOAc in hexanes) to furnish 2-(4-(4-methoxyphenyl)cyclohexyl)acetaldehyde (609 mg, 52%) as a colorless oil.

34F. 1,1,1-Trifluoro-3-(4-(4-methoxyphenyl)cyclohexyl)propan-2-ol

A solution of 2-(4-(4-methoxyphenyl)cyclohexyl)acetaldehyde (34E, 609 mg, 2.62 mmol) and TMS-$CF_3$ (0.58 mL, 3.93 mmol) in THF (6 mL) was treated with a 1M solution of TBAF in THF (15.72 mL, 15.72 mmol) at 0° C. The mixture was allowed to warm to rt for 16 h, then quenched with aqueous 2N HCl (3 mL) over 30 minutes. The mixture was partitioned between EtOAc and water and the layers were separated. The organic layers were washed with brine, dried over sodium sulfate and concentrated under reduced pressure to afford a residue which was purified using silica gel chromatography (15% EtOAc in hexanes) to deliver 1,1,1-trifluoro-3-(4-(4-methoxyphenyl)cyclohexyl)propan-2-ol (565 mg, 71%) as a colorless oil.

34G. 1,1,1-Trifluoro-3-(4-(4-methoxyphenyl)cyclohexyl)propan-2-one

To a solution of 1,1,1-trifluoro-3-(4-(4-methoxyphenyl) cyclohexyl)propan-2-ol (34F, 565 mg, 1.89 mmol) in $CH_2Cl_2$ (19 mL) was added sodium bicarbonate (476 mg, 5.67) followed by Dess-Martin periodinane (1.04 g, 2.46 mmol) at 0° C. The mixture was stirred at rt for 16 h, then diluted with $CH_2Cl_2$ and washed with water. The mixture was concentrated under reduced pressure and the residue was purified using silica gel chromatography (10% EtOAc in hexanes) to afford 1,1,1-trifluoro-3-(4-(4-methoxyphenyl) cyclohexyl)propan-2-one (356 mg, 63%) as a colorless oil which crystallized upon standing.

34H. N-(4-Chlorophenyl)-1,1,1-trifluoro-3-(4-(4-methoxyphenyl)cyclohexyl)propan-2-imine and (Z)-4-chloro-N-(3,3,3-trifluoro-1-(4-(4-methoxyphenyl) cyclohexyl)prop-1-en-2-yl)aniline A mixture of 1,1,1-trifluoro-3-(4-(4-methoxyphenyl)cyclohexyl)propan-2-one (34G, 178 mg, 0.59 mmol), 4-fluoroaniline (0.14 mL, 1.19 mmol) and p-TsOH (5 mg, 0.03 mmol), dissolved in toluene (5 mL), was heated to reflux utilizing a Dean-Stark trap for 16 h. The mixture was concentrated under reduced pressure to afford a residue which was purified by column chromatography on neutral alumina (7% EtOAc/hexanes) to give a mixture of imine N-(4-chlorophenyl)-1,1,1-trifluoro-3-(4-(4-methoxyphenyl) cyclohexyl)propan-2-imine and (Z)-4-chloro-N-(3,3,3-trifluoro-1-(4-(4-methoxyphenyl)cyclohexyl)prop-1-en-2-yl) aniline as a viscous, colorless oil.

Example 34

4-Fluoro-N-(1,1,1-trifluoro-3-(4-(4-methoxyphenyl) cyclohexyl)propan-2-yl)aniline To a mixture of the product of 34H (N-(4-chlorophenyl)-1,1,1-trifluoro-3-(4-(4-methoxyphenyl)cyclohexyl)propan-2-imine and (Z)-4-chloro-N-(3,3,3-trifluoro-1-(4-(4-methoxyphenyl)cyclohexyl)prop-1-en-2-yl)aniline) (34H, 160 mg, 0.41 mmol) in MeOH (10 mL), at rt, was added sodium borohydride (46 mg, 1.2 mmol). The resultant mixture was stirred at rt for 1.5 h before being quenched with satd. aq. ammonium chloride then extracted with dichloromethane. The combined organic phases were dried over sodium sulfate and concentrated under reduced pressure. The resultant residue was purified by preparative HPLC (Varian ProStar using Hamilton C18 PRP-1 column (15×250 mm) with flow rate of 20 mL/min, Mobile Phase A: 0.5% formic acid in water; Mobile Phase B: 0.5% formic acid in acetonitrile; 0% to 100% B gradient elution during 30 minutes) to give a residue. The residue was diluted with 2M HCl in diethyl ether and concentrated under reduced pressure to give the HCl salt of the desired compound as a racemic mixture of cis/trans isomers. $^1$H NMR (300 MHz; CDCl$_3$): δ 7.16-7.08 (m, 2H), 6.95-6.81 (m, 4H), 6.65-6.59 (m, 2H), 3.93-3.85 (m, 1H), 3.85-3.71 (m, 3H), 3.41 (d, J=9.0 Hz, 1H), 2.55-2.50 (m, 1H), 2.41 (tt, J=12.3, 3.0 Hz, 1H), 2.17-2.08 (m, 1H), 1.99-1.00 (m, 9H) ppm. m/z 396.15 (M+H)$^+$.

Example 35

4-Chloro-N-(1,1,1-trifluoro-3-(4-(4-methoxyphenyl)cyclohexyl)propan-2-yl)aniline hydrogenchloride

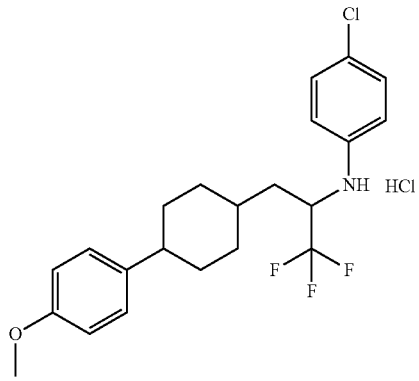 [SMILES: COc1ccc(C2CCC(CC(Nc3ccc(Cl)cc3)C(F)(F)F)CC2)cc1 ; Cl]

Prepared utilizing the procedures used to afford 4-fluoro-N-(1,1,1-trifluoro-3-(4-(4-methoxyphenyl)cyclohexyl)propan-2-yl)aniline replacing 4-fluoroaniline with 4-chloroaniline. MS(ES): m/z=412.10 [M+H]$^+$. t$_R$=2.94 min (Method M).

Example 36

2-(4-Cyanophenyl)-N-((trans)-4-phenylcyclohexyl)acetamide

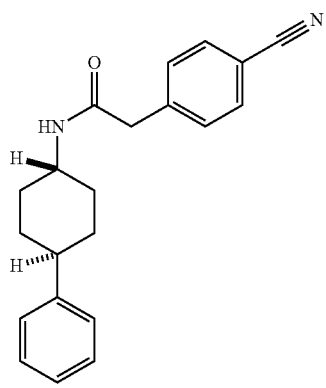 [SMILES: N#Cc1ccc(CC(=O)N[C@H]2CC[C@H](c3ccccc3)CC2)cc1]

The following compound was made in the manner of General Procedure A, employing trans-4-phenyl-cyclohexanamine (PCT Publication No. WO 2001/092204) (138 mg, 0.79 mmol), 2-(4-cyanophenyl)acetic acid (138 mg, 0.86 mmol), 1-[bis(dimethylamino)methylene]-1H-1,2,3-triazolo[4,5-b]pyridinium 3-oxid hexafluorophosphate (360 mg, 0.95 mmol), and DMF (4 mL). The residue was purified to by preparative TLC (33% EtOAc in hexanes), followed by preparative HPLC (Varian ProStar using Hamilton C18 PRP-1 column (15×250 mm) with flow rate of 20 mL/min, Mobile Phase A: 0.5% formic acid in water; Mobile Phase B: 0.5% formic acid in acetonitrile; 0% to 100% B gradient elution during 30 minutes) to give the desired product. $^1$H NMR (300 MHz; CDCl$_3$): δ 7.64 (dd, J=8.4, 1.8 Hz, 2H), 7.40 (dd, J=8.4, 1.8 Hz, 2H), 7.32-7.24 (m, 2H), 7.21-7.16 (m, 3H), 5.31 (d, J=7.5 Hz, 1H), 3.89-3.79 (m, 1H), 3.60 (s, 2H), 2.45 (tt, J=16.0, 3.6 Hz, 1H), 2.10-1.90 (m, 4H), 1.66-1.56 (m, 2H), 1.30-1.16 (m, 2H) ppm. m/z 319 (M+H)$^+$.

Example 37

2-(4-Chlorophenyl)-N-((trans)-4-phenylcyclohexyl)propanamide

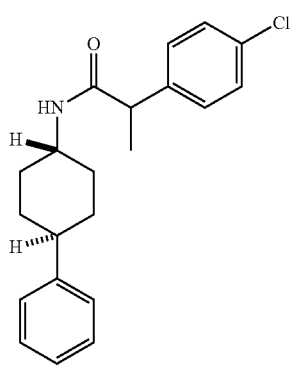 [SMILES: CC(C(=O)N[C@H]1CC[C@H](c2ccccc2)CC1)c1ccc(Cl)cc1]

The following compound was made in the manner of General Procedure A, employing trans-4-phenyl-cyclohexanamine (PCT Publication No. WO 2001/092204) (138 mg, 0.79 mmol), 2-(4-chlorophenyl)propanoic acid (158 mg, 0.86 mmol), 1-[bis(dimethylamino)methylene]-1H-1,2,3-triazolo[4,5-b]pyridinium 3-oxid hexafluorophosphate (360 mg, 0.95 mmol), and DMF (4 mL). The residue was purified to by preparative TLC (33% EtOAc in hexanes) to give a residue. The residue was further purified by preparative HPLC (Varian ProStar using Hamilton C18 PRP-1 column (15×250 mm) with flow rate of 20 mL/min, Mobile Phase A: 0.5% formic acid in water; Mobile Phase B: 0.5% formic acid in acetonitrile; 0% to 100% B gradient elution during 30 minutes) to give the desired product as a racemic mixture. $^1$H NMR (300 MHz; CDCl$_3$): δ 7.34-7.14 (m, 9H), 5.16 (d, J=7.8 Hz, 1H), 3.86-3.75 (m, 1H), 3.48 (q, J=7.2 Hz, 1H), 2.42 (tt, J=12.3, 3.3 Hz, 1H), 2.09-1.84 (m, 4H), 1.68-1.52 (m, 2H), 1.49 (d, J=7.2 Hz, 3H), 1.26-1.06 (m, 2H) ppm. m/z 342 (M+H)$^+$.

Example 38

2-(4-Chlorophenyl)-N-((trans)-4-(quinolin-4-yl)cyclohexyl)acetamide

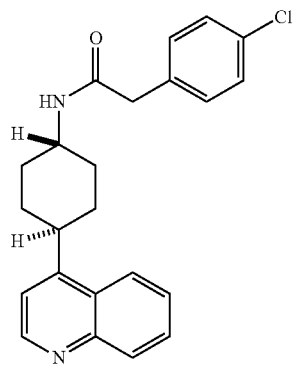 [SMILES: O=C(Cc1ccc(Cl)cc1)N[C@H]1CC[C@H](c2ccnc3ccccc32)CC1]

38A. 4-(1,4-Dioxaspiro[4.5]dec-7-en-8-yl)quinoline 1,4-Dioxaspiro[4.5]dec-7-en-8-yl trifluoromethanesulfonate (*Bioorg. Med. Chem. Lett.,* 24:5377 (2014)) (6.9 g, 23.9 mmol) was placed in a 500 mL round bottomed flask, followed by quinolone-4-boronic acid (4.55 g, 26.3 mmol), Pd(PPh$_3$)$_4$ (1.39 g, 1.2 mmol, 5 mol %), KBr (2.85 g, 23.94 mmol) and sodium carbonate (6.34 g, 59.85 mmol). The flask was evacuated and backfilled with N$_2$ three times, before degassed dioxane (100 mL) and water (10 mL) were added to the solids and the mixture was stirred and heated to 90° C. under N$_2$ atmosphere. After 16 h, the mixture was cooled to rt, and SiO$_2$ was added. The mixture was concentrated under reduced pressure and the residue was purified by silica gel column chromatography (0% to 100% EtOAc in hexanes) to give 4-(1,4-dioxaspiro[4.5]dec-7-en-8-yl)quinoline (3.2 g, 50%).

38B. 4-(1,4-Dioxaspiro[4.5]decan-8-yl)quinolone

A mixture 4-(1,4-dioxaspiro[4.5]dec-7-en-8-yl)quinolone (3.2 g, 12.0 mmol), NaHCO$_3$ (500 mg, 6.0 mmol), and MeOH (70 mL) was purged with N$_2$ (g), before 20 wt. % of Pd/C (dry activated, 10 wt. %) was added to the mixture. H$_2$ (g) was bubbled through the solution until complete disappearance of the starting material. The mixture was purged with N$_2$ (g), filtered through CELITE®, and the filtrate was concentrated under reduced pressure. The residue was purified by flash chromatography to give 4-(1,4-dioxaspiro[4.5]decan-8-yl)quinolone (2.9 g, 90%).

38C. 4-(Quinolin-4-yl)cyclohexan-1-one

To a mixture of 4-(1,4-dioxaspiro[4.5]decan-8-yl)quinolone (3.0 g, 11 mmol) in acetone (30 mL) was added 3M aqueous HCl (30 mL). After the mixture was stirred at rt for 24 h, it was concentrated under reduced pressure and NaHCO$_3$ (sat. aqueous solution) was added to adjust the pH above 8.0. The mixture was then extracted with EtOAc. The combined organic layers were dried with Na$_2$SO$_4$, and concentrated under reduced pressure to furnish 4-(quinolin-4-yl)cyclohexan-1-one as a yellow oil (2.3 g, 90%), which solidified upon standing.

38D. 4-(Quinolin-4-yl)cyclohexan-1-amine

The desired amine was made through reductive amination of 4-(quinolin-4-yl)cyclohexan-1-one with ammonium acetate and sodium cyanoborohydride to give 4-(quinolin-4-yl)cyclohexan-1-amine.

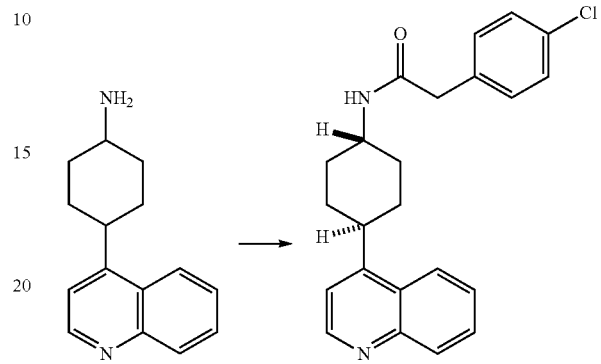

38E. 2-(4-Chlorophenyl)-N-((trans)-4-(quinolin-4-yl)cyclohexyl)acetamide

General Procedure A was employed using 4-(quinolin-4-yl)cyclohexan-1-amine, and 2-(4-chlorophenyl)acetic acid. The residue was purified using preparative HPLC (Varian ProStar using Hamilton C18 PRP-1 column (15×250 mm) with flow rate of 20 mL/min, Mobile Phase A: 0.5% formic acid in water; Mobile Phase B: 0.5% formic acid in acetonitrile; 0% to 100% B gradient elution during 30 minutes) to give the desired compound as a white powder. $^1$H NMR (400 MHz; CD$_3$OD): δ 8.77-8.74 (m, 1H), 8.26-8.21 (m, 1H), 8.05-8.01 (m, 1H), 7.79-7.73 (m, 1H), 7.68-7.63 (m, 1H), 7.49-7.45 (m, 1H), 7.34-7.27 (m, 4H), 3.82-3.77 (m, 1H), 3.50-3.42 (m, 3H), 2.13-2.03 (m, 4H), 1.82-1.70 (m, 2H), 1.65-1.60 (m, 2H) ppm. m/z 379 (M+H)$^+$.

Example 40

N—((R)-1-(((1s,4S)-4-(6-Fluoroquinolin-4-yl)cyclohexyl)ethyl)-3-methylbenzenesulfonamide

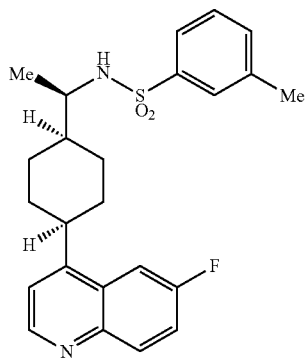 [SMILES: Cc1cccc(S(=O)(=O)N[C@H](C)[C@H]2CC[C@@H](c3ccnc4ccc(F)cc43)CC2)c1]

Preparation 40A:

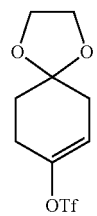

To a stirred solution of 1,4-dioxaspiro[4.5]decan-8-one (300 g, 1920.86 mmol, 1.0 eq) and phenyltrifluoromethanesulfonimide (823.47 g, 2305.03 mmol, 1.2 eq) in MTBE (7.5 L) under $N_2$ at −78° C. was added 2.0 M NaHMDS in THF (1152.2 mL, 2305.03 mmol, 1.2 eq) over 70 minutes, and the mixture was stirred for an additional 60 minutes. The reaction mixture was warmed to room temperature and stirred overnight until TLC showed complete consumption of the starting material. The mixture was quenched with aqueous $KHSO_4$ (100 ml), filtrated to remove the solid and concentrated the filtrate completely. To the residue was added 3 L MTBE, then washed with 5% NaOH (1.5 L×3). The organic phase was concentrated to obtain 567 g crude Preparation 40A (light yellow oil, yield 102%). The crude can be used directly in next step without further purification.

Preparation 40A: $^1$H NMR (400 MHz, $CDCl_3$): δ (ppm) 5.65 (t, J=4.0 Hz, 1H), 3.98 (d, J=1.5 Hz, 4H), 2.53 (s, 2H), 2.40 (s, 2H), 1.90 (t, J=6.6 Hz, 2H)

Preparation 40B:

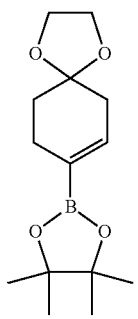

A mixture of crude Preparation 40A (600 g, 2.08 mol, 1 eq), $B_2Pin_2$ (687.1 g, 2.71 mol, 1.3 eq), KOAc (613 g, 6.24 mol, 3 eq), NaBr (86 g 0.833 mol, 0.4 eq) and Pd(dppf)Cl$_2$ (76 g, 0.1 mol, 0.05 eq) in dioxane (6.5 L) was heated to reflux overnight. Once the reaction was complete, the mixture was concentrated and purified by FCC (2%→10%→20% EtOAc/PE) to give Preparation 40B (369 g, 66%).

Preparation 40B: LC-MS: 267.1 (M+1)+, $^1$H NMR (400 MHz, $CDCl_3$) δ 6.46 (s, 1H), 3.98 (s, 4H), 2.37-2.35 (m, 4H), 1.74-1.60 (t, 2H), 1.24 (s, 12H).

Preparation 40C:

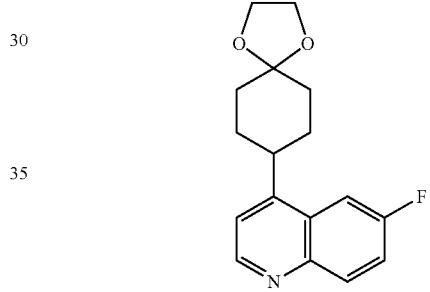

A mixture of Preparation 40B (368 g, 1.38 mol, 1.3 eq), 4-Chloro-6-fluoroquinoline (195 g, 1.07 mol, 1 eq), $K_2CO_3$ (445 g, 3.22 mol, 3 eq) and Pd(PPh$_3$)$_4$ (25 g, 22 mmol, 0.02 eq) in dioxane-water (3 L, 4:1) was heated to reflux overnight. The solution was then concentrated and extracted with EtOAc. Purification by FCC (38% EtOAc/petroleum ether) gave Preparation 40C (236 g, 77%).

Preparation 40C: LC-MS: 286.1 (M+1)+, $^1$H NMR (400 MHz, $CDCl_3$) δ 8.80-8.29 (d, 1H), 8.11-8.07 (q, 1H), 7.63-7.61 (q, 1H), 7.47-7.46 (q, 1H), 7.26-7.22 (m, 1H), 5.75-5.74 (m, 1H), 4.08-4.05 (m, 4H), 2.63-2.59 (m, 2H), 2.59-2.53 (m, 2H), 2.0-1.97 (m, 2H).

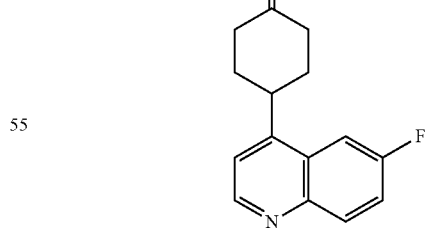

Preparation 40D:

To Preparation 40C (125 g, 0.44 mol) in IPA (2 L) at 55° C. was added 10% Pd/C and the mixture was stirred under an atmosphere of $H_2$ overnight. The mixture was filtered and concentrated to give crude Preparation 40D (130 g), which was used directly in the next step.

Preparation 40E:

Preparation 40D (100 g, 0.348 mol) was treated with 4 N HCl (300 mL) in acetone (1200 mL) at 45° C. overnight. The mixture was monitored by TLC. Then the solution was concentrated in vacuo. The residue was adjusted to pH 9 with 6 N NaOH. and the mixture was partitioned between ethyl acetate and water. The organic layer was washed with brine, dried over anhydrous Na₂SO₄, filtered and concentrated to give light yellow solid, which was then purified by silica gel column using hexanes and ethyl acetate (from 20 percent ethyl acetate to 70% ethyl acetate) to afford Preparation 40E as a white solid, (47 g+20 g mixture, yield >55%). Preparation 40E: LC-MS: 244.0 (M+1)+, ¹H NMR (400 MHz, CDCl₃) δ 8.84 (d, J=4.6 Hz, 1H), 8.16 (dd, J=9.3, 5.7 Hz, 1H), 7.72 (dd, J=10.3, 2.8 Hz, 1H), 7.52 (ddd, J=9.2, 7.8, 2.7 Hz, 1H), 7.29 (d, J=4.6 Hz, 1H), 3.69 (ddd, J=12.1, 9.0, 3.3 Hz, 1H), 2.77-2.54 (m, 4H), 2.37 (ddd, J=13.4, 5.9, 3.0 Hz, 2H), 2.04 (qd, J=12.6, 5.3 Hz, 2H).

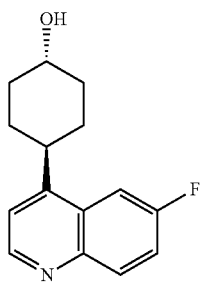 [SMILES: O[C@H]1CC[C@H](c2ccnc3ccc(F)cc32)CC1]

Preparation 40F:

Preparation 40E (57.8 g, 237.8 mmol) was dissolved in EtOH (240 mL) and cooled to 0° C. NaBH₄ (9.94 g, 261.6 mmol) was added portionwise maintaining the temperature within a range of 0-10° C. (exothermic reaction). The resulting suspension was stirred for 20 minutes. An LC/MS of an aliquot of the reaction mixture indicated consumption of ketone (m/z (M+H)+=244). The reaction was quenched at 0° C. by the slow addition of acetone (58 mL) over 15 minutes (exotherm). The reaction was poured slowly onto 500 mL of saturated aqueous ammonium chloride and 500 g of ice. The resulting aqueous solution was extracted with EtOAc (3×300 mL) and the combined organic fractions were washed with saturated aqueous ammonium chloride (250 mL) and saturated aqueous sodium chloride (250 mL). The organic portion was dried over anhydrous sodium sulfate and concentrated under reduced pressure. Sufficient silica to adsorb the oil was added and diluted with 10% MeOH in CH₂Cl₂. A similar quantity of silica was used as a silica plug to purify the material. The silica plug was washed with 10% MeOH in CH₂Cl₂ until UV-active material no longer could be detected by TLC (7:3 EtOAc/Hexanes, R_f=0.4). The filtrate was concentrated then suspended in 500 mL of toluene and concentrated again. Crude Preparation 40F was isolated as a yellow solid (58.2 g) that was used in the subsequent step without further purification.

Preparation 40G:

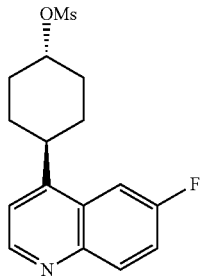 [SMILES: CS(=O)(=O)O[C@H]1CC[C@H](c2ccnc3ccc(F)cc32)CC1]

To Preparation 40F (58.2 g, 237.8 mmol) was added MeCN (125 mL) and pyridine (38.7 mL, 480 mmol) and the reaction mixture was cooled to 5° C. using an ice/water bath. Methanesulfonyl chloride (26.0 mL, 336 mmol) was added dropwise at 5° C. (exothermic reaction), the reaction mixture stirred for 1 hr at 5° C. and then brought up to room temperature and stirred for an additional 16 h during which time a white precipitate formed. The heterogeneous mixture was quenched by the addition of saturated aqueous ammonium chloride (200 mL) and extracted with CH₂Cl₂ (3×300 mL). The combined organic fractions were dried over anhydrous sodium sulfate and concentrated under reduced pressure. Excess pyridine was removed by azeotroping from toluene (3×300 mL). The crude material was recrystallized from H₂O/MeOH as follows: 1 mL/mmol of H₂O was added and the slurry was heated to 120° C. in an oil bath. MeOH was added until the solids went into solution (~0.5 L). After cooling white crystals were collected by filtration to give Preparation 40G (58.6 g, >20:1 dr, 76% over two steps). m/z (M+H)+=324.1. ¹H-NMR (400 MHz; CDCl₃): δ 8.82 (dd, J=4.6, 0.2 Hz, 1H), 8.15-8.11 (m, 1H), 7.64-7.61 (m, 1H), 7.52-7.46 (m, 1H), 7.25 (s, 1H), 4.78 (tt, J=10.9, 5.2 Hz, 1H), 3.24-3.16 (m, 1H), 3.07 (d, J=1.0 Hz, 3H), 2.42-2.38 (m, 2H), 2.16-2.12 (m, 2H), 1.93-1.66 (m, 4H).

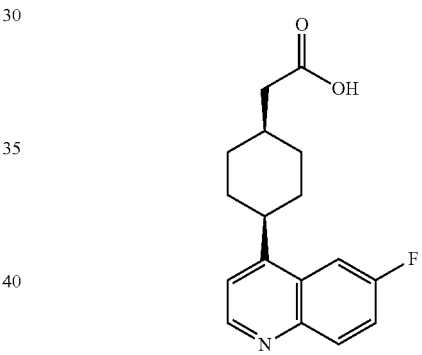

Preparation 40H:

Di-tert-butyl malonate (33.5 mL, 150 mmol) was added dropwise to a stirred suspension of NaH (6.0 g, 60% suspension in oil, 150 mmol) in 1,2-dimethoxyethane (100 mL) under Ar, cooled in a water-ice bath. After stirring for 10 min, Preparation 40G (16.2 g, 50 mmol) was added and the reaction was heated at 85° C. for 20 h. After this time, acetic acid (100 mL) was added, the reaction flask was fitted with a distillation head and the temperature was raised to 130° C. 1,2-dimethoxyethane was distilled off under atmospheric pressure until the distillate was acidic (~100 mL). The distillation head was removed, a reflux condenser was attached, water (20 mL) was added and the reaction heated at 130° C. for 12 h. The reaction was concentrated under reduced pressure and poured onto 200 g of ice and 100 mL of saturated aqueous NaOAc. Preparation 40H was isolated as a white solid by filtration and further dried by refluxing with toluene in a Dean-Stark apparatus (11.0 g, 76%). m/z (M+H)+=288.2. ¹H-NMR (400 MHz; DMSO-d₆): δ 12.05 (bs, 1H), 8.79 (d, J=4.5 Hz, 1H), 8.06 (dd, J=9.2, 5.8 Hz, 1H), 7.94 (dd, J=11.0, 2.8 Hz, 1H), 7.66-7.61 (m, 1H), 7.50 (d, J=4.6 Hz, 1H), 2.41 (d, J=7.6 Hz, 2H), 2.28-2.23 (m, 1H), 1.87-1.78 (m, 2H), 1.73-1.64 (m, 6H).

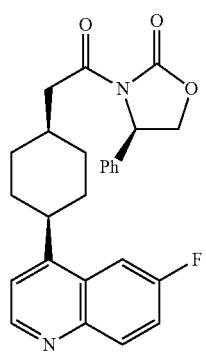 [SMILES: O=C(C[C@H]1CC[C@@H](c2ccnc3ccc(F)cc32)CC1)N1C(=O)OC[C@H]1c1ccccc1]

Preparation 40I:

To a solution of Preparation 40H (1.4 g, 4.8 mmol) in THF (15 mL) was added NEt₃ (1.3 mL, 9.6 mmol). The reaction mixture was cooled to 0° C. and trimethylacetyl chloride (0.713 mL, 5.8 mmol) was added dropwise and the resulting solution stirred for 30 min at 0° C. In a separate flask, (R)-4-phenyloxazolidin-2-one (3, 1.01 g, 6.24 mmol) in THF (45 mL) at 0° C. was treated with 1 M LiHMDS solution in THF (dropwise addition of 6.24 mL, 6.24 mmol) and stirred at 0° C. The lithiate was added via cannula to the first flask. The reaction mixture was allowed to warm to rt and was stirred for 3 hours. LC/MS indicated the complete consumption of the starting carboxylic acid and formation of the desired imide. The reaction mixture was poured onto saturated aqueous ammonium chloride (50 mL) and the layers were separated. The aqueous layer was extracted with EtOAc (3×50 mL). The combined organic extracts were dried over anhydrous sodium sulfate and chromatographed on silica using EtOAc/Hexanes 0 to 100% gradient to give Preparation 40I as a white foam in 83% yield. m/z (M+H)⁺ =433.3. ¹H-NMR (400 MHz; CDCl₃): δ 8.80 (d, J=4.5 Hz, 1H), 8.11 (dd, J=9.1, 5.7 Hz, 1H), 7.63 (dd, J=10.5, 2.5 Hz, 1H), 7.48-7.43 (m, 1H), 7.40-7.30 (m, 6H), 5.47-5.44 (m, 1H), 4.71 (t, J=8.9 Hz, 1H), 4.31-4.28 (m, 1H), 3.20-3.11 (m, 3H), 2.49-2.46 (m, 1H), 1.82-1.67 (m, 6H).

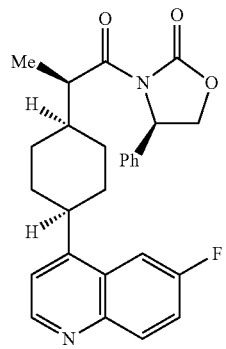 [SMILES: C[C@@H](C(=O)N1C(=O)OC[C@H]1c1ccccc1)[C@H]1CC[C@@H](c2ccnc3ccc(F)cc32)CC1]

Preparation 40J:

A solution of Preparation 40I (21.6 g, 50 mmol) in anhydrous THF (200 mL) was cooled to −40° C. (using acetonitrile/dry ice bath, some precipitation occurs) and 2 M NaHMDS solution in THF (30 mL, 60 mmol) was added over 5 min (a 5-8° C. rise in temperature was observed). The resulting yellow reaction mixture was stirred for 10 min, became homogeneous, and MeI (10.6 g, 75 mmol) was added dropwise over 2 min (a 10° C. rise in temperature was observed). The reaction mixture was stirred for 1 h at −40° C. and LC/MS indicated the complete consumption of the starting material and formation of the desired methyl imide. The reaction mixture was rapidly diluted with saturated aqueous ammonium chloride solution (400 mL) and the biphasic mixture was stirred for 15 min. ᶦPrOAc (100 mL) was added, the layers were separated, and the aqueous layer was extracted with ᶦPrOAc (3×50 mL). The combined organic extracts were dried over anhydrous magnesium sulfate filtered, and concentrated. The resulting residue was recrystallized by dissolving in 400 mL hot acetone and adding H₂O until a milky solution formed followed to re-dissolving with heating (~3:1 acetone/H₂O). Preparation 40J was obtained as white needles (15.04 g, 2 crops, 68%). m/z (M+H)⁺=447.3. ¹H-NMR (400 MHz; CDCl₃): δ 8.81 (d, J=4.6 Hz, 1H), 8.10 (dd, J=9.2, 5.7 Hz, 1H), 7.65 (dd, J=10.6, 2.7 Hz, 1H), 7.47-7.42 (m, 1H), 7.41-7.29 (m, 6H), 5.47 (dd, J=8.8, 3.8 Hz, 1H), 4.69 (t, J=8.9 Hz, 1H), 4.38-4.30 (m, 1H), 4.26 (dd, J=8.9, 3.9 Hz, 1H), 3.26-3.21 (m, 1H), 2.18-2.15 (m, 1H), 1.93-1.64 (m, 8H), 1.09 (d, J=6.9 Hz, 3H).

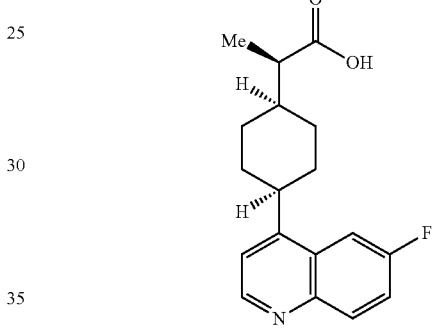

Preparation 40K:

To a solution of Preparation 40J (82.0 g, 183.6 mmol) in THF (610 mL) at 0° C. was added aqueous H₂O₂ (35 wt %, 82 mL) and LiOH (7.04 g, 293.8 mmol) in H₂O (189 mL). The resulting reaction mixture was allowed to slowly warm to rt and stirred overnight. The reaction was cooled to 0° C. and saturated aqueous sodium bisulfite solution (250 mL) was added. After stirring for 30 min, the THF was removed under reduced pressure. Acetic acid (34 mL) was added followed by EtOAc (300 mL). The layers were separated, and the aqueous layer was extracted with EtOAc (3×500 mL). The combined organic extracts were dried over anhydrous Na₂SO₄, filtered, and concentrated under reduced pressure. The brown crude reaction mixture was suspended in MeCN (400 mL) and the suspension was brought to reflux with vigorous stirring. After cooling to rt, the solids were collected by filtration washing with additional MeCN. Preparation 40K was obtained as a white solid (45.4 g, 82%). m/z (M+H)⁺=302.2. ¹H-NMR (400 MHz; DMSO-d6): δ 12.10 (s, 1H), 8.79 (d, J=4.5 Hz, 1H), 8.07 (dd, J=9.2, 5.9 Hz, 1H), 7.97-7.94 (m, 1H), 7.67-7.62 (m, 1H), 7.49 (d, J=4.5 Hz, 1H), 3.41-3.36 (m, 1H), 2.73-2.65 (m, 1H), 1.83-1.61 (m, 9H), 1.08 (d, J=6.8 Hz, 3H). Chiral HPLC, >99% ee (ChiralPak IC-3, 3 μM, 4.6×250 mm, 15 min isocratic 70% heptane 30% i-PrOH with 230 nm detection) at a flow rate of 0.75 mL/min the desired enantiomer had a retention time of 8.6 min with the undesired enantiomer eluting at 9.5 min.

Preparation 40L:

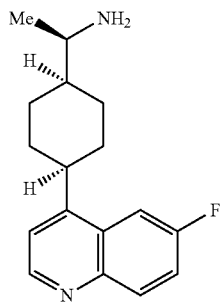 [SMILES: C[C@@H](N)[C@H]1CC[C@@H](c2ccnc3ccc(F)cc32)CC1]

Preparation 40K (2 g, 6.64 mmol) was taken up in toluene (22.12 ml) and diphenyl phosphorazidate (2.009 g, 7.30 mmol) and triethylamine (1.110 ml, 7.96 mmol) were added. Vial sealed and heated to 70° C. After 2 hours, the reaction was cooled to room temperature and concentrated under reduced pressure. Crude residue was taken up in 40 mL THF and 40 mL of water and lithium hydroxide (1.589 g, 66.4 mmol) was added. The reaction was stirred at room temperature for 1 hour. The reaction was acidified with 1N HCl (white precipitate forms) and extracted with EtOAc. The aqueous portion was then basified with 1N NaOH (precipitate forms) and extracted with EtOAc 5 times. Basic extracts were concentrated in vacuo to give 40L (1.68 g, 6.17 mmol, 93% yield). LC-MS Anal. Calc'd for $C_{17}H_{21}FN_2$ 272.17. found [M+H] 273.1 $T_r$=0.50 min (Method A). $^1$H NMR (400 Mhz, chloroform-d) δ: 8.80 (d, J=4.6 Hz, 1H), 8.11 (dd, J=9.3, 5.7 Hz, 1H), 7.67 (dd, J=10.6, 2.8 Hz, 1H), 7.46 (ddd, J=9.2, 8.0, 2.8 Hz, 1H), 7.32 (d, J=4.5 Hz, 1H), 3.27-3.37 (m, 1H), 3.13 (dq, J=9.3, 6.3 Hz, 1H), 2.01-2.10 (m, 1H), 1.67-1.92 (m, 6H), 1.37-1.55 (m, 4H), 1.15 (d, J=6.4 Hz, 3H).

Example 40

N—((R)-1-((1s,4S)-4-(6-Fluoroquinolin-4-yl)cyclohexyl)ethyl)-3-methylbenzenesulfonamide Preparation 40L (20 mg, 0.073 mmol) was dissolved DCM (0.2 mL) and added to a vial containing phenyl sulfonyl chloride (26 mg, 0.147 mmol) and DCM (0.2 mL) followed directly after with the addition of DIPEA (64.1 μl, 0.367 mmol). The reaction was stirred at room temperature overnight. After overnight, the reaction was concentrated in vacuo, taken up in 2 mL DMF, filtered, and purified via HPLC to give Example 40 (12.2 mg, 0.28 mmol, 39%) LC-MS Anal. Calc'd for $C_{24}H_{27}FN_2O_2S$ 426.18. found [M+H] 427.3 $T_r$=2.065 min (Method B). $^1$H NMR (500 MHz, DMSO-d$_6$) δ: 8.82 (d, J=4.5 Hz, 1H), 8.08 (dd, J=9.2, 5.8 Hz, 1H), 7.90 (dd, J=10.9, 2.5 Hz, 1H), 7.60-7.72 (m, 3H), 7.50 (d, J=8.5 Hz, 1H), 7.45 (t, J=7.7 Hz, 1H), 7.38 (d, J=7.6 Hz, 1H), 7.32 (d, J=4.5 Hz, 1H), 3.29 (t, J=10.5 Hz, 1H), 2.35 (s, 3H), 1.64-1.83 (m, 3H), 1.41-1.64 (m, 4H), 1.23-1.41 (m, 2H), 0.92 (d, J=6.4 Hz, 3H).

Examples 41 to 46

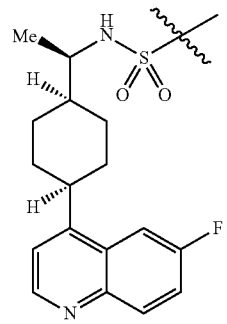 [SMILES: *S(=O)(=O)N[C@H](C)[C@H]1CC[C@@H](c2ccnc3ccc(F)cc32)CC1]

Examples 41 to 46 were prepared from Preparation 40L following the procedure for Example 40 using the corresponding sulfonyl chlorides.

| Ex. No. | Name | R | Tr (min)$^{(Method\ B)}$ | [M + H]$^+$ |
|---|---|---|---|---|
| 41 | N-((R)-1-((1s,4S)-4-(6-fluoroquinolin-4-yl)cyclohexyl)ethyl)-4-methylbenzenesulfonamide | 4-Me-phenyl | 2.065 | 427.3 |
| 42 | 2-chloro-N-((R)-1-((1s,4S)-4-(6-fluoroquinolin-4-yl)cyclohexyl)ethyl)benzenesulfonamide | 2-Cl-phenyl | 2.085 | 447.2 |
| 43 | 4-chloro-N-((R)-1-((1s,4S)-4-(6-fluoroquinolin-4-yl)cyclohexyl)ethyl)benzenesulfonamide | 4-Cl-phenyl | 2.126 | 447.2 |

| Ex. No. | Name | R | Tr (min)(Method B) | [M + H]+ |
|---|---|---|---|---|
| 44 | 3-chloro-N-((R)-1-((1s,4S)-4-(6-fluoroquinolin-4-yl)cyclohexyl)ethyl)benzenesulfonamide | 3-chlorophenyl | 2.124 | 447.2 |
| 45 | N-((R)-1-((1s,4S)-4-(6-fluoroquinolin-4-yl)cyclohexyl)ethyl)-3-methoxybenzenesulfonamide | 3-methoxyphenyl | 1.995 | 443.3 |
| 46 | N-((R)-1-((1s,4S)-4-(6-fluoroquinolin-4-yl)cyclohexyl)ethyl)-4-methoxybenzenesulfonamide | 4-methoxyphenyl | 1.975 | 443.3 |

Example 47

4-Chloro-N—((R)-1-((1s,4S)-4-(6-fluoroquinolin-4-yl)cyclohexyl)ethyl)benzamide

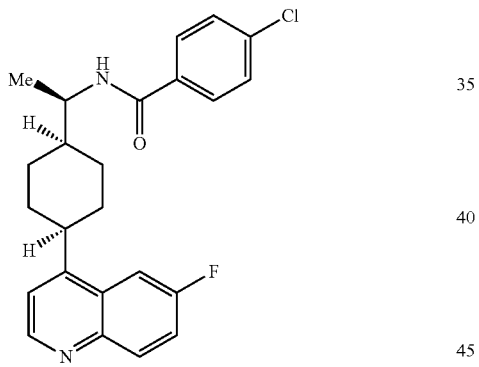

Preparation 40L (4 mg, 0.015 mmol) was taken up in DMF (147 μl) and HOBT (2.92 mg, 0.019 mmol), EDC (3.66 mg, 0.019 mmol), 4-chlorobenzoic acid (4.60 mg, 0.029 mmol) and TEA (10.23 μl, 0.073 mmol) were added and reaction stirred at room temperature overnight. The reaction was then diluted with 1.8 mL DMF and purified via preparative HPLC to give Example 47 (2.3 mg, 0.006 mmol, 38%). LC-MS Anal. Calc'd for $C_{24}H_{24}ClFN_2$ 410.16. found [M+H] 411.0 $T_r$=2.057 min (Method B). $^1$H NMR (500 MHz, DMSO-$d_6$) δ: 8.82 (d, J=4.5 Hz, 1H), 8.36 (d, J=8.8 Hz, 1H), 8.08 (dd, J=9.2, 5.8 Hz, 1H), 7.95 (dd, J=11.0, 2.7 Hz, 1H), 7.86 (d, J=8.6 Hz, 2H), 7.65 (td, J=8.7, 2.7 Hz, 1H), 7.52 (d, J=8.5 Hz, 2H), 7.47 (d, J=4.5 Hz, 1H), 4.42 (d, J=6.6 Hz, 1H), 1.74-1.91 (m, 6H), 1.56-1.73 (m, 4H), 1.18 (d, J=6.5 Hz, 3H).

Examples 48 to 69

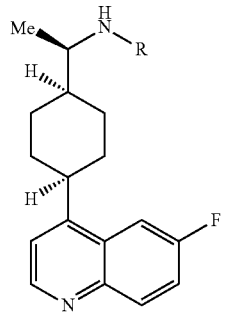

Examples 48 to 69 were prepared from Preparation 40L following the procedure for Example 47 using the corresponding benzoic acids.

| Ex. No. | Name | R | Tr (min)(Method B) | [M + H]+ |
|---|---|---|---|---|
| 48 | N-((R)-1-((1s,4S)-4-(6-fluoroquinolin-4-yl)cyclohexyl)ethyl)benzamide | benzoyl | 1.875 | 377.1 |

-continued

| Ex. No. | Name | R | Tr (min)(Method B) | [M + H]+ |
|---|---|---|---|---|
| 49 | N-((R)-1-((1s,4S)-4-(6-fluoroquinolin-4-yl)cyclohexyl)ethyl)-2-methylbenzamide | 2-methylbenzoyl | 1.949 | 391.1 |
| 50 | N-((R)-1-((1s,4S)-4-(6-fluoroquinolin-4-yl)cyclohexyl)ethyl)-3-methyl benzamide | 3-methylbenzoyl | 2.004 | 391.3 |
| 51 | N-((R)-1-((1s,4S)-4-(6-fluoroquinolin-4-yl)cyclohexyl)ethyl)-4-methylbenzamide | 4-methylbenzoyl | 2.035 | 391.3 |
| 52 | N-((R)-1-((1s,4S)-4-(6-fluoroquinolin-4-yl)cyclohexyl)ethyl)-2-methoxybenzamide | 2-methoxybenzoyl | 2.055 | 407.3 |
| 53 | N-((R)-1-((1s,4S)-4-(6-fluoroquinolin-4-yl)cyclohexyl)ethyl)-3-methoxybenzamide | 3-methoxybenzoyl | 1.955 | 407.3 |
| 54 | 2-fluoro-N-((R)-1-((1s,4S)-4-(6-fluoroquinolin-4-yl)cyclohexyl)ethyl)benzamide | 2-fluorobenzoyl | 1.971 | 395.1 |
| 55 | 3-fluoro-N-((R)-1-((1s,4S)-4-(6-fluoroquinolin-4-yl)cyclohexyl)ethyl)benzamide | 3-fluorobenzoyl | 1.985 | 395.3 |
| 56 | 2-chloro-N-((R)-1-((1s,4S)-4-(6-fluoroquinolin-4-yl)cyclohexyl)ethyl)benzamide | 2-chlorobenzoyl | 1.985 | 411.3 |
| 57 | 3-chloro-N-((R)-1-((1s,4S)-4-(6-fluoroquinolin-4-yl)cyclohexyl)ethyl)benzamide | 3-chlorobenzoyl | 2.115 | 411.2 |

-continued

| Ex. No. | Name | R | Tr (min)$^{(Method\ B)}$ | [M + H]$^+$ |
|---|---|---|---|---|
| 59 | 3,4-dichloro-N-((R)-1-((1s,4S)-4-(6-fluoroquinolin-4-yl)cyclohexyl)ethyl)benzamide | 3,4-dichlorobenzoyl | 2.277 | 445.2 |
| 60 | 4-fluoro-N-((R)-1-((1s,4S)-4-(6-fluoroquinolin-4-yl)cyclohexyl)ethyl)benzamide | 4-fluorobenzoyl | 1.955 | 395.3 |
| 61 | N-((R)-1-((1s,4S)-4-(6-fluoroquinolin-4-yl)cyclohexyl)ethyl)-[1,1'-biphenyl]-3-carboxamide | 3-phenylbenzoyl | 2.307 | 453.3 |
| 66 | 3,5-dichloro-N-((R)-1-((1s,4S)-4-(6-fluoroquinolin-4-yl)cyclohexyl)ethyl)benzamide | 3,5-dichlorobenzoyl | 2.348 | 445.2 |
| 67 | N-((R)-1-((1s,4S)-4-(6-fluoroquinolin-4-yl)cyclohexyl)ethyl)picolinamide | picolinoyl | 1.945 | 378.1 |
| 68 | N-((R)-1-((1s,4S)-4-(6-fluoroquinolin-4-yl)cyclohexyl)ethyl)-4-methoxybenzamide | 4-methoxybenzoyl | 1.914 | 407.3 |
| 69 | N-((R)-1-((1s,4S)-4-(6-fluoroquinolin-4-yl)cyclohexyl)ethyl)-[1,1'-biphenyl]-2-carboxamide | 2-phenylbenzoyl | 2.206 | 453.3 |

Example 70

N—((R)-1-((1s,4S)-4-(6-fluoroquinolin-4-yl)cyclohexyl)ethyl)-[1,1'-biphenyl]-4-carboxamide

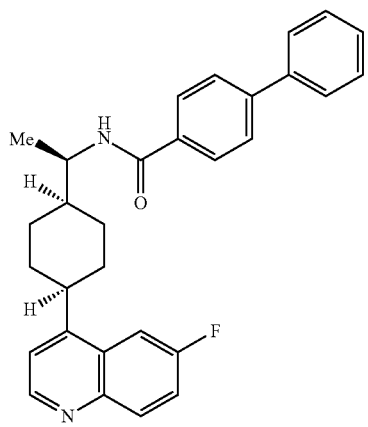 [SMILES: C[C@@H](NC(=O)c1ccc(-c2ccccc2)cc1)[C@H]1CC[C@@H](c2ccnc3ccc(F)cc32)CC1]

Example 70

N—((R)-1-((cis)-4-(6-fluoroquinolin-4-yl)cyclohexyl)ethyl)-[1,1'-biphenyl]-4-carboxamide Preparation 40L (50 mg, 0.184 mmol) was taken up in DMF (1836 μl) and HOBT (36.5 mg, 0.239 mmol), EDC (45.8 mg, 0.239 mmol), [1,1'-biphenyl]-4-carboxylic acid (54.6 mg, 0.275 mmol) and TEA (128 μl, 0.918 mmol) were added and reaction stirred at room temperature for 3 hours. Reaction diluted with EtOAc and washed with 5:1 water/aqueous saturated NaHCO$_3$ solution. The combined organic extracts were dried with sodium sulfate, filtered and concentrated in vacuo. The crude residue was purified via silica gel flash column chromatography to give Example 70 (63 mg, 0.132 mmol, 72.0% yield). LC-MS Anal. Calc'd for C$_{30}$H$_{29}$FN$_2$O, 452.23. found [M+H] 453.3 T$_r$=2.297 min (Method B). $^1$H NMR (400 MHz, CHLOROFORM-d) δ: 8.82 (d, J=4.5 Hz, 1H), 8.13 (dd, J=9.2, 5.7 Hz, 1H), 7.85 (d, J=8.6 Hz, 2H), 7.64-7.70 (m, 3H), 7.58-7.64 (m, J=7.0 Hz, 2H), 7.36-7.50 (m, 5H), 5.91 (d, J=9.2 Hz, 1H), 4.58-4.70 (m, 1H), 3.30 (tt, J=10.6, 3.6 Hz, 1H), 1.96-2.15 (m, 3H), 1.80 (br. s., 6H), 1.33 (d, J=6.6 Hz, 3H).

Example 71

4-Chloro-N-(1-((trans)-4-(quinolin-4-yloxy)cyclohexyl)propyl)benzamide

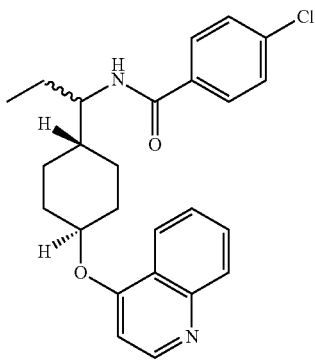 [SMILES: CCC(NC(=O)c1ccc(Cl)cc1)[C@H]1CC[C@H](Oc2ccnc3ccccc23)CC1]

Intermediate 71A. Ethyl 2-(1,4-dioxaspiro[4.5]decan-8-ylidene)acetate

Triethyl phosphonoacetate (21.79 ml, 109 mmol) was added to a suspension of sodium hydride (3.84 g, 96 mmol) in THF (64.0 ml) and 0° C. Reaction was stirred at room temperature for 30 minutes. After 30 minutes, the reaction was recooled to 0° C. and a solution of 1,4-dioxaspiro[4.5]decan-8-one (10 g, 64.0 mmol) in 5 mL THF was added. The reaction was then stirred at room temperature for 30 minutes prior to quenching with water. The mixture was extracted with DCM three times. Combined organic extracts were dried with sodium sulfate, filtered, and concentrated in vacuo. Crude residue was purified via silica gel chromatography to give Intermediate 71A (13.88 g, 61.3 mmol, 96% yield). TLC: product stains as purple spot in anisaldehyde (Rf=0.75 in 1:1 Hex/EtOAc). $^1$H NMR (400 MHz, chloroform-d) δ: 5.65 (s, 1H), 4.13 (q, J=7.2 Hz, 2H), 3.92-3.99 (m, 4H), 2.94-3.02 (m, 2H), 2.31-2.40 (m, 2H), 1.71-1.79 (m, 4H), 1.26 (t, J=7.2 Hz, 3H).

Intermediate 71B. Ethyl 2-(1,4-dioxaspiro[4.5]decan-8-yl)acetate

Intermediate 71A (13.88 g, 61.3 mmol) was taken up in EtOAc (61.3 ml) and was added to a Parr hydrogenation bottle containing wet 10% palladium on carbon (1.306 g, 12.27 mmol) (54% w/w water) under an atmosphere of nitrogen. The reaction bottle was purged and back-filled with nitrogen three times, and then with hydrogen. After filling the bottle with hydrogen to 50 psi, the bottle was placed in a Parr shaker and shaken. After 4 hours, the reaction was filtered over pressed CELITE® and concentrated in vacuo to give Intermediate 71B (13.78 g, 60.4 mmol, 98% yield). LC-MS Anal. Calc'd for C$_{12}$H$_{20}$O$_4$ 228.14. found [M+H] 229.1 T$_r$=0.83 min (Method A). $^1$H NMR (400 MHz, chloroform-d) δ: 4.11 (q, J=7.2 Hz, 2H), 3.88-3.95 (m, 4H), 2.2.1 (d, J=7.0 Hz, 2H), 1.83 (dqd, J=11.0, 7.5, 3.5 Hz, 1H), 1.68-1.78 (m, 4H), 1.50-1.61 (m, 2H), 1.27-1.35 (m, 2H), 1.24 (t, J=7.2 Hz, 3H).

Intermediate 71C. Ethyl 2-(1,4-dioxaspiro[4.5]decan-8-yl)butanoate

Diisopropylamine (2.347 ml, 16.63 mmol) taken up in dry THF (15.99 ml) (under N$_2$ atmosphere) and cooled to −78° C. n-BuLi (6.14 ml, 15.35 mmol) (2.5 M in hexanes) was added over ~5 minutes at −78° C. After stirring for 45 minutes, reaction was warmed to room temperature for 10 minutes and returned to −78° C. Then, 1,3-dimethyltetrahydropyrimidin-2(1H)-one (1.541 ml, 12.79 mmol) was added followed by a solution of Intermediate 71B (2.92 g, 12.79 mmol) in THF (15.99 ml) (dropwise over ~5 minutes). After 1 hour, iodoethane (1.125 ml, 14.07 mmol) (neat) was added dropwise over ~5 minutes. Reaction stirred another 2 hours at −78° C. before slowly warming to room temperature. The reaction was then stirred over night at room temperature. The reaction was quenched by pouring into 1:1 water/brine and extracting with EtOAc. Combined organics washed with brine, dried with sodium sulfate, filtered and concentrated in vacuo. Crude residue was purified via silica gel column chromatography to give Intermediate 71C (2.27 g, 8.86 mmol, 69% yield). TLC: product stains as purple spot in anisaldehyde (Rf=0.80 in 1:1 hex/EtOAc). $^1$H NMR (400 MHz, chloroform-d) δ: 4.14 (q, J=7.5 Hz, 2H), 3.88-3.95 (m, 4H), 2.09 (td, J=8.4, 5.6 Hz, 1H), 1.69-1.83 (m, 4H), 1.45-1.64 (m, 6H), 1.33-1.42 (m, 1H), 1.25 (t, J=7.1 Hz, 3H), 0.86 (t, J=7.5 Hz, 3H).

Intermediate 71D. Ethyl 2-(4-oxocyclohexyl)butanoate

Intermediate 71C (2.00 g, 7.80 mmol) was taken up in THF (39.0 ml) and hydrochloric acid, 1M (39.0 ml) was added. Reaction stirred at room temperature for 2 hours. The reaction was concentrated in vacuo, diluted with water and extracted with EtOAc. The combined organic extracts were dried with sodium sulfate, filtered and concentrated in vacuo. The crude material was purified on silica gel column chromatography to give Intermediate 71D (1.47 g, 6.92 mmol, 89% yield). TLC: product stains faintly pink in anisaldehyde (Rf=0.65 in 1:1 Hex/EtOAc). $^1$H NMR (400 MHz, chloroform-d) δ: 4.15 (q, J=7.1 Hz, 2H), 2.25-2.42 (m, 4H), 2.18 (ddd, J=9.3, 7.8, 5.2 Hz, 1H), 2.10 (ddt, J=13.1, 6.2, 3.3 Hz, 1H), 1.90-2.03 (m, 2H), 1.56-1.70 (m, 2H), 1.38-1.56 (m, 2H), 1.25 (t, J=7.2 Hz, 3H), 0.89 (t, J=7.4 Hz, 3H).

Intermediate 71E. Ethyl 2-((trans)-4-hydroxycyclohexyl)butanoate

Intermediate 71D (1.47 g, 6.92 mmol) was dissolved in EtOH (13.85 ml) and cooled to 0° C. NaBH$_4$ (0.314 g, 8.31 mmol) was added and the reaction was then allowed to stir at 0° C. for 1 hour. The reaction was quenched with saturated aqueous NH$_4$Cl and extracted with EtOAc. Combined organic extracts were dried with sodium sulfate, filtered, and concentrated in vacuo. The crude material was purified via silica gel column chromatography to give Intermediate 71E (1.22 g, 5.69 mmol, 82% yield) along with (138 mg, 0.644 mmol, 9.30% yield) of the cis-isomer. $^1$H NMR (400 MHz, chloroform-d) δ: 4.14 (q, J=7.1 Hz, 2H), 3.53 (t, J=10.5 Hz, 1H), 1.92-2.08 (m, 2H), 1.80-1.89 (m, 1H), 1.63-1.70 (m, 1H), 1.52-1.62 (m, 4H), 1.37-1.52 (m, 2H), 1.26 (t, J=7.2 Hz, 3H), 0.95-1.17 (m, 2H), 0.87 (t, J=7.4 Hz, 3H).

Intermediate 71F. Ethyl 2-((trans)-4-(quinolin-4-yloxy)cyclohexyl)butanoate

Intermediate 71E (100 mg, 0.467 mmol) was taken up in DMSO (933 µl) and NaH (22.40 mg, 0.933 mmol) was added slowly, portionwise at rt. After 1 hour, 4-bromoquinoline (117 mg, 0.560 mmol) was added and the reaction was heated to 80° C. After 16 hours, the reaction was quenched with ammonium chloride and extracted with EtOAc. The combined organic extracts were dried with sodium sulfate, filtered, concentrated in vacuo. The crude residue was purified via silica gel column chromatography to give Intermediate 71F (89 mg, 0.261 mmol, 55.9% yield). LC-MS Anal. Calc'd for $C_{21}H_{27}NO_3$ 341.20. found [M+H] 342.3 $T_r$=0.84 min (Method A).

Intermediate 71G. 2-((trans)-4-(Quinolin-4-yloxy)cyclohexyl)butanoic acid

Intermediate 71F (89 mg, 0.261 mmol) was taken up in THF (1043 µl), Water (1043 µl), and MeOH (521 µl). Lithium hydroxide (62.4 mg, 2.61 mmol) was added and reaction stirred at 60° C. for 24 hours. The reaction was concentrated in vacuo, diluted with water, acidified with acetic acid added (precipitate forms), and extracted with EtOAc. The combined organic extracts were dried with sodium sulfate, filtered and concentrated in vacuo to give Intermediate 71G (74 mg, 0.236 mmol, 91% yield). LC-MS Anal. Calc'd for $C_{19}H_{23}NO_3$ 313.17. found [M+H] 314.2 $T_r$=0.69 min (Method A).

Intermediate 71H. 1-((trans)-4-(Quinolin-4-yloxy)cyclohexyl)propan-1-amine

Intermediate 71G (190 mg, 0.606 mmol) was taken up in toluene (2021 µl) in a vial and diphenyl phosphorazidate (184 mg, 0.667 mmol) and TEA (101 µl, 0.728 mmol) were added. The vial sealed and heated to 80° C. After 2 h, the reaction was cooled to room temperature and concentrated under reduced pressure. The crude residue was taken up in 1 mL THF and 1 mL of water and LiOH (145 mg, 6.06 mmol) was added. Reaction stirred at room temperature for 1 hour. The reaction was acidified with 1N HCl (white precipitate forms) and extracted with EtOAc to remove DPPA related impurities. Then, the reaction was basified with 1N NaOH (precipitate forms again) and extracted with EtOAc (×5). Basic extracts were concentrated in vacuo to give Intermediate 71H (35 mg, 0.123 mmol, 20.30% yield). LC-MS Anal. Calc'd for $C_{18}H_{24}N_2O$, 284.19. found [M+H] 285.2 $T_r$=0.55 min (Method A).

Example 71

4-Chloro-N-(1-((trans)-4-(quinolin-4-yloxy)cyclohexyl)propyl)benzamide

Intermediate 71H (35 mg, 0.123 mmol) was taken up in DMF (1231 µl) and HOBT (24.50 mg, 0.160 mmol), EDC (30.7 mg, 0.160 mmol), 4-chlorobenzoic acid (38.5 mg, 0.246 mmol) and TEA (86 µl, 0.615 mmol) were added and reaction was stirred at rt. After 2 hours, the reaction was diluted with DMF filtered and purified via preparative HPLC to give Example 71 (24.6 mg, 0.058, 46.8% yield). LC-MS Anal. Calc'd for $C_{25}H_{27}ClN_2O_2$ 422.18. found [M+H] 423.3 $T_r$=0.82 min (Method A). $^1$H NMR (500 MHz, DMSO-d$_6$) δ: 8.67 (d, J=5.2 Hz, 1H), 8.15 (d, J=9.0 Hz, 1H), 8.11 (d, J=8.2 Hz, 1H), 7.87-7.94 (m, 3H), 7.72 (t, J=7.6 Hz, 1H), 7.49-7.58 (m, 3H), 7.10 (d, J=5.2 Hz, 1H), 4.62 (t, J=10.2 Hz, 1H), 3.74-3.85 (m, J=8.9 Hz, 1H), 2.21 (d, J=10.1 Hz, 2H), 1.86 (t, J=14.3 Hz, 2H), 1.39-1.71 (m, 5H), 1.28 (q, J=12.3 Hz, 2H), 0.85 (t, J=7.2 Hz, 3H).

Enantiomer 1 and Enantiomer 2

Enantiomer 1

Example 71

4-Chloro-N-(1-((trans)-4-(quinolin-4-yloxy)cyclohexyl)propyl)benzamide (Homochiral, Stereochemistry Unknown)

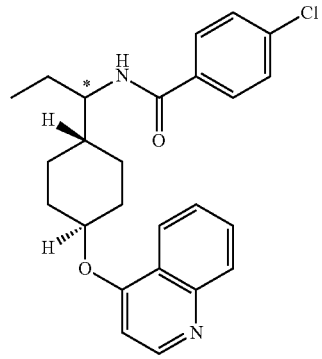 [SMILES: CCC(NC(=O)c1ccc(Cl)cc1)[C@H]1CC[C@H](Oc2ccnc3ccccc23)CC1]

Enantiomer 2

Example 71

4-Chloro-N-(1-((trans)-4-(quinolin-4-yloxy)cyclohexyl)propyl)benzamide (Homochiral, Stereochemistry Unknown)

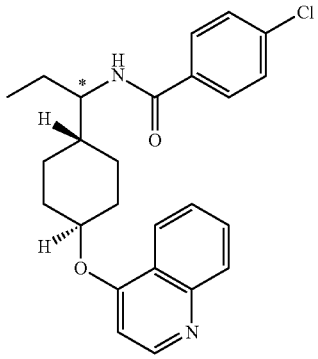

Example 71 Enantiomer 1 and Enantiomer 2

Chiral separation of the racemic sample (Method C) gave Enantiomer 1 $T_r$=5.195 min (Method D) and Enantiomer 2 $T_r$=8.226 min (Method D) Absolute stereochemistry was not determined.

Enantiomer 1: MS(ES): m/z=423.3 [M+H]$^+$. $T_r$=2.126 min (Method A). $^1$H NMR (500 MHz, DMSO-$d_6$) δ: 8.78 (d, J=5.1 Hz, 1H), 8.14-8.22 (m, 2H), 7.97 (d, J=8.2 Hz, 1H), 7.89 (d, J=8.2 Hz, 2H), 7.82 (t, J=7.6 Hz, 1H), 7.62 (t, J=7.5 Hz, 1H), 7.54 (d, J=8.3 Hz, 2H), 7.25 (d, J=5.6 Hz, 1H), 4.65-4.75 (m, 1H), 3.75-3.84 (m, J=8.8 Hz, 1H), 2.22 (d, J=10.4 Hz, 2H), 1.81-1.92 (m, 2H), 1.43-1.70 (m, 5H), 1.28 (q, J=12.2 Hz, 2H), 0.85 (t, J=7.2 Hz, 3H).

Enantiomer 2: MS(ES): m/z=423.3[M+H]$^+$. $T_r$=2.126 min (Method A). $^1$H NMR (500 MHz, DMSO-$d_6$) δ: 8.67 (d, J=5.0 Hz, 1H), 8.16 (d, J=9.0 Hz, 1H), 8.11 (d, J=8.2 Hz, 1H), 7.85-7.94 (m, 3H), 7.72 (t, J=7.3 Hz, 1H), 7.54 (d, J=8.2 Hz, 3H), 7.09 (d, J=5.2 Hz, 1H), 4.61 (t, J=10.1 Hz, 1H), 3.75-3.83 (m, J=8.5 Hz, 1H), 2.21 (d, J=10.2 Hz, 2H), 1.85 (t, J=14.0 Hz, 2H), 1.39-1.69 (m, 5H), 1.22-1.33 (m, 2H), 0.85 (t, J=7.1 Hz, 3H).

Example 72

4-Chloro-N-(1-((trans)-4-((8-(trifluoromethyl)quinolin-4-yl)oxy)cyclohexyl)propyl)benzamide

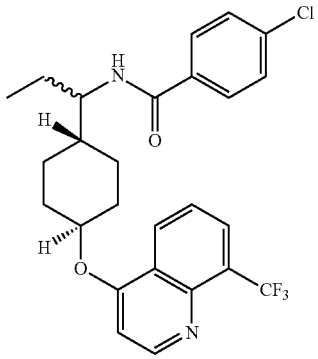 [SMILES: CCC(NC(=O)c1ccc(Cl)cc1)[C@H]1CC[C@H](Oc2ccnc3c(C(F)(F)F)cccc23)CC1]

Example 72 was prepared from Intermediate 71E and the analogous procedures outlined to make 71F, 71G, 71H, and Example 71 except that 4-chloro-8-(trifluoromethyl)quinoline was used in part F. LC-MS Anal. Calc'd for $C_{26}H_{26}ClF_3N_2O_2$ 490.16. found [M+H] 491.2 $T_r$=0.99 min (Method A). $^1$H NMR (500 MHz, DMSO-$d_6$) δ: 8.80 (d, J=5.0 Hz, 1H), 8.40 (d, J=8.2 Hz, 1H), 8.17 (d, J=8.9 Hz, 1H), 8.14 (d, J=7.2 Hz, 1H), 7.88 (d, J=8.2 Hz, 2H), 7.65 (t, J=7.8 Hz, 1H), 7.53 (d, J=8.2 Hz, 2H), 7.24 (d, J=5.1 Hz, 1H), 4.66 (t, J=10.0 Hz, 1H), 3.74-3.84 (m, J=6.6 Hz, 1H), 2.21 (d, J=10.2 Hz, 2H), 1.85 (t, J=13.5 Hz, 2H), 1.40-1.71 (m, 5H), 1.27 (q, J=12.1 Hz, 2H), 0.84 (t, J=7.0 Hz, 3H).

Example 73 and Example 74

(trans)-N-(4-Chlorobenzyl)-4-(6-fluoroquinolin-4-yl)cyclohexanecarboxamide (cis)-N-(4-Chlorobenzyl)-4-(6-fluoroquinolin-4-yl)cyclohexanecarboxamide (Homochiral, Absolute and Relative Stereochemistry Unassigned)

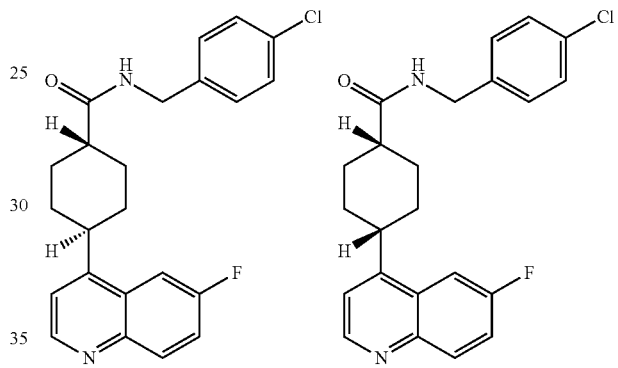

Intermediate 73A. 1,4-Dioxaspiro[4.5]dec-7-en-8-yl trifluoromethane sulfonate

To a stirred solution of 1,4-dioxaspiro[4.5]decan-8-one (300 g, 1920.86 mmol, 1.0 eq) and N-phenyltrifluoromethanesulfonimide (823.47 g, 2305.03 mmol, 1.2 eq) in MTBE (7.5 L) under nitrogen atmosphere at −78° C. was added 2.0 M NaHMDS in THF (1152.2 mL, 2305.03 mmol, 1.2 eq) over 70 minutes, and the mixture was stirred for an additional 60 minutes. The reaction mixture was warmed to room temperature and stirred overnight until TLC showed complete consumption of the starting material. The mixture was quenched with aqueous KHSO$_4$ (100 ml), filtrated to remove the solid and concentrated the filtrate completely. To the residue was added 3 L MTBE, then washed with 5% NaOH (1.5 L×3). The organic phase was concentrated to obtain Intermediate 34A (567 g, light yellow oil, yield 102% yield). TLC Rf: 0.7 (PE/EtOAc=10/1, KMnO$_4$). $^1$H NMR (400 MHz, CDCl$_3$): δ (ppm) 5.65 (t, J=4.0 Hz, 1H), 3.98 (d, J=1.5 Hz, 4H), 2.53 (s, 2H), 2.40 (s, 2H), 1.90 (t, J=6.6 Hz, 2H).

Intermediate 73B. 4,4,5,5-Tetramethyl-2-(1,4-dioxaspiro[4.5]dec-7-en-8-yl)-1,3,2-dioxaborolane A mixture of Intermediate 73A (600 g, 2.08 mol, 1 eq), B$_2$Pin$_2$ (687.1 g, 2.71 mol, 1.3 eq), KOAc (613 g, 6.24 mol, 3 eq), NaBr (86 g 0.833 mol, 0.4 eq) and Pd(dppf)Cl$_2$ (76 g, 0.1 mol, 0.05 eq) in dioxane (6.5 L) was heated to reflux overnight. Once the reaction was complete, the mixture was concentrated and purified by via silica gel column chromatography to give Intermediate 73B (369 g, 66% yield). LC-MS Anal. Calc'd for $C_{14}H_{23}BO_4$ 266.17. found [M+H] 267.1. $^1$H NMR (400 MHz, $CDCl_3$) δ 6.46 (s, 1H), 3.98 (s, 4H), 2.37-2.35 (m, 4H), 1.74-1.60 (t, 2H), 1.24 (s, 12H).

Intermediate 73C. 6-Fluoro-4-(1,4-dioxaspiro[4.5] dec-7-en-8-yl)quinoline

A mixture of Intermediate 73B (368 g, 1.38 mol, 1.3 eq), 4-chloro-6-fluoroquinoline (195 g, 1.07 mol, 1 eq), $K_2CO_3$ (445 g, 3.22 mol, 3 eq) and $Pd(PPh_3)_4$ (25 g, 22 mmol, 0.02 eq) in dioxane-water (3 L, 4:1) was heated to reflux overnight. The solution was concentrated and extracted with EtOAc. The crude residue was purified via silica gel column chromatography to give Intermediate 73C (236 g, 77% yield). LC-MS Anal. Calc'd for $C_{17}H_{16}FNO_2$ 285.12. found [M+H] 286.1. $^1$H NMR (400 MHz, $CDCl_3$) δ 8.80-8.29 (d, 1H), 8.11-8.07 (q, 1H), 7.63-7.61 (q, 1H), 7.47-7.46 (q, 1H), 7.26-7.22 (m, 1H), 5.75-5.74 (m, 1H), 4.08-4.05 (m, 4H), 2.63-2.59 (m, 2H), 2.59-2.53 (m, 2H), 2.0-1.97 (m, 2H).

Intermediate 73D. 6-Fluoro-4-(1,4-dioxaspiro[4.5] decan-8-yl)quinoline

To Intermediate 73C (125 g, 0.44 mol) in IPA (2 L) at 55° C. was added 10% Pd/C and the mixture was stirred under an atmosphere of $H_2$ overnight. The mixture was filtered and concentrated to give crude Intermediate 73D (128 g, 100% yield), which was used directly in the next step. LC-MS Anal. Calc'd for $C_{17}H_{18}FNO_2$ 287.13. found [M+H] 288.2, rt=0.62 min (Method A).

Intermediate 73E. 4-(6-Fluoroquinolin-4-yl)cyclohexanone

Intermediate 73D (100 g, 0.348 mol) was treated with 4 N HCl (300 mL) in acetone (1200 mL) at 45° C. for overnight. Then the solution was concentrated in vacuo. The residue was adjusted pH 9 with 6 N NaOH. The mixture was partitioned between ethyl acetate and water. The organic layer was washed with brine, dried over anhydrous $Na_2SO_4$, filtered and concentrated to give light yellow solid, which was then purified by silica gel column chromatography to afford Intermediate 73E as white solid (67 g, 55% yield). LC-MS Anal. Calc'd for $C_{15}H_{14}FNO$, 243.11. found [M+H] 244.0. $^1$H NMR (400 MHz, $CDCl_3$) δ 8.84 (d, J=4.6 Hz, 1H), 8.16 (dd, J=9.3, 5.7 Hz, 1H), 7.72 (dd, J=10.3, 2.8 Hz, 1H), 7.52 (ddd, J=9.2, 7.8, 2.7 Hz, 1H), 7.29 (d, J=4.6 Hz, 1H), 3.69 (ddd, J=12.1, 9.0, 3.3 Hz, 1H), 2.77-2.54 (m, 4H), 2.37 (ddd, J=13.4, 5.9, 3.0 Hz, 2H), 2.04 (qd, J=12.6, 5.3 Hz, 2H).

Intermediate 73F. 4-(6-Fluoroquinolin-4-yl)cyclohexanecarbonitrile

To a solution of Intermediate 73E (500 mg, 2.055 mmol) and 1-((isocyanomethyl)sulfonyl)-4-methylbenzene (522 mg, 2.67 mmol) in DMSO (10.100 ml) and methanol (0.202 ml) was added potassium 2-methylpropan-2-olate (554 mg, 4.93 mmol). After the addition was complete, the reaction mixture was stirred room temperature. After 1 hour, the reaction was diluted with diethyl ether (30 mL) and washed with water (20 ml). The organic layer was dried with anhydrous $MgSO_4$, concentrated under reduced pressure. The crude material was purified via silica gel column chromatography to give Intermediate 73F (280 mg, 1.101 mmol, 53.6% yield) as a mixture of cis and trans isomers (~2:1 ratio). LC-MS Anal. Calc'd for $C_{16}H_{15}FN_2$ 254.12. found [M+H] 255.1, rt=0.60 (first elution diastereomer) and 0.62 min (second eluting diastereomer) (Method A).

Intermediate 73G. 4-(6-Fluoroquinolin-4-yl)cyclohexanecarboxylic acid

Intermediate 73F (280 mg, 1.101 mmol) taken up in methanol (5505 µl) and hydrochloric acid, 37% (5505 µl). Reaction heated at 70° C. After 48 hours, the reaction was slowly added to 100 mL water and basified with sodium bicarbonate (sat aq). The aqueous was extracted with EtOAc. The combined organics were dried with sodium sulfate, filtered, and concentrated in vacuo to give crude methyl 4-(6-fluoroquinolin-4-yl)cyclohexanecarboxylate. This crude material was taken up in THF (4260 µl), Water (4260 µl), MeOH (2130 µl) and lithium hydroxide (255 mg, 10.65 mmol) was added. Reaction stirred at room temperature for 1 hour. The reaction was then concentrated, acidified with 1N HCl and extracted with EtOAc. The combined organics were dried with sodium sulfate, filtered, and concentrated in vacuo to give a crude residue. This crude residue was purified via silica gel column chromatography to give Intermediate 73G (mixture of cis and trans) (63 mg, 0.231 mmol, 21.64% yield). LC-MS Anal. Calc'd for $C_{16}H_{16}FNO_2$ 273.1. found [M+H] 274.1, rt=0.55 (Method A).

Example 73 and Example 74

N-(4-Chlorobenzyl)-4-(6-fluoroquinolin-4-yl)cyclohexanecarboxamide (Mixture of Cis- and Trans-Isomers)

Intermediate 73G (15 mg, 0.055 mmol) was dissolved in thionyl chloride (40.1 µl, 0.549 mmol) and DMF (2.125 µl, 0.027 mmol) was added. Reaction stirred at room temperature for 1 hour. After, the reaction was concentrated in vacuo, taken up in toluene, concentrated again and placed on high vac. After 15 minutes, the crude acyl chloride was taken up in ACN (274 µl) and added to a solution of (4-chlorophenyl)methanamine (15.54 mg, 0.110 mmol) in ACN (274 µl) and TEA (38.2 µl, 0.274 mmol) at 0° C. Reaction was then allowed to warm to room temperature. After 1 hour, the reaction was diluted with water and extracted with EtOAc. Organics were dried with sodium sulfate, filtered, and concentrated in vacuo. Crude residue taking up in DMF filtered, and purified via preparative HPLC to give two diastereomers.

The first eluting diastereomer, Example 73 (4.9 mg, 0.012 mmol, 22% yield). LC-MS Anal. Calc'd for $C_{23}H_{22}ClFN_2O$, 396.14. found [M+H] 397.0, rt=1.891 (Method B). $^1$H NMR (500 MHz, DMSO-$d_6$) δ: 8.80 (d, J=4.4 Hz, 1H), 8.40 (t, J=5.7 Hz, 1H), 8.08 (dd, J=9.0, 5.9 Hz, 1H), 7.99 (d, J=9.8 Hz, 1H), 7.66 (t, J=8.6 Hz, 1H), 7.45 (d, J=4.3 Hz, 1H), 7.37 (d, J=8.2 Hz, 2H), 7.26 (d, J=8.1 Hz, 2H), 4.26 (d, J=5.8 Hz, 2H), 3.33 (t, J=11.9 Hz, 1H), 2.32 (t, J=11.9 Hz, 1H), 1.92 (t, J=11.2 Hz, 4H), 1.71-1.83 (m, 2H), 1.56 (q, J=12.3 Hz, 2H).

The second eluting enantiomer, Example 74 (3.6 mg, 0.009 mmol, 17% yield) LC-MS Anal. Calc'd for $C_{23}H_{22}ClFN_2O$, 396.14. found [M+H] 397.0, rt=1.940 (Method B). $^1$H NMR (500 MHz, DMSO-$d_6$) δ: 8.78 (d, J=4.3 Hz, 1H), 8.37 (t, J=5.5 Hz, 1H), 8.07 (dd, J=8.9, 6.0 Hz, 1H), 7.95 (d, J=10.8 Hz, 1H), 7.65 (t, J=8.6 Hz, 1H), 7.36 (d, J=8.0 Hz, 2H), 7.23-7.31 (m, 3H), 4.27 (d, J=5.7 Hz, 2H), 3.33 (br. s., 1H), 2.61 (br. s., 1H), 2.01-2.13 (m, 2H), 1.74-1.85 (m, 4H), 1.65-1.74 (m, 2H).

Example 75 and Example 76

(trans)-N-(4-Chlorophenyl)-4-(6-fluoroquinolin-4-yl)cyclohexanecarboxamide (cis)-N-(4-Chlorophenyl)-4-(6-fluoroquinolin-4-yl)cyclohexanecarboxamide (Homochiral, Absolute and Relative Stereochemistry Unassigned)

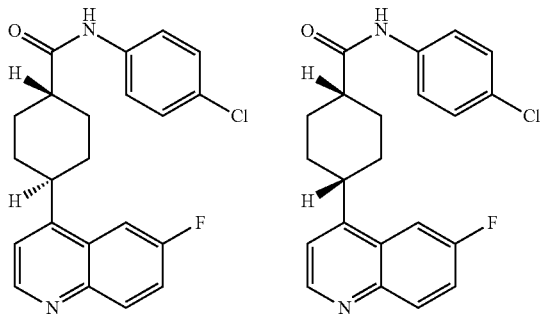 [SMILES: O=C(Nc1ccc(Cl)cc1)[C@H]1CC[C@H](c2ccnc3ccc(F)cc32)CC1 ; O=C(Nc1ccc(Cl)cc1)[C@H]1CC[C@@H](c2ccnc3ccc(F)cc32)CC1]

Example 75 and Example 76 were made from Intermediate 73G utilizing the procedure to make Example 73 and Example 74.

First eluting diastereomer: (7.1 mg, 0.018 mmol, 34% yield) LC-MS Anal. Calc'd for $C_{22}H_{20}ClFN_2O$, 382.13. found [M+H] 383.2, rt=2.011 (Method B). $^1$H NMR (500 MHz, DMSO-$d_6$) δ: 10.00 (s, 1H), 8.78 (d, J=4.4 Hz, 1H), 8.07 (dd, J=9.1, 5.8 Hz, 1H), 7.96 (d, J=8.8 Hz, 1H), 7.59-7.68 (m, 3H), 7.39 (d, J=4.4 Hz, 1H), 7.33 (d, J=8.8 Hz, 2H), 3.37 (br. s., 1H), 2.78 (br. s., 1H), 2.09 (d, J=12.1 Hz, 2H), 1.81-2.00 (m, 4H), 1.75 (d, J=11.4 Hz, 2H).

Second eluting diastereomer: (8.4 mg, 0.021 mmol, 39% yield) LC-MS Anal. Calc'd for $C_{22}H_{20}ClFN_2O$, 382.13. found [M+H] 383.0, rt=1.988 (Method B). $^1$H NMR (500 MHz, DMSO-$d_6$) δ: 10.09 (s, 1H), 8.81 (d, J=4.4 Hz, 1H), 8.08 (dd, J=9.0, 5.9 Hz, 1H), 8.01 (d, J=8.9 Hz, 1H), 7.61-7.71 (m, 3H), 7.46 (d, J=4.4 Hz, 1H), 7.34 (d, J=8.7 Hz, 2H), 3.36 (t, J=11.9 Hz, 1H), 2.41-2.48 (m, 1H) (triplet buried under DMSO), 1.97 (d, J=9.7 Hz, 4H), 1.76-1.88 (m, 2H), 1.54-1.65 (m, 2H).

Example 77a (±)-4-Chloro-N-(1-((cis)-4-(pyridin-4-yloxy)cyclohexyl)propyl)benzamide

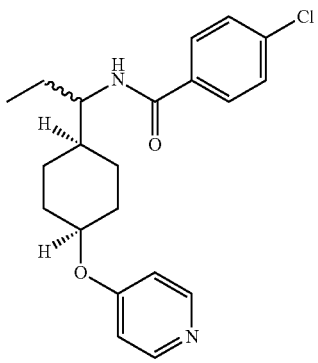 [SMILES: CCC(NC(=O)c1ccc(Cl)cc1)[C@H]1CC[C@@H](Oc2ccncc2)CC1]

Intermediate 77A. Ethyl 2-((cis)-4-(pyridin-4-yloxy)cyclohexyl)butanoate

Intermediate 71E (100 mg, 0.467 mmol) was dissolved in THF (1867 µl) and pyridin-4-ol (98 mg, 1.027 mmol) and triphenylphosphine (269 mg, 1.027 mmol) were added. Solution was cooled to 0° C. in an ice bath. Diisopropyl azodicarboxylate (200 µl, 1.027 mmol) was added and the reaction was allowed to stir at room temperature once the addition was complete. Stirred at room temperature for 16 hours. Reaction was concentrated in vacuo and purified via silica gel column chromatography to give Intermediate 77A (89 mg, 0.205 mmol, 43.9% yield). LC-MS Anal. Calc'd for $C_{17}H_{25}NO_3$ 291.18. found [M+H] 292.3 $T_r$=0.84 min (Method A). $^1$H NMR (400 MHz, chloroform-d) δ: 8.34-8.42 (m, 2H), 6.71-6.79 (m, 2H), 4.57-4.64 (m, 1H), 4.15 (q, J=7.1 Hz, 2H), 2.14 (ddd, J=9.8, 7.9, 4.6 Hz, 1H), 1.97-2.07 (m, 2H), 1.38-1.69 (m, 9H), 1.24-1.29 (m, 3H), 0.88 (t, J=7.4 Hz, 3H)

Intermediate 77B. 2-((cis)-4-(Pyridin-4-yloxy)cyclohexyl)butanoic acid

Intermediate 77A (89 mg, 0.305 mmol) was taken up in THF (244 µl), water (244 µl), and MeOH (122 µl). Lithium hydroxide (73.1 mg, 3.05 mmol) was added and the reaction stirred at 60° C. for 16 hours. Lithium hydroxide (73.1 mg, 3.05 mmol) was again added and the reaction stirred for another 24 hours at 60° C. The reaction was concentrated in vacuo, diluted with water and extracted with EtOAc. The aqueous layer was then treated with AcOH and extracted with EtOAc. LCMS shows Product remains in aqueous layer. Extracted again with 7:3 chloroform:propanol. LCMS Shows product was successfully extracted from the aqueous layer. The combined organic layers were dried with sodium sulfate, filtered, and concentrated in vacuo to give Intermediate 77B (73 mg, 0.277 mmol, 91% yield). Material was not further purified. LC-MS Anal. Calc'd for $C_{15}H_{21}NO_3$ 263.15. found [M+H] 264.2 $T_r$=0.58 min (Method A).

Intermediate 77C. 1-((cis)-4-(Pyridin-4-yloxy)cyclohexyl)propan-1-amine

Intermediate 77B (35 mg, 0.133 mmol) was taken up in toluene (443 µl) and diphenyl phosphorazidate (40.2 mg, 0.146 mmol) and TEA (22.23 µl, 0.159 mmol) added. The reaction vial was sealed (vented with needle while reaching temperature) and heated to 80° C. After 2 h, the reaction was cooled to room temperature and concentrated under reduced pressure. The crude residue was taken up in 1 mL THF and 1 mL of water LiOH (31.8 mg, 1.329 mmol) was added. The reaction stirred at room temperature overnight. The reaction was acidified with 1N HCl and extracted with EtOAc (extracts discarded). The aqueous portion was then basified with 1N NaOH and extracted with EtOAc (x2). The combined basic, organic extracts were dried with sodium sulfate, filtered and concentrated in vacuo to give Intermediate 77C (25 mg, 0.107 mmol, 80% yield). LC-MS Anal. Calc'd for $C_{14}H_{22}N_2O$, 234.17. found [M+H] 235.1 $T_r$=0.43 min (Method A).

Example 77a (±)-4-Chloro-N-(1-((cis)-4-(pyridin-4-yloxy)cyclohexyl)propyl)benzamide Intermediate 77C (25 mg, 0.107 mmol) was taken up in DMF (1067 µl) and HOBT (21.24 mg, 0.139 mmol), EDC (26.6 mg, 0.139 mmol), 4-chlorobenzoic acid (33.4 mg, 0.213 mmol) and TEA (74.3 μl, 0.533 mmol) were added and reaction stirred at room temperature. After 2 hours, the reaction was diluted with DMF to bring total volume to 2 mL, filtered, and purified via preparative HPLC to give Example 77a (23.2 mg, 0.062 mmol, 58% yield). LC-MS Anal. Calc'd for $C_{21}H_{25}ClN_2O_2$ 372.16. found [M+H] 373.3 $T_r$=0.73 min (Method A). $^1$H NMR (500 MHz, DMSO-d$_6$) δ: 8.30 (d, J=5.6 Hz, 2H), 8.17 (d, J=9.1 Hz, 1H), 7.81 (d, J=8.3 Hz, 2H), 7.51 (d, J=8.3 Hz, 2H), 6.91 (d, J=5.6 Hz, 2H), 4.69 (br. s., 1H), 1.88 (d, J=12.0 Hz, 2H), 1.25-1.68 (m, 9H), 0.81 (t, J=7.2 Hz, 3H).

Examples 77b and c

4-Chloro-N—((R)-1-((cis)-4-(pyridin-4-yloxy)cyclohexyl)propyl)benzamide 4-Chloro-N—((S)-1-((cis)-4-(pyridin-4-yloxy)cyclohexyl)propyl)benzamide (Homochiral, Absolute and Relative Stereochemistry Unassigned)

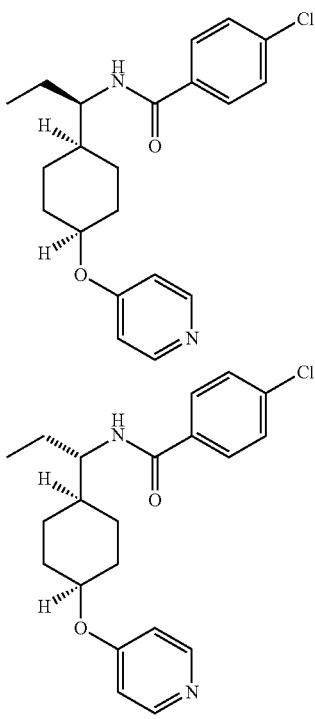

Example 77b and Example 77c

Chiral separation of the racemic Example 77a (Method E) gave Example 77b $T_r$=3.391 min (Method F) and Example 77c $T_r$=3.851 min (Method F) Absolute stereochemistry was not determined.

Example 77b

MS(ES): m/z=373.3 [M+H]$^+$. $T_r$=1.783 min (Method B). $^1$H NMR (500 MHz, DMSO-d$_6$) δ: 8.34 (d, J=4.9 Hz, 2H), 8.12 (d, J=9.0 Hz, 1H), 7.84 (d, J=8.3 Hz, 2H), 7.53 (d, J=8.3 Hz, 2H), 6.94 (d, J=5.5 Hz, 2H), 4.71 (br. s., 1H), 1.89 (br. s., 2H), 1.27-1.69 (m, 10H), 0.83 (t, J=7.2 Hz, 3H).

Example 77c

MS(ES): m/z=373.3 [M+H]$^+$. $T_r$=1.793 min (Method B). $^1$H NMR (500 MHz, DMSO-d$_6$) δ: 8.34 (d, J=3.6 Hz, 2H), 8.12 (d, J=9.0 Hz, 1H), 7.84 (d, J=8.3 Hz, 2H), 7.53 (d, J=8.4 Hz, 2H), 6.95 (d, J=5.4 Hz, 2H), 4.72 (br. s., 1H), 1.86-1.94 (m, J=5.0 Hz, 2H), 1.29-1.68 (m, 10H), 0.83 (t, J=7.2 Hz, 3H).

Example 78

(±)-4-Chloro-N-(1-((cis)-4-((6-(trifluoromethyl)quinolin-4-yl)oxy)cyclohexyl)propyl)benzamide

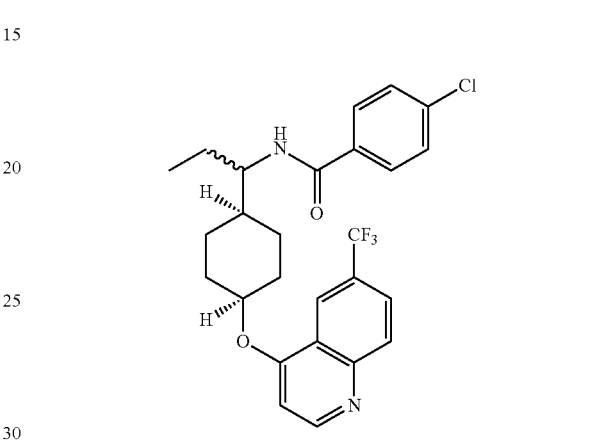

Example 78 was synthesized from Intermediate 71E following the same procedures used to make Intermediates 77A, 77B, 77C and Example 77a using 4-hydroxy-6-trifluoromethyl quinoline rather than pyridin-4-ol in the synthesis of 77A. LC-MS Anal. Calc'd for $C_{26}H_{26}ClF_3N_2O_2$ 490.16. found [M+H] 491.2 $T_r$=0.86 min (Method A). $^1$H NMR (500 MHz, DMSO-d$_6$) δ: 8.81 (d, J=5.2 Hz, 1H), 8.36 (s, 1H), 8.16 (d, J=9.0 Hz, 1H), 8.12 (d, J=8.8 Hz, 1H), 7.96 (d, J=8.2 Hz, 1H), 7.81 (d, J=8.3 Hz, 2H), 7.45 (d, J=8.4 Hz, 2H), 7.15 (d, J=5.3 Hz, 1H), 4.98 (br. s., 1H), 2.07 (t, J=15.6 Hz, 2H), 1.37-1.74 (m, 9H), 0.82 (t, J=7.2 Hz, 3H).

Example 79a (±)-4-Chloro-N-(1-((cis)-4-((2-(trifluoromethyl)quinolin-4-yl)oxy)cyclohexyl)propyl)benzamide

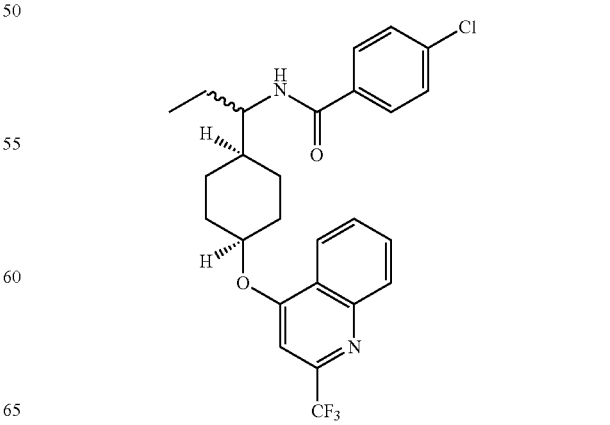

Example 79a was synthesized from Intermediate 71E following the same procedures used to make Intermediates 77A, 77B, 77C and Example 77a using 4-hydroxy-2-trifluoromethyl quinoline rather than pyridin-4-ol in the synthesis of 77A. LC-MS Anal. Calc'd for $C_{26}H_{26}ClF_3N_2O_2$ 490.16. found [M+H] 491.2 $T_r$=1.13 min (Method A). $^1$H NMR (500 MHz, DMSO-$d_6$) δ: 8.17 (d, J=8.3 Hz, 1H), 8.14 (d, J=9.1 Hz, 1H), 8.05 (d, J=8.4 Hz, 1H), 7.81-7.91 (m, 3H), 7.50-7.58 (m, 3H), 7.39 (s, 1H), 5.18 (br. s., 1H), 2.07 (t, J=13.9 Hz, 2H), 1.40-1.74 (m, 9H), 0.85 (t, J=7.2 Hz, 3H).

Examples 79b and c

4-Chloro-N—((R)-1-((cis)-4-(2-(trifluoromethyl)quinolin-4-yloxy)cyclohexyl)propyl)benzamide and 4-Chloro-N—((S)-1-((cis)-4-(2-(trifluoromethyl)quinolin-4-yloxy)cyclohexyl)propyl)benzamide (Homochiral, Absolute and Relative Stereochemistry Unassigned)

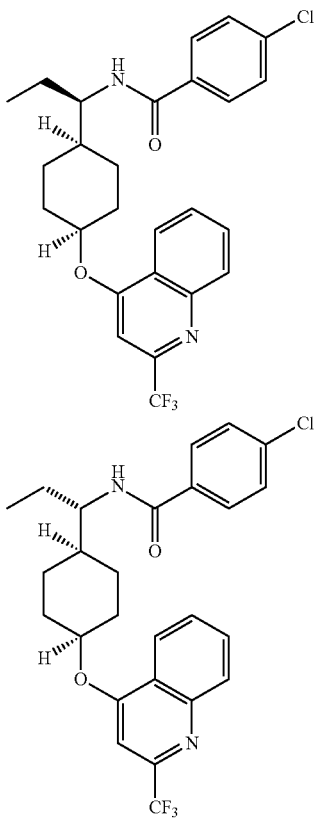

Example 79b and Example 79c

Chiral separation of the racemic Example 79a (Method G) gave Example 79b $T_r$=3.998 min (Method H) and Example 79c $T_r$=5.009 min (Method H) Absolute stereochemistry was not determined.

Example 79b

MS(ES): m/z=491.3 [M+H]$^+$. $T_r$=2.438 min (Method B). $^1$H NMR (500 MHz, DMSO-$d_6$) δ: 8.11-8.20 (m, 2H), 0.8.05 (d, J=8.3 Hz, 1H), 7.81-7.89 (m, J=7.0 Hz, 3H), 7.49-7.57 (m, 3H), 7.37 (s, 1H), 5.16 (br. s., 1H), 3.83 (br. s., 1H), 2.06 (t, J=13.4 Hz, 2H), 1.56-1.76 (m, 6H), 1.39-1.56 (m, 3H), 0.84 (t, J=6.9 Hz, 3H)

Example 79c

MS(ES): m/z=491.3 [M+H]$^+$. $T_r$=2.438 min (Method B). $^1$H NMR (500 MHz, DMSO-$d_6$) δ: 8.16 (t, J=8.8 Hz, 2H), 8.04 (d, J=8.5 Hz, 1H), 7.85 (m, 3H), 7.49-7.56 (m, 3H), 7.37 (s, 1H), 5.15 (br. s., 1H), 3.83 (br. s., 1H), 2.00-2.11 (m, 2H), 1.56-1.73 (m, 6H), 1.40-1.55 (m, 3H), 0.84 (t, J=7.2 Hz, 3H)

Example 80

4-Chloro-N-(1-(cis-4-(quinolin-4-yloxy)cyclohexyl)propyl)benzamide

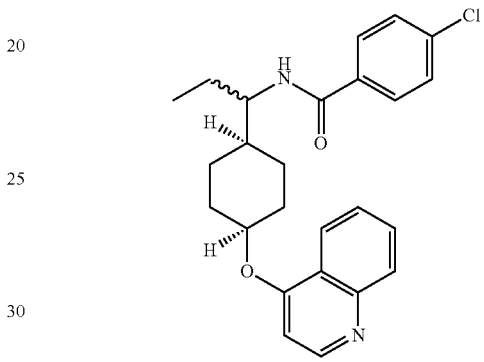

Example 80 was synthesized from Intermediate 71E following the same procedures used to make Intermediates 77A, 77B, 77C and Example 77 using 4-hydroxyquinoline rather than pyridin-4-ol as in the synthesis of 77A. LC-MS Anal. Calc'd for $C_{25}H_{27}ClN_2O_2$ 422.18. found [M+H] 423.2 $T_r$=0.78 min (Method A). $^1$H NMR (500 MHz, DMSO-$d_6$) δ: 8.66 (d, J=5.0 Hz, 1H), 8.14 (d, J=9.0 Hz, 1H), 8.08 (d, J=8.1 Hz, 1H), 7.90 (d, J=8.3 Hz, 1H), 7.85 (d, J=8.2 Hz, 2H), 7.70 (t, J=7.4 Hz, 1H), 7.52 (d, J=8.2 Hz, 2H), 7.36 (t, J=7.5 Hz, 1H), 7.00 (d, J=5.1 Hz, 1H), 4.95 (br. s., 1H), 2.06 (t, J=13.9 Hz, 2H), 1.38-1.71 (m, 9H), 0.84 (t, J=7.0 Hz, 3H).

Example 81

4-Chloro-N-((1-(6-fluoroquinolin-4-yl)-4-hydroxypiperidin-4-yl)methyl)benzamide

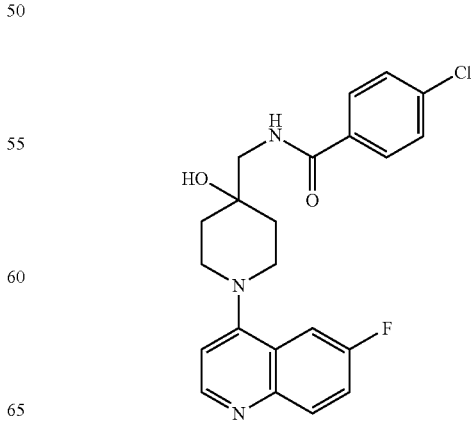

81A. tert-Butyl 4-((4-chlorobenzamido)methyl)-4-hydroxypiperidine-1-carboxylate A solution of tert-butyl 4-(aminomethyl)-4-hydroxypiperidine-1-carboxylate (0.25 g, 1.086 mmol) and 4-chlorobenzoic acid (0.204 g, 1.303 mmol) in DMF (2 mL) was treated with triethylamine (0.454 mL, 3.26 mmol) followed by BOP (0.576 g, 1.303 mmol). The reaction was stirred for 2 h then quenched with dil. aq. HOAc. This resulted in the formation of a precipitate, so the mixture was filtered and rinsed with water. It was then suspended in dil. aq. sodium bicarbonate, sonicated, then filtered, rinsed with water, and air-dried to afford tert-butyl 4-((4-chlorobenzamido)methyl)-4-hydroxypiperidine-1-carboxylate (0.38 g, 90% yield) as a colorless solid, mp 172-173° C. MS(ES): m/z=369 [M+H]$^+$. $t_R$=0.93 min (Method A).

81B. 4-Chloro-N-((4-hydroxypiperidin-4-yl)methyl)benzamide, HCl

A solution of HCl (3.56 ml, 14.23 mmol) in dioxane was treated with tert-butyl 4-((4-chlorobenzamido)methyl)-4-hydroxypiperidine-1-carboxylate (0.35 g, 0.949 mmol). Initially, material dissolved as it was added, but eventually, a gum formed. This was stirred for 15 min. then ~3 mL of dichloromethane was added and stirring was continued for 2 h. During this time, product took on the form of a finely-divided suspension. Concentration under reduced pressure afforded 4-chloro-N-((4-hydroxypiperidin-4-yl)methyl)benzamide, HCl (0.29 g, quantitative yield) as a white powder. MS(ES): m/z=269 [M+H]$^+$. $t_R$=0.55 min (Method A).

Example 81

4-Chloro-N-((1-(6-fluoroquinolin-4-yl)-4-hydroxypiperidin-4-yl)methyl)benzamide A suspension of 4-chloro-6-fluoroquinoline (0.119 g, 0.655 mmol) and 4-chloro-N-((4-hydroxypiperidin-4-yl)methyl)benzamide, HCl (0.2 g, 0.655 mmol) in NMP (1 mL) was treated with DIEA (0.286 mL, 1.638 mmol) and heated to 135° C. for 5 h. After about 45 min. the reaction had become homogeneous. The reaction was cooled to ~80° C. and treated with ~3 mL of 5% aq. HOAc resulting in the formation of a precipitate. This was stirred briefly, filtered, rinsed several times with water and once with 10% EtOAc-hexanes, and air-dried to afford 4-chloro-N-((1-(6-fluoroquinolin-4-yl)-4-hydroxypiperidin-4-yl)methyl)benzamide (0.21 g, 74% yield) as an off-white solid, mp 91-94° C. MS(ES): m/z=414 [M+H]$^+$. $t_R$=0.68 min (Method A). $^1$H NMR (400 MHz, DMSO-d$_6$) δ 8.67 (d, 1H, J=4.9 Hz), 8.46 (t, 1H, J=6.1 Hz), 7.99-8.04 (m, 1H), 7.94 (d, 2H, J=8.7 Hz), 7.55-7.63 (m, 4H), 7.05 (d, 1H, J=5.0 Hz), 4.71 (s, 1H), 3.42 (d, 2H, J=6.1 Hz), 3.24-3.31 (m, integration obscured by water peak), 3.10-3.18 (m, 2H), 1.85-1.94 (m, 2H), 1.67-1.72 (m, 2H).

Example 84

N-([1,1'-Biphenyl]-4-yl)-4-(6-fluoroquinolin-4-yl)piperazine-1-carboxamide

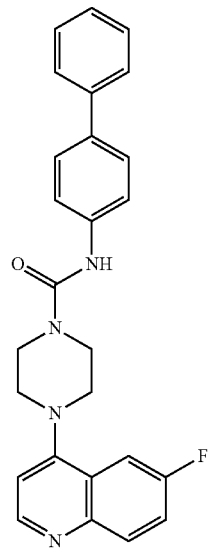 [SMILES: O=C(Nc1ccc(-c2ccccc2)cc1)N1CCN(c2ccnc3ccc(F)cc23)CC1]

84A. tert-Butyl 4-(6-fluoroquinolin-4-yl)piperazine-1-carboxylate

To a homogeneous mixture of 4-chloro-6-fluoroquinoline (500.0 mg, 2.8 mmol) in NMP (5 mL), in a sealable vial, was added 1-Boc-piperazine (750.0 mg, 4.0 mmol) followed by DIPEA (2 mL, 11.6 mmol). After the addition was complete, the vial was capped and the mixture was stirred at 120° C. After 15 hours, the reaction was cooled to room temperature then partitioned between water and Et$_2$O. The layers were separated and the aqueous layer was extracted twice more with Et$_2$O then once with EtOAc. These organic extracts were combined with the original organic layer and were washed with brine, dried (Na$_2$SO$_4$), filtered and concentrated in vacuo to afford the crude product as an oil. Purification by Isco chromatography afforded tert-butyl 4-(6-fluoroquinolin-4-yl)piperazine-1-carboxylate as a solid (719.3 mg; 77% yield). MS(ES): m/z=332 [M+H]$^+$. $t_R$=0.70 min (Method A). $^1$H NMR (400 MHz, DMSO-d$_6$) δ 8.70 (d, J=4.9 Hz, 1H), 8.04 (dd, J=9.2, 5.6 Hz, 1H), 7.76-7.58 (m, 2H), 7.07 (d, J=5.0 Hz, 1H), 3.71-3.54 (m, 4H), 3.14-3.01 (m, 4H), 1.44 (s, 9H).

84B. 6-Fluoro-4-(piperazin-1-yl)quinoline

To a homogeneous mixture of tert-butyl 4-(6-fluoroquinolin-4-yl)piperazine-1-carboxylate (700.0 mg, 2.1 mmol) in anhydrous dioxane (4 mL), at room temperature under nitrogen, was added HCl (4N in dioxane, 10 mL, 40.0 mmol). After 6 hours, a precipitate had formed which was isolated by vacuum filtration, rinsed with anhydrous dioxane and dried under vacuum to afford the title compound (508.0 mg, 79% yield) as an HCl salt which was used without further purification. MS(ES): m/z=232 [M+H]$^+$. $t_R$=0.38 min (Method A).

84 N-([1,1'-Biphenyl]-4-yl)-4-(6-fluoroquinolin-4-yl)piperazine-1-carboxamide To a heterogeneous mixture of the HCl salt of 6-fluoro-4-(piperazin-1-yl)quinoline (84B, 25.0 mg, 0.09 mmol) in anhydrous DMF (1 mL), at room temperature, was added DIPEA (0.05 mL, 0.29 mmol) followed by 4-isocyanato-1,1'-biphenyl (23.0 mg, 0.12 mmol). The resulting mixture was stirred for 96 hours, before being diluted with DMF, passed through a syringe filter, then purified via preparative HPLC/MS to afford the title compound (12.9 mg; 21% yield). MS(ES): m/z=427 [M+H]$^+$. $t_R$=1.55 min (Method I). $^1$H NMR (500 MHz, DMSO-d$_6$) δ 8.69 (d, J=6.5 Hz, 1H), 8.07 (dd, J=9.2, 5.1 Hz, 1H), 7.99-7.96 (m, 1H), 7.93-7.90 (m, 1H), 7.63 (d, J=7.7 Hz, 2H), 7.58-7.57 (m, 4H), 7.44-7.41 (m, 2H), 7.33-7.26 (m, 2H), 7.20 (d, J=6.6 Hz, 1H), 3.87-3.81 (m, 4H), 3.81-3.73 (m, 4H).

Example 86

N-((1-(6-Fluoroquinolin-4-yl)piperidin-4-yl)methyl)-4-methylbenzamide

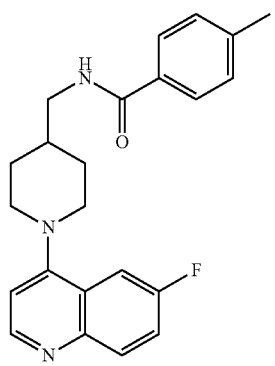 [SMILES: Cc1ccc(C(=O)NCC2CCN(c3ccnc4ccc(F)cc34)CC2)cc1]

86A. tert-Butyl ((1-(6-fluoroquinolin-4-yl)piperidin-4-yl)methyl)carbamate

To a homogeneous mixture of 4-chloro-6-fluoroquinoline (220.0 mg, 1.2 mmol) in anhydrous NMP (4 mL), in a sealable vial, was added tert-butyl (piperidin-4-ylmethyl)carbamate (350.0 mg, 1.6 mmol) followed by DIPEA (0.8 mL, 4.6 mmol). The vial was sealed and the mixture was stirred at 60° C. for 2 hours, then at 90° C. for 17 hours before being stirred at 120° C. for 24 hours. After cooling to room temperature, the reaction mixture was purified by Isco silica gel chromatography to afford tert-butyl ((1-(6-fluoroquinolin-4-yl)piperidin-4-yl)methyl)carbamate as an off-white solid (323.7 mg; 74% yield). MS(ES): m/z=360 [M+H]$^+$. $t_R$=0.71 min (Method A). $^1$H NMR (400 MHz, DMSO-d$_6$) δ 8.66 (d, J=5.0 Hz, 1H), 8.01 (dd, J=9.1, 5.7 Hz, 1H), 7.66-7.51 (m, 2H), 7.01 (d, J=4.9 Hz, 1H), 6.93 (t, J=5.7 Hz, 1H), 3.48 (d, J=12.2 Hz, 2H), 2.94 (t, J=6.3 Hz, 2H), 2.76 (t, J=11.2 Hz, 2H), 1.80 (d, J=11.1 Hz, 2H), 1.67-1.55 (m, 1H), 1.51-1.42 (m, 2H), 1.40 (s, 9H).

86B. (1-(6-Fluoroquinolin-4-yl)piperidin-4-yl)methanamine

To a homogeneous mixture of tert-butyl ((1-(6-fluoroquinolin-4-yl)piperidin-4-yl)methyl)carbamate (308.1 mg, 0.9 mmol) in DCM (10 mL), under nitrogen atmosphere, was added TFA (1.2 mL, 15.6 mmol). The resultant mixture was stirred at ambient temperature for 45 minutes before being concentrated in vacuo to afford the TFA salt of the title compound as a gold oil, which was used without further purification. MS(ES): m/z=260 [M+H]$^+$. $t_R$=0.43 min (Method A).

Example 86

N-((1-(6-Fluoroquinolin-4-yl)piperidin-4-yl)methyl)-4-methylbenzamide

To a homogeneous mixture of the TFA salt of (1-(6-fluoroquinolin-4-yl)piperidin-4-yl)methanamine (86B, 41.8 mg, 0.09 mmol), 4-methylbenzoic acid (14.0 mg, 0.1 mmol) and DIPEA (0.06 mL, 0.3 mmol) in anhydrous THF (1 mL), dioxane (0.5 mL) and DMF (0.5 mL), under nitrogen atmosphere, was added PyBOP (44.6 mg, 0.09 mmol). After stirring at ambient temperature for 15 hours, the mixture was diluted with DMSO, passed through a syringe filter, then purified via preparative HPLC/MS to afford the title compound (21.1 mg; 65% yield). MS(ES): m/z=378 [M+H]$^+$. $t_R$=1.25 min (Method I). $^1$H NMR (500 MHz, DMSO-d$_6$) δ 8.63-8.53 (m, 2H), 7.97 (dd, J=8.9, 5.7 Hz, 1H), 7.70 (d, J=7.9 Hz, 2H), 7.63-7.51 (m, 2H), 7.25 (d, J=7.8 Hz, 2H), 7.00 (d, J=4.8 Hz, 1H), 3.47 (d, J=11.4 Hz, 2H), 2.76 (t, J=11.6 Hz, 2H), ~2.53 (m, integration, exact chemical shift range obscured by solvent peak), 2.31 (s, 3H), 1.87-1.73 (m, 3H), 1.55-1.41 (m, 2H).

Example 87

3,4-Dichloro-N-((1-(6-fluoroquinolin-4-yl)piperidin-4-yl)methyl)benzamide

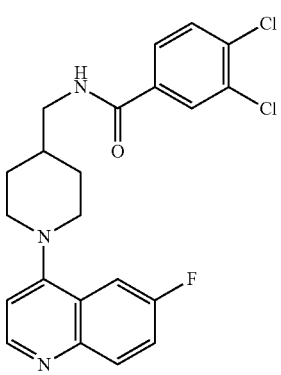 [SMILES: O=C(NCC1CCN(c2ccnc3ccc(F)cc23)CC1)c1ccc(Cl)c(Cl)c1]

To a heterogeneous mixture of the TFA salt of (1-(6-fluoroquinolin-4-yl)piperidin-4-yl)methanamine (86B, 41.8 mg, 0.09 mmol) in anhydrous THF (1 mL) and dioxane (0.5 mL), under nitrogen atmosphere, was added DIPEA (0.06 mL, 0.3 mmol) followed by 3,4-dichlorobenzoyl chloride (18.9 mg, 0.09 mmol). After stirring at ambient temperature for 16 hours, the mixture was diluted with DMF, filtered through a syringe filter, then purified via preparative HPLC/MS to afford the title compound (23.1 mg; 62% yield). MS(ES): m/z=432 [M+H]$^+$. $t_R$=1.51 min (Method I). $^1$H NMR (500 MHz, DMSO-d$_6$) δ 8.83-8.76 (m, 1H), 8.63 (d, J=4.8 Hz, 1H), 8.07 (s, 1H), 7.99 (dd, J=8.8, 5.7 Hz, 1H), 7.82 (d, J=8.2 Hz, 1H), 7.73 (d, J=8.4 Hz, 1H), 7.64-7.54 (m, 2H), 7.01 (d, J=4.8 Hz, 1H), 3.71-3.44 (m, 2H), 3.34-3.21 (m, 2H), 2.76 (t, J=11.7 Hz, 2H), 1.88-1.75 (m, 3H), 1.56-1.45 (m, 2H).

Examples 88 to 90

Reaction of the TFA salt of (1-(6-fluoroquinolin-4-yl)piperidin-4-yl)methanamine with an appropriate acid chloride, under the conditions described for Example 87 (Scheme 1, below), afforded compounds of the invention shown in Table 1 below.

Scheme 1

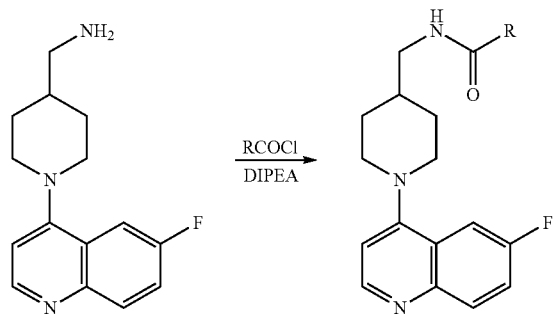

TABLE 1

| Ex. No. | R | (M + H)$^+$ | $t_R$ (min.)$^{Method}$ |
|---|---|---|---|
| 88 | ![4-chlorophenyl] | 398 | 1.31$^1$ |
| 89 | ![4-fluorophenyl] | 382 | 1.19$^1$ |
| 90 | ![3-chlorophenyl] | 398 | 1.33$^1$ |

Example 91

1-(1-(6-Fluoroquinolin-4-yl)piperidin-4-yl)-3-(p-tolyl)urea

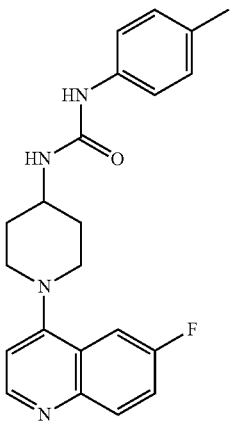 [SMILES: Cc1ccc(NC(=O)NC2CCN(c3ccnc4ccc(F)cc34)CC2)cc1]

91A. tert-Butyl (1-(6-fluoroquinolin-4-yl)piperidin-4-yl)carbamate

To a homogeneous mixture of 4-chloro-6-fluoroquinoline (200.0 mg, 1.1 mmol) in anhydrous NMP (5 mL), in a sealable vial, was added 4-Boc-aminopiperidine (309.0 mg, 1.5 mmol) followed by DIPEA (0.8 mL, 4.6 mmol). The vial was sealed and the mixture was stirred at 120° C. for 15 hours. After cooling to room temperature, the reaction mixture was partitioned between EtOAc and water. The layers were separated and the aqueous layer was extracted twice more with EtOAc. The organic extracts were combined, washed with brine, dried (Na$_2$SO$_4$), filtered and concentrated in vacuo to afford the crude product which was used without further purification, based on quantitative yield. MS(ES): m/z=346 [M+H]$^+$. $t_R$=0.70 min (Method A).

91B. 1-(6-Fluoroquinolin-4-yl)piperidin-4-amine

To a homogeneous mixture of tert-butyl (1-(6-fluoroquinolin-4-yl)piperidin-4-yl)carbamate (380.0 mg, 1.1 mmol) in dioxane (2 mL), under nitrogen atmosphere, was added 4M HCl in dioxane (2 mL, 8.0 mmol). The resultant mixture was stirred at ambient temperature for 6 hours, during which time a precipitate formed. Vacuum filtration afforded the HCl salt of the title compound as a pale yellow solid (358 mg, 100% yield) which was used without further purification. MS(ES): m/z=246 [M+H]$^+$. $t_R$=0.42 min (Method A).

Example 91

1-(1-(6-Fluoroquinolin-4-yl)piperidin-4-yl)-3-(p-tolyl)urea

To a heterogeneous mixture of the HCl salt of 1-(6-fluoroquinolin-4-yl)piperidin-4-amine (91B, 30.0 mg, 0.09 mmol) in anhydrous THF (1 mL), at room temperature, was added DIPEA (0.05 mL, 0.29 mmol) followed by 1-isocyanato-4-methylbenzene (15.1 mg, 0.11 mmol). The resulting mixture was stirred for 88 hours, before being diluted with DMSO, passed through a syringe filter, then purified via preparative HPLC/MS to afford the title compound (21.7 mg; 60% yield). MS(ES): m/z 379 [M+H]$^+$. $t_R$=1.30 min (Method I). $^1$H NMR (500 MHz, DMSO-d$_6$) δ 8.67 (d, J=2.5 Hz, 1H), 8.29 (s, 1H), 8.11-7.96 (m, 1H), 7.70-7.57 (m, 2H), 7.27 (d, J=7.3 Hz, 2H), 7.12-6.97 (m, 3H), 6.23 (d, J=7.2 Hz, 1H), 3.79-3.68 (m, 1H), 3.53-3.37 (m, 2H), 3.05-2.90 (m, 2H), 2.21 (s, 3H), 2.11-1.98 (m, 2H), 1.81-1.65 (m, 2H).

Example 92

1-(4-Chloro-2-fluorophenyl)-3-(1-(6-fluoroquinolin-4-yl)piperidin-4-yl)urea

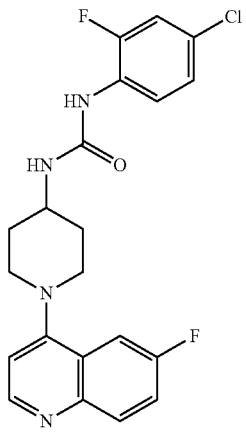 [SMILES: O=C(Nc1ccc(Cl)cc1F)NC1CCN(c2ccnc3ccc(F)cc23)CC1]

Example 92 (19.3 mg; 49% yield) was prepared following a procedure analogous to that for the synthesis of Example 91, except that 4-chloro-2-fluoro-1-isocyanatobenzene (19.4 mg, 0.11 mmol) was used instead of 1-isocyanato-4-methylbenzene. MS(ES): m/z=417 [M+H]$^+$. T$_r$=1.42 min (Method I). $^1$H NMR (500 MHz, DMSO-d$_6$) δ 8.67 (d, J=4.8 Hz, 1H), 8.39 (s, 1H), 8.16 (t, J=8.9 Hz, 1H), 8.02 (dd, J=9.9, 5.6 Hz, 1H), 7.68-7.56 (m, 2H), 7.39 (d, J=11.2 Hz, 1H), 7.17 (d, J=8.8 Hz, 1H), 7.06 (d, J=4.7 Hz, 1H), 6.84 (d, J=7.3 Hz, 1H), 3.82-3.70 (m, 1H), 3.50-3.37 (m, 2H), 2.98 (t, J=10.8 Hz, 2H), 2.12-2.01 (m, 2H), 1.78-1.65 (m, 2H).

Example 93

1-(4-Fluorophenyl)-3-(1-(6-fluoroquinolin-4-yl)piperidin-4-yl)urea

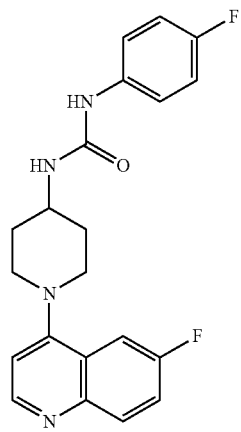 [SMILES: O=C(Nc1ccc(F)cc1)NC1CCN(c2ccnc3ccc(F)cc23)CC1]

Example 93 (21.8 mg; 61% yield) was prepared following a procedure analogous to that for the synthesis of Example 91, except that 1-fluoro-4-isocyanatobenzene (15.5 mg, 0.11 mmol) was used instead of 1-isocyanato-4-methylbenzene. MS(ES): m/z=383 [M+H]$^+$. T$_r$=1.18 min (Method I). $^1$H NMR (500 MHz, DMSO-d$_6$) δ 8.57 (d, J=6.1 Hz, 1H), 8.44 (s, 1H), 8.00 (dd, J=9.2, 5.2 Hz, 1H), 7.84-7.71 (m, 2H), 7.35 (dd, J=8.4, 4.9 Hz, 2H), 7.15 (d, J=6.3 Hz, 1H), 7.05 (t, J=8.7 Hz, 2H), 6.31 (d, J=7.5 Hz, 1H), 3.86-3.85 (m, 3H), 3.35 (t, J=11.1 Hz, 2H), 2.07-2.00 (m, 2H), 1.74-1.61 (m, 2H).

Example 97 trans-N-(4-Methoxybenzyl)-4-phenylcyclohexanamine

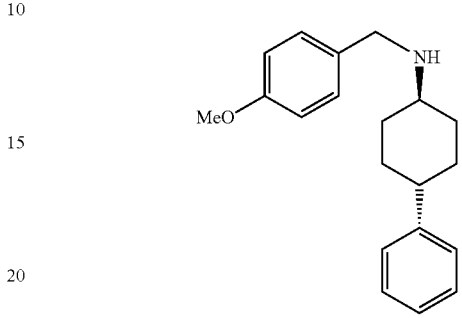

A suspension of trans-4-phenylcyclohexanone (2 g, 11.48 mmol) in DCM (30 mL) was treated with (4-methoxyphenyl)methanamine (1.575 g, 11.48 mmol) and magnesium perchlorate (0.128 g, 0.574 mmol). After stirring at rt for 16 h Na$_2$SO$_4$ was added and stirring continued at rt for 1 hr. The mixture was filtered washed with MeOH and the mother liquor was conc. to yield a yellow viscous oil. The oil was dissolved in MeOH (10 mL), and treated with NaBH$_4$ (0.651 g, 17.22 mmol) in portions, then stirred at rt for 30 min until the reaction was done. The reaction was quenched with water (75 ml) and extracted with EtOAc (3×). The combined organic extracts were dried, filtered, and concentrated. The yellow residue was purified on an ISCO silica column (40 g), eluting with (DCM:10% MeOH in DCM contain 2.5% NH$_4$OH=0%-70%) in 20 mins. to yield (1r,4r)-N-(4-methoxybenzyl)-4-phenylcyclohexanamine (870 mg, 2.94 mmol, 25%) $^1$H NMR (500 MHz, chloroform-d) δ 7.32-7.22 (m, 3H), 7.22-7.10 (m, 4H), 6.92-6.77 (m, 2H), 3.84-3.70 (m, 5H), 2.60-2.46 (m, 2H), 2.15-2.02 (m, 2H), 1.97-1.82 (m, 2H), 1.49 (qd, J=12.9, 3.0 Hz, 2H), 1.36-1.15 (m, 2H) MS: Anal. Calc'd for C$_{20}$H$_{25}$NO 295.194. found [M+H] 296.1 LC: tr=1.4 min (Method I)

Example 119

1-(4-Chlorophenyl)-3-(trans-4-(6-fluoroquinolin-4-yl)cyclohexyl)urea

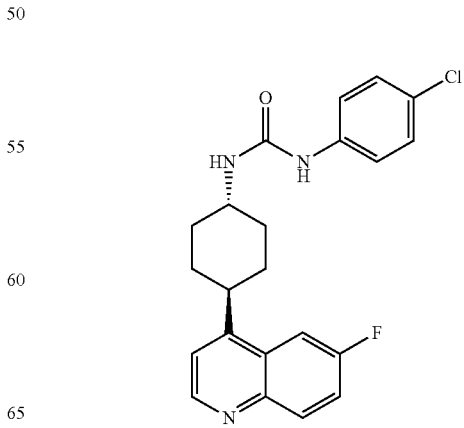

119A.
trans-4-(6-Fluoroquinolin-4-yl)cyclohexanamine

To a solution of 4-(6-fluoroquinolin-4-yl)cyclohexanone (350 mg, 1.439 mmol) in EtOH (6 mL) in a microwave vial was added ammonium acetate (1663 mg, 21.58 mmol). The resulting suspension was treated with sodium cyanoborohydride (108 mg, 1.726 mmol). The reaction was capped and microwaved at 130° C. for 5 min. The reaction was cooled to RT and diluted with MeOH and purified by preparative HPLC (PHENOMENEX® Luna 5μ 30×100 mm), 40 mL/min flow rate with gradient of 0% B-100% B over 12 minutes. Hold at 100% B for 2 min. (A: 0.1% TFA in water/MeOH (90:10), B: 0.1% TFA in water/MeOH (10:90) monitoring at 254 nm. Fractions containing the product were combined and concentrated to give trans-4-(6-fluoroquinolin-4-yl)cyclohexanamine (310 mg, 0.624 mmol, 43.4% yield) $^1$H NMR (400 MHz, DMSO-d$_6$) δ 8.88 (d, J=4.6 Hz, 1H), 8.19-8.05 (m, 2H), 7.92 (br. s., 3H), 7.73 (td, J=8.7, 2.8 Hz, 1H), 7.53 (d, J=4.6 Hz, 1H), 3.36 (br. s., 1H), 3.22-3.02 (m, 1H), 2.09 (br. s., 2H), 1.96 (br. s., 2H), 1.77-1.52 (m, 4H) MS: Anal. Calc'd for C$_{15}$H$_{17}$FN$_2$ 244.138. found [M+H] 245.1 LC: t$_r$=0.42 min (Method A)

Example 119

1-(4-Chlorophenyl)-3-(trans-4-(6-fluoroquinolin-4-yl)cyclohexyl)urea

To a solution of trans-4-(6-fluoroquinolin-4-yl)cyclohexanamine (20 mg, 0.042 mmol) in THF (0.5 mL) at RT was added 1-chloro-4-isocyanatobenzene (9.76 mg, 0.064 mmol). The reaction was stirred at RT for 3 h. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 22 minutes, then a 5-minute hold at 100% B; Flow: 20 mL/min. Fractions containing the desired product were combined and dried via centrifugal evaporation. The yield of the product was 11.4 mg (0.029 mmol, 67%) $^1$H NMR (400 MHz, DMSO-d$_6$) δ 8.82 (d, J=4.5 Hz, 1H), 8.50 (s, 1H), 8.10 (dd, J=9.3, 5.9 Hz, 1H), 8.03 (dd, J=11.1, 2.8 Hz, 1H), 7.68 (td, J=8.7, 2.8 Hz, 1H), 7.50 (d, J=4.5 Hz, 1H), 7.46-7.35 (m, 2H), 7.33-7.19 (m, 2H), 6.19 (d, J=7.7 Hz, 1H), 3.70-3.52 (m, 1H), 3.42-3.34 (m, 1H), 2.04 (d, J=9.3 Hz, 2H), 1.92 (d, J=12.1 Hz, 2H), 1.79-1.63 (m, 2H), 1.61-1.45 (m, 2H) MS: Anal. Calc'd for C$_{22}$H$_{21}$ClFN$_3$O, 397.136. found [M+H] 398.2 LC: t$_r$=1.39 min (Method I).

These compounds were obtained following the procedures in Example 119 using the corresponding isocyanates.

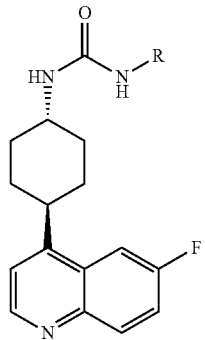

| Ex. No. | Name | R | Tr (min)$^{Method\ I}$ | [M + H]$^+$ |
|---|---|---|---|---|
| 120 | 1-(4-chloro-2-fluorophenyl)-3-(trans-4-(6-fluoroquinolin-4-yl)cyclohexyl)urea | 2-F, 4-Cl phenyl | 1.46 | 416.0 |
| 121 | 1-(4-cyanophenyl)-3-trans-4-(6-fluoroquinolin-4-yl)cyclohexyl)urea | 4-CN phenyl | 1.16 | 389.1 |
| 122 | 1-(2,4-difluorophenyl)-3-(trans-4-(6-fluoroquinolin-4-yl)cyclohexyl)urea | 2,4-diF phenyl | 1.25 | 399.9 |
| 123 | 1-(3,4-difluorophenyl)-3-(trans-4-(6-fluoroquinolin-4-yl)cyclohexyl)urea | 3,4-diF phenyl | 1.37 | 400.2 |

| Ex. No. | Name | R | Tr (min)^Method 1 | [M + H]+ |
|---|---|---|---|---|
| 124 | 1-(4-fluorophenyl)-3-(trans-4-(6-fluoroquinolin-4-yl)cyclohexyl)urea | | 1.26 | 382.3 |

Example 125

1-(4-Chlorophenyl)-3-(cis-4-(6-fluoroquinolin-4-yl)cyclohexyl)urea

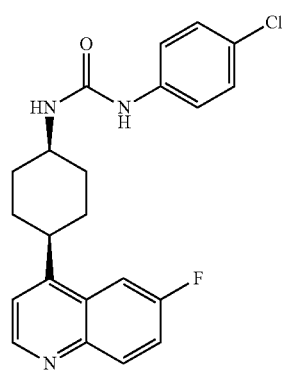 [SMILES: O=C(Nc1ccc(Cl)cc1)N[C@H]1CC[C@@H](c2ccnc3ccc(F)cc32)CC1]

125A.
cis-4-(6-Fluoroquinolin-4-yl)cyclohexanamine

To a solution of 4-(6-fluoroquinolin-4-yl)cyclohexanone (350 mg, 1.439 mmol) in EtOH (6 mL) in a microwave vial was added ammonium acetate (1663 mg, 21.58 mmol). To the resulting suspension was added sodium cyanoborohydride (108 mg, 1.726 mmol). The reaction was capped and microwaved at 130° C. for 5 min. The reaction was cooled to RT and diluted with MeOH and purified by preparative HPLC (PHENOMENEX® Luna 5μ 30×100 mm), 40 mL/min flow rate with gradient of 0% B-100% B over 12 minutes Hold at 100% B for 2 min. (A: 0.1% TFA in water/MeOH (90:10), B: 0.1% TFA in water/MeOH (10:90) monitoring at 254 nm. Fractions containing the product were combined and concentrated to give cis-4-(6-fluoroquinolin-4-yl)cyclohexanamine (100 mg, 0.201 mmol, 14% yield) $^1$H NMR (400 MHz, DMSO-$d_6$) δ 8.94 (d, J=4.6 Hz, 1H), 8.19-8.03 (m, 2H), 7.94 (br. s., 1H), 7.74 (td, J=8.7, 2.8 Hz, 1H), 7.60 (d, J=4.8 Hz, 1H), 3.59 (br. s., 1H), 3.49 (t, J=11.0 Hz, 1H), 2.10-1.82 (m, 6H), 1.75 (d, J=10.8 Hz, 2H) MS: Anal. Calc'd for $C_{15}H_{17}FN_2$ 244.138. found [M+H] 245.1 LC: $t_r$=0.45 min (Method A).

Example 125

1-(4-Chlorophenyl)-3-(cis-4-(6-fluoroquinolin-4-yl)cyclohexyl)urea

To a solution of cis-4-(6-fluoroquinolin-4-yl)cyclohexanamine (25 mg, 0.053 mmol) in THF (0.5 mL) at RT was added 1-chloro-4-isocyanatobenzene (16.27 mg, 0.106 mmol). The reaction was stirred at RT for 2 h. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 22 minutes, then a 5-minute hold at 100% B; Flow: 20 mL/min. Fractions containing the desired product were combined and dried via centrifugal evaporation. The yield of the product was 14.7 mg (0.034 mmol, 64%) $^1$H NMR (500 MHz, DMSO-$d_6$) δ 8.95 (d, J=4.5 Hz, 1H), 8.56 (s, 1H), 8.21-8.08 (m, 2H), 7.78 (t, J=8.5 Hz, 1H), 7.63 (d, J=4.4 Hz, 1H), 7.43 (d, J=8.3 Hz, 2H), 7.27 (d, J=7.4 Hz, 2H), 6.69 (d, J=7.4 Hz, 1H), 4.01 (br. s., 1H), 3.59 (d, J=9.4 Hz, 1H), 1.96-1.78 (m, 4H), 1.76 (br. s., 4H) MS: Anal. Calc'd for $C_{22}H_{21}ClFN_3O$, 397.136. found [M+H] 398.2 LC: tr=1.44 min (Method I).

Example 130 trans-N-Benzyl-4-(6-fluoroquinolin-4-yl)cyclohexanamine

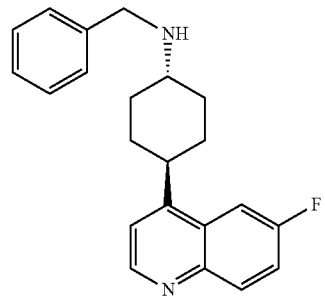 [SMILES: Fc1ccc2nccc([C@H]3CC[C@H](NCc4ccccc4)CC3)c2c1]

To a solution of 4-(6-fluoroquinolin-4-yl)cyclohexanone (100 mg, 0.411 mmol) and benzylamine (66 mg, 0.617 mmol) in $CH_2Cl_2$ (2 mL) at RT was added acetic acid (0.024 mL, 0.411 mmol), followed by sodium triacetoxyborohydride (131 mg, 0.617 mmol). The reaction was stirred at RT for 4 h. Then it was diluted with MeOH and purified with prep HPLC (Phen Luna 5u 30×100 mm), 40 mL/min flow rate with gradient of 0% B-100% B over 12 minutes Hold at 100% B for 2 min. (A: 0.1% TFA in water/MeOH (90:10), B: 0.1% TFA in water/MeOH (10:90) monitoring at 254 nm. Evaporation of the product containing fractions gave (1r,4r)-N-benzyl-4-(6-fluoroquinolin-4-yl)cyclohexanamine (150 mg). An aliquot (15 mg) of this material was further purified under the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 10-50% B over 18 minutes, then a 5-minute hold at 100% B; Flow: 20 mL/min. Fractions containing the desired product were combined and dried via centrifugal evaporation. The yield of the product was 3.1 mg, $^1$H NMR (500 MHz, DMSO-d$_6$) δ 8.78 (br d, J=4.2 Hz, 1H), 8.08 (br dd, J=8.8, 6.0 Hz, 1H), 7.96 (br d, J=10.6 Hz, 1H), 7.72-7.62 (m, 1H), 7.43 (br d, J=7.0 Hz, 3H), 7.37 (br t, J=7.3 Hz, 2H), 7.34-7.25 (m, 1H), 3.94 (s, 1H), 3.74-3.63 (m, 1H), 3.29 (br s, 1H), 2.78 (br s, 1H), 2.14 (br s, 2H), 1.99-1.84 (m, 3H), 1.55 (br s, 4H). MS: Anal. Calc'd for C$_{22}$H$_{23}$FN$_2$ 334.185. found [M+H] 335.1 LC: tr=0.78 min (Method I).

Example 131 cis-N-Benzyl-4-(6-fluoroquinolin-4-yl)cyclohexanamine

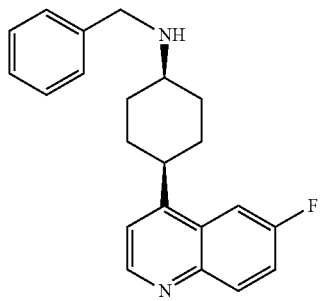 [SMILES: Fc1ccc2nccc([C@H]3CC[C@@H](NCc4ccccc4)CC3)c2c1]

Example 131 was obtained following the procedures in Example 130 using the corresponding cis-4-(6-fluoroquinolin-4-yl)cyclohexanone and benzylamine. $^1$H NMR (500 MHz, DMSO-d$_6$) δ 8.84 (d, J=3.8 Hz, 1H), 8.14-8.04 (m, 1H), 8.00 (d, J=10.8 Hz, 1H), 7.67 (t, J=8.7 Hz, 1H), 7.55-7.46 (m, 3H), 7.41 (t, J=7.2 Hz, 2H), 7.35 (d, J=7.2 Hz, 1H), 4.01 (br. s., 2H), 3.41 (br. s., 1H), 3.17 (br. s., 1H), 2.09-1.99 (m, 2H), 1.99-1.80 (m, 4H), 1.67 (d, J=12.0 Hz, 2H). MS: Anal. Calc'd for C$_{22}$H$_{23}$FN$_2$ 334.185. found [M+H] 335.2 LC: t$_r$=0.90 min (Method I).

Example 139

2-(4-(((trans-4-(6-Fluoroquinolin-4-yl)cyclohexyl)amino)methyl)phenyl)acetic acid

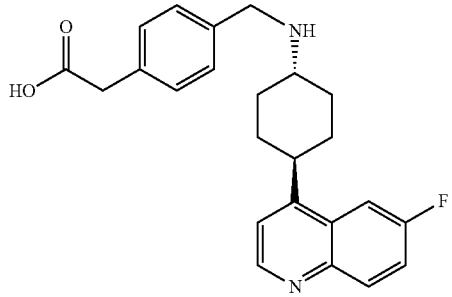 [SMILES: O=C(O)Cc1ccc(CN[C@H]2CC[C@H](c3ccnc4ccc(F)cc43)CC2)cc1]

Example 139 was obtained following the procedures in Example 130 using the corresponding trans-4-(6-fluoroquinolin-4-yl)cyclohexanone and 2-(4-(aminomethyl)phenyl) acetic acid hydrochloride $^1$H NMR (500 MHz, DMSO-d$_6$) δ 8.91 (br. s., 2H), 8.83 (d, J=3.9 Hz, 1H), 8.20-8.08 (m, 1H), 8.03 (d, J=10.7 Hz, 1H), 7.71 (t, J=8.3 Hz, 1H), 7.48 (d, J=7.9 Hz, 3H), 7.35 (d, J=7.3 Hz, 2H), 4.21 (br. s., 2H), 3.60 (d, J=19.4 Hz, 2H), 3.41-3.28 (m, 1H), 3.21 (br. s., 1H), 2.28 (d, J=10.6 Hz, 2H), 2.01 (d, J=11.3 Hz, 2H), 1.81-1.59 (m, 4H) MS: Anal. Calc'd for C$_{24}$H$_{25}$FN$_2$O$_2$ 392.190. found [M+H] 393.1 LC: tr=0.72 min (Method I).

Example 140

2-(4-(((cis-4-(6-Fluoroquinolin-4-yl)cyclohexyl)amino)methyl)phenyl)acetic acid

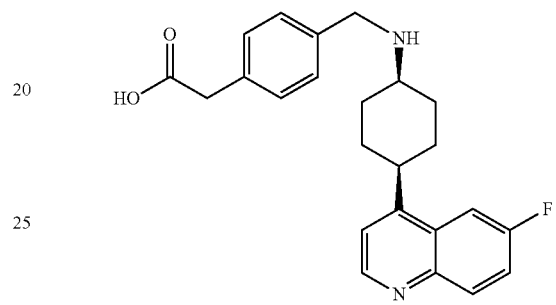

Example 140 was obtained following the procedures in Example 130 using the corresponding cis-4-(6-fluoroquinolin-4-yl)cyclohexanone and 2-(4-(aminomethyl)phenyl)acetic acid hydrochloride $^1$H NMR (500 MHz, DMSO-d$_6$) δ 8.81 (d, J=4.2 Hz, 1H), 8.16-8.03 (m, 1H), 7.98 (d, J=9.6 Hz, 1H), 7.73-7.60 (m, 1H), 7.51 (d, J=4.3 Hz, 1H), 7.42-7.29 (m, J=7.6 Hz, 2H), 7.26-7.08 (m, J=7.5 Hz, 2H), 3.81 (br. s., 1H), 3.64 (br. s., 1H), 3.49 (s, 1H), 3.34 (br. s., 1H), 3.16 (s, 1H), 2.99 (br. s., 1H), 2.01-1.87 (m, 4H), 1.83-1.68 (m, 2H), 1.61 (d, J=11.9 Hz, 2H). MS: Anal. Calc'd for C$_{24}$H$_{25}$FN$_2$O$_2$ 392.190. found [M+H] 393.2 LC: tr=0.79 min (Method I).

Example 144

2-(4-Chlorophenyl)-N-(trans-4-(6-fluoroquinolin-4-yl)cyclohexyl)acetamide

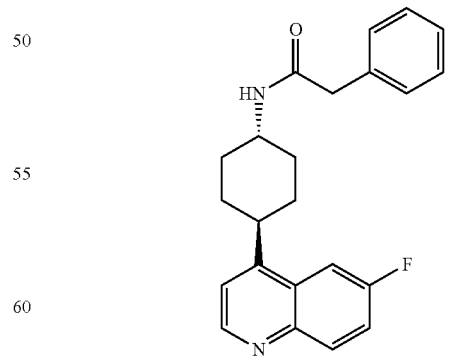

To a solution of trans-4-(6-fluoroquinolin-4-yl)cyclohexanamine (20 mg, 0.042 mmol) (Intermediate 119A) in THF (0.5 mL) at RT was added 2-(4-chlorophenyl)acetyl chloride (16.02 mg, 0.085 mmol), followed by triethylamine (0.024 mL, 0.169 mmol). The reaction was stirred at RT for 3 h. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 50-100% B over 20 minutes, then a 5-minute hold at 100% B; Flow: 20 mL/min. Fractions containing the desired product were combined and dried via centrifugal evaporation. The yield of the product was 11.5 mg (0.029 mmol, 68%) $^1$H NMR (500 MHz, DMSO-$d_6$) δ 8.76 (d, J=4.5 Hz, 1H), 8.25 (d, J=7.7 Hz, 1H), 8.07 (dd, J=9.1, 5.8 Hz, 1H), 7.93 (d, J=8.8 Hz, 1H), 7.71-7.58 (m, 1H), 7.46 (d, J=4.4 Hz, 1H), 7.36-7.30 (m, J=8.2 Hz, 2H), 7.29-7.13 (m, J=8.2 Hz, 2H), 3.94-3.81 (m, 2H), 3.61 (d, J=7.3 Hz, 1H), 3.25 (t, J=11.2 Hz, 1H), 1.88 (t, J=13.7 Hz, 4H), 1.66-1.43 (m, 4H) MS: Anal. Calc'd for $C_{23}H_{22}ClFN_2O$, 396.140. found [M+H] 397.0 LC: $t_r$=1.37 min (Method I).

| Ex. No. | Name | R | Tr (min)$^{Method\ 1}$ | [M + H]$^+$ |
|---|---|---|---|---|
| 145 | 2-(4-chlorophenyl)-N-(trans-4-(6-fluoroquinolin-4-yl)cyclohexyl)propanamide | | 1.52 | 411.1 |
| 146 | 4-chloro-N-(trans-4-(6-fluoroquinolin-4-yl)cyclohexyl)benzamide | | 1.42 | 383.2 |
| 147 | 2-(4-chlorophenyl)-N-(cis-4-(6-fluoroquinolin-4-yl)cyclohexyl)acetamide | | 1.75 | 397.2 |

-continued

| Ex. No. Name | R | Tr (min)$^{Method\ 1}$ | [M + H]$^+$ |
|---|---|---|---|
| 148 2-(4-chlorophenyl)-N-(cis-4-(6-fluoroquinolin-4-yl)cyclohexyl)propanamide | | 1.47 | 411.2 |
| 149 4-chloro-N-(cis-4-(6-fluoroquinolin-4-yl)cyclohexyl)benzamide | | 1.30 | 383.3 |

These compounds were obtained following the procedures in Example 144 using the corresponding amines and acid chloride.

Example 157 a, b, c, d, e

4-Chloro-N-(1-(4-(2-methylpyridin-4-yl)cyclohexyl)ethyl)benzamide 4-Chloro-N—((S)-1-(cis-4-(2-methylpyridin-4-yl)cyclohexyl)ethyl)benzamide 4-Chloro-N—((R)-1-(cis-4-(2-methylpyridin-4-yl)cyclohexyl)ethyl)benzamide 4-Chloro-N—((S)-1-(trans-4-(2-methylpyridin-4-yl)cyclohexyl)ethyl)benzamide 4-Chloro-N—((R)-1-(trans-4-(2-methylpyridin-4-yl)cyclohexyl)ethyl)benzamide

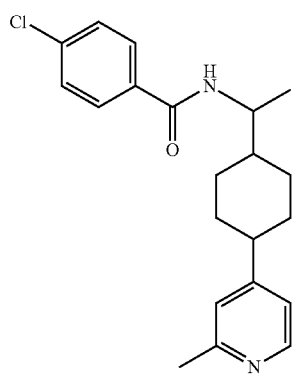

-continued

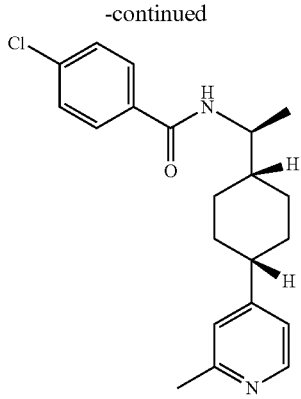

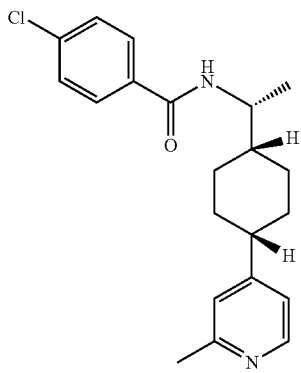 [SMILES: Cc1cc([C@H]2CC[C@H]([C@@H](C)NC(=O)c3ccc(Cl)cc3)CC2)ccn1]

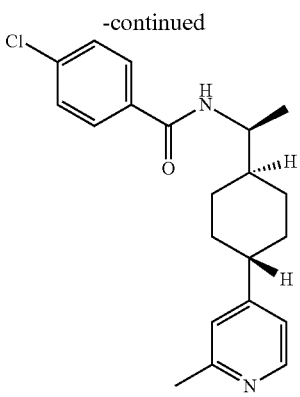

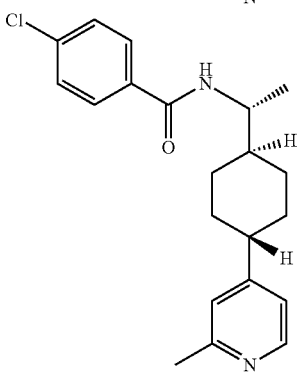

157A. Ethyl 2-(1,4-dioxaspiro[4.5]decan-8-ylidene)propanoate

To a suspension of NaH (0.307 g, 7.68 mmol) in THF (8 mL) cooled at 0° C. was added ethyl 2-(diethoxyphosphoryl)propanoate (1.830 g, 7.68 mmol) slowly. After 30 min, 1,4-dioxaspiro[4.5]decan-8-one (1 g, 6.40 mmol) was added. The resulting mixture was stirred at 0° C. for 2 h, then warmed to RT overnight. The mixture was quenched with water and the THF was removed in vacuo. The residue was dissolved in EtOAc, washed with water and brine. The solution was dried over Na$_2$SO$_4$, filtered and concentrated. The crude material was purified by ISCO (EtOAc/Hex 0-30%). Fractions containing the product were concentrated to yield ethyl 2-(1,4-dioxaspiro[4.5]decan-8-ylidene)propanoate (1.2 g, 78% yield) a light yellow oil. $^1$H NMR (400 MHz, CHLOROFORM-d) δ 4.19 (q, J=7.1 Hz, 2H), 4.03-3.89 (m, 4H), 2.68-2.53 (m, 2H), 2.46-2.28 (m, 2H), 1.89 (s, 3H), 1.78-1.66 (m, 4H), 1.30 (t, J=7.1 Hz, 3H).

157B. Ethyl 2-(1,4-dioxaspiro[4.5]decan-8-yl)propanoate

A suspension of ethyl 2-(1,4-dioxaspiro[4.5]decan-8-ylidene)propanoate (500 mg, 2.081 mmol) and 10% palladium on carbon (25 mg, 0.024 mmol) in EtOAc (5 mL) was hydrogenated in a Parr shaker at 45 psi for 6 h. The catalyst was filtered and the filtrate was concentrated to yield ethyl 2-(4-(3-methylpyridin-4-yl)cyclohexyl)propanoate (450 mg, 89% yield) as a light oil. $^1$H NMR (400 MHz, CHLOROFORM-d) δ 4.12 (dtt, J=10.7, 7.1, 3.6 Hz, 2H), 3.98-3.81 (m, 4H), 2.35-2.17 (m, 1H), 1.83-1.68 (m, 3H), 1.66-1.45 (m, 4H), 1.43-1.28 (m, 2H), 1.27-1.22 (m, 3H), 1.14-1.07 (m, 3H)

157C. Ethyl 2-(4-oxocyclohexyl)propanoate

To a solution of ethyl 2-(1,4-dioxaspiro[4.5]decan-8-yl)propanoate (450 mg, 1.857 mmol) in THF (5 mL) was added 1M hydrogen chloride (aqueous) (0.929 mL, 3.71 mmol). The mixture was heated at 50° C. for 6 h. The reaction mixture was concentrated. The residue was dissolved in EtOAc, washed with water (2×), and brine. The solution was dried over Na$_2$SO$_4$ and concentrated. The crude material was purified with ISCO (EtOAc/Hex 0-30%). Fractions containing product were concentrated to yield ethyl 2-(4-oxocyclohexyl)propanoate (290 mg, 79% yield) as a clear oil. $^1$H NMR (400 MHz, CHLOROFORM-d) δ 4.22-4.06 (m, 2H), 2.46-2.30 (m, 5H), 2.13-1.91 (m, 3H), 1.56-1.42 (m, 2H), 1.31-1.24 (m, 3H), 1.18 (d, J=7.1 Hz, 3H).

157D. Ethyl 2-(4-(((trifluoromethyl)sulfonyl)oxy) cyclohex-3-en-1-yl)propanoate Ethyl 2-(4-oxocyclohexyl)propanoate (200 mg, 1.01 mmol) and 2,6-di-tert-butyl-4-methylpyridine (238 mg, 1.16 mmol) were dissolved in dry DCM (10 ml). To the reaction mixture trifluoromethanesulfonic anhydride (0.186 mL, 1.11 mmol) was added dropwise and stirred for 2 h. The suspension was filtered and the filtrate was diluted with DCM, washed with 1N HCl (2×), satd. sodium bicarbonate solution, water, and brine. The solution was dried over Na$_2$SO$_4$ and concentrated to yield ethyl 2-(4-(((trifluoromethyl)sulfonyl)oxy)cyclohex-3-en-1-yl)propanoate (320 mg, 96% yield) as a brown oil. $^1$H NMR (400 MHz, CHLOROFORM-d) δ 5.73 (t, J=6.1 Hz, 1H), 4.28-4.05 (m, 2H), 2.52-2.17 (m, 4H), 2.08-1.79 (m, 3H), 1.49 (dt, J=11.1, 6.6 Hz, 1H), 1.31-1.20 (m, 3H), 1.19-1.04 (m, 3H)

157E. Ethyl 2-(4-(4,4,5,5-tetramethyl-1,3,2-dioxaborolan-2-yl)cyclohex-3-en-1-yl)propanoate To a solution of ethyl 2-(4-(((trifluoromethyl)sulfonyl)oxy)cyclohex-3-en-1-yl)propanoate (300 mg, 0.908 mmol) in DMSO (5 mL) was added 4,4,4',4',5,5,5',5'-octamethyl-2,2'-bi(1,3,2-dioxaborolane) (230 mg, 0.908 mmol) and potassium acetate (267 mg, 2.72 mmol). After the mixture was degassed with N$_2$ for 10 minutes, PdCl$_2$(dppf) (19.9 mg, 0.027 mmol) was added. The mixture was heated at 80° C. overnight. The mixture was partitioned between EtOAc and water. The organic phase was concentrated and purified by ISCO silica gel column. Fractions containing product were concentrated to yield ethyl 2-(4-(4,4,5,5-tetramethyl-1,3,2-dioxaborolan-2-yl)cyclohex-3-en-1-yl)propanoate (168 mg, 60% yield) as a brown oil. $^1$H NMR (400 MHz, CHLOROFORM-d) δ 6.66-6.40 (m, 1H), 4.31-4.00 (m, 2H), 2.34-2.26 (m, 1H), 2.25-2.19 (m, 1H), 2.19-2.04 (m, 2H), 1.95-1.75 (m, 3H), 1.73-1.60 (m, 1H), 1.29-1.24 (m, 15H), 1.13 (dd, J=11.6, 7.0 Hz, 3H)

157F. Ethyl 2-(4-(2-methylpyridin-4-yl)cyclohex-3-en-1-yl)propanoate

To a solution of ethyl 2-(4-(4,4,5,5-tetramethyl-1,3,2-dioxaborolan-2-yl)cyclohex-3-en-1-yl)propanoate (120 mg, 0.389 mmol) in dioxane (3 mL) was added 4-bromo-2-methylpyridine (67.0 mg, 0.389 mmol), water (1 mL) and Na$_2$CO$_3$ (165 mg, 1.557 mmol). The mixture was degassed with N2 for 10 minutes. Pd(Ph$_3$P)$_4$ (22.49 mg, 0.019 mmol) was then added. The mixture was heated to 100° C. for 16 h. The cooled mixture was diluted with EtOAc, washed with water and brine. The solution was dried over Na$_2$SO$_4$, filtered and evaporated. The crude material was purified by ISCO silica gel chromatography (0-50% EtOAc/Hexane). Fractions containing product were concentrated to yield ethyl 2-(4-(2-methylpyridin-4-yl)cyclohex-3-en-1-yl)propanoate (100 mg, 0.366 mmol, 94% yield) as a yellow oil. $^1$H NMR (400 MHz, chloroform-d) δ 8.61-8.11 (m, 1H), 7.09-6.68 (m, 2H), 4.15 (qdd, J=7.1, 3.3, 1.8 Hz, 2H), 2.71-2.57 (m, 1H), 2.53 (d, J=5.3 Hz, 3H), 2.47-2.35 (m, 0.5H), 2.29 (t, J=7.1 Hz, 0.5H), 1.98-1.75 (m, 3H), 1.67-1.38 (m, 4H), 1.32-1.22 (m, 4H), 1.21-1.09 (m, 4H).

157G Ethyl 2-(4-(2-methylpyridin-4-yl)cyclohexyl)propanoate

Ethyl 2-(4-(2-methylpyridin-4-yl)cyclohex-3-en-1-yl)propanoate (100 mg, 0.366 mmol) was dissolved in MeOH (5 mL). Ammonium formate (115 mg, 1.829 mmol) and palladium on carbon (10%) (10.51 mg, 0.099 mmol) were added. The vessel was equipped with a reflux condenser, evacuated and flushed with N$_2$ three times. The reaction was then heated to reflux. After one hour, the reaction was cooled and filtered. The filtrate was concentrated in vacuo. The residue was dissolved in EtOAc, washed with sodium bicarbonate solution, water, and brine. The solution was dried over Na$_2$SO$_4$, filtered and concentrated. The crude product was used directly in the next step.

157H. 2-(4-(2-Methylpyridin-4-yl)cyclohexyl)propanoic acid

To a mixture of ethyl 2-(4-(2-methylpyridin-4-yl)cyclohexyl)propanoate (320 mg, 1.162 mmol) in THF (2 mL), MeOH (2 mL) and water was added LiOH (278 mg, 11.62 mmol). The mixture was heated at 70° C. for 4 h. LC-MS indicated the completion of the reaction. The mixture was cooled to RT, neutralized with 1N HCl until pH-4, and extracted with EtOAc 3 times. The combined organic phases were washed with water and brine. The solution was dried over Na$_2$SO$_4$ and concentrated. $^1$H NMR (400 MHz, chloroform-d) δ 8.41 (d, J=5.3 Hz, 1H), 7.09-6.94 (m, 2H), 2.75-2.59 (m, 1H), 2.54 (d, J=3.5 Hz, 3H), 2.44 (br. s., 1H), 2.35 (t, J=7.0 Hz, 1H), 1.98-1.82 (m, 3H), 1.77-1.61 (m, 4H), 1.56-1.39 (m, 1H), 1.20 (d, J=6.7 Hz, 3H); MS: Anal. Calc'd for C$_{15}$H$_{21}$NO$_2$ 247.16. found [M+H] 248.08 LC: t$_r$=0.55 min.

157I. 1-(4-(2-Methylpyridin-4-yl)cyclohexyl)ethanamine 2-(4-(2-Methylpyridin-4-yl)cyclohexyl)propanoic acid (240 mg, 0.970 mmol) (157B) was taken up in toluene (5 ml) and diphenyl phosphorazidate (0.230 mL, 1.067 mmol) and triethylamine (0.162 mL, 1.164 mmol) were added. The vial was sealed and heated to 70° C. After about 2 h, the reaction was cooled to rt and concentrated under reduced pressure. The crude residue was taken up in 40 mL THF and 40 mL of water and lithium hydroxide (1.589 g, 66.4 mmol) was added. The reaction was stirred at rt. LCMS after 1 hour shows that the isocyanate was consumed. The reaction was acidified with 1N HCl (white precipitate forms) and extracted with EtOAc to remove DPPA related impurities. The solution was made basic with 1N NaOH (precipitate forms again) and extracted with EtOAc (×5). The basic extracts were concentrated in vacuo to give 1-(4-(2-methylpyridin-4-yl)cyclohexyl)ethanamine (140 mg, 0.641 mmol, 66.1% yield) as a yellow oil. $^1$H NMR (400 MHz, chloroform-d) δ 8.65-8.17 (m, 1H), 7.08-6.86 (m, 2H), 2.97 (dd, J=8.6, 6.4 Hz, 0.5H), 2.79-2.62 (m, 1H), 2.52 (d, J=2.8 Hz, 3H), 2.48-2.33 (m, 0.5H), 2.03-1.90 (m, 2H), 1.90-1.68 (m, 4H), 1.50-1.11 (m, 3H), 1.08 (dd, J=6.4, 2.8 Hz, 3H). MS: Anal. Calc'd for C$_{14}$H$_{22}$N$_2$ 218.18. found [M+H] 219.2 LC: t$_r$=0.43 min.

Example 157a

4-Chloro-N-(1-(4-(2-methylpyridin-4-yl)cyclohexyl)ethyl)benzamide

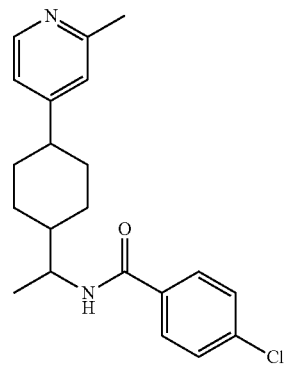 [SMILES: Cc1cc(C2CCC(C(C)NC(=O)c3ccc(Cl)cc3)CC2)ccn1]

To a solution of 1-(4-(2-methylpyridin-4-yl)cyclohexyl)ethanamine (100 mg, 0.458 mmol) (157I) in THF (2 mL) was added 4-chlorobenzoic acid (108 mg, 0.687 mmol), HOBT (140 mg, 0.916 mmol), EDC (176 mg, 0.916 mmol) and TEA (0.192 mL, 1.374 mmol). The mixture was stirred at RT overnight. The reaction mixture was filtered and purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 25-100% B over 20 minutes, then a 4-minute hold at 100% B; Flow: 20 mL/min. Fractions containing the desired product were combined and dried via centrifugal evaporation to yield 4-chloro-N-(1-(4-(2-methylpyridin-4-yl)cyclohexyl)ethyl)benzamide (136.8 mg, 84% yield). $^1$H NMR (500 MHz, DMSO-d$_6$) δ 8.52-8.20 (m, 2H), 7.84 (dd, J=10.6, 8.7 Hz, 2H), 7.52 (dd, J=8.4, 2.4 Hz, 2H), 7.27-6.85 (m, 2H), 4.24 (br. s., 0.5H), 3.87 (d, J=7.4 Hz, 0.5H), 3.62-3.37 (m, 1H), 2.42 (d, J=9.1 Hz, 3H), 1.94-1.31 (m, 8H), 1.20-1.02 (m, 4H).

Example 157b, c, d, e

4-Chloro-N-(1-(4-(2-methylpyridin-4-yl)cyclohexyl)ethyl)benzamide (Homochiral with Absolute and Relative Stereochemistry not Determined)

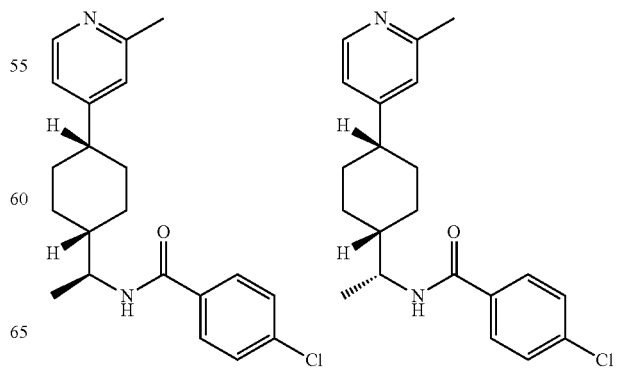

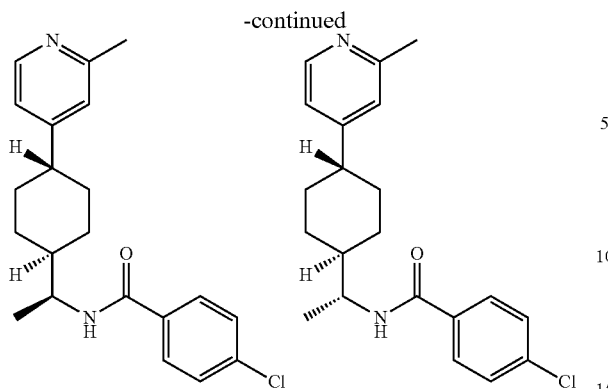

The material was further purified through chiral separation. An approximately 140 mg sample was resolved. The material was purified via preparative SFC with the following conditions: Column: Chiral AD 25×3 cm ID, 5-µm particles; Mobile Phase: 70/30 $CO_2$/MeOH; Detector Wavelength: 220 nm; Flow: 85 mL/min. The fractions ("Peak-1" $t_r$=10.117, "Peak-2" $t_r$=11.355, "Peak-3" $t_r$=14.873 and "Peak-4" $t_r$=18.312; analytical conditions: Column: Chiral AD 250×4.6 mm ID, 5 µm particles; Mobile Phase: 70/30 $CO_2$/MeOH Flow: 2.0 mL/min) were collected in MeOH.

157b First eluting isomer: $^1$H NMR (500 MHz, DMSO-$d_6$) δ 8.44-8.18 (m, 2H), 7.84 (d, J=8.3 Hz, 2H), 7.52 (d, J=8.3 Hz, 2H), 7.24-6.96 (m, 2H), 4.26 (d, J=6.9 Hz, 1H), 2.60 (br. s., 1H), 2.43 (s, 3H), 1.84-1.36 (m, 9H), 1.14 (d, J=6.5 Hz, 3H). MS: Anal. Calc'd for $C_{21}H_{25}ClN_2O$, 356.17. found [M+H] 357.0 LC: $t_r$=1.826 (Method A).

157c Second eluting isomer: $^1$H NMR (500 MHz, DMSO-$d_6$) δ 8.48-8.19 (m, 2H), 7.81 (d, J=8.3 Hz, 2H), 7.50 (d, J=8.3 Hz, 2H), 7.27-6.82 (m, 2H), 4.24 (d, J=6.9 Hz, 1H), 2.60 (br. s., 1H), 2.42 (s, 3H), 1.83-1.37 (m, 9H), 1.13 (d, J=6.4 Hz, 3H). MS: Anal. Calc'd for $C_{21}H_{25}ClN_2O$, 356.17. found [M+H] 356.9 LC: t, =1.864 (Method A).

157d Third eluting isomer: $^1$H NMR (500 MHz, DMSO-$d_6$) δ 8.28 (d, J=5.6 Hz, 2H), 7.86 (d, J=8.4 Hz, 2H), 7.52 (d, J=8.4 Hz, 2H), 7.23-6.87 (m, 2H), 3.87 (d, J=6.4 Hz, 1H), 2.40 (s, 4H), 1.96-1.71 (m, 4H), 1.58-1.28 (m, 3H), 1.21-0.99 (m, 5H). MS: Anal. Calc'd for $C_{21}H_{25}ClN_2O$, 356.17. found [M+H] 356.9 LC: $t_r$=1.857 (Method A).

157e Fourth eluting isomer: $^1$H NMR (500 MHz, DMSO-$d_6$) δ 8.28 (d, J=4.9 Hz, 2H), 7.86 (d, J=8.3 Hz, 2H), 7.52 (d, J=8.3 Hz, 2H), 7.24-6.84 (m, 2H), 4.06-3.74 (m, 1H), 2.46-2.28 (m, 4H), 1.95-1.71 (m, 4H), 1.61-1.29 (m, 3H), 1.21-1.02 (m, 5H) MS: Anal. Calc'd for $C_{21}H_{25}ClN_2O$, 356.17. found [M+H] 356.8 LC: $t_r$=1.857 (Method A).

The following compounds were obtained using the procedures in Example 157.

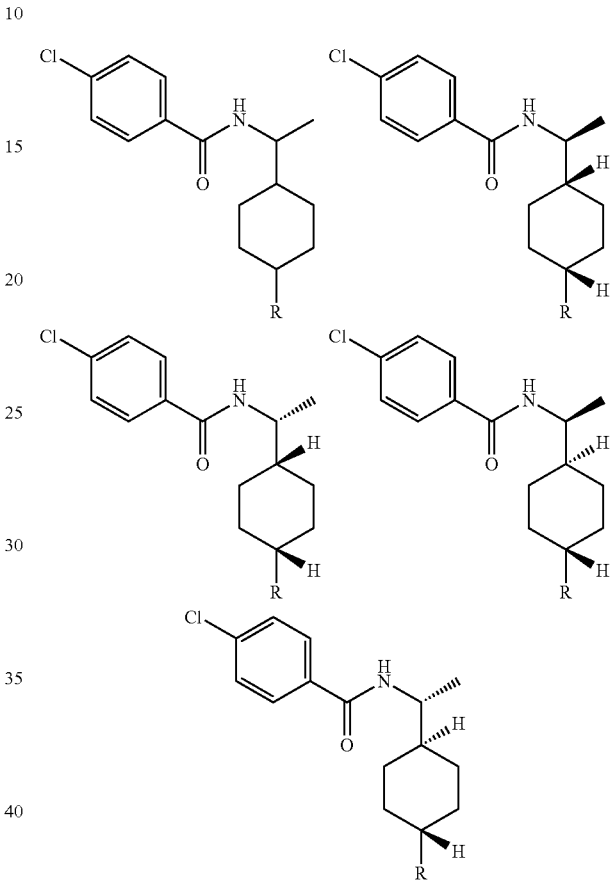

| Ex. No. | Name | R | Tr $(min)^{Method}$ | $[M + H]^+$ | Stereochemistry |
|---|---|---|---|---|---|
| 158a | 4-chloro-N-(1-(4-(2-fluoro-3-methylpyridin-4-yl)cyclohexyl)ethyl)benzamide | | $2.075^A$ | 375.2 | Diastereomer Mixture |
| 158b | 4-chloro-N-(1-(4-(2-fluoro-3-methylpyridin-4-yl)cyclohexyl)ethyl)benzamide | | $14.485^W$ | 375.1 | Homochiral with absolute and relative stereochemistry not determined |

-continued

| Ex. No. | Name | R | Tr (min)$^{Method}$ | [M + H]$^+$ | Stereochemistry |
|---|---|---|---|---|---|
| 158c | 4-chloro-N-(1-(4-(2-fluoro-3-methylpyridin-4-yl)cyclohexyl)ethyl)benzamide | 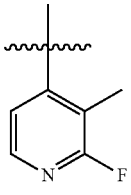 [SMILES: *c1ccnc(F)c1C] | 17.193$^W$ | 375.2 | Homochiral with absolute and relative stereochemistry not determined |
| 158d | 4-chloro-N-(1-(4-(2-fluoro-3-methylpyridin-4-yl)cyclohexyl)ethyl)benzamide | 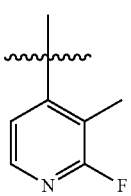 [SMILES: *c1ccnc(F)c1C] | 19.497$^W$ | 375.2 | Homochiral with absolute and relative stereochemistry not determined |
| 158e | 4-chloro-N-(1-(4-(2-fluoro-3-methylpyridin-4-yl)cycloheyxl)ethyl)benzamide | 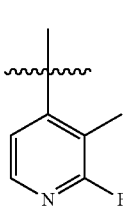 [SMILES: *c1ccnc(C)c1C] | 21.901$^W$ | 375.1 | Homochiral with absolute and relative stereochemistry not determined) |
| 159a | 4-chloro-N-(1-(4-(2,3-dimethylpyridin-4-yl)cyclohexyl)ethyl)benzamide | 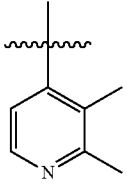 [SMILES: *c1ccnc(C)c1C] | 1.899$^A$ | 370.9 | Diastereomer Mixture |
| 159b | 4-chloro-N-(1-(4-(2,3-dimethylpyridin-4-yl)cyclohexyl)ethyl)benzamide | 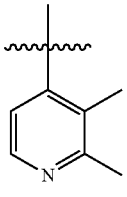 [SMILES: *c1ccnc(C)c1C] | 7.917$^X$ | 371.3 | Homochiral with absolute and relative stereochemistry not determined) |
| 159c | 4-chloro-N-(1-(4-(2,3-dimethylpyridin-4-yl)cyclohexyl)ethyl)benxamide | 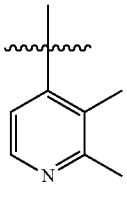 [SMILES: *c1ccnc(C)c1C] | 8.920$^X$ | 371.2 | Homochiral with absolute and relative stereochemistry not determined) |
| 159d | 4-chloro-N-(1-(4-(2,3-dimethylpyridin-4-yl)cyclohexyl)ethyl)benzamide | 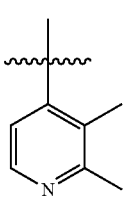 | 10.505$^X$ | 371.2 | Homochiral with absolute and relative stereochemistry not determined) |

| Ex. No. | Name | R | Tr (min)$^{Method}$ | [M + H]$^+$ | Stereochemistry |
|---|---|---|---|---|---|
| 159e | 4-chloro-N-(1-(4-(2,3-dimethylpyridin-4-yl)cyclohexyl)ethyl)benzamide | 2,3-dimethylpyridin-4-yl | 11.426$^X$ | 371.2 | Homochiral with absolute and relative sterochemistry not determined) |
| 160a | 4-chloro-N-(1-(4-(3-methylpyridin-4-yl)cyclohexyl)ethyl)benzamide | 3-methylpyridin-4-yl | 1.912$^A$ | 357.2 | Diastereomer Mixture |
| 160b | 4-chloro-N-(1-(4-(3-methylpyridin-4-yl)cyclohexyl)ethyl)benzamide | 3-methylpyridin-4-yl | 10.662$^O$ | 357.3 | Homochiral with absolute and relative stereochemistry not determined) |
| 160c | 4-chloro-N-(1-(4-(3-methylpyridin-4-yl)cyclohexyl)ethyl)benzamide | 3-methylpyridin-4-yl | 13.158$^Y$ | 357.2 | Homochiral with absolute and relative stereochemistry not deterermined) |
| 160d | 4-chloro-N-(1-(4-(3-methylpyridin-4-yl)cyclohexyl)ethyl)benzamide | 3-methylpyridin-4-yl | 14.889$^Y$ | 357.2 | Homochiral with absolute and relative stereochemistry not determined) |
| 160e | 4-chloro-N-(1-(4-(3-methylpyridin-4-yl)cyclohexyl)ethyl)benzamide | 3-methylpyridin-4-yl | 19.795$^Y$ | 357.3 | Homochiral with absolute and relative stereochemistry not determined) |
| 161a | 4-choro-N-(1-(4-(3-fluoropyridin-4-yl)cyclohexyl)ethyl)benzamide | 3-fluoropyridin-4-yl | 7.542$^Z$ | 361.2 | Homochiral with absolute and relative stereochemistry not determined) |

-continued

| Ex. No. | Name | R | Tr (min)^Method | [M + H]+ | Stereochemistry |
|---|---|---|---|---|---|
| 161b | 4-chloro-N-(1-(4-_(3-fluoropyridin-4-yl)cyclohexyl)ethyl)benzamide | 3-fluoropyridin-4-yl | 8.044^Z | 361.4 | Homochiral with absolute and relative stereochemistry not determined) |
| 161c | 4-chloro-N-(1-(4-(3-fluoropyridin-4-yl)cyclohexyl)ethyl)benzamide | 3-fluoropyridin-4-yl | 10.057^Z | 361.2 | Homochiral with absolute and relative stereochemistry not determined) |
| 161d | 4-chloro-N-(1-(4-(3-fluoropyridin-4-yl)cyclohexyl)ethyl)benzamide | 3-fluoropyridin-4-yl | 11.177^Z | 361.3 | Homochiral with absolute and relative sterochemistry not determined) |

Example 163

5-Ethoxy-N—((R)-1-(cis-4-(6-fluoroquinolin-4-yl)cyclohexyl)ethyl)picolinamide

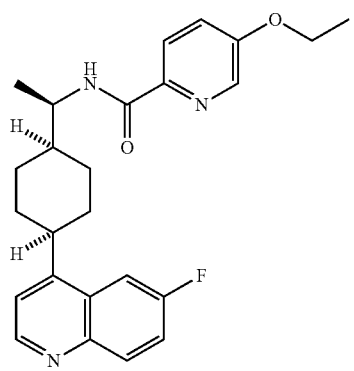 [SMILES: CCOc1ccc(C(=O)N[C@H](C)[C@H]2CC[C@@H](c3ccnc4ccc(F)cc43)CC2)nc1]

163A. Methyl 5-ethoxypicolinate

To a solution of methyl 5-hydroxypicolinate (0.1 g, 0.653 mmol) in DMF (2 mL) were added EtI (0.06 mL, 0.72 mmol), and $K_2CO_3$ (0.135 g, 0.980 mmol). The reaction mixture was stirred at rt for 2 h. The reaction mixture was diluted with saturated $NaHCO_3$ solution and ethyl acetate. The organic layer was separated and concentrated in vacuo to give Intermediate 163A (white solid, 0.09 g, 0.497 mmol, 76% yield). LC-MS Anal. Calc'd for $C_9H_{11}NO_3$ 181.07. found [M+H] 182.1, $T_r$=0.66 min (Method A). $^1$H NMR (400 MHz, methanol-$d_4$) δ: 8.29 (d, J=2.6 Hz, 1H), 8.11 (dd, J=8.6, 0.4 Hz, 1H), 7.48 (dd, J=8.7, 3.0 Hz, 1H), 4.20 (q, J=7.0 Hz, 2H), 3.94 (s, 3H), 1.45 (t, J=6.9 Hz, 3H).

163B. 5-Ethoxypicolinic acid

To a solution of methyl 5-ethoxypicolinate (0.09 g, 0.497 mmol) in THF (1 mL) and MeOH (1 mL) was added lithium hydroxide solution (1.49 mL, 2.98 mmol). The reaction mixture was stirred at rt for 3 h. The reaction mixture was diluted with 1 N HCl solution and ethyl acetate. The organic layer was separated and dried over $MgSO_4$. The filtrate was concentrated in vacuo to give Intermediate 163B (white solid, 0.06 g, 0.359 mmol, 72.3% yield). LC-MS Anal. Calc'd for $C_8H_9NO_3$ 167.06. found [M+H] 168.1, $T_r$=0.49 min (Method A). $^1$H NMR (400 MHz, DMSO-$d_6$) δ: 12.75 (br. s., 1H), 8.35 (d, J=2.6 Hz, 1H), 8.01 (d, J=8.6 Hz, 1H), 7.48 (dd, J=8.8, 2.9 Hz, 1H), 4.19 (q, J=6.9 Hz, 2H), 1.37 (t, J=6.9 Hz, 3H)

Example 163

5-Ethoxy-N—((R)-1-(cis-4-(6-fluoroquinolin-4-yl)cyclohexyl)ethyl)picolinamide

To a solution of 5-ethoxypicolinic acid (14.36 mg, 0.086 mmol) in DMF (1 mL) was added HATU (33 mg, 0.086 mmol). The reaction mixture was stirred at rt for 5 min, followed by addition of (R)-1-(cis-4-(6-fluoroquinolin-4-yl)cyclohexyl)ethanamine (18 mg, 0.066 mmol) Intermediate 40L and N-methylmorpholine (0.032 mL, 0.264 mmol). The resulting mixture was stirred at rt for 2 h. The reaction mixture was concentrated in vacuo and the residue was dissolved in MeOH, filtered, and purified via preparative HPLC to give Example 163 (16 mg, 0.038 mmol, 57% yield). LC-MS Anal. Calc'd for $C_{25}H_{28}FN_3O_2$ 421.22. found [M+H] 422.3. $T_r$=1.63 min (Method I). $^1$H NMR (500

MHz, DMSO-d$_6$) δ: 8.81 (d, J=4.4 Hz, 1H), 8.36 (d, J=9.6 Hz, 1H), 8.26 (d, J=2.4 Hz, 1H), 8.07 (dd, J=9.1, 5.8 Hz, 1H), 7.99-7.85 (m, 2H), 7.73-7.59 (m, 1H), 7.55-7.39 (m, 2H), 4.39 (d, J=6.6 Hz, 1H), 4.14 (q, J=6.9 Hz, 2H), 3.71-3.52 (m, 1H), 1.94-1.52 (m, 9H), 1.34 (t, J=6.9 Hz, 3H), 1.19 (d, J=6.4 Hz, 3H).

Example 164a, b, c, d

4-Chloro-N—((R)-1-(cis-4-(6-fluoroquinolin-4-yl)cyclohexyl)propyl)benzamide 4-Chloro-N—((S)-1-(cis-4-(6-fluoroquinolin-4-yl)cyclohexyl)propyl)benzamide 4-Chloro-N—((R)-1-(trans-4-(6-fluoroquinolin-4-yl)cyclohexyl)propyl)benzamide 4-Chloro-N—((S)-1-(trans-4-(6-fluoroquinolin-4-yl)cyclohexyl)propyl)benzamide (Homochiral with Absolute and Relative Stereochemistry not Determined)

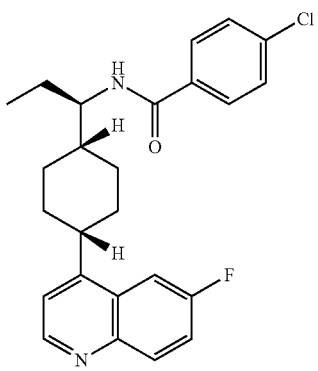

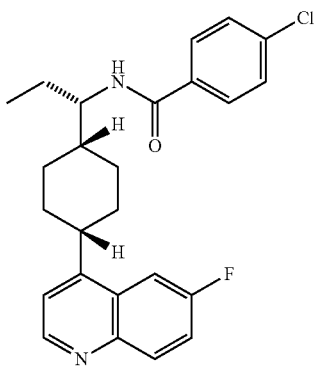

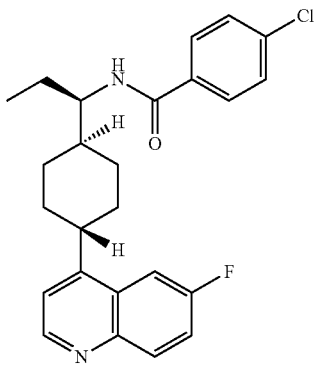

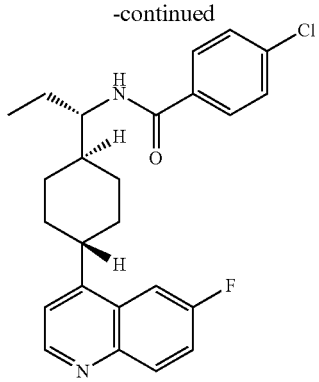

164A. Ethyl 2-(1,4-dioxaspiro[4.5]decan-8-ylidene)acetate

To the flask containing sodium hydride (46.1 g, 1153 mmol) was added THF (1200 mL) at 0° C. under nitrogen. Then triethyl phosphonoacetate (258 g, 1153 mmol) was added dropwise. The reaction mixture was stirred at 0° C. for 30 minutes. Then 1,4-dioxaspiro[4.5]decan-8-one (150 g, 960 mmol) was added and stirred at 0° C. for 2 h. The reaction mixture was warmed to rt and stirred for 16 h. The reaction was quenched with water (500 mL) and the mixture was concentrated in vacuo. The residue was extracted with ethyl acetate (3×1000 mL). The combined, organic layers were washed with water (500 mL) and brine (500 mL) successively. The filtrate was dried over sodium sulfate and concentrated in vacuo. The crude material was purified through flash column chromatography, eluting with 0-30% ethyl acetate in petroleum ether to give Intermediate 164A (pale yellow oil, 135 g, 597 mmol, 62.1% yield). LC-MS Anal. Calc'd for $C_{12}H_{18}O_4$, 226.12 found [M+H]. $^1$H NMR (400 MHz, chloroform-d) δ: 5.66 (s, 1H), 4.14 (q, J=7.2 Hz, 2H), 4.02-3.82 (m, 4H), 3.24-2.86 (m, 2H), 2.63-2.27 (m, 2H), 1.98-1.68 (m, 4H), 1.27 (t, J=7.2 Hz, 3H).

164B. Ethyl 2-(1,4-dioxaspiro[4.5]decan-8-yl)acetate

Ethyl 2-(1,4-dioxaspiro[4.5]decan-8-ylidene)acetate (13.88 g, 61.3 mmol) was taken up in EtOAc (61.3 ml) and was added to a Parr hydrogenation bottle containing 10% palladium on carbon (1.306 g, 12.27 mmol) (54% w/w water) under an atmosphere of nitrogen. The reaction bottle was purged with nitrogen, then with hydrogen. After filling the bottle with hydrogen to 50 psi, the bottle was placed in a Parr shaker and shaken. After 4 hours, the reaction mixture was filtered over pressed CELITE® and concentrated in vacuo to give Intermediate 164B ethyl 2-(1,4-dioxaspiro[4.5]decan-8-yl)acetate (colorless oil, 13.78 g, 60.4 mmol, 98% yield). LC-MS Anal. Calc'd for $C_{12}H_{20}O_4$ 228.14. found [M+H] 229.1. $T_r$=0.83 min (Method A). $^1$H NMR (400 MHz, chloroform-d) δ: 4.31-4.08 (m, 2H), 4.00-3.86 (m, 4H), 2.22 (d, J=7.0 Hz, 2H), 1.91-1.79 (m, 1H), 1.78-1.70 (m, 4H), 1.63-1.50 (m, 2H), 1.37-1.14 (m, 5H).

164C. Ethyl 2-(4-oxocyclohexyl)acetate

In a 10 liter reactor was taken ethyl 2-(1,4-dioxaspiro[4.5]decan-8-yl)acetate (67.5 g, 296 mmol) in acetone (5000 mL). To the reaction mixture was added 1 M HCl solution (1183 mL, 1183 mmol) and the resulting mixture was heated under reflux for 2 h. The reaction mixture was concentrated to remove acetone. The residue was extracted with ethyl acetate (3×1000 mL). Combined organic layer was washed with water and brine. The organic layer was dried over sodium sulfate and concentrated in vacuo. The crude material was purified through flash column chromatography, eluting with 0-20% ethyl acetate in petroleum ether to give Intermediate 164C (pale yellow liquid, 40 g, 217 mmol, 73.4% yield). GC-MS Anal. Calc'd for $C_{10}H_{16}O_3$, 184.11 found [M] 184. $T_r$=10.03 min (Method J).

164D. Ethyl 2-(4-(trifluoromethylsulfonyloxy)cyclohex-3-enyl)acetate

A 2 liter 4 neck flask was charged with 2,6-di-tert-butyl-4-methylpyridine (84 g, 407 mmol) in dichloromethane (500 mL) under nitrogen. $Tf_2O$ (55.0 mL, 326 mmol) was added dropwise. Then a solution of ethyl 2-(4-oxocyclohexyl) acetate (50 g, 271 mmol) in dichloromethane (500 mL) was added slowly. After completion of the addition, the reaction mixture was stirred at rt overnight. The reaction mixture was diluted with 1000 mL of dichloromethane and washed with water and sodium carbonate solution and then water. The organic layer was dried over sodium sulfate and concentrated in vacuo. The crude material was purified through flash column chromatography, eluting with 0-10% ethyl acetate in petroleum ether to give Intermediate 164D (pale yellow oil, 65 g, 206 mmol, 76% yield). GC-MS Anal. Calc'd for $C_{11}H_{15}F_3O_5S$, 316.06 found [M] 317. $T_r$=10.16 min (Method J).

164E. Ethyl 2-(4-(4,4,5,5-tetramethyl-1,3,2-dioxaborolan-2-yl)cyclohex-3-enyl)acetate In 2 liter 4 neck flask was taken ethyl 2-(4-(((trifluoromethyl)sulfonyl)oxy)cyclohex-3-en-1-yl)acetate (120 g, 379 mmol), BISPIN (106 g, 417 mmol), and potassium acetate (112 g, 1138 mmol) in 1,4-dioxane (1200 mL) under nitrogen. Nitrogen was purged inside the reaction mixture for 10 minutes. Then 1,1'-bis(diphenylphosphino)ferrocene-palladium dichloride dichloromethane complex (15.49 g, 18.97 mmol) was added. The reaction mixture was heated at 80° C. for 16 h. The reaction mixture was concentrated. The residue was partitioned between ethyl acetate and water, filtered through CELITE® bed. The organic layer was separated and the aqueous layer was extracted with ethyl acetate (3×). Combined organic layer was washed with water, brine, and dried over sodium sulfate and concentrated in vacuo. The crude material was purified through flash column chromatography, eluting with 0-10% ethyl acetate in petroleum ether to give Intermediate 164E (pale yellow oil, 56 g, 190 mmol, 50.2% yield). GC-MS Anal. Calc'd for $C_{16}H_{27}BO_4$, 294.20 found [M] 295.3. $T_r$=1.10 min (Method A). $^1$H NMR (400 MHz, chloroform-d) δ: 6.52 (dd, J=4.1, 1.9 Hz, 1H), 4.14 (q, J=7.1 Hz, 2H), 2.62-1.97 (m, 6H), 1.94-1.68 (m, 2H), 1.33-1.21 (m, 16H).

164F. Ethyl 2-(4-(6-fluoroquinolin-4-yl)cyclohex-3-en-1-yl)acetate

Ethyl 2-(4-(4,4,5,5-tetramethyl-1,3,2-dioxaborolan-2-yl) cyclohex-3-en-1-yl)acetate (Intermediate 164E) (5 g, 17.00 mmol) was taken up in dioxane (28.3 ml) and water (7.08 ml). 4-Chloro-6-fluoroquinoline (2.57 g, 14.15 mmol) was added followed by $K_2CO_3$ (5.87 g, 42.5 mmol). Mixture was bubbled with nitrogen gas for 5 minutes before the addition of $Pd(Ph_3P)_4$ (0.327 g, 0.283 mmol). After the addition, the reaction was evacuated and backfilled with $N_2$ three times and then sealed (sealed vial parafilmed) and heated to 100° C. for 16 hours. The reaction was concentrated in vacuo and purified directly via silica gel flash column chromatography to give Intermediate 164F (4.22 g, 13.47 mmol, 95% yield). LC-MS Anal. Calc'd for $C_{19}H_{20}FNO_2$ 313.15. found [M+H] 314.1 $T_r$=0.75 min (Method A).

164G. Ethyl 2-(4-(6-fluoroquinolin-4-yl)cyclohexyl)acetate

Intermediate 164F (4.22 g, 13.47 mmol) was dissolved in MeOH (67.3 ml) and ammonium formate (4.25 g, 67.3 mmol) was added. The vessel was equipped with a reflux condenser and evacuated and flushed with nitrogen gas 3 times. Then palladium on carbon (0.143 g, 1.347 mmol) (wet, Degussa type) was added and the reaction was heated to reflux for 1 hour. The reaction was cooled, concentrated in vacuo, and diluted with DCM. Solids were filtered off and the filtrate was concentrated to give crude Intermediate 164G (4.20 g, 13.32 mmol, 99% yield) as a mixture of cis- and trans-diastereomers. LC-MS Anal. Calc'd for $C_{19}H_{22}FNO_2$ 315.16. found [M+H] 316.2 $T_r$=0.76 min (Method A).

164H. Ethyl 2-(4-(6-fluoroquinolin-4-yl)cyclohexyl)butanoate

To the flask containing THF (6 mL) was added lithium diisopropylamide (2.0 M solution in THF) (3.17 mL, 6.34 mmol) at −78° C., followed by addition of 1,3-dimethyltetrahydropyrimidin-2(1H)-one (0.573 mL, 4.76 mmol) and a solution of ethyl 2-(4-(6-fluoroquinolin-4-yl)cyclohexyl)acetate (1.0 g, 3.17 mmol) in THF (10 mL) dropwise at −78° C. The resulting mixture turned into a brown solution and was stirred at −78° C. for 1 h, then iodoethane (0.51 mL, 6.34 mmol) was added slowly. The reaction mixture was then stirred at ice bath temperature for 1 h, warmed to rt overnight. The reaction was quenched by pouring into water and extracting with EtOAc. The combined organic layers were washed with brine, dried with $MgSO_4$, filtered and concentrated in vacuo. The residue was dissolved in DCM and purified by silica gel flash chromatography, eluting with 0-20% ethyl acetate in hexane to give Intermediate 164H (oil, 0.81 g, 2.359 mmol, 74.4% yield). LC-MS Anal. Calc'd for $C_{21}H_{26}FNO_2$, 343.19 found [M+H] 344.3. $T_r$=0.87-0.88 min (Method A). $^1$H NMR (400 MHz, chloroform-d) δ: 8.88-8.77 (m, 1H), 8.18-8.06 (m, 1H), 7.66 (dd, J=10.6, 2.6 Hz, 1H), 7.47 (ddd, J=9.2, 8.0, 2.9 Hz, 1H), 7.36 (d, J=4.6 Hz, 1H), 4.25-4.15 (m, 2H), 3.34-3.09 (m, 1H), 2.70-2.16 (m, 1H), 2.13-1.49 (m, 13H), 1.36-1.24 (m, 3H), 1.00-0.90 (m, 3H).

164I. 2-(4-(6-Fluoroquinolin-4-yl)cyclohexyl)butanoic acid

To a solution of ethyl 2-(4-(6-fluoroquinolin-4-yl)cyclohexyl)butanoate (0.81 g, 2.359 mmol) in THF (4 mL) and MeOH (7 mL) was added 2.0 M LiOH solution (7.1 mL, 14.2 mmol) slowly. The reaction mixture was stirred at rt overnight. The next day, more LiOH solution (7.1 mL, 14.2 mmol) was added to the reaction and the resulting mixture was heated at 70° C. for 28 h. The reaction mixture was cooled and ethyl acetate was added. The aqueous layer was separated and to the aqueous layer was added 1N HCl solution to adjust pH to 5-6. The resulting mixture was diluted with water and $CHCl_3$: 2-propanol (2:1). The organic layer was separated and dried over $MgSO_4$. The filtrate was concentrated in vacuo to give Intermediate 164I as a mixture of cis- and trans-(3:2) isomers (0.64 g, 2.029 mmol, 86% yield). LC-MS Anal. Calc'd for $C_{19}H_{22}FNO_2$ 315.16 found [M+H] 316.3. $T_r$=0.72 min (Method A). $^1$H NMR (400 MHz, chloroform-d) δ: 8.83 (d, J=4.4 Hz, 1H), 8.30-8.03 (m, 1H), 7.67 (dd, J=10.6, 2.4 Hz, 1H), 7.48 (ddd, J=9.2, 7.9, 2.6

Hz, 1H), 7.38 (d, J=4.6 Hz, 1H), 7.32-7.27 (m, 1H), 3.37-3.07 (m, 1H), 2.77-2.21 (m, 1H), 2.11-1.30 (m, 11H), 1.07-1.00 (m, 3H).

164J. 1-(4-(6-Fluoroquinolin-4-yl)cyclohexyl)propan-1-amine

To a suspension of 2-(4-(6-fluoroquinolin-4-yl)cyclohexyl)butanoic acid (0.31 g, 0.983 mmol) in toluene (8 mL) were added diphenylphosphoryl azide (0.245 mL, 1.13 mmol) and triethylamine (0.15 mL, 1.28 mmol). The reaction mixture turned into clear solution after addition of TEA. The vial was sealed and heated to 70° C. for 2.5 h. The reaction mixture was concentrated under reduced pressure. To the residue was added THF (10 mL) and 2.0 M lithium hydroxide solution (4.91 mL, 9.83 mmol) and the resulting mixture was stirred at rt for 1 h. The reaction mixture was acidified with 1N HCl (white precipitate forms) and extracted with EtOAc to remove DPPA related impurities. Then the aqueous layer was basified with 1N NaOH (precipitate forms again) and extracted with EtOAc four times. The basic extracts were combined, dried over MgSO$_4$ and the filtrate was concentrated in vacuo to give colorless oil as a mixture of cis- and trans-, dried on high vacuum over night to give Intermediate 164J (oil, 0.245 g, 0.855 mmol, 87% yield). LC-MS Anal. Calc'd for $C_{18}H_{23}FN_2$ 286.19. found [M+H] 287.3. T$_r$=0.54 min, 0.55 min (Method A). $^1$H NMR (400 MHz, chloroform-d) δ: 8.81 (d, J=4.6 Hz, 1H), 8.12 (dd, J=9.1, 5.8 Hz, 1H), 7.67 (dd, J=10.6, 2.6 Hz, 1H), 7.47 (ddd, J=9.2, 8.0, 2.9 Hz, 1H), 7.37-7.28 (m, 1H), 3.41-3.09 (m, 1H), 2.97-2.50 (m, 1H), 2.19-1.23 (m, 11H), 1.06-0.93 (m, 3H).

Example 164

4-Chloro-N-(1-(4-(6-fluoroquinolin-4-yl)cyclohexyl)propyl)benzamide

To a solution of 4-chlorobenzoic acid (42.6 mg, 0.272 mmol) in DMF (2 mL) was added HATU (104 mg, 0.272 mmol). The reaction mixture was stirred at rt for 10 min, followed by addition of 1-(4-(6-fluoroquinolin-4-yl)cyclohexyl)propan-1-amine (60 mg, 0.210 mmol) (Intermediate 164J) in THF (0.5 mL) and N-methyl morpholine (0.10 mL, 0.838 mmol). The resulting mixture was stirred at rt for 2 h. The reaction mixture was concentrated in vacuo and the residue was dissolved in MeOH, filtered, and purified via preparative HPLC to give a mixture containing the four isomers. The isomers were further separated by preparative SFC (Method C) to give:

First eluting Example 164a (15 mg, 0.035 mmol, 16.7% yield). LC-MS Anal. Calc'd for $C_{25}H_{26}ClFN_2O$, 424.17 found [M+H] 424.9 T$_r$=1.57 min (Method I). $^1$H NMR (500 MHz, DMSO-d$_6$) δ: 8.82 (d, J=3.9 Hz, 1H), 8.19 (d, J=9.1 Hz, 1H), 8.12-8.03 (m, 1H), 7.94 (d, J=10.3 Hz, 1H), 7.86 (d, J=8.0 Hz, 2H), 7.65 (t, J=7.9 Hz, 1H), 7.52 (d, J=8.0 Hz, 2H), 7.46 (d, J=3.5 Hz, 1H), 4.27 (d, J=8.0 Hz, 1H), 3.37 (br. s., 1H), 1.92-1.54 (m, 10H), 1.40 (d, J=6.2 Hz, 1H), 0.86 (t, J=6.9 Hz, 3H).

Second eluting Example 164b (8.6 mg, 0.020 mmol, 9.6% yield). LC-MS Anal. Calc'd for $C_{25}H_{26}ClFN_2O$, 424.17 found [M+H] 424.9 T$_r$=1.55 min (Method I). $^1$H NMR (500 MHz, DMSO-d$_6$) δ: 8.78 (d, J=4.5 Hz, 1H), 8.17 (d, J=9.0 Hz, 1H), 8.07 (dd, J=9.0, 5.8 Hz, 1H), 7.97 (d, J=9.0 Hz, 1H), 7.90 (d, J=8.3 Hz, 2H), 7.71-7.59 (m, 1H), 7.54 (d, J=8.3 Hz, 2H), 7.43 (d, J=4.4 Hz, 1H), 3.80 (br. s., 1H), 3.27 (t, J=11.3 Hz, 1H), 1.97-1.81 (m, 4H), 1.74-1.29 (m, 7H), 0.86 (t, J=7.2 Hz, 3H).

Third eluting Example 164c (6.5 mg, 0.015 mmol, 6.9% yield). LC-MS Anal. Calc'd for $C_{25}H_{26}ClFN_2O$, 424.17 found [M+H] 425.0 T$_r$=1.55 min (Method I). $^1$H NMR (500 MHz, DMSO-d$_6$) δ: 8.78 (d, J=4.4 Hz, 1H), 8.17 (d, J=9.1 Hz, 1H), 8.07 (dd, J=8.9, 5.8 Hz, 1H), 7.97 (d, J=8.9 Hz, 1H), 7.90 (d, J=8.3 Hz, 2H), 7.71-7.60 (m, 1H), 7.54 (d, J=8.3 Hz, 2H), 7.43 (d, J=4.3 Hz, 1H), 3.81 (br. s., 1H), 3.36-3.21 (m, 1H), 1.90 (d, J=12.5 Hz, 4H), 1.73-1.28 (m, 7H), 0.86 (t, J=7.1 Hz, 3H).

Fourth eluting Example 164d (13.9 mg, 0.032 mmol, 15.5% yield). LC-MS Anal. Calc'd for $C_{25}H_{26}ClFN_2O$, 424.17 found [M+H] 425.1 T$_r$=1.58 min (Method I). $^1$H NMR (500 MHz, DMSO-d$_6$) δ: 8.82 (d, J=4.3 Hz, 1H), 8.19 (d, J=9.1 Hz, 1H), 8.08 (dd, J=9.0, 5.9 Hz, 1H), 7.95 (d, J=9.5 Hz, 1H), 7.87 (d, J=8.3 Hz, 2H), 7.65 (t, J=7.4 Hz, 1H), 7.53 (d, J=8.3 Hz, 2H), 7.46 (d, J=4.3 Hz, 1H), 4.28 (d, J=7.8 Hz, 1H), 3.37 (br. s., 1H), 1.92-1.53 (m, 10H), 1.39 (dt, J=14.7, 7.6 Hz, 1H), 0.87 (t, J=7.1 Hz, 3H).

Example 165a, b, c, d

4-Cyano-N—((R)-1-(cis-4-(6-fluoroquinolin-4-yl)cyclohexyl)propyl)benzamide 4-Cyano-N—((S)-1-(cis-4-(6-fluoroquinolin-4-yl)cyclohexyl)propyl)benzamide 4-Cyano-N—((R)-1-(trans-4-(6-fluoroquinolin-4-yl)cyclohexyl)propyl)benzamide 4-Cyano-N—((S)-1-(trans-4-(6-fluoroquinolin-4-yl)cyclohexyl)propyl)benzamide (Homochiral with Absolute and Relative Stereochemistry not Determined)

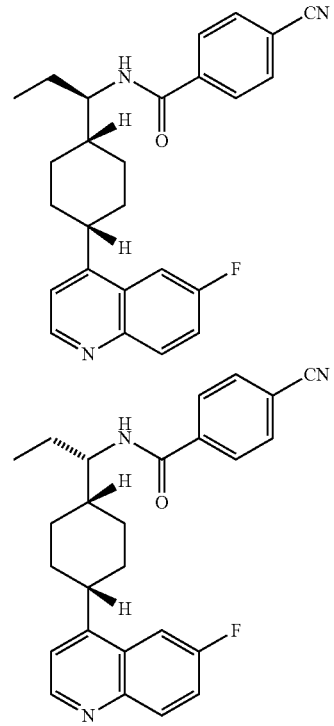

-continued

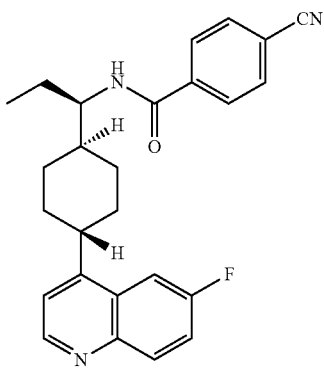

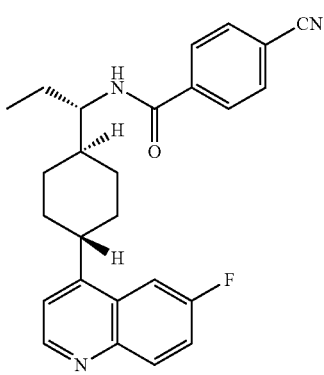

Example 165

4-Cyano-N-(1-(4-(6-fluoroquinolin-4-yl)cyclohexyl)propyl)benzamide

To a solution of 4-cyanobenzoic acid (33.4 mg, 0.227 mmol) in DMF (2 mL) was added HATU (86 mg, 0.227 mmol). The reaction mixture was stirred at rt for 10 min, followed by addition of 1-(4-(6-fluoroquinolin-4-yl)cyclohexyl)propan-1-amine (50 mg, 0.175 mmol) (Intermediate 164J) in THF (0.5 mL) and N-methyl morpholine (0.10 mL, 0.838 mmol). The resulting mixture was stirred at rt for 2 h. The reaction mixture was concentrated in vacuo and the residue was dissolved in MeOH, filtered, and purified via preparative HPLC to give a mixture containing the four isomers. The isomers were further separated by preparative SFC (Method K) to give:

First eluting Example 165a (10.7 mg, 0.025 mmol, 14.6% yield). LC-MS Anal. Calc'd for $C_{26}H_{26}FN_3O$, 415.21 found [M+H] 416.2, $T_r$=1.40 min (Method B). $^1$H NMR (500 MHz, DMSO-$d_6$) δ: 8.82 (d, J=4.4 Hz, 1H), 8.37 (d, J=9.1 Hz, 1H), 8.08 (dd, J=9.0, 5.8 Hz, 1H), 8.02-7.87 (m, 5H), 7.69-7.58 (m, 1H), 7.46 (d, J=4.4 Hz, 1H), 4.29 (d, J=8.2 Hz, 1H), 3.53-3.42 (m, 1H), 1.96-1.56 (m, 10H), 1.50-1.31 (m, 1H), 0.88 (t, J=7.2 Hz, 3H).

Second eluting Example 165b (5.7 mg, 0.014 mmol, 7.8% yield). LC-MS Anal. Calc'd for $C_{26}H_{26}FN_3O$, 415.21 found [M+H] 416.0, $T_r$=1.51 min (Method I). $^1$H NMR (500 MHz, DMSO-$d_6$) δ: 8.78 (d, J=4.5 Hz, 1H), 8.34 (d, J=9.0 Hz, 1H), 8.13-7.99 (m, 3H), 7.99-7.86 (m, 3H), 7.74-7.57 (m, 1H), 7.43 (d, J=4.4 Hz, 1H), 3.81 (br. s., 1H), 3.27 (t, J=11.4 Hz, 1H), 2.00-1.81 (m, 4H), 1.76-1.30 (m, 7H), 0.87 (t, J=7.2 Hz, 3H).

Third eluting Example 165c (5.5 mg, 0.013 mmol, 7.5% yield). LC-MS Anal. Calc'd for $C_{26}H_{26}FN_3O$, 415.21 found [M+H] 416.0, $T_r$=1.51 min (Method I). $^1$H NMR (500 MHz, DMSO-$d_6$) δ: 8.79 (d, J=4.5 Hz, 1H), 8.34 (d, J=8.9 Hz, 1H), 8.13-8.00 (m, 3H), 7.99-7.86 (m, 3H), 7.72-7.55 (m, 1H), 7.43 (d, J=4.5 Hz, 1H), 3.82 (d, J=9.0 Hz, 1H), 3.28 (t, J=11.7 Hz, 1H), 1.99-1.80 (m, 4H), 1.75-1.29 (m, 7H), 0.87 (t, J=7.2 Hz, 3H).

Fourth eluting Example 165d (12 mg, 0.029 mmol, 16.4% yield). LC-MS Anal. Calc'd for $C_{26}H_{26}FN_3O$, 415.21 found [M+H] 416.0, $T_r$=1.52 min (Method I). $^1$H NMR (500 MHz, DMSO-$d_6$) δ: 8.81 (d, J=4.4 Hz, 1H), 8.38 (d, J=9.1 Hz, 1H), 8.08 (dd, J=9.1, 5.8 Hz, 1H), 8.01-7.88 (m, 5H), 7.70-7.60 (m, 1H), 7.47 (d, J=4.4 Hz, 1H), 4.28 (d, J=8.4 Hz, 1H), 3.49-3.28 (m, 1H), 1.96-1.56 (m, 10H), 1.48-1.31 (m, 1H), 0.87 (t, J=7.2 Hz, 3H).

Examples 176 to 196

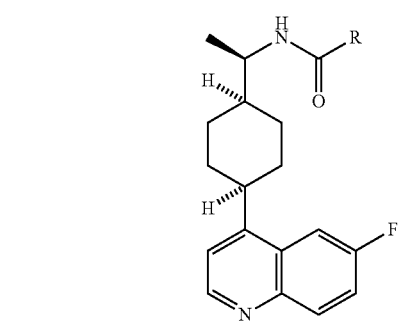

Examples 176 to 196 were prepared from Intermediate 40L following the procedure for Example 164 using the corresponding acid.

| Ex. No. Name | R | Tr (min)$^{Method\ 1*}$ | [M + H]$^+$ |
|---|---|---|---|
| 176 4-cyano-N-((R)-1-(cis-4-(6-fluoroquinolin-4-yl)cyclohexyl)ethyl)benzamide | 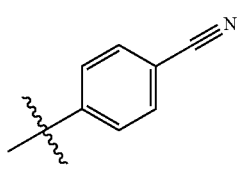 [SMILES: *c1ccc(C#N)cc1] | 1.31 | 402.2 |

-continued
| Ex. No. Name | R | Tr (min)^(Method 1*) | [M + H]+ |
|---|---|---|---|
| 178 5-(3-fluoro-4-methoxyphenyl)-N-((R)-1-(cis-4-(6-fluoroquinolin-4-yl)cyclohexyl)ethyl)picolinamide | 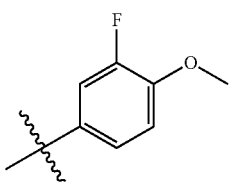 [SMILES: *c1ccc(OC)c(F)c1] | 1.83 | 502.3 |
| 194 (R)-1-(cis-4-(6-fluoroquinolin-4-yl)cyclohexyl)-N-methylethanamine | 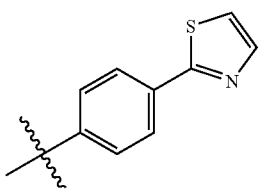 [SMILES: *c1ccc(-c2nccs2)cc1] | 1.40 | 459.9 |
| 195 N-((R)-1-(cis-4-(6-fluoroquinolin-4-yl)cyclohexyl)ethyl)-4-(1H-pyrrol-1-yl)benzamide | 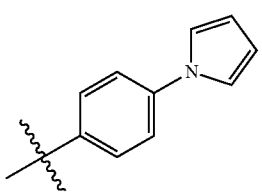 [SMILES: *c1ccc(-n2cccc2)cc1] | 1.56 | 442.0 |
| 196 N-((R)-1-(cis-4-(6-fluoroquinolin-4-yl)cyclohexyl)ethyl)-4-(1H-imidazol-1-yl)benzamide | 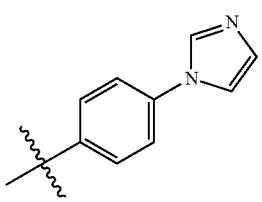 [SMILES: *c1ccc(-n2ccnc2)cc1] | 0.95 | 443.3 |
*unless otherwise noted

Example 197

4-chloro-N-(1-(4-(pyrazolo[1,5-a]pyrimidin-7-yl)cyclohexyl)ethyl)benzamide, 4-chloro-N—((R)-1-(cis-4-(pyrazolo[1,5-a]pyrimidin-7-yl)cyclohexyl)ethyl)benzamide, 4-Chloro-N—((S)-1-(cis-4-(pyrazolo[1,5-a]pyrimidin-7-yl)cyclohexyl)ethyl)benzamide, 4-chloro-N—((R)-1-(trans-4-(pyrazolo[1,5-a]pyrimidin-7-yl)cyclohexyl)ethyl)benzamide, 4-Chloro-N—((S)-1-(trans-4-(pyrazolo[1,5-a]pyrimidin-7-yl)cyclohexyl)ethyl)benzamide Absolute and Relative Stereochemistry Unknown, Arbitrarily Assigned

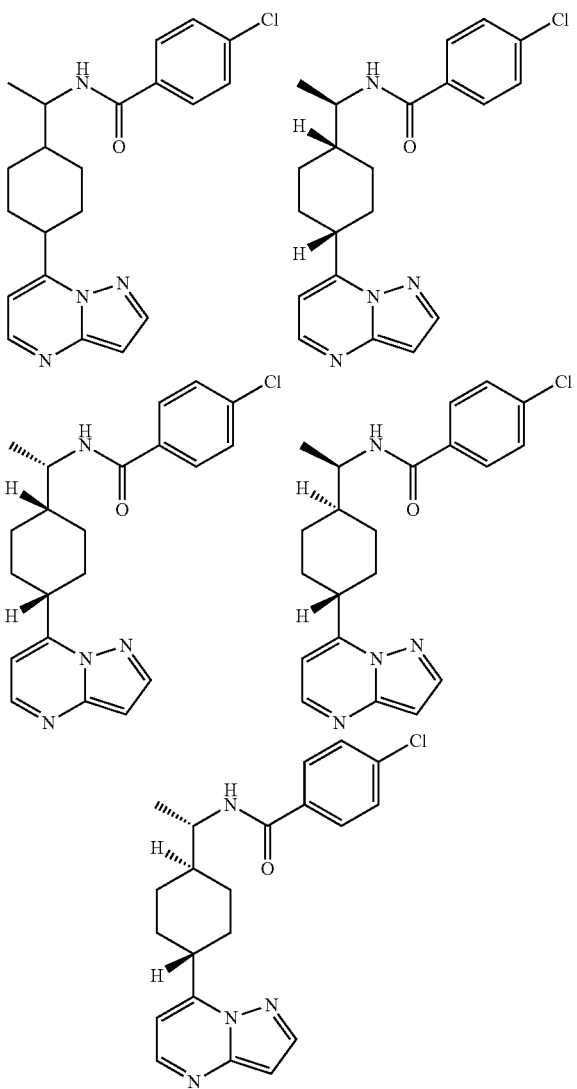

197A. ethyl 2-(1,4-dioxaspiro[4.5]decan-8-ylidene)propanoate

To a suspension of NaH (0.307 g, 7.68 mmol) in THF (8 mL) cooled at 0° C. was added ethyl 2-(diethoxyphosphoryl)propanoate (1.830 g, 7.68 mmol) slowly. After 30 min, 1,4-dioxaspiro[4.5]decan-8-one (1 g, 6.40 mmol) was added. The resulting mixture was stirred at 0° C. for 2 hours, then warmed up to room temperature for overnight. The mixture was quenched with water, THF was removed under reduced pressure. The residue was dissolved in EtOAc, washed with water, brine, dried over Na$_2$SO$_4$ and concentrated. The crude was purified by ISCO (EtOAc/Hex 0-30%). Fractions containing the product were concentrated to yield Intermediate 197A (1.2 g, 78% yield) a light yellow oil. $^1$H NMR (400 MHz, CHLOROFORM-d) δ 4.19 (q, J=7.1 Hz, 2H), 4.03-3.89 (m, 4H), 2.68-2.53 (m, 2H), 2.46-2.28 (m, 2H), 1.89 (s, 3H), 1.78-1.66 (m, 4H), 1.30 (t, J=7.1 Hz, 3H)

197B. ethyl 2-(1,4-dioxaspiro[4.5]decan-8-yl)propanoate

A suspension of Intermediate 143A (500 mg, 2.081 mmol) (1A) and 10% palladium on carbon (25 mg, 0.024 mmol) in EtOAc (5 mL) was hydrogenated in a Parr shaker at 45 psi for 6 h. The catalyst was filtered, and the filtrate was concentrated to yield Intermediate 197B (450 mg, 89% yield) as a light oil. $^1$H NMR (400 MHz, CHLOROFORM-d) δ 4.12 (dtt, J=10.7, 7.1, 3.6 Hz, 2H), 3.98-3.81 (m, 4H), 2.35-2.17 (m, 1H), 1.83-1.68 (m, 3H), 1.66-1.45 (m, 4H), 1.43-1.28 (m, 2H), 1.27-1.22 (m, 3H), 1.14-1.07 (m, 3H)

197C. ethyl 2-(4-oxocyclohexyl)propanoate

To a solution of ethyl 2-(1,4-dioxaspiro[4.5]decan-8-yl)propanoate (450 mg, 1.857 mmol) (1B) in THF (5 mL) was added 1M hydrogen chloride (aqueous) (0.929 mL, 3.71 mmol). The mixture was heated to 50° C. for 6 h. The reaction mixture was concentrated. The residue was dissolved in EtOAc, washed with water (2×), brine, dried over Na$_2$SO$_4$ and concentrated. The crude was purified with ISCO (EtOAc/Hex 0-30%). Fractions containing product were concentrated to yield Intermediate 197C (290 mg, 79% yield) as a clear oil. $^1$H NMR (400 MHz, CHLOROFORM-d) δ 4.22-4.06 (m, 2H), 2.46-2.30 (m, 5H), 2.13-1.91 (m, 3H), 1.56-1.42 (m, 2H), 1.31-1.24 (m, 3H), 1.18 (d, J=7.1 Hz, 3H)

197D. ethyl 2-(4-(((trifluoromethyl)sulfonyl)oxy)cyclohex-3-en-1-yl)propanoate Intermediate 143C (200 mg, 1.01 mmol) (1C) and 2,6-di-tert-butyl-4-methylpyridine (238 mg, 1.16 mmol) were dissolved in dry DCM (10 ml). To the reaction mixture trifluoromethanesulfonic anhydride (0.186 mL, 1.11 mmol) was added dropwise and stirred for 2 h. The suspension was filtered and the filtrate was diluted with DCM, washed with 1N HCl (2×), satd. sodium bicarb solution, water, brine and dried over Na$_2$SO$_4$ and concentrated to yield Intermediate 197D (320 mg, 96% yield) as a brown oil. $^1$H NMR (400 MHz, CHLOROFORM-d) δ 5.73 (t, J=6.1 Hz, 1H), 4.28-4.05 (m, 2H), 2.52-2.17 (m, 4H), 2.08-1.79 (m, 3H), 1.49 (dt, J=11.1, 6.6 Hz, 1H), 1.31-1.20 (m, 3H), 1.19-1.04 (m, 3H)

197E. ethyl 2-(4-(4,4,5,5-tetramethyl-1,3,2-dioxaborolan-2-yl)cyclohex-3-en-1-yl)propanoate To a solution of Intermediate 143D (300 mg, 0.908 mmol) (1D) in DMSO (5 mL) was added 4,4,4',4',5,5,5',5'-octamethyl-2,2'-bi(1,3,2-dioxaborolane) (230 mg, 0.908 mmol) and potassium acetate (267 mg, 2.72 mmol). After the mixture was degassed with N$_2$ for 10 min, PdCl$_2$(dppf) (19.9 mg, 0.027 mmol) was added. The mixture was heated to 80° C. for overnight. The mixture was partitioned between EtOAc and water. The organic phase was concentrated and purified by ISCO. Fractions containing product were concentrated to yield Intermediate 197E (168 mg, 60% yield) as a brown oil. $^1$H NMR (400 MHz, CHLOROFORM-d) δ 6.66-6.40 (m, 1H), 4.31-4.00 (m, 2H), 2.34-2.26 (m, 1H), 2.25-2.19 (m, 1H), 2.19-2.04 (m, 2H), 1.95-1.75 (m, 3H), 1.73-1.60 (m, 1H), 1.29-1.24 (m, 15H), 1.13 (dd, J=11.6, 7.0 Hz, 3H)

197F. Ethyl 2-(4-(pyrazolo[1,5-a]pyrimidin-7-yl)cyclohex-3-en-1-yl)propanoate A mixture of 7-chloropyrazolo[1,5-a]pyrimidine (0.193 g, 1.260 mmol), Intermediate 143E (0.400 g, 1.298 mmol), $Na_2CO_3$ (0.534 g, 5.04 mmol), and $Pd(Ph_3P)_4$ (0.073 g, 0.063 mmol) in dioxane (11.67 ml) and water (3.89 ml) was heated at 100° C. overnight. The reaction was quenched with water and diluted with EtOAc. Layers were separated. The aqueous phase was extracted with EtOAc (3×). The organics were combined, dried over $Na_2SO_4$, filtered, and concentrated to afford a brown residue. Purification of the crude material by silica gel chromatography using an ISCO machine (40 g column, 40 mL/min, 0-70% EtOAc in hexanes over 16 min, $t_r$=10.5 min) gave 197F (0.224 g, 0.748 mmol, 59.4% yield) as a yellow residue. ESI MS (M+H)$^+$=300.2. HPLC Peak $t_r$=0.95 minutes. HPLC conditions: method A.

197G. Ethyl 2-(4-(pyrazolo[1,5-a]pyrimidin-7-yl)cyclohexyl)propanoate

To a solution of 143F (0.224 g, 0.748 mmol) in MeOH (3.74 ml) was added ammonium formate (0.236 g, 3.74 mmol) followed by Pd/C (0.021 g, 0.202 mmol). The reaction was heated at 70° C. for 1 h. The reaction was filtered through CELITE® and the filter cake washed with $CH_2Cl_2$. The filtrate was concentrated. The crude material was taken up in EtOAc and washed with a sat. aq. solution of $NaHCO_3$ (1×). The organic phase was dried over $Na_2SO_4$, filtered, and concentrated to afford 197G (220 mg, 98%) as a yellow residue. ESI MS (M+H)$^+$=302.2. HPLC Peak $t_r$=0.94 minutes. HPLC conditions: method A.

197H. 2-(4-(Pyrazolo[1,5-a]pyrimidin-7-yl)cyclohexyl)propanoic acid

To a solution of 197G (0.1112 g, 0.369 mmol) in THF (1.318 ml) and MeOH (0.527 ml) was added lithium hydroxide (3.69 ml, 3.69 mmol). The reaction was heated at 70° C. for 2.5 h, then allowed to cool to rt. The reaction was adjusted to pH 7 with 1N HCl, then diluted with EtOAc. Layers were separated. The aqueous phase was extracted with EtOAc (5×). The organic phases were combined, dried over $Na_2SO_4$, filtered, and concentrated to afford 197H (82.7 mg, 82%) as a yellow residue. ESI MS (M+H)$^+$=274.1. HPLC Peak $t_r$=0.73 minutes. HPLC conditions: method A.

197I. 1-(4-(Pyrazolo[1,5-a]pyrimidin-7-yl)cyclohexyl)ethanamine 197H (0.0823 g, 0.301 mmol) was taken up in toluene (1.004 ml) in a reaction vial and diphenyl phosphorazidate (0.071 ml, 0.331 mmol) and triethylamine (0.050 ml, 0.361 mmol) were added. The vial was sealed and heated to 80° C. After about 2 h, the reaction was cooled to rt. The crude residue taken up in 1 mL THF and 1 mL of water and lithium hydroxide (0.072 g, 3.01 mmol) were added. The reaction was stirred at rt. The reaction was acidified to pH=1 with 1N HCl and extracted with EtOAc to remove DPPA related impurities. The organic layer was discarded. The aqueous layer was then basified to pH=12 with 1N NaOH and extracted with EtOAc (3×). The combined organic phases were dried with sodium sulfate, filtered, and concentrated in vacuo to give 197I (46.5 mg, 0.190 mmol, 63.2% yield) as an orange residue. ESI MS (M+H)$^+$=245.2. HPLC Peak $t_r$=0.52 minutes. HPLC conditions: method A.

Example 197a

(+/−)-Cis- and trans-4-chloro-N-(1-(4-(pyrazolo[1,5-a]pyrimidin-7-yl)cyclohexyl)ethyl)benzamide To a solution of 197I (46.5 mg, 0.190 mmol) in THF (1359 μl) at rt was added 4-chlorobenzoic acid (89 mg, 0.571 mmol), followed by 1-(3-dimethylaminopropyl)-3-ethylcarbodiimide hydrochloride (109 mg, 0.571 mmol), 4-hydroxybenzotriazole (77 mg, 0.571 mmol) and Hunig's Base (133 μl, 0.761 mmol). The reaction was stirred at rt for 16 h. The reaction was concentrated, then purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-70% B over 20 minutes, then a 5-minute hold at 100% B; Flow: 20 mL/min. Fractions containing the desired product were combined and dried via centrifugal evaporation to afford the title compound as a mixture of 4 isomers (22.5 mg, 30%). ESI MS (M+H)$^+$=383.0. HPLC Peak $t_r$=1.714 minutes. Purity=98%. HPLC conditions: method B.

Approximately 20.6 mg of Example 197a was resolved by the following method. The isomeric mixture was purified via preparative SFC with the following conditions: Column: Chiral AD, 25×3 cm ID, 5-μm particles; Mobile Phase A: 70/30 $CO_2$/MeOH; Detector Wavelength: 220 nm; Flow: 85 mL/min. The fractions ("Peak-1" $t_r$=7.485, "Peak-2" $t_r$=9.868, "Peak-3" $t_r$=11.635, "Peak-4" $t_r$=16.651; analytical conditions: Column: Chiral AD, 250×4.6 mm ID, 5-μm particles; Mobile Phase A: 70/30 $CO_2$/MeOH; Flow: 2.0 mL/min) were collected in MeOH. The stereoisomeric purity of each fraction was estimated to be greater than 99% based on the prep-SFC chromatograms. Each diasteromer or enantiomer was further purified via preparative LC/MS:

Example 197b, first eluting isomer: The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-70% B over 20 minutes, then a 5-minute hold at 100% B; Flow: 20 mL/min. Fractions containing the desired product were combined and dried via centrifugal evaporation to afford Isomer 1 (5.0 mg, 6.6%). ESI MS (M+H)+=383.3. HPLC Peak $t_r$=1.764 minutes. Purity=96%. HPLC conditions: B. Absolute stereochemistry not determined.

Example 197c, second eluting isomer: The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-70% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 35-65% B over 25 minutes, then a 2-minute hold at 65% B; Flow: 20 mL/min. Fractions containing the desired product were combined and dried via centrifugal evaporation to afford Isomer 2 (5.2 mg, 7.0%). ESI MS (M+H)+=383.1. HPLC Peak $t_r$=1.726 minutes. Purity=98%. HPLC conditions: B. Absolute stereochemistry not determined.

Example 197d, third eluting isomer: The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-70% B over 20 minutes, then a 5-minute hold at 100% B; Flow: 20 mL/min. Fractions containing the desired product were combined and dried via centrifugal evaporation to afford Isomer 3 (4.7 mg, 6.3%). ESI MS (M+H)+=383.2. HPLC Peak $t_r$=1.848 minutes. Purity=97%. HPLC conditions: B. Absolute stereochemistry not determined.

Example 197e, fourth eluting isomer: The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-70% B over 20 minutes, then a 5-minute hold at 100% B; Flow: 20 mL/min. Fractions containing the desired product were combined and dried via centrifugal evaporation to afford Isomer 4 (4.5 mg, 5.9%). ESI MS (M+H)+=383.2. HPLC Peak $t_r$=1.806 minutes. Purity=96%. HPLC conditions: B. Absolute stereochemistry not determined.

Example 198

4-chloro-N—((R)-1-((1s,4S)-4-(6-fluoroquinolin-4-yl)cyclohexyl)but-3-en-1-yl)benzamide

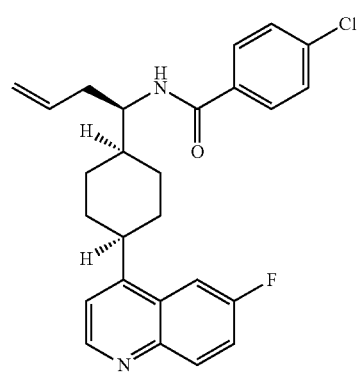 [SMILES: C=CC[C@@H](NC(=O)c1ccc(Cl)cc1)[C@H]1CC[C@@H](c2ccnc3ccc(F)cc32)CC1]

198A. (R)-3-((R)-2-((1s,4S)-4-(6-fluoroquinolin-4-yl)cyclohexyl)pent-4-enoyl)-4-phenyloxazolidin-2-one

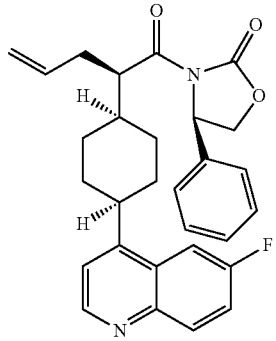 [SMILES: C=CC[C@@H](C(=O)N1C(=O)OC[C@H]1c1ccccc1)[C@H]1CC[C@@H](c2ccnc3ccc(F)cc32)CC1]

To a solution of Preparation 40I (50 mg, 0.116 mmol) in THF (2 mL) at −40° C. was added NaHMDS (1M in THF) (0.139 mL, 0.139 mmol) drop wise. The mixture was stirred at −40° C. to −30° C. for 15 min. Then 3-bromoprop-1-ene (28.0 mg, 0.231 mmol) in THF (0.5 mL) was added drop wise. The reaction was stirred at −20° C. for 16 h. The reaction was quenched at −20° C. by pouring it into saturated NH4Cl solution. The aqueous was extracted with EtOAc. The organic was washed with brine, dried over MgSO$_4$, filtered and concentrated to give a crude material. This crude material was added MeOH and filtered to remove the solid. The filtrate was purified with prep HPLC (Phen Luna 5u 30×100 mm), 40 mL/min flow rate with gradient of 20% B-100% B over 10 minutes Hold at 100% B for 5 min. (A: 0.1% TFA in water/MeOH (90:10), B: 0.1% TFA in water/MeOH (10:90) monitoring at 254 nm. Combined fractions (tr=9.428 min) containing the product. After concentration, (R)-3-((R)-2-((1s, 4S)-4-(6-fluoroquinolin-4-yl)cyclohexyl)pent-4-enoyl)-4-phenyloxazolidin-2-one (25 mg, 0.052 mmol, 44.8% yield) was obtained as white solid. $^1$H NMR (400 MHz, CHLOROFORM-d) δ 9.12 (d, J=5.5 Hz, 1H), 8.64 (dd, 5.0 Hz, 1H), 8.01-7.89 (m, 2H), 7.89-7.75 (m, 1H), 7.47-7.31 (m, 5H), 5.62-5.45 (m, 2H), 4.84-4.76 (m, 1H), 4.76-4.68 (m, 1H), 4.68-4.52 (m, 1H), 4.36 (dd, J=9.0, 3.9 Hz, 1H), 3.55-3.33 (m, 1H), 2.49-2.35 (m, 1H), 2.33-2.21 (m, 2H), 2.12-1.97 (m, 2H), 1.93-1.65 (m, 6H) LC-MS: M+H=473.3 (tr=0.90 min) (Method A)

198B: (R)-2-((1s,4S)-4-(6-fluoroquinolin-4-yl)cyclohexyl)pent-4-enoic acid

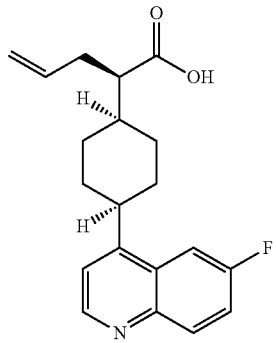 [SMILES: C=CC[C@@H](C(=O)O)[C@H]1CC[C@@H](c2ccnc3ccc(F)cc32)CC1]

To a solution of Preparation 198A (250 mg, 0.529 mmol) in THF (2 mL) at 0° C. was added 2.0 M LiOH in H$_2$O (0.476 mL, 0.952 mmol), followed by 30% H$_2$O$_2$ (0.360 mL, 3.17 mmol). The reaction was stirred at 0° C. for 10 min. Then it was warmed up to RT and stirred at RT for 16 h. The reaction was carefully quenched at 0° C. by addition of saturated Na2SO3. The pH was adjusted to 5~6 with 1N HCl and the mixture was extracted with EtOAc. The combined organics were dried over MgSO4, filtered and concentrated. The crude material was purified with prep HPLC (9 injections) (Phen Luna 5u 30×100 mm), 40 mL/min flow rate with gradient of 20% B-100% B over 10 minutes Hold at 100% B for 5 min. (A: 0.1% TFA in water/MeOH (90:10), B: 0.1% TFA in water/MeOH (10:90) monitoring at 254 nm. 1B (78 mg, 0.236 mmol, 44.6% yield) was obtained as white solid. $^1$H NMR (400 MHz, CHLOROFORM-d) δ 9.22 (br. s., 1H), 8.63 (dd, J=9.0, 5.0 Hz, 1H), 7.98-7.75 (m, 4H), 5.85 (dd, J=16.9, 9.7 Hz, 1H), 5.25-5.03 (m, 2H), 3.50 (br. s., 1H), 2.89-2.75 (m, 1H), 2.54-2.32 (m, 2H), 2.16 (d, J=10.1 Hz, 1H), 2.06 (d, J=13.2 Hz, 1H), 2.01-1.71 (m, 6H) LC-MS: M+H=328 (tr=0.69 min) (Method A)

198C: (R)-1-((1s,4S)-4-(6-fluoroquinolin-4-yl)cyclohexyl)but-3-en-1-amine

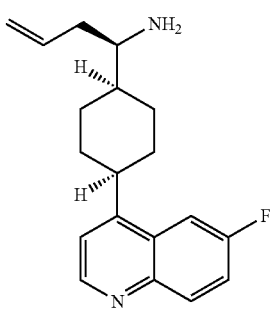 [SMILES: C=CC[C@@H](N)[C@H]1CC[C@@H](c2ccnc3ccc(F)cc32)CC1]

Preparation 198B (55 mg, 0.168 mmol) taken up in toluene (1 mL) and diphenylphosphoryl azide (0.040 mL, 0.185 mmol) and triethylamine (0.028 mL, 0.202 mmol) was added. Vial sealed and heated to 70 C. After about 3 h, diphenylphosphoryl azide (0.040 mL, 0.185 mmol) and triethylamine (0.028 mL, 0.202 mmol) were added. The reaction was heated for another 3 h. The reaction was cooled to rt and concentrated under reduced pressure. Crude residue taken up in THF (0.2 mL) and 2M LiOH (0.840 mL, 1.680 mmol). Reaction stirred at rt for 16 h. LCMS shows isocyanate consumed. New peak with M+1 of desired at rt=0.56 min. Reaction acidified with 1N HCl (white precipitate forms) to pH1 and extracted EtOAc to remove DPPA related impurities. The material was purified with prep HPLC (Phen Luna 5u 30×100 mm), 40 mL/min flow rate with gradient of 0% B-100% B over 10 minutes Hold at 100% B for 5 min. (A: 0.1% TFA in water/MeOH (90:10), B: 0.1% TFA in water/MeOH (10:90) monitoring at 254 nm. Preparation 198C was obtained (30 mg, 0.040 mmol, 23.77% yield) was obtained. LC-MS: M+H=299.2 (TR=0.56 min) (Method A).

Example 198

4-chloro-N—((R)-1-41 s, 4S)-4-(6-fluoroquinolin-4-yl)cyclohexyl)but-3-en-1-yl)benzamide To a solution of Preparation 198C (15 mg, 0.029 mmol) in THF (0.5 mL) at RT was added Hunig's Base (0.015 mL, 0.086 mmol), followed by 4-chlorobenzoyl chloride (9.98 mg, 0.057 mmol). The reaction as stirred at RT for 2 h. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 50-100% B over 20 minutes, then a 10-minute hold at 100% B; Flow: 20 mL/min. Fractions containing the desired product were combined and dried via centrifugal evaporation. The yield of the product 1 was 3.8 mg (8.70 umol, 30.5%).

$^1$H NMR (500 MHz, DMSO-d$_6$) δ 8.82 (d, J=4.4 Hz, 1H), 8.27 (d, J=9.0 Hz, 1H), 8.09 (dd, J=9.0, 5.9 Hz, 1H), 7.95 (d, J=10.9 Hz, 1H), 7.84 (d, J=8.3 Hz, 2H), 7.66 (t, J=7.5 Hz, 1H), 7.57-7.43 (m, 3H), 5.90-5.73 (m, 1H), 5.07 (d, J=17.2 Hz, 1H), 4.98 (d, J=10.1 Hz, 1H), 4.42 (d, J=8.9 Hz, 1H), 3.39 (br. s., 1H), 2.26-2.13 (m, 1H), 1.94-1.71 (m, 7H), 1.68 (br. s., 1H), 1.62 (d, J=11.1 Hz, 1H) LC-MS: M+H=437.3 tr=2.23 min (Method B)

Example 199

N—((R)-1-((Is, 4S)-4-(6-fluoroquinolin-4-yl)cyclohexyl)but-3-en-1-yl)-[1,1'-biphenyl]-4-carboxamide

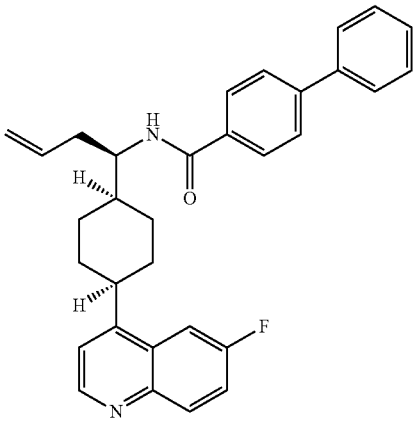 [SMILES: C=CC[C@@H](NC(=O)c1ccc(-c2ccccc2)cc1)[C@H]1CC[C@@H](c2ccnc3ccc(F)cc32)CC1]

Example 199 was obtained following the procedures in Example 198 using 198C and [1,1'-biphenyl]-4-carbonyl chloride. $^1$H NMR (500 MHz, DMSO-d$_6$) δ 8.83 (d, J=4.5 Hz, 1H), 8.25 (d, J=9.2 Hz, 1H), 8.09 (dd, J=9.1, 5.8 Hz, 1H), 8.01-7.84 (m, 3H), 7.80-7.61 (m, 5H), 7.54-7.45 (m, 3H), 7.45-7.27 (m, 1H), 5.90-5.79 (m, 1H), 5.10 (d, J=17.4 Hz, 1H), 5.00 (d, J=9.8 Hz, 1H), 4.46 (d, J=7.9 Hz, 1H), 3.40 (br. s., 1H), 2.31-2.16 (m, 1H), 2.01-1.78 (m, 6H), 1.75 (br. s., 2H), 1.69 (br. s., 1H), 1.63 (d, J=12.2 Hz, 1H) LC-MS: M+H=470.3 tr=2.41 min (Method B)

Example 200 and Example 201

(Chiral) N-1-((1s,4S)-4-(quinolin-3-yl)cyclohexyl)propyl)-[1,1'-biphenyl]-4-carboxamide

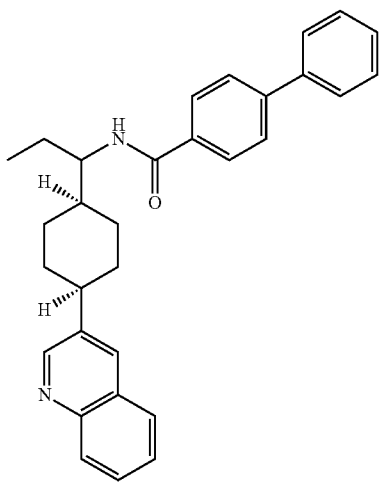

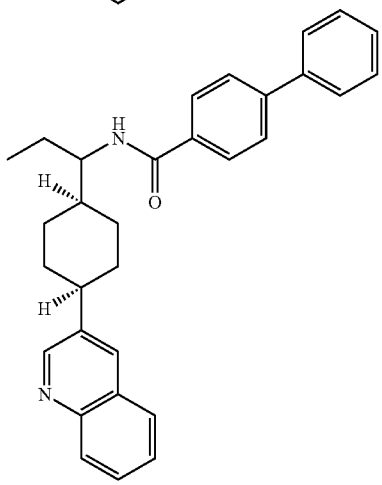

200A: ethyl 2-(4-(quinolin-3-yl)cyclohex-3-en-1-yl)acetate

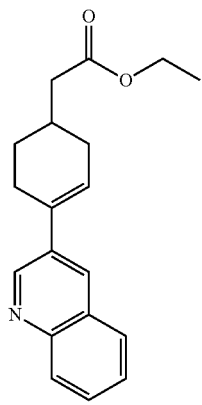 [SMILES: CCOC(=O)CC1CC=C(c2cnc3ccccc3c2)CC1]

Ethyl 2-(4-(4,4,5,5-tetramethyl-1,3,2-dioxaborolan-2-yl)cyclohex-3-en-1-yl)acetate (5.26 g, 17.88 mmol) was taken up in Dioxane (40 mL) and Water (10.00 mL). 3-bromoquinoline (3.1 g, 14.90 mmol) was added followed by potassium carbonate (6.18 g, 44.7 mmol). Mixture was bubble with N2 for 5 minutes before addition of tetrakis(triphenylphosphine)palladium(0) (0.344 g, 0.298 mmol). After addition, reaction was evacuated and backfilled with $N_2$ three times and then sealed and heated to 100° C. for 16 h. The Reaction was diluted with EtOAc and water. Organic was separated and washed with brine, dried over $MgSO_4$, filtered and concentrated in vacuo and purified directly via ISCO (120 g column, 85 mL/min, 0-30% EtOAc in hexanes) to give Preparation 200A (4.47 g, 14.38 mmol, 96% yield). 1H NMR (400 MHz, CHLOROFORM-d) δ 9.05 (d, J=2.3 Hz, 1H), 8.09 (d, J=8.4 Hz, 1H), 8.02 (d, J=2.2 Hz, 1H), 7.86-7.76 (m, 1H), 7.67 (ddd, J=8.4, 6.9, 1.5 Hz, 1H), 7.58-7.45 (m, 1H), 6.38-6.18 (m, 1H), 4.20 (q, J=7.1 Hz, 2H), 2.67-2.56 (m, 2H), 2.55-2.43 (m, 1H), 2.42-2.35 (m, 2H), 2.30-2.18 (m, 1H), 2.12-1.92 (m, 2H), 1.57 (ddt, J=12.8, 10.8, 7.9 Hz, 1H), 1.36-1.27 (m, 3H) LC-MS: M+H=296.2 tr=0.74 min (Method A)

200B: ethyl 2-(4-(quinolin-3-yl)cyclohexyl)acetate

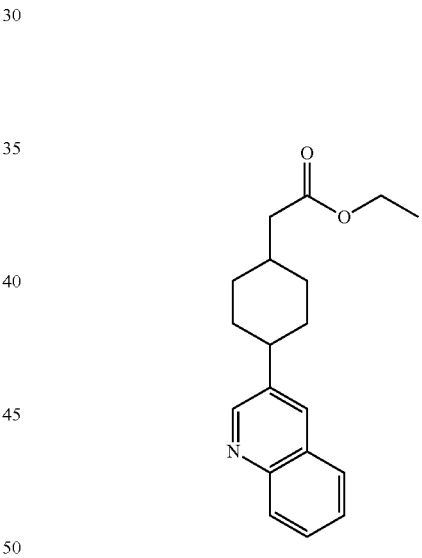

Preparation 200A (3.5 g, 11.85 mmol) was dissolved in MeOH (70 mL) and ammonium formate (3.74 g, 59.2 mmol) was added. The vessel was equipped with a reflux condenser and vacated and flushed with $N_2$ 3 times. Then, 10% Pd/C (1.256 g, 1.185 mmol) was added and the reaction was heated at 70° C. LCMS after 1 hour shows reduction complete. Reaction cooled, solids were filtered off and the filtrate was concentrated to give crude material. This crude material was purified with ISCO 120 g, 85 mL/min. 0-50% EtOAc/Hexane. Preparation 200B (0.71 g, 2.308 mmol, 19.48% yield) was eluted with 10% EtOAc/Hexane. LC-MS: M+H=302.2 tr=0.81 min (Method A)

200C: ethyl 2-(4-(quinolin-3-yl)cyclohexyl)butanoate

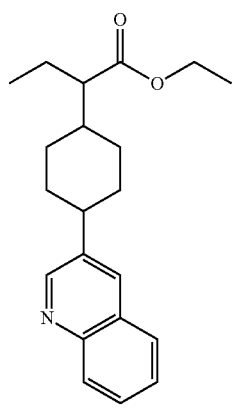 [SMILES: CCOC(=O)C(CC)C1CCC(c2cnc3ccccc3c2)CC1]

To a solution of Preparation 200B (920 mg, 3.09 mmol) in THF (10 mL) at 0° C. was added 1M NaHMDS in THF (7.73 mL, 7.73 mmol) drop wise. The mixture was stirred at 0° C. for 30 min. Then iodoethane (0.3 mL, 3.75 mmol) was added drop wise. The resulting mixture was stirred at 0° C. for 45 min. [The color of the solution does not change much]. Iodoethane (0.4 mL, 5.00 mmol) was added drop wise and the reaction was stirred at 0° C. [The color of the solution turned to a little darker]. After 1 h, iodoethane (0.15 mL, 1.875 mmol) was added and the reaction was stirred at RT for 2 h. LC-MS shows desired product formed but still there is starting material left. The reaction was poured into a saturated $NH_4Cl$ solution. EtOAc was added and organic was separated and washed with brine, dried over $MgSO_4$, filtered and concentrated to give a crude material. This crude material was purified with ISCO 80 g column, 60 mL/min. 0-30% EtOAc/Hexane in 40 min. The desired product was eluted with 25% EtOAc/Hexane. Combined fractions 5-11. After concentration, Preparation 200C (386 mg, 1.174 mmol, 38.0% yield) was obtained as clear liquid. LC-MS; M+H=326.2 (TR=0.81, 0.82 min) (Method A)

200D: 2-(4-(quinolin-3-yl)cyclohexyl)butanoic acid

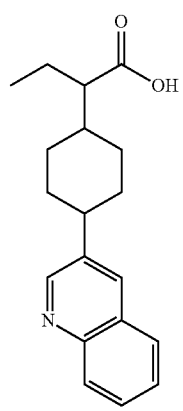 [SMILES: CCC(C(=O)O)C1CCC(c2cnc3ccccc3c2)CC1]

To a solution of Preparation 200C (385 mg, 1.183 mmol) in THF (1 mL) and MeOH (5 mL) at rt was added 2M LiOH (5.91 mL, 11.83 mmol) and 1M NaOH (2.366 mL, 2.366 mmol). The reaction was stirred at 60° C. for 48 h. LC-MS still shows a little bit of starting material and methylester. Cooled to RT. The mixture was adjusted to pH 5 with concentrated HCl. Extracted the aqueous layer with EtOAc. The organic was separated and washed with brine, dried over $MgSO_4$, filtered and concentrated to give Preparation 200D (400 mg, 1.076 mmol, 91% yield) as white solid. LC-MS: M+H=298.2 (tr=0.67 min) (Method A)

200E: 1-(4-(quinolin-3-yl)cyclohexyl)propan-1-amine

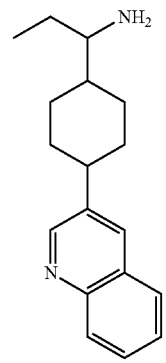 [SMILES: CCC(N)C1CCC(c2cnc3ccccc3c2)CC1]

Preparation 200D (200 mg, 0.673 mmol) taken up in toluene (2 mL) and diphenylphosphoryl azide (0.290 mL, 1.345 mmol) and triethylamine (0.187 mL, 1.345 mmol) added. Vial sealed and heated to 70 C for 16 h. The reaction was cooled to RT and concentrated under reduced pressure. Crude residue taken up in THF (2 mL) and 2M LiOH (2.354 mL, 4.71 mmol). Reaction stirred at RT for 3 days. LCMS shows isocyanate consumed. New peak with M+1 of desired at RT=0.50 min. Reaction acidified with 1N HCl to pH1 and extracted EtOAc to remove DPPA related impurities. Then the aqueous layer was adjusted to pH 10 with 2M LiOH. Extracted with EtOAc (3×). Combined organics were washed with brine, dried over $MgSO_4$, filtered and concentrated to give Preparation 200E (110 mg, 0.398 mmol, 59.1% yield) as clear liquid. LC-MS: M+H=269.2 (tr=0.50 min) (Method A)

Example 200a and Example 200b

N-(1-((1r,4r)-4-(quinolin-3-yl)cyclohexyl)propyl)-[1,1'-biphenyl]-4-carboxamide and N-(1-((1r,4r)-4-(quinolin-3-yl)cyclohexyl)propyl)-[1,1'-biphenyl]-4-carboxamide (Relative and Absolute Stereochemistry No Confirmed, Arbitrarily Assigned)

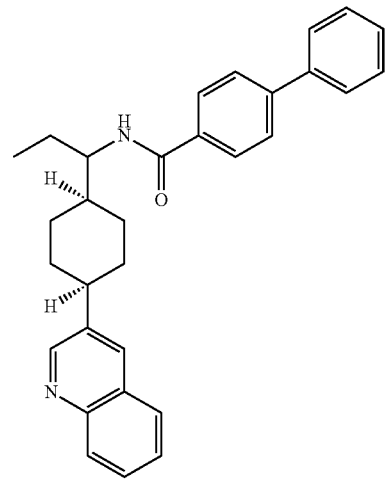

-continued

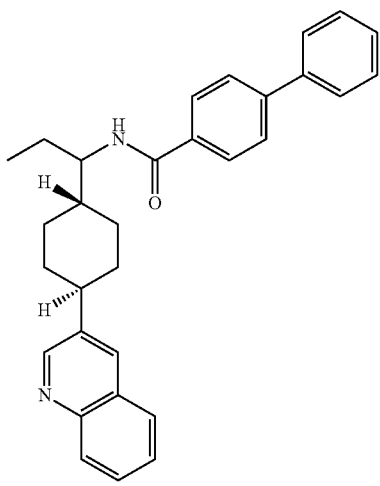

To a solution of 1-(3-dimethylaminopropyl)-3-ethylcarbodiimide hydrochloride (102 mg, 0.533 mmol) in DMF (4 mL) at RT was added [1,1'-biphenyl]-4-carboxylic acid (162 mg, 0.820 mmol), 1-(3-dimethylaminopropyl)-3-ethylcarbodiimide hydrochloride (102 mg, 0.533 mmol),1-hydroxybenzotriazole (82 mg, 0.533 mmol) and triethylamine (0.171 mL, 1.230 mmol). The reaction was stirred at RT for 16 h. The reaction was diluted with EtOAc and water. Organic was separated and washed with brine, dried over MgSO$_4$, filtered and concentrated to dryness. The crude material was purified with ISCO 40 g column, 40 mL/min, 0-70% EtOAc/Hexane in 40 min. 3F (90 mg, 0.197 mmol, 48%) was eluted with 60% EtOAc/Hexane.

Example 200a $^1$H NMR (400 MHz, CHLOROFORM-d) δ 8.86 (d, J=2.2 Hz, 1H), 8.15-8.01 (m, 2H), 7.89-7.77 (m, 3H), 7.74-7.58 (m, 5H), 7.58-7.47 (m, 3H), 7.47-7.34 (m, 1H), 5.81 (d, J=9.8 Hz, 1H), 4.56-4.27 (m, 1H), 2.96 (br. s., 1H), 2.26-2.09 (m, 1H), 2.01-1.78 (m, 8H), 1.77-1.64 (m, 1H), 1.52-1.36 (m, 1H), 1.08-0.96 (m, 3H) LC-MS: M+H=449.3 (tr=0.88 min) (Method A)

Example 200b (65 mg, 0.142 mmol, 35%) was eluted with 70% EtOAc/Hexane. $^1$H NMR (400 MHz, CHLOROFORM-d) δ 8.83 (d, J=2.3 Hz, 1H), 8.09 (d, J=8.4 Hz, 1H), 7.96-7.85 (m, 3H), 7.79 (d, J=8.3 Hz, 1H), 7.73-7.61 (m, 5H), 7.58-7.47 (m, 3H), 7.45-7.31 (m, 1H), 5.92 (d, J=9.5 Hz, 1H), 4.21-4.01 (m, 1H), 2.82-2.55 (m, 1H), 2.18-1.95 (m, 4H), 1.83 (ddd, J=14.0, 7.4, 4.5 Hz, 11-1), 1.75-1.47 (m, 4H), 1.47-1.32 (m, 2H), 1.05 (t, J=7.4 Hz, 3H) LC-MS: M+H=449.3 (tr=0.88 min) (Method A)

Examples 200c and 200d

N—((R)-1-((1s,4S)-4-(quinolin-3-yl)cyclohexyl)propyl)-[1,1'-biphenyl]-4-carboxamide and N—((S)-1-((1s,4R)-4-(quinolin-3-yl)cyclohexyl)propyl)-[1,1'-biphenyl]-4-carboxamide (Absolute and Relative Stereochemistry not Confirmed, Arbitrarily Assigned)

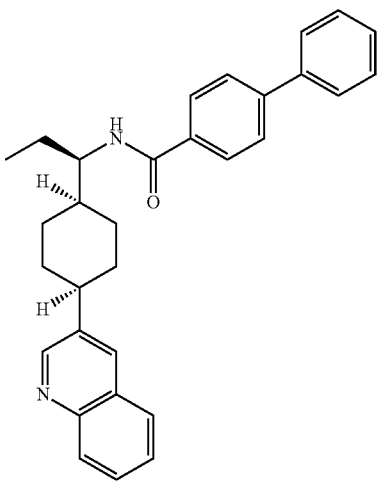

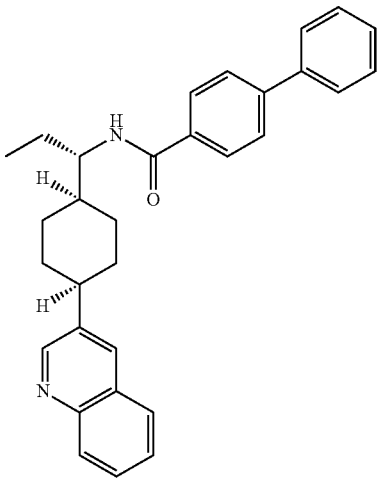

The racemate Example 200a was purified via preparative SFC with the following conditions: Column: Chiral AD-H 25×3 cm ID, 5-μm particles; Mobile Phase A: 50/50 CO2/MeOH; Detector Wavelength: 220 nm; Flow: 85 mL/min. The fractions ("Peak-1" tr=10.78 min (Example 200c) and "Peak-2" tr=23.917 min (Example 200d);

$^1$H NMR (400 MHz, CHLOROFORM-d) δ 8.86 (d, J=2.2 Hz, 1H), 8.15-8.01 (m, 2H), 7.89-7.77 (m, 3H), 7.74-7.58 (m, 5H), 7.58-7.47 (m, 3H), 7.47-7.34 (m, 1H), 5.81 (d, J=9.8 Hz, 1H), 4.56-4.27 (m, 1H), 2.96 (br. s., 1H), 2.26-2.09 (m, 1H), 2.01-1.78 (m, 8H), 1.77-1.64 (m, 1H), 1.52-1.36 (m, 1H), 1.08-0.96 (m, 3H) LC-MS: M+H=449.3 (tr=0.88 min) (Method A)

Examples 201 and 202

N—((R)-1-((1r,4R)-4-(quinolin-3-yl)cyclohexyl)propyl)-[1,1'-biphenyl]-4-carboxamide and N—((S)-1-((1r,4S)-4-(quinolin-3-yl)cyclohexyl)propyl)-[1,1'-biphenyl]-4-carboxamide (Absolute and Relative Stereochemistry not Confirmed, Arbitrarily Assigned)

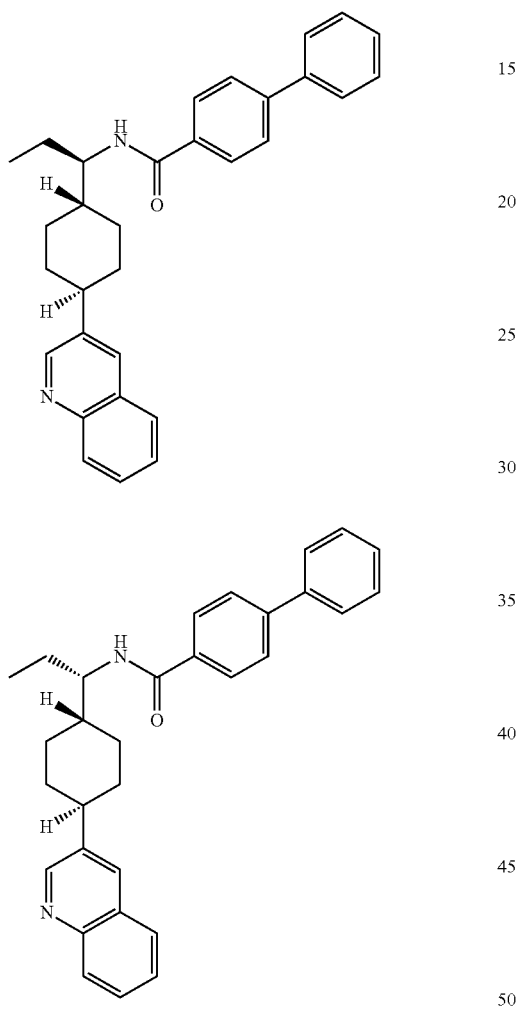

The racemate Example 200b was purified via preparative SFC with the following conditions: Column: Chiral IC-H 25×3 cm ID, 5-μm particles; Mobile Phase A: 50/50 CO2/MeOH; Detector Wavelength: 220 nm; Flow: 85 mL/min. The fractions ("Peak-1" tr=10.811 min (Example 201) and "Peak-2" tr=10.842 min (Example 202);

$^1$H NMR (400 MHz, CHLOROFORM-d) δ 8.83 (d, J=2.3 Hz, 1H), 8.09 (d, J=8.4 Hz, 1H), 7.96-7.85 (m, 3H), 7.79 (d, J=8.3 Hz, 1H), 7.73-7.61 (m, 5H), 7.58-7.47 (m, 3H), 7.45-7.31 (m, 1H), 5.92 (d, J=9.5 Hz, 1H), 4.21-4.01 (m, 1H), 2.82-2.55 (m, 1H), 2.18-1.95 (m, 4H), 1.83 (ddd, J=14.0, 7.4, 4.5 Hz, 1H), 1.75-1.47 (m, 4H), 1.47-1.32 (m, 2H), 1.05 (t, J=7.4 Hz, 3H) LC-MS: M+H=449.2 (tr=0.86 min) (Method A)

Example 203

4-chloro-N—((R)-1-(cis-4-(quinolin-3-yl)cyclohexyl)propyl)benzamide 4-Chloro-N—((S)-1-(cis-4-(quinolin-3-yl)cyclohexyl)propyl)benzamide 4-chloro-N—((R)-1-(trans-4-(quinolin-3-yl)cyclohexyl)propyl)benzamide 4-Chloro-N—((S)-1-(trans-4-(quinolin-3-yl)cyclohexyl)propyl)benzamide Absolute and Relative Stereochemistry Unknown

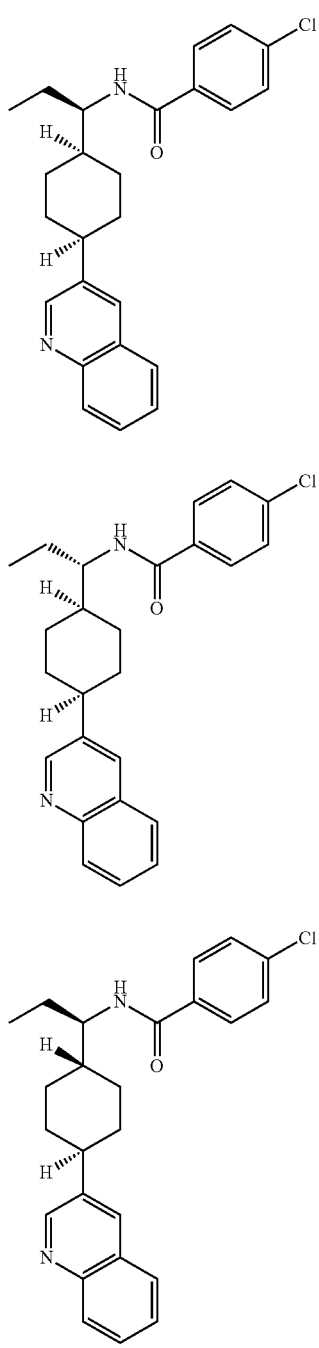

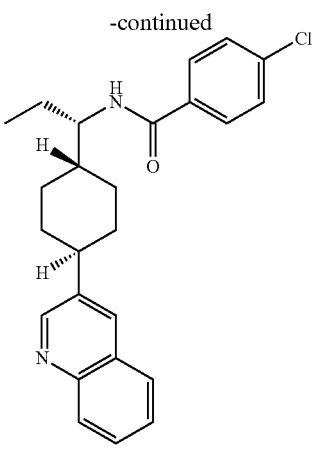

Examples 203a-d were obtained following the procedures in Examples 200 and 201 using 200E and 4-chlorobenzoyl chloride. The racemate was purified via preparative SFC with the following conditions: Column: Chiral IC-H 25×3 cm ID, 5-μm particles; Mobile Phase A: 65/35 CO2/MeOH; Detector Wavelength: 220 nm; Flow: 85 mL/min. The fractions ("Peak-1" tr=5.98 min (Example 203a) and "Peak-2" tr=6.29 min (Example 203b); ("Peak-3" tr=8.0 min (Example 203c) and "Peak-4" tr=9.0 min (Example 203d);

Examples 203a and 203b $^1$H NMR (400 MHz, CHLOROFORM-d) δ 8.86 (d, J=2.2 Hz, 1H), 8.16-8.00 (m, 2H), 7.80 (d, J=8.2 Hz, 1H), 7.73-7.63 (m, 3H), 7.59-7.46 (m, 1H), 7.45-7.35 (m, 2H), 5.71 (d, J=10.0 Hz, 1H), 4.49-4.23 (m, 1H), 3.06-2.83 (m, 1H), 2.24-2.05 (m, 1H), 2.00-1.83 (m, 5H), 1.83-1.73 (m, 3H), 1.73-1.63 (m, 1H), 1.51-1.35 (m, 1H), 1.00 (t, J=7.4 Hz, 3H) LC-MS: M+H=407.2 (tr=0.81 min) (Method A)

Examples 203c and 203d $^1$H NMR (400 MHz, CHLOROFORM-d) δ 8.86 (d, J=2.2 Hz, 1H), 8.16-8.00 (m, 2H), 7.80 (d, J=8.2 Hz, 1H), 7.73-7.63 (m, 3H), 7.59-7.46 (m, 1H), 7.45-7.35 (m, 2H), 5.71 (d, J=10.0 Hz, 1H), 4.49-4.23 (m, 1H), 3.06-2.83 (m, 1H), 2.24-2.05 (m, 1H), 2.00-1.83 (m, 5H), 1.83-1.73 (m, 3H), 1.73-1.63 (m, 1H), 1.51-1.35 (m, 1H), 1.00 (t, J=7.4 Hz, 3H) LC-MS: M+H=407.2 (tr=0.81 min) (Method A)

Example 207 rac-4-chloro-N-(1-((trans)-4-((3-chloro-2-methyl-pyridin-4-yl)oxy)cyclohexyl)ethyl)benzamide

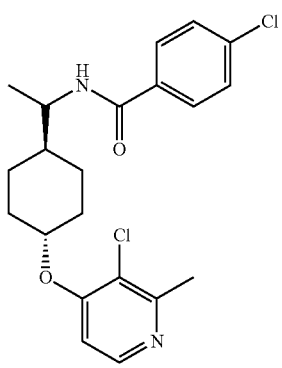 [SMILES: Cc1nccc(O[C@H]2CC[C@H](C(C)NC(=O)c3ccc(Cl)cc3)CC2)c1Cl]

207A. rac-ethyl 2-((trans)-4-((3-chloro-2-methyl-pyridin-4-yl)oxy)cyclohexyl)propanoate A solution of ethyl rac-2-((trans)-4-hydroxycyclohexyl)propanoate (1.001 g, 5 mmol) in THF (4 mL) was cooled to 0° C. and treated with potassium hexamethyldisilazide (5.50 mL, 5.50 mmol) over 1 min. The reaction was stirred 10 min. then treated with 3,4-dichloro-2-methylpyridine (0.851 g, 5.25 mmol). The reaction was stirred 40 min. at 0° C. then quenched with aq. ammonium chloride. The phases were stirred together 1 h then extracted with 1:1 EtOAc-hexane, and the organic extract was dried and stripped to afford an oil. Prep. HPLC afforded rac-ethyl 2-((trans)-4-((3-chloro-2-methylpyridin-4-yl)oxy)cyclohexyl)propanoate (0.47 g, 29% yield) as a golden oil. MS (ES): m/z=326 [M+H]$^+$. $t_R$=0.78 min (Method A).

207B. rac-2-((trans)-4-((3-chloro-2-methylpyridin-4-yl)oxy)cyclohexyl)propanoic acid A solution of Preparation 207A (0.42 g, 1.289 mmol) in THF (4 mL) was treated with lithium hydroxide (0.154 g, 6.45 mmol) in water (4 mL). Methanol, ~4 mL was added to give a single phase, and the reaction was stirred for 1 h at 50° C. The reaction was then cooled and stirred at RT. Most of the solvent was removed under a stream of nitrogen, and the reaction was diluted to ~6 ml with water. This cloudy suspension was filtered, and the filtrate solution pH was adjusted to ~5.5 with aq. HOAc. The resulting precipitate was filtered, rinsed with water, and air-dried to afford rac-2-((trans)-4-((3-chloro-2-methylpyridin-4-yl)oxy)cyclohexyl)propanoic acid (0.16 g, 42% yield) as a white solid. MS (ES): m/z=298 [M+H]$^+$. $t_R$=0.63 min (Method A).

207C. rac-1-((trans)-4-((3-chloro-2-methylpyridin-4-yl)oxy)cyclohexyl)ethanamine A solution of Preparation 207B (0.26 g, 0.873 mmol) in toluene (4.37 ml) was treated with triethylamine (0.158 ml, 1.135 mmol) followed by diphenylphosphinyl azide (0.244 g, 1.004 mmol). The solution was warmed to 70° C. (much bubbling). After 30 min., the solution was cooled and stripped. The residue was re-dissolved in THF (5 mL) and added to a solution of lithium hydroxide (0.836 g, 34.9 mmol) in 20 mL of water and 8 mL of THF. This mixture was stirred at RT for 30 min. then it was diluted with ether and washed twice with 1M aq. HCl. The combined aqueous phases were drained into sat. aq. sodium carbonate (final pH~12), and this mixture was ext. with EtOAc then 3:1 chloroform-IPA. These two organic extracts were combined, dried, and stripped to afford rac-1-((trans)-4-((3-chloro-2-methylpyridin-4-yl)oxy)cyclohexyl)ethanamine (0.18 g, 77% yield) an oil. MS (ES): m/z=269 [M+H]$^+$. $t_R$=0.47 min (Method A).

Example 207 rac-4-chloro-N-(1-((trans)-4-((3-chloro-2-methyl-pyridin-4-yl)oxy)cyclohexyl)ethyl)benzamide A solution of Preparation 207C (0.01 g, 0.037 mmol) and 4-chlorobenzoic acid (6.99 mg, 0.045 mmol) in DMF (0.25 mL) was treated with triethylamine (0.016 mL, 0.112 mmol) followed by BOP (0.021 g, 0.048 mmol). The reaction was stirred 2 h at RT then quenched with one drop of water and diluted with DMF to 2 mL. This solution was then purified by prep. HPLC. Concentration of the appropriate fractions afforded 0.0088 g (50%) of the title compound. MS (ES): m/z=407 [M+H]$^+$. $t_R$=2.05 min (Method B).

Examples 208-210

Bop coupling (Scheme 9, below) of amine 207C (prepared in the preceeding example) with the appropriate benzoic acids under the conditions described for the conversion of 207C to Example 207 affords compounds of the invention shown in Table 1 below. (All entries are racemic with trans relative stereochemistry at the cyclohexyl.)

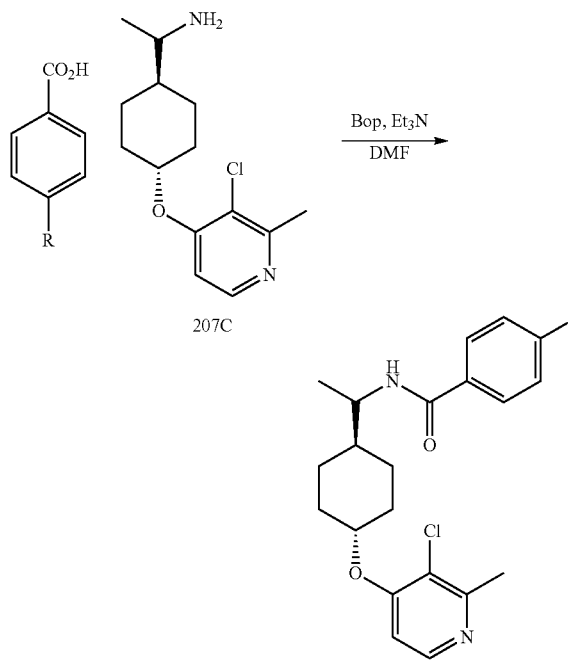

Scheme 9

TABLE 1

| Ex.# | R | (M + H)⁺ | $t_R$ (min., Method B) | BMT# |
|---|---|---|---|---|
| Example 208 | F | 391 | 1.93 | BMT-267222 |
| Example 209 | OMe | 403 | 1.83 | BMT-267223 |
| Example 210 | Me | 387 | 1.96 | BMT-267225 |

TABLE 2

Examples 211-225 were prepared following the procedures in Example 157 using the corresponding pyridyl halide (absolute and relative stereochemistry unknown)

| Example 211 | 4-chloro-N-(1-(4-(2-(trifluoromethyl)pyridin-4-yl)cyclohexyl)ethyl)benzamide | | 2.194$^B$ | 411.1 | Diastereomer Mixture |
| Example 212 | 4-chloro-N-(1-(4-(2-(trifluoromethyl)pyridin-4-yl)cyclohexyl)ethyl)benzamide | | 9.502$^{AC}$ | 411.3 | Homochiral |

TABLE 2-continued

Examples 211-225 were prepared following the procedures in Example 157 using the corresponding pyridyl halide (absolute and relative stereochemistry unknown)

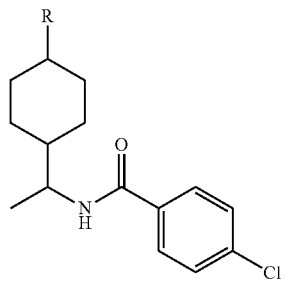

| Example | Name | R | | | |
|---|---|---|---|---|---|
| Example 213 | 4-chloro-N-(1-(4-(2-(trifluoromethyl)pyridin-4-yl)cyclohexyl)ethyl)benzamide | 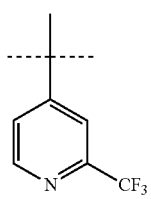 | 11.583^{AC} | 411.3 | Homochiral |
| Example 214 | 4-chloro-N-(1-(4-(2-(trifluoromethyl)pyridin-4-yl)cyclohexyl)ethyl)benzamide | 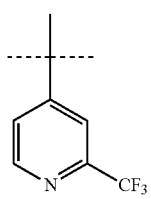 | 12.382^{AC} | 411.3 | Homochiral |
| Example 215 | 4-chloro-N-(1-(4-(2-(trifluoromethyl)pyridin-4-yl)cyclohexyl)ethyl)benzamide | 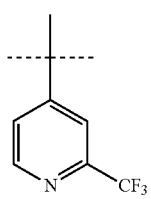 | 13.169^{AC} | 411.3 | Homochiral |
| Example 216 | 4-chloro-N-(1-(4-(6-(trifluoromethyl)pyridin-3-yl)cyclohexyl)ethyl)benzamide | 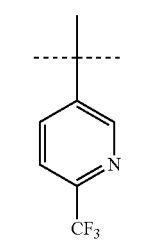 | 2.169^{B} | 411.1 | Diastereomer Mixture |
| Example 217 | 4-chloro-N-(1-(4-(6-(trifluoromethyl)pyridin-3-yl)cyclohexyl)ethyl)benzamide | 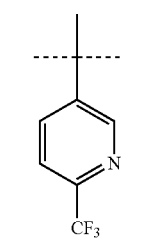 | 8.665^{AD} | 411.1 | Homochiral |

TABLE 2-continued

Examples 211-225 were prepared following the procedures in Example 157 using the corresponding pyridyl halide (absolute and relative stereochemistry unknown)

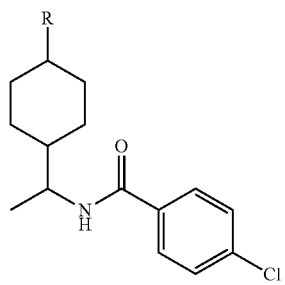

| Example 218 | 4-chloro-N-(1-(4-(6-(trifluoromethyl)pyridin-3-yl)cyclohexyl)ethyl)benzamide | 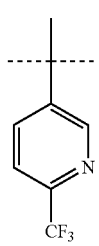 | 9.315$^{AD}$ | 411.1 | Homochiral |
| --- | --- | --- | --- | --- | --- |
| Example 219 | 4-chloro-N-(1-(4-(6-(trifluoromethyl)pyridin-3-yl)cyclohexyl)ethyl)benzamide | 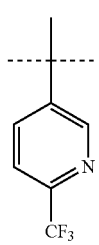 | 11.473$^{AD}$ | 411.1 | Homochiral |
| Example 220 | 4-chloro-N-(1-(4-(6-(trifluoromethyl)pyridin-3-yl)cyclohexyl)ethyl)benzamide | 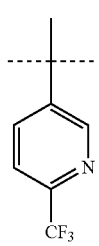 | 14.545$^{AD}$ | 411.1 | Homochiral |
| Example 221 | N-(1-(4-(2-fluoro-3-methylpyridin-4-yl)cyclohexyl)ethyl)-[1,1'-biphenyl]-4-carboxamide | 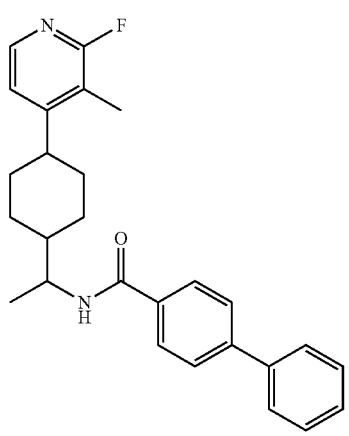 [SMILES: Cc1c(C2CCC(C(C)NC(=O)c3ccc(-c4ccccc4)cc3)CC2)ccnc1F] | 2.310$^{B}$ | 417.2 | Diastereomer Mixture |

TABLE 2-continued

Examples 211-225 were prepared following the procedures in Example 157 using the corresponding pyridyl halide (absolute and relative stereochemistry unknown)

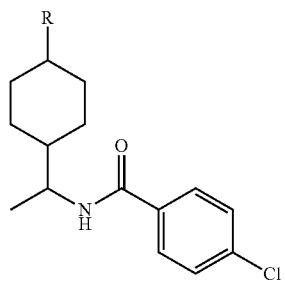

| Example 222 | N-(1-(4-(2-fluoro-3-methylpyridin-4-yl)cyclohexyl)ethyl)-[1,1'-biphenyl]-4-carboxamide | 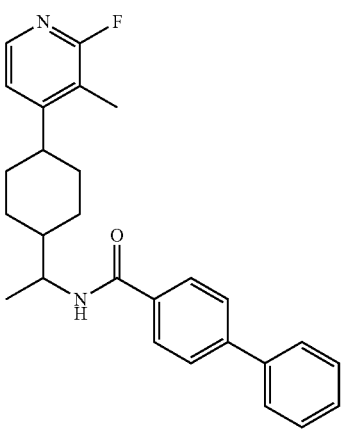 [SMILES: Cc1c(C2CCC(C(C)NC(=O)c3ccc(-c4ccccc4)cc3)CC2)ccnc1F] | 12.645$^{AE}$ | 417.2 | Homochiral |
| Example 223 | N-(1-(4-(2-fluoro-3-methylpyridin-4-yl)cyclohexyl)ethyl)-[1,1'-biphenyl]-4-carboxamide | 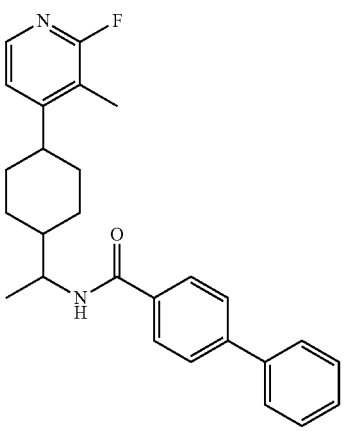 [SMILES: Cc1c(C2CCC(C(C)NC(=O)c3ccc(-c4ccccc4)cc3)CC2)ccnc1F] | 14.189$^{AE}$ | 417.2 | Homochiral |
| Example 224 | N-(1-(4-(2-fluoro-3-methylpyridin-4-yl)cyclohexyl)ethyl)-[1,1'-biphenyl]-4-carboxamide | 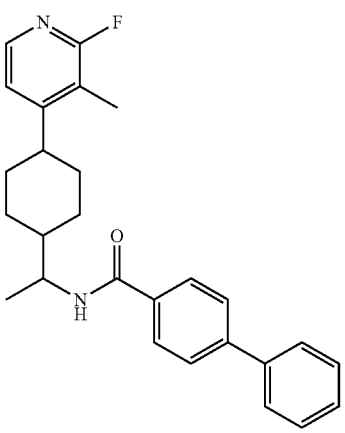 [SMILES: Cc1c(C2CCC(C(C)NC(=O)c3ccc(-c4ccccc4)cc3)CC2)ccnc1F] | 15.726$^{AE}$ | 417.2 | Homochiral |

TABLE 2-continued

Examples 211-225 were prepared following the procedures in Example 157 using the corresponding pyridyl halide (absolute and relative stereochemistry unknown)

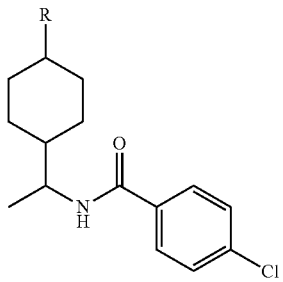

| Example 225 | N-(1-(4-(2-fluoro-3-methylpyridin-4-yl)cyclohexyl)ethyl)-[1,1'-biphenyl]-4-carboxamide | 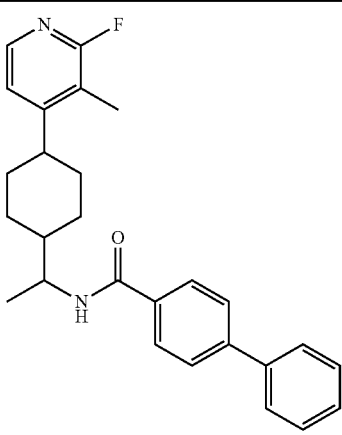 | 21.565[AE] | 417.2 | Homochiral |

Example 226

4-Chloro-N-((1-(6-fluoroquinolin-4-yl)-4-methylpiperidin-4-yl)methyl)benzamide

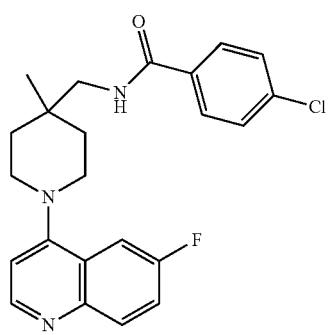 [SMILES: CC1(CNC(=O)c2ccc(Cl)cc2)CCN(c2ccnc3ccc(F)cc23)CC1]

226A. tert-Butyl 4-((4-chlorobenzamido)methyl)-4-methylpiperidine-1-carboxylate To a homogeneous mixture of tert-butyl 4-(aminomethyl)-4-methylpiperidine-1-carboxylate (53.0 mg, 0.23 mmol) in anhydrous DCM (2 mL), under nitrogen atmosphere, was added DIPEA (0.17 mL, 0.97 mmol) followed by 4-chlorobenzoyl chloride (0.05 mL, 0.390 mmol). The resulting mixture was stirred at ambient temperature for 4 hours, before being partitioned between DCM and water. The layers were separated and the aqueous layer was extracted twice more with DCM. These organic extracts were combined with the original organic layer and were concentrated in vacuo to afford the title compound as an amber residue, which was used in the next step without purification. MS(ES): m/z=367 [M+H]$^+$. $t_R$=1.00 min (Method A).

226B. 4-Chloro-N-((4-methylpiperidin-4-yl)methyl)benzamide

To a homogeneous mixture of tert-butyl 4-((4-chlorobenzamido)methyl)-4-methylpiperidine-1-carboxylate (226A, 0.23 mmol) in anhydrous dioxane (3 mL), under nitrogen atmosphere, was added HCl (4N in dioxane, 0.5 mL, 2.0 mmol). The resulting mixture was stirred at ambient temperature for 45 hours before being partitioned between water and EtOAc. The layers were separated and the aqueous layer was extracted once more with EtOAc. The organic layers were combined and washed with water, and this aqueous layer was added to the original aqueous layer. The combined aqueous layer was lyophilized to afford the HCl salt of title compound as a brown residue which was used without further purification. MS (ES): m/z=267 [M+H]$^+$. $t_R$=0.59 min (Method A).

Example 226

4-Chloro-N-((1-(6-fluoroquinolin-4-yl)-4-methylpiperidin-4-yl)methyl)benzamide

To a sealable flask charged with 4-chloro-6-fluoroquinoline (15.0 mg, 0.08 mmol) was added a homogeneous mixture of the HCl salt of 4-chloro-N-((4-methylpiperidin-4-yl)methyl)benzamide (226B, 23.4 mg, 0.09 mmol) and DIPEA (0.07 mL, 0.40 mmol) in anhydrous NMP (1 mL). The vial was sealed and the mixture was stirred at 120° C. After 65 hours, the reaction mixture was cooled to room temperature, diluted with DMF, passed through a syringe filter then purified via preparative HPLC/MS to afford the title compound (19.4 mg; 57% yield). MS(ES): m/z=412 [M+H]$^+$. $t_R$=1.91 min (Method B). $^1$H NMR (500 MHz, DMSO-d$_6$) δ 8.63-8.53 (m, 2H), 8.00 (dd, J=9.1, 5.3 Hz, 1H), 7.85 (d, J=8.4 Hz, 2H), 7.81-7.71 (m, 2H), 7.52 (d, J=8.3 Hz, 2H), 7.10 (d, J=6.3 Hz, 1H), 3.71-3.60 (m, 1H), 3.55-3.43 (m, 1H), 3.31 (d, J=6.1 Hz, 2H), 2.95-2.85 (m, 1H), 2.56-2.54 (m, 1H), 1.79-1.68 (m, 2H), 1.58-1.49 (m, 2H), 1.04 (s, 3H).

Example 227

4-Chloro-N-((4-methyl-1-(2-(trifluoromethyl)pyridin-4-yl)piperidin-4-yl)methyl)benzamide

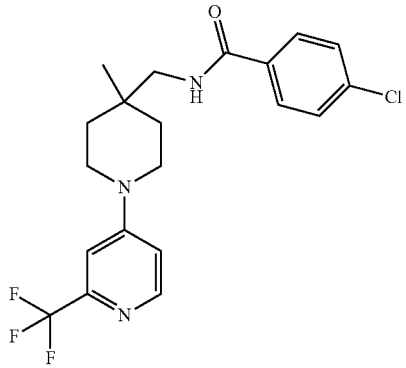 [SMILES: CC1(CNC(=O)c2ccc(Cl)cc2)CCN(c2ccnc(C(F)(F)F)c2)CC1]

Example 227 (13.9 mg; 41% yield) was prepared following a procedure analogous to that for the synthesis of Example 226 except that 4-chloro-2-(trifluoromethyl)pyridine was used instead of 4-chloro-6-fluoroquinoline, in the final step. MS(ES): m/z=412 [M+H]$^+$. $t_R$=1.96 min (Method B). $^1$H NMR (500 MHz, DMSO-d$_6$) δ 8.57-8.48 (m, 1H), 8.19 (d, J=5.9 Hz, 1H), 7.78 (d, J=8.3 Hz, 2H), 7.49 (d, J=8.4 Hz, 2H), 7.13 (s, 1H), 7.01-6.91 (m, 1H), 3.74-3.54 (m, 2H), 3.34-3.24 (m, 2H), 3.21 (d, J=6.2 Hz, 2H), 1.55-1.43 (m, 2H), 1.39-1.30 (m, 2H), 0.96 (s, 3H).

Example 228

N-((4-Methyl-1-(2-(trifluoromethyl)pyridin-4-yl)piperidin-4-yl)methyl)-[1,1'-biphenyl]-4-carboxamide

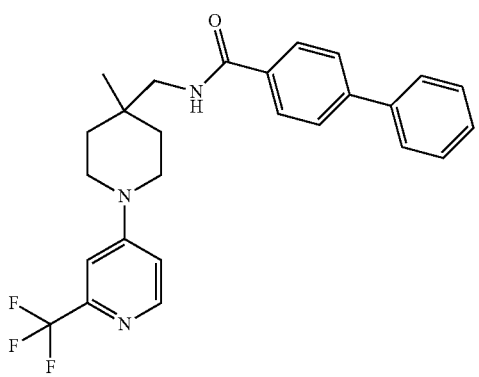 [SMILES: CC1(CNC(=O)c2ccc(-c3ccccc3)cc2)CCN(c2ccnc(C(F)(F)F)c2)CC1]

Example 228 (15.6 mg; 44% yield) was prepared following a procedure analogous to that for the synthesis of Example 227 except that [1,1'-biphenyl]-4-carbonyl chloride was used instead of 4-chlorobenzoyl chloride, in the initial step. MS(ES): m/z=454 [M+H]$^+$. $t_R$=2.12 min (Method B). $^1$H NMR (500 MHz, DMSO-d$_6$) δ 8.49 (t, Hz, 1H), 8.21 (d, J=6.0 Hz, 1H), 7.90 (d, J=8.2 Hz, 2H), 7.79-7.65 (m, 4H), 7.48 (t, J=7.5 Hz, 2H), 7.44-7.36 (m, 1H), 7.16 (s, 1H), 7.04-6.94 (m, 1H), 3.69-3.53 (m, 2H), 3.31 (t, J=9.8 Hz, 2H), 3.25 (d, J=6.1 Hz, 2H), 1.59-1.48 (m, 2H), 1.41-1.32 (m, 2H), 0.99 (s, 3H).

Example 229

(+/−)-4-chloro-N-(1-((1r,4r)-4-((2-(trifluoromethyl)pyridin-4-yl)oxy)cyclohexyl)ethyl)benzamide

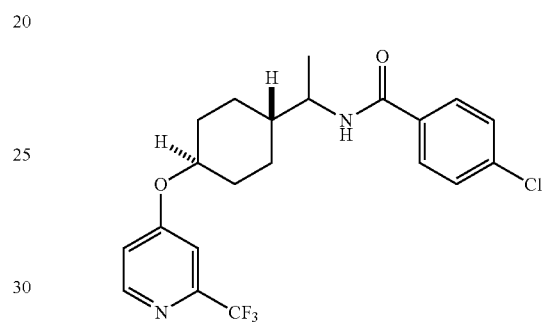

Preparation 229A. ethyl 2-((1r,4r)-4-((2-(trifluoromethyl)pyridin-4-yl)oxy)cyclohexyl)propanoate

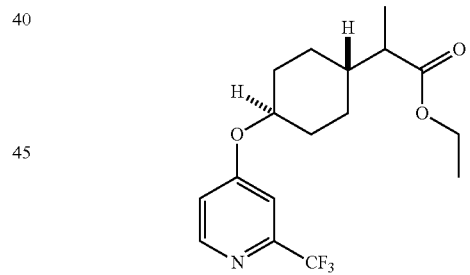

To a solution of ethyl 2-((1r,4r)-4-hydroxycyclohexyl)propanoate (0.1294 g, 0.646 mmol) in DMF (1.077 ml) was added NaH (0.043 g, 1.077 mmol). After 30 min, 4-bromo-2-(trifluoromethyl)pyridine (0.071 ml, 0.538 mmol) as added. The reaction was heated at 80° C. overnight. Reaction quenched with a sat. aq. soln of NH$_4$Cl and diluted with EtOAc. Layers were separated. The aqueous phase was extracted with EtOAc (2×). The combined organic phases were washed with water, dried over Na$_2$SO$_4$, filtered, and concentrated to afford a brown residue. Purification of the crude material by silica gel chromatography using an ISCO machine (40 g column, 40 mL/min, 0-30% EtOAc in hexanes over 14 min, t$_r$=9.5 min) gave the title compound (0.0646 g, 0.187 mmol, 34.7% yield) as a colorless residue. ESI MS (M+H)+=346.2. HPLC Peak tr=1.09 minutes. HPLC conditions: A.

Preparation 229B. 2-((1r,4r)-4-((2-(trifluoromethyl)pyridin-4-yl)oxy)cyclohexyl)propanoic acid

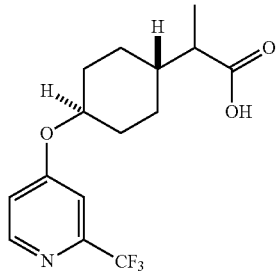 [SMILES: CC(C(=O)O)[C@H]1CC[C@H](Oc2ccnc(C(F)(F)F)c2)CC1]

To a solution of Preparation 229A (0.0437 g, 0.127 mmol) in THF (0.452 ml) and MeOH (0.181 ml) was added lithium hydroxide (1.265 ml, 1.265 mmol). The reaction was heated at 70° C. for 2 h, then allowed to cool to rt. The reaction was adjusted to pH 7 with 1N HCl, then diluted with EtOAc. Layers were separated. The aqueous phase was extracted with EtOAc (3×). The organic phases were combined, dried over $Na_2SO_4$, filtered, and concentrated to afford the title compound as a colorless residue (18.2 mg, 45% yield). ESI MS (M+H)+=318.1. HPLC Peak $t_r$=0.89 minutes. HPLC conditions: A.

Preparation 229C. 1-((1r,4r)-4-((2-(trifluoromethyl)pyridin-4-yl)oxy)cyclohexyl)ethanamine

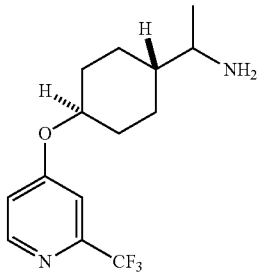 [SMILES: CC(N)[C@H]1CC[C@H](Oc2ccnc(C(F)(F)F)c2)CC1]

Preparation 229B (18.2 mg, 0.057 mmol) taken up in toluene (191 μl) and diphenyl phosphorazidate (13.59 μl, 0.063 mmol) and triethylamine (9.59 μl, 0.069 mmol) added. The vial was sealed and heated to 80° C. After about 2 h, the reaction was cooled to rt. The reaction heated an addition 2 h, then allowed to cool to rt. To this reaction was added 1 mL THF and 1 mL of water and lithium hydroxide (13.74 mg, 0.574 mmol). The reaction stirred at rt overnight. The reaction was acidified to pH=1 with 1N HCl (~5.5 mL) and extracted with EtOAc to remove DPPA related impurities. Then, the aqueous phase was basified to pH=12 with 1N NaOH and extracted with EtOAc (3×). The organic extracts were dried with sodium sulfate, filtered, and concentrated in vacuo to give the title compound (3.8 mg, 0.013 mmol, 22.98% yield) as a yellow residue.

Example 229

(+/−)-4-chloro-N-(1-((1r,4r)-4-((2-(trifluoromethyl)pyridin-4-yl)oxy)cyclohexyl)ethyl)benzamide To a solution of Preparation 229C (3.8 mg, 0.013 mmol) in THF (132 μl) at rt was added Hunig's base (6.91 μl, 0.040 mmol), followed by 4-chlorobenzoyl chloride (3.38 μl, 0.026 mmol). The reaction was stirred at rt for 2 h. The crude material was purified via preparative LC/MS with the following conditions: Column: XBridge C18, 19×150 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 25-100% B over 20 minutes, then a 5-minute hold at 100% B; Flow: 20 mL/min. Fractions containing the desired product were combined and dried via centrifugal evaporation to afford the title compound (2.5 mg, 44%). ESI MS (M+H)+=427.2. HPLC Peak $t_r$=2.101 minutes. Purity=100%. HPLC conditions: B.

Example 230

N-(1-((1s,4s)-4-(6-(trifluoromethyl)quinolin-4-yl)cyclohexyl)propyl)biphenyl-4-carboxamide

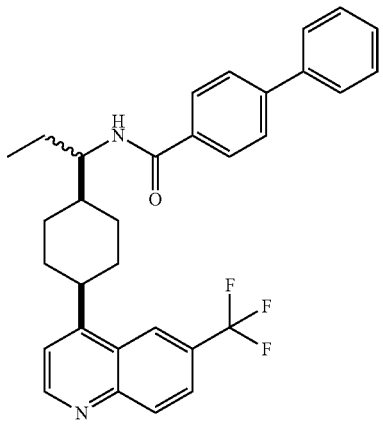

230A. ethyl 2-(4-(6-(trifluoromethyl)quinolin-4-yl)cyclohex-3-enyl)acetate

To a solution of 4-chloro-6-(trifluoromethyl)quinoline (2.05 g, 8.85 mmol), ethyl 2-(4-(4,4,5,5-tetramethyl-1,3,2-dioxaborolan-2-yl)cyclohex-3-en-1-yl)acetate (3.12 g, 10.62 mmol) in 1,4-dioxane (35 mL) was added potassium carbonate (3.67 g, 26.6 mmol) and water (7 mL). The reaction mixture was purged with nitrogen stream for 3 min, followed by addition of $Pd(Ph_3P)_4$ (0.409 g, 0.354 mmol). The resulting mixture was heated at 100° C. under nitrogen stream for over night. The reaction mixture was cooled down and diluted with ethyl acetate and saturated $NaHCO_3$ solution. The organic layer was separated and washed with sat. $NaHCO_3$ solution, and dried over $MgSO_4$. The filtrate was concentrated in vacuo and the residue was purified via silica gel flash column chromatography, eluting with 0-50% ethyl acetate in hexane to give Intermediate 230A (oil, 3.0 g, 8.26 mmol, 93% yield). LC-MS Anal. Calc'd for $C_{20}H_{20}F_3NO_2$, 363.14. found [M+H] 364.5. $T_r$=0.97 min (Method A). $^1$H NMR (400 MHz, CHLOROFORM-d) δ: 8.95 (d, J=4.5 Hz, 1H), 8.31 (s, 1H), 8.22 (d, J=8.8 Hz, 1H), 7.87 (dd, J=8.8, 2.0 Hz, 1H), 7.29 (d, J=4.5 Hz, 1H), 5.86 (dd, J=2.8, 1.7 Hz, 1H), 4.20 (q, J=7.2 Hz, 2H), 2.65-2.24 (m, 5H), 2.15-1.96 (m, 2H), 1.73-1.54 (m, 2H), 1.36-1.29 (m, 3H)

230B. Ethyl 2-(4-(6-(trifluoromethyl)quinolin-4-yl)cyclohexyl)acetate

The reaction mixture of ethyl 2-(4-(6-(trifluoromethyl)quinolin-4-yl)cyclohex-3-en-1-yl)acetate (3.0 g, 8.26 mmol), ammonium formate (2.08 g, 33.0 mmol) in MeOH (50 mL) was purged with nitrogen stream for 3 min, followed by addition of Pd—C (0.88 g, 0.41 mmol). The resulting mixture was heated at 85° C. for 2 h. The reaction mixture was cooled down. The reaction mixture was filtered through a CELITE® pad and the filter cake was washed with MeOH. The filtrate was concentrated in vacuo. The residue was extracted with ethyl acetate and washed with saturated $NaHCO_3$ solution, brine successively. The organic layer was dried over $MgSO_4$ and the filtrate was concentrated in vacuo to give Intermediate 230B (oil, 2.6 g, 7.12 mmol, 86% yield) as a mixture of cis- and trans-diastereomers. LC-MS Anal. Calc'd for $C_{20}H_{22}F_3NO_2$ 365.16. found [M+H] 366.2. $T_r$=0.94 min (Method A). $^1$H NMR (400 MHz, CHLOROFORM-d) δ: 9.05-8.85 (m, 1H), 8.36 (s, 1H), 8.24 (d, J=8.8 Hz, 1H), 7.88 (dd, J=8.9, 1.7 Hz, 1H), 7.51-7.33 (m, 1H), 4.29-4.03 (m, 2H), 3.51-3.23 (m, 1H), 2.61-2.29 (m, 2H), 2.12-1.35 (m, 9H), 1.32-1.21 (m, 3H)

230C ethyl 2-((1s,4s)-4-(6-(trifluoromethyl)quinolin-4-yl)cyclohexyl)butanoate To the flask containing THF (15 mL) was added lithium diisopropylamide (2.0 M solution in THF) (7.65 mL, 15.30 mmol) at −78° C., followed by addition of 1,3-dimethyltetrahydropyrimidin-2(1H)-one (1.29 mL, 10.67 mmol) and a solution of ethyl 2-(4-(6-(trifluoromethyl)quinolin-4-yl)cyclohexyl)acetate (2.6 g, 7.12 mmol) in THF (10 mL) dropwise at −78° C. The resulting mixture turned into dark brown solution and stirred at −78° C. for 1 h, then iodoethane (1.14 mL, 14.23 mmol) was added slowly. The reaction mixture was warmed to rt and stirred for 3 h. The reaction was quenched by pouring into water and extracted with EtOAc. Combined organics was washed with brine, dried with $MgSO_4$, filtered and the filtrate was concentrated in vacuo. The extract was purified via silica gel flash column chromatography, eluting with 0-20% ethyl acetate in hexane to give the minor isomer and the major isomer as cis Intermediate 230C (oil, 1.1 g, 2.77 mmol, 39% yield). LC-MS Anal. Calc'd for $C_{22}H_{26}F_3NO_2$ 393.19. found [M+H] 394.3. $T_r$=0.97 min (Method A). $^1$H NMR (400 MHz, CHLOROFORM-d) δ: 8.97 (d, J=4.6 Hz, 1H), 8.37 (s, 1H), 8.24 (d, J=8.8 Hz, 1H), 7.88 (dd, J=8.8, 2.0 Hz, 1H), 7.46 (d, J=4.6 Hz, 1H), 4.20 (q, J=7.2 Hz, 2H), 3.57-3.32 (m, 1H), 2.64 (td, J=10.8, 4.0 Hz, 1H), 2.14-1.58 (m, 11H), 1.29 (t, J=7.2 Hz, 3H), 0.95 (t, J=7.4 Hz, 3H).

230D. 2-((1s,4s)-4-(6-(trifluoromethyl)quinolin-4-yl)cyclohexyl)butanoic acid To the reaction mixture of ethyl 2-((1s,4s)-4-(6-(trifluoromethyl)quinolin-4-yl)cyclohexyl)butanoate (1.1 g, 2.80 mmol) in THF (20 mL) and MeOH (8 mL) was added lithium hydroxide solution (2.0 M solution) (13.98 mL, 28.0 mmol). The resulting mixture was heated at 65° C. over the weekend. The reaction mixture was cooled down and diluted with water. To the mixture was added 1 N HCl solution to adjust pH to about 5. White solid crashed out at pH 5-6. The resulting mixture was extracted with ethyl acetate twice. The organic layer was separated and washed with brine, dried over $MgSO_4$. The filtrate was concentrated in vacuo to give Intermediate 230D as a racemate (yellow solid, 0.93 g, 2.55 mmol, 91% yield). LC-MS Anal. Calc'd for $C_{20}H_{22}F_3NO_2$ 365.16. found [M+H] 366.3. $T_r$=0.81 min (Method A). $^1$H NMR (400 MHz, DMSO-$d_6$) δ: 12.10 (br. s., 1H), 8.99 (d, J=4.6 Hz, 1H), 8.57 (s, 1H), 8.23 (d, J=8.8 Hz, 1H), 8.00 (dd, J=8.7, 1.9 Hz, 1H), 7.65 (d, J=4.6 Hz, 1H), 3.61 (d, J=10.3 Hz, 1H), 1.96-1.54 (m, 11H), 1.49-1.29 (m, 1H), 0.90 (t, J=7.4 Hz, 3H)

230E 1-((1s,4s)-4-(6-(trifluoromethyl)quinolin-4-yl)cyclohexyl)propan-1-amine To a suspension of 2-((1s,4s)-4-(6-(trifluoromethyl)quinolin-4-yl)cyclohexyl)butanoic acid (0.58 g, 1.587 mmol) in toluene (15 mL) were added diphenylphosphoryl azide (0.40 mL, 1.83 mmol) and triethylamine (0.24 mL, 2.06 mmol). The reaction mixture turned into clear solution after addition of TEA. The reaction mixture was heated to 70° C. for 2 h. The reaction was cooled to rt. The reaction mixture was concentrated under reduced pressure. To the residue was added THF (15 mL) and 2.0 M lithium hydroxide solution (7.94 mL, 15.87 mmol) and the resulting mixture was stirred at rt for 4 h. The reaction mixture was acidified with 1N HCl (white precipitate forms) and extracted with EtOAc to remove DPPA related impurities. Then the aqueous layer was basified with 1N NaOH (precipitate forms again) and extracted with EtOAc four times. The organic extracts were combined, dried over $MgSO_4$ and the filtrate was concentrated in vacuo to give light yellow oil, dried on high vacuum over night to give Intermediate 230E (oil, 0.47 g, 1.397 mmol, 88% yield). LC-MS Anal. Calc'd for $C_{19}H_{23}F_3N_2$, 336.18. found [M+H] 337.2. $T_r$=0.68 min (Method A). $^1$H NMR (400 MHz, CHLOROFORM-d) δ: 8.95 (d, J=4.6 Hz, 1H), 8.38 (s, 1H), 8.24 (d, J=8.8 Hz, 1H), 7.88 (dd, J=8.8, 1.8 Hz, 1H), 7.45 (d, J=4.6 Hz, 1H), 3.57-3.44 (m, 1H), 2.90 (td, J=8.5, 3.0 Hz, 1H), 2.22-1.20 (m, 13H), 1.01 (d, J=15.0 Hz, 3H)

Example 230 N-(1-((1s,4s)-4-(6-(trifluoromethyl)quinolin-4-yl)cyclohexyl)propyl)biphenyl-4-carboxamide To a solution of [1,1'-biphenyl]-4-carboxylic acid (21.2 mg, 0.107 mmol) in DMF (1.5 mL) was added HATU (44 mg, 0.116 mmol). The reaction mixture was stirred at rt for 10 min, followed by addition of a solution of 1-((1s,4s)-4-(6-(trifluoromethyl)quinolin-4-yl)cyclohexyl)propan-1-amine (30 mg, 0.089 mmol) in THF (0.8 mL) and DIPEA (0.03 mL, 0.178 mmol). The reaction mixture was stirred at rt for 2 h. and was concentrated in vacuo. The residue was dissolved in MeOH, filtered, and purified via preparative HPLC to give a racemic Example 230 (33 mg, 0.063 mmol, 71% yield). LC-MS Anal. Calc'd for $C_{32}H_{31}F_3N_2O$, 516.24. found [M+H] 517.0. $T_r$=2.02 min (Method B). $^1$H NMR (500 MHz, DMSO-$d_6$) δ: 9.01 (d, J=4.5 Hz, 1H), 8.55 (s, 1H), 8.30-8.21 (m, 1H), 8.17 (d, J=9.3 Hz, 1H), 8.03-7.91 (m, 3H), 7.79-7.67 (m, 4H), 7.61 (d, J=4.5 Hz, 1H), 7.48 (t, J=7.4 Hz, 2H), 7.43-7.37 (m, 1H), 4.33 (d, J=8.7 Hz, 1H), 4.02-3.49 (m, 1H), 1.99-1.33 (m, 11H), 0.90 (t, J=7.0 Hz, 3H)

Example 231a-e (Absolute and Relative Stereochemistry Unknown)
4-chloro-N-(1-(4-(6-(difluoromethyl)pyridin-2-yl)cyclohexyl)propyl)benzamide

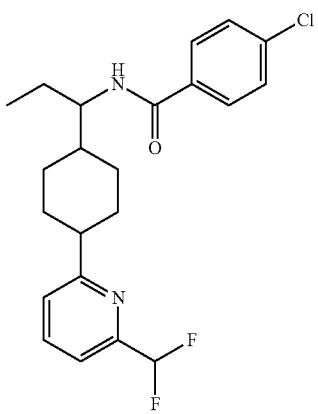

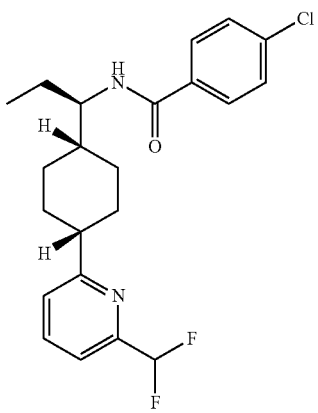

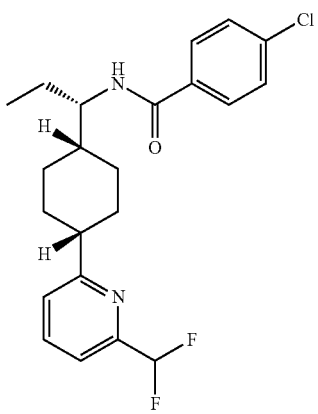 [SMILES: CC[C@H](NC(=O)c1ccc(Cl)cc1)[C@H]1CC[C@H](c2cccc(C(F)F)n2)CC1]

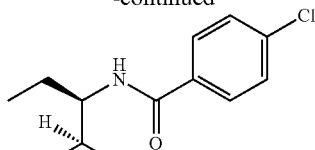

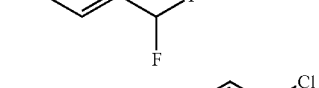

231A. ethyl 2-(4-(6-(difluoromethyl)pyridin-2-yl)cyclohex-3-enyl)acetate

To the reaction mixture of 2-bromo-6-(difluoromethyl)pyridine (1.55 g, 7.45 mmol), ethyl 2-(4-(4,4,5,5-tetramethyl-1,3,2-dioxaborolan-2-yl)cyclohex-3-en-1-yl)acetate (2.52 g, 8.57 mmol) in 1,4-Dioxane (20 mL) was added $K_2CO_3$ (7.45 mL, 22.36 mmol) solution and the resulting mixture was purged with nitrogen stream for 3 min, followed by addition of $Pd(Ph_3P)_4$ (0.431 g, 0.373 mmol) and the reaction mixture was further purged with nitrogen stream and then heated at 110° C. under nitrogen for 20 h. The reaction mixture was diluted with brine and ethyl acetate. The organic layer was separated, dried over $MgSO_4$. The filtrate was concentrated in vacuo and the residue was purified via silica gel flash column chromatography, eluting with 0-20% ethyl acetate in hexane to give Intermediate 231A (oil, 2.2 g, 7.45 mmol, 99% yield). LC-MS Anal. Calc'd for $C_{16}H_{19}F_2NO_2$, 295.14. found [M+H] 296.2. $T_r$=1.10 min (Method A). $^1$H NMR (400 MHz, METHANOL-$d_4$) δ: 7.92-7.80 (m, 1H), 7.60 (dd, J=8.0, 0.8 Hz, 1H), 7.47 (d, J=7.7 Hz, 1H), 6.71 (dd, J=3.1, 2.0 Hz, 1H), 6.65-6.44 (m, 1H), 4.20-4.08 (m, 2H), 2.79-2.65 (m, 1H), 2.56-2.39 (m, 2H), 2.36 (d, J=7.0 Hz, 2H), 2.20-1.92 (m, 3H), 1.48 (dtd, J=13.0, 10.6, 5.5 Hz, 1H), 1.30-1.22 (m, 3H)

231B. ethyl 2-(4-(6-(difluoromethyl)pyridin-2-yl)cyclohexyl)acetate

The reaction mixture of crude ethyl 2-(4-(6-(difluoromethyl)pyridin-2-yl)cyclohex-3-en-1-yl)acetate (2.1 g, 7.11 mmol), ammonium formate (1.794 g, 28.4 mmol) in MeOH (40 mL) was purged with nitrogen stream for 3 min, followed by addition of 5% Pd—C (0.757 g, 0.356 mmol). The resulting mixture was heated at 85° C. for 2 h. The reaction mixture was cooled down. The reaction mixture was filtered and the filter cake was washed with MeOH. The filtrate was concentrated in vacuo. The residue was extracted with ethyl acetate and washed with saturated NaHCO$_3$ solution, brine successively. The organic layer was dried over MgSO$_4$ and the filtrate was concentrated in vacuo to give Intermediate 231B (oil, 1.8 g, 6.05 mmol, 85% yield) as a mixture of cis- and trans-diastereomers. LC-MS Anal. Calc'd for C$_{16}$H$_{21}$F$_2$NO$_2$, 297.15 found 298.2 [M+H]. T$_r$=1.09 min (Method A). $^1$H NMR (400 MHz, CHLOROFORM-d) δ: 7.75 (t, J=7.8 Hz, 1H), 7.55-7.42 (m, 1H), 7.34-7.23 (m, 1H), 6.98 (dd, J=14.0, 7.8 Hz, 1H), 6.80-6.42 (m, 1H), 4.33-4.04 (m, 2H), 2.91-2.59 (m, 1H), 2.55-2.36 (m, 2H), 2.34-2.20 (m, 1H), 2.07-1.52 (m, 8H), 1.32-1.23 (m, 3H)

231C ethyl 2-(4-(6-(difluoromethyl)pyridin-2-yl) cyclohexyl)butanoate

To the flask containing THF (8 mL) was added lithium diisopropylamide (2.0 M solution in THF) (3.70 mL, 7.40 mmol) at −78° C., followed by addition of 1,3-dimethyltetrahydropyrimidin-2(1H)-one (0.81 mL, 6.73 mmol) and a solution of ethyl 2-(4-(6-(difluoromethyl)pyridin-2-yl)cyclohexyl)acetate (1.0 g, 3.36 mmol) in THF (10 mL) dropwise at −78° C. The resulting mixture turned into brown solution and was stirred at −78° C. for 1 h, then iodoethane (0.54 mL, 6.73 mmol) was added slowly. The reaction mixture was then stirred at −78° C. for 0.5 h, warmed to rt for 20 h. To the reaction mixture was added more lithium diisopropylamide (2.0 M solution in THF) (3.70 mL, 7.40 mmol) (1.8 mL) at ice bath temperature. The reaction mixture was stirred at ice bath temperature for 2 h. The reaction was quenched by pouring into water and extracted with EtOAc. Combined organics were washed with brine, dried with sodium sulfate, filtered and concentrated in vacuo. The extract was purified via silica gel flash column chromatography, eluting with 0-16% ethyl acetate in hexane to give Intermediate 231C (oil, 0.365 g, 1.122 mmol, 33% yield). LC-MS Anal. Calc'd for C$_{18}$H$_{25}$F$_2$NO$_2$, 325.18 found [M+H] 326.3. T$_r$=1.12 min (Method A). $^1$H NMR (400 MHz, CHLOROFORM-d) δ: 7.82-7.69 (m, 1H), 7.45 (d, J=7.5 Hz, 1H), 7.32 (d, J=7.9 Hz, 0.5H), 7.26-7.21 (m, 0.5H), 6.84-6.33 (m, 1H), 4.17 (qd, J=7.1, 5.9 Hz, 2H), 2.90 (dt, J=8.8, 4.4 Hz, 0.5H), 2.70 (tt, J=12.2, 3.4 Hz, 0.5H), 2.53-2.36 (m, 0.5H), 2.18-2.09 (m, 0.5H), 2.06-1.73 (m, 5H), 1.71-1.57 (m, 4H), 1.55-1.44 (m, 1H), 1.27 (dt, J=12.8, 7.2 Hz, 4H), 0.90 (t, J=7.4 Hz, 3H)

231D. 2-(4-(6-(difluoromethyl)pyridin-2-yl)cyclohexyl)butanoic acid

To the reaction mixture of ethyl 2-(4-(6-(difluoromethyl) pyridin-2-yl)cyclohexyl)butanoate (0.4 g, 1.229 mmol) in THF (6 mL) and MeOH (3 mL) was added LiOH solution (6.15 mL, 18.44 mmol) at rt. The reaction mixture was then heated 60° C. over night. To the reaction mixture was added more THF (4 mL) and LiOH solution (6.15 mL, 18.44 mmol) and the reaction mixture was heated at 60° C. for another 3 days. To the reaction mixture was added 2 N HCl solution to adjust pH to about 5-6 and the resulting mixture was extracted with ethyl acetate twice. The organic layer was separated and dried over MgSO$_4$. The filtrate was concentrated in vacuo to give Intermediate 231D (yellow solid, 0.37 g, 1.22 mmol, 99% yield). LC-MS Anal. Calc'd for C$_{16}$H$_{21}$F$_2$NO$_2$, 297.15. found [M+H] 298.3, T$_r$=0.96 min (Method A).
$^1$H NMR (400 MHz, METHANOL-d$_4$) δ: 7.86 (td, J=7.8, 1.5 Hz, 1H), 7.50-7.37 (m, 2H), 6.86-6.47 (m, 1H), 2.99-2.84 (m, 0.5H), 2.72 (tt, J=12.2, 3.4 Hz, 0.5H), 2.53-2.37 (m, 0.5H), 2.15-1.42 (m, 10.5H), 1.36-1.12 (m, 1H), 0.94 (td, J=7.4, 2.9 Hz, 3H)

231E. 1-(4-(6-(difluoromethyl)pyridin-2-yl)cyclohexyl)propan-1-amine

To a suspension of 2-(4-(6-(difluoromethyl)pyridin-2-yl) cyclohexyl)butanoic acid (0.32 g, 1.076 mmol) in Toluene (8 mL) were added diphenylphosphoryl azide (0.27 mL, 1.24 mmol) and triethylamine (0.17 mL, 1.40 mmol). The reaction mixture in a sealed vial turned into clear solution after addition of TEA. The reaction mixture was heated to 70° C. for 2.5 h. The reaction mixture was concentrated under reduced pressure. To the residue was added THF (10 mL) and 2.0 M lithium hydroxide solution (5.4 mL, 10.76 mmol) and the resulting mixture was stirred at rt for 1 h. The reaction mixture was acidified with 1N HCl (white precipitate forms) and extracted with EtOAc to remove DPPA related impurities. Then the aqueous layer was basified with 1N NaOH (precipitate forms again) and extracted with EtOAc 3 times. The basic extracts were combined, dried over MgSO$_4$ and the filtrate was concentrated in vacuo to give colorless oil, dried on high vacuum over night to give Intermediate 231E (oil, 95 mg, 0.35 mmol, 33% yield). LC-MS Anal. Calc'd for C$_{15}$H$_{22}$F$_2$N$_2$, 268.17. found [M+H] 269.5. T$_r$=0.71 min (Method A).
$^1$H NMR (400 MHz, METHANOL-d$_4$) δ: 7.84 (td, J=7.8, 2.2 Hz, 1H), 7.54-7.34 (m, 2H), 6.82-6.39 (m, 1H), 2.98 (dt, J=7.6, 3.5 Hz, 0.5H), 2.80-2.64 (m, 1H), 2.49 (dt, J=8.1, 4.7 Hz, 0.5H), 2.21-1.17 (m, 11H), 0.96 (q, J=7.4 Hz, 3H)

Example 231

Four Isomers 4-chloro-N-(1-(4-(6-(difluoromethyl) pyridin-2-yl)cyclohexyl)propyl)benzamide To a solution of 4-chlorobenzoic acid (30.1 mg, 0.192 mmol) in DMF (1 mL) was added HATU (79 mg, 0.208 mmol). The reaction mixture was stirred at rt for 3 min, followed by addition of a solution of Intermediate 231C (43 mg, 0.160 mmol) in THF (1 mL) and DIPEA (0.1 mL, 0.50 mmol). The reaction mixture was stirred at rt for 1 h. and was concentrated in vacuo. The residue was dissolved in MeOH, filtered, and purified via preparative HPLC to give a mixture of diastereomers Example 231a.

The isomers were further separated by preparative SFC (Method R) to give first eluate Example 231b (11.3 mg, 0.027 mmol, 16.8% yield). LC-MS Anal. Calc'd for C$_{22}$H$_{25}$ClF$_2$N$_2$O, 406.16. found [M+H] 406.9. T$_r$=2.15 min (Method B). $^1$H NMR (500 MHz, DMSO-d$_6$) δ: 8.11 (d, J=9.1 Hz, 1H), 7.90 (t, J=7.8 Hz, 1H), 7.82 (d, J=8.3 Hz, 2H), 7.57-7.41 (m, 4H), 7.02-6.68 (m, 1H), 4.02 (d, J=9.6 Hz, 1H), 2.86 (br. s., 1H), 2.02-1.82 (m, 2H), 1.77-1.26 (m, 9H), 0.82 (t, J=7.2 Hz, 3H).

Second eluate Example 231c (10.5 mg, 0.025 mmol, 15.8% yield). LC-MS Anal. Calc'd for C$_{22}$H$_{25}$ClF$_2$N$_2$O, 406.16. found [M+H] 407.2. T$_r$=2.28 min (Method B). $^1$H NMR (500 MHz, DMSO-d$_6$) δ: 8.09 (d, J=9.1 Hz, 1H), 7.92 (t, J=7.8 Hz, 1H), 7.84 (d, J=8.4 Hz, 2H), 7.59-7.38 (m, 4H), 7.04-6.73 (m, 1H), 4.03 (d, J=8.1 Hz, 1H), 2.88 (br. s., 1H), 2.06-1.24 (m, 11H), 0.83 (t, J=7.2 Hz, 3H)

Third eluate Example 231d (8 mg, 0.019 mmol, 12.0% yield). LC-MS Anal. Calc'd for $C_{22}H_{25}ClF_2N_2O$, 406.16. found [M+H] 407.0. $T_r$=2.12 min (Method B). $^1$H NMR (500 MHz, DMSO-$d_6$) δ: 8.15 (d, J=9.1 Hz, 1H), 7.95-7.77 (m, 3H), 7.52 (d, J=8.3 Hz, 2H), 7.49-7.35 (m, 2H), 7.05-6.59 (m, 1H), 3.75 (d, J=9.1 Hz, 1H), 2.79-2.58 (m, 1H), 1.97-1.77 (m, 4H), 1.71-1.36 (m, 5H), 1.17 (br. s., 2H), 0.84 (t, J=7.2 Hz, 3H).

Fourth eluate Example 231E (8.9 mg, 0.021 mmol, 13.4% yield). LC-MS Anal. Calc'd for $C_{22}H_{25}ClF_2N_2O$, 406.16. found [M+H] 406.9. $T_r$=2.12 min (Method B). $^1$H NMR (500 MHz, DMSO-$d_6$) δ: 8.15 (d, J=9.0 Hz, 1H), 7.96-7.80 (m, 3H), 7.53 (d, J=8.3 Hz, 2H), 7.48 (d, J=7.6 Hz, 1H), 7.43 (d, J=7.7 Hz, 1H), 6.99-6.72 (m, 1H), 3.75 (d, J=9.1 Hz, 1H), 2.78-2.58 (m, 1H), 1.99-1.77 (m, 4H), 1.70-1.38 (m, 5H), 1.17 (br. s., 2H), 0.84 (t, J=7.2 Hz, 3H)

Example 232

N—((R)-1-((1s,4S)-4-(6-fluoroquinolin-4-yl)cyclohexyl)ethyl)-4-(5-methyl-1,3,4-oxadiazol-2-yl)benzamide

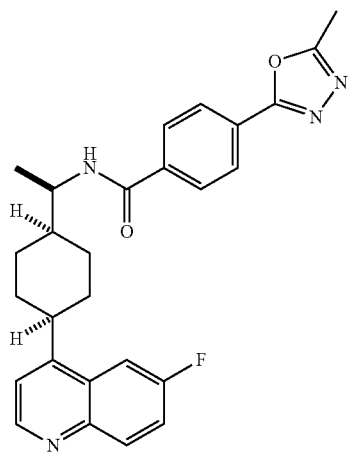 [SMILES: Cc1nnc(-c2ccc(C(=O)N[C@H](C)[C@H]3CC[C@@H](c4ccnc5ccc(F)cc54)CC3)cc2)o1]

232A. 4-bromo-N—((R)-1-((1s,4S)-4-(6-fluoroquinolin-4-yl)cyclohexyl)ethyl)benzamide To a solution of 4-bromobenzoic acid (354 mg, 1.762 mmol) in DMF (6 mL) was added HATU (670 mg, 1.762 mmol). The reaction mixture was stirred at rt for 5 min, followed by addition of a solution of (R)-1-((1s,4S)-4-(6-fluoroquinolin-4-yl)cyclohexyl)ethanamine (400 mg, 1.469 mmol) in THF (3 mL) and DIPEA (0.77 mL, 4.41 mmol). The reaction mixture was stirred at rt for 3 h. The reaction mixture was diluted with ethyl acetate and saturated NaHCO$_3$ solution. The organic layer was separated and washed with brine, dried over MgSO$_4$. The filtrate was concentrated in vacuo. and the residue was purified via silica gel flash column chromatography, eluting with 0-70% ethyl acetate in hexane to give Intermediate 232A (white solid, 0.55 g, 1.208 mmol, 82% yield). LC-MS Anal. Calc'd for $C_{24}H_{24}BrFN_2O$, 454.1. found [M+H] 455.1, 457.1. $T_r$=0.85 min (Method A). $^1$H NMR (400 MHz, CHLOROFORM-d) δ: 8.82 (d, J=4.5 Hz, 1H), 8.12 (dd, J=9.3, 5.7 Hz, 1H), 7.73-7.63 (m, 3H), 7.62-7.56 (m, 2H), 7.47 (ddd, J=9.2, 8.0, 2.8 Hz, 1H), 7.42 (d, J=4.5 Hz, 1H), 5.85 (d, J=9.3 Hz, 1H), 4.61 (tq, J=9.7, 6.5 Hz, 1H), 3.45-3.17 (m, 2.15-1.68 (m, 9H), 1.32 (d, J=6.6 Hz, 3H)

232B. N—((R)-1-((1s,4S)-4-(6-fluoroquinolin-4-yl)cyclohexyl)ethyl)-4-(4,4,5,5-tetramethyl-1,3,2-dioxaborolan-2-yl)benzamide To a solution of 4-bromo-N—((R)-1-((1s,4S)-4-(6-fluoroquinolin-4-yl)cyclohexyl)ethyl)benzamide (0.55 g, 1.208 mmol) in 1,4-dioxane (20 mL) were added potassium acetate (0.356 g, 3.62 mmol) and bis(pinacolato)diboron (0.368 g, 1.449 mmol). The reaction mixture was purged with nitrogen stream for 3 min, followed by addition of PdCl$_2$(dppf) (0.088 g, 0.121 mmol). The reaction mixture was heated at 90° C. over night. The reaction mixture was cooled down and diluted with saturated NaHCO$_3$ solution and ethyl acetate. The organic layer was separated and washed with brine, dried over MgSO$_4$. The filtrate was concentrated in vacuo. to give crude Intermediate 232B as boronic ester and acid mixture (black solid, 0.6 g, 1.208 mmol, 99% yield). LC-MS Anal. Calc'd for $C_{30}H_{36}BFN_2O_3$, 502.28. found [M+H] 503.5. $T_r$=0.87 min (Method A).

Example 232

N—((R)-1-((1s,4S)-4-(6-fluoroquinolin-4-yl)cyclohexyl)ethyl)-4-(5-methyl-1,3,4-oxadiazol-2-yl)benzamide To the reaction mixture of 2-bromo-5-methyl-1,3,4-oxadiazole (15.57 mg, 0.096 mmol) and crude N—((R)-1-((1s,4S)-4-(6-fluoroquinolin-4-yl)cyclohexyl)ethyl)-4-(4,4,5,5-tetramethyl-1,3,2-dioxaborolan-2-yl)benzamide (40 mg, 0.080 mmol) in dioxane (2 mL) was added Na$_2$CO$_3$ (2.0 M solution) (0.12 mL, 0.24 mmol). The reaction mixture was purged with nitrogen stream for 2 min, followed by addition of PdCl$_2$(dppf) (5.8 mg, 0.0080 mmol). The resulting mixture in the sealed tube was heated at 90° C. for 16 h. The reaction mixture was diluted with ethyl acetate and sat. NaHCO$_3$ solution. The organic layer was separated and concentrated in vacuo. The residue was dissolved in DMF, filtered, and purified via preparative HPLC to give Example 232 (17 mg, 0.037 mmol, 46.1% yield). LC-MS Anal. Calc'd for $C_{27}H_{27}FN_4O_2$ 458.21. found [M+H] 458.9. $T_r$=1.23 min (Method I). $^1$H NMR (500 MHz, DMSO-$d_6$) δ: 8.83 (d, J=4.5 Hz, 1H), 8.47 (d, J=8.8 Hz, 1H), 8.14-8.00 (m, 5H), 7.97 (d, J=8.8 Hz, 1H), 7.66 (t, J=7.4 Hz, 1H), 7.48 (d, J=4.3 Hz, 1H), 4.46 (br. s., 1H), 3.38 (br. s., 1H), 2.59 (s, 3H), 1.96-1.54 (m, 9H), 1.22 (d, J=6.4 Hz, 3H)

Examples 233-253

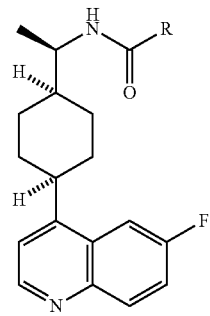

Examples 233-253 were prepared from Intermediate 40L following the procedure for Example 47 using the corresponding acid or following the procedure for Example 231.

| Ex. No. | Name | R | Tr (min)^{Method 1*} | [M + H]^+ |
|---|---|---|---|---|
| Example 233 | N-((R)-1-((1s,4S)-4-(6-fluoroquinolin-4-yl)cyclohexyl)ethyl)-4-(pyrazin-2-yl)benzamide | 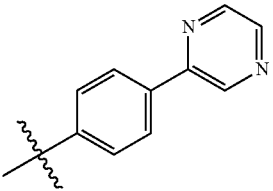 [SMILES: *c1ccc(-c2cnccn2)cc1] | 1.47 | 455.0 |
| Example 234 | N-((R)-1-((1s,4S)-4-(6-fluoroquinolin-4-yl)cyclohexyl)ethyl)-4-(pyrimidin-5-yl)benzamide | 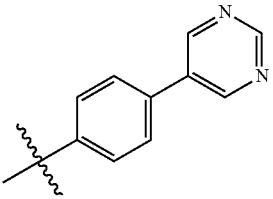 [SMILES: *c1ccc(-c2cncnc2)cc1] | 1.20 | 454.9 |
| Example 235 | N-((R)-1-((1s,4S)-4-(6-fluoroquinolin-4-yl)cyclohexyl)ethyl)-4-(1-methyl-1H-imidazol-4-yl)benzamide | 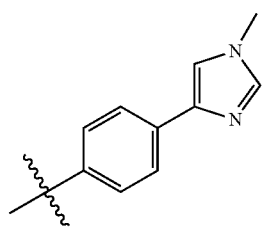 [SMILES: *c1ccc(-c2cn(C)cn2)cc1] | 0.98 | 457.0 |
| Example 236 | N-((R)-1-((1s,4S)-4-(6-fluoroquinolin-4-yl)cyclohexyl)ethyl)-4-(2-methoxypyrimidin-4-yl)benzamide | 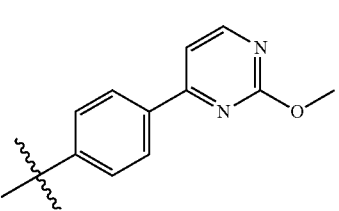 [SMILES: *c1ccc(-c2ccnc(OC)n2)cc1] | 1.45 | 485.1 |
| Example 237 | N-((R)-1-((1s,4S)-4-(6-fluoroquinolin-4-yl)cyclohexyl)ethyl)-4-(6-methylsulfonyl)pyridin-3-yl)benzamide | 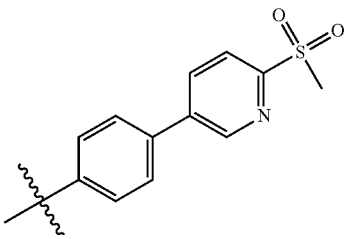 [SMILES: *c1ccc(-c2ccc(S(C)(=O)=O)nc2)cc1] | 1.31 | 532.1 |
| Example 238 | N-((R)-1-((1s,4S)-4-(6-fluoroquinolin-4-yl)cyclohexyl)ethyl)-4-(2-methylthiazol-5-yl)benzamide | 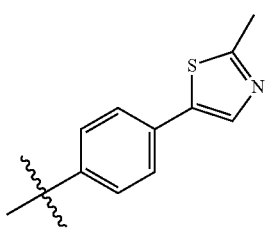 [SMILES: *c1ccc(-c2cnc(C)s2)cc1] | 1.48 | 473.9 |

-continued

| Ex. No. | Name | R | Tr (min)$^{Method\ 1*}$ | [M + H]$^+$ |
|---|---|---|---|---|
| Example 239 | N-((R)-1-((1s,4S)-4-(6-fluoroquinolin-4-yl)cyclohexyl)ethyl)-4-(5-methoxypyridin-2-yl)benzamide | | 1.21 | 483.9 |
| Example 240 | 4-(2-cyanopyrimidin-5-yl)-N-((R)-1-((1s,4S)-4-(6-fluoroquinolin-4-yl)cyclohexyl)ethyl)benzamide | | 1.55 | 480.4 |
| Example 241 | N-((R)-1-((1s,4S)-4-(6-fluoroquinolin-4-yl)cyclohexyl)ethyl)-4-(2-methoxythiazol-4-yl)benzamide | | 1.67 | 489.8 |
| Example 242 | N-((R)-1-((1s,4S)-4-(6-fluoroquinolin-4-yl)cyclohexyl)ethyl)-4'-(2-hydroxypropan-2-yl)biphenyl-4-carboxamide | | 1.56 | 511.0 |
| Example 243 | N-((R)-1-((1s,4S)-4-(6-fluoroquinolin-4-yl)cyclohexyl)ethyl)-4-(thiazol-4-yl)benzamide | | 1.51 | 460.0 |
| Example 244 | N-((R)-1-((1s,4S)-4-(6-fluoroquinolin-4-yl)cyclohexyl)ethyl)-4-(1,3,4-oxadiazol-2-yl)benzamide | | 1.16 | 444.9 |
| Example 245 | N-((R)-1-((1s,4S)-4-(6-fluoroquinolin-4-yl)cyclohexyl)ethyl)-4-(6-methoxypyridin-3-yl)benzamide | | 1.63 | 484.4 |

-continued

| Ex. No. | Name | R | Tr (min)<sup>Method 1*</sup> | [M + H]⁺ |
|---|---|---|---|---|
| Example 246 | N-((R)-1-((1s,4S)-4-(6-fluoroquinolin-4-yl)cyclohexyl)ethyl)-4-morpholinobenzamide | 4-morpholinophenyl | 1.29 | 462.1 |
| Example 247 | 4-cyclopropyl-N-((R)-1-((1s,4S)-4-(6-fluoroquinolin-4-yl)cyclohexyl)ethyl)benzamide | 4-cyclopropylphenyl | 1.56 | 416.9 |
| Example 248 | N-((R)-1-((1s,4S)-4-(6-fluoroquinolin-4-yl)cyclohexyl)ethyl)-4-(1-methylcyclopropyl)benzamide | 4-(1-methylcyclopropyl)phenyl | 1.67 | 431.0 |
| Example 249 | N-((R)-1-((1s,4S)-4-(6-fluoroquinolin-4-yl)cyclohexyl)ethyl)-4-(trifluoromethyl)benzamide | 4-(trifluoromethyl)phenyl | 1.58 | 444.9 |
| Example 250 | N-((R)-1-((1s,4S)-4-(6-fluoroquinolin-4-yl)cyclohexyl)ethyl)-4-(oxazol-5-yl)benzamide | 4-(oxazol-5-yl)phenyl | 1.27 | 444.0 |
| Example 251 | N-((R)-1-((1s,4S)-4-(6-fluoroquinolin-4-yl)cyclohexyl)ethyl)-4-(1-methyl-1H-1,2,4-triazol-5-yl)benzamide | 4-(1-methyl-1H-1,2,4-triazol-5-yl)phenyl | 1.24 | 458.3 |
| Example 252 | N-((R)-1-((1s,4S)-4-(6-fluoroquinolin-4-yl)cyclohexyl)ethyl)-4-(5-methylthiazol-2-yl)benzamide | 4-(5-methylthiazol-2-yl)phenyl | 1.53 | 474.1 |

-continued

| Ex. No. | Name | R | Tr (min)$^{Method\ 1*}$ | [M + H]$^+$ |
|---|---|---|---|---|
| Example 253 | 4-(5-cyanothiazol-2-yl)-N-((R)-1-((1s,4S)-4-(6-fluoroquinolin-4-yl)cyclohexyl)ethyl)benzamide | 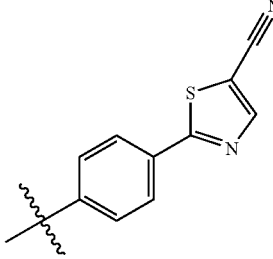 | 1.61 | 485.2 |

*unless otherwise noted

Examples 254-256

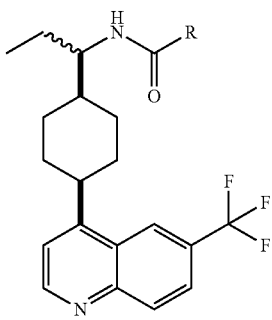

Examples 257-263

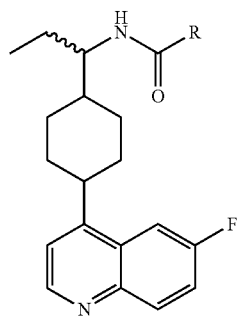

Examples 254-256 were prepared from Intermediate 230E following the procedure for Example 230 using the corresponding acid.

Examples 257-263 were prepared from Intermediate 164J following the procedure for Example 164 using the corresponding acid.

| Ex. No. | Name | R | Tr (min)$^{Method\ 1*}$ | [M + H]$^+$ |
|---|---|---|---|---|
| Example 254 | 4-chloro-N-(1-((1s,4s)-4-(6-(trifluoromethyl)quinolin-4-yl)cylcohexyl)propyl)benzamide | 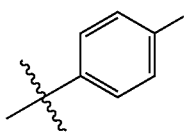 | 1.81 | 474.8 |
| Example 255 | 4-(1H-pyrrol-1-yl)-N-(1-((1s,4S)-4-(6-(trifloromethyl)quinolin-4-yl)cyclohexyl)propyl)benzamide | 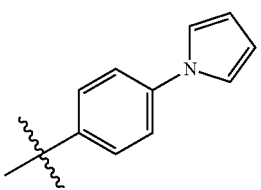 [SMILES: *c1ccc(-n2cccc2)cc1] | 1.89 | 506.1 |
| Example 256 | 6-methoxy-N-(1-((1s,4S)-4-(6-(trifluoromethyl)quinolin-4-yl)cylcohexyl)propyl)nicotinamide | 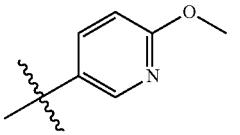 [SMILES: *c1ccc(OC)nc1] | 1.56 | 471.9 |

*unless otherwise noted

| Ex. No. | Stereochemistry | Name | R | Tr (min)$^{Method\ 1*}$ | [M + H]$^+$ |
|---|---|---|---|---|---|
| Example 257 | Diastereomer mixture | N-(1-(4-(6-fluoroquinolin-4-yl)cyclohexyl)propyl)-4-(thiazol-2-yl)benzamide | | 1.53-1.56 | 474.3 |
| Example 258 | Diastereomer mixture | N-(1-(4-(6-fluoroquinolin-4-yl)cyclohexyl)propyl)biphenyl-4-carboxamide | | 1.79-1.83 | 467.0 |
| Example 259 Isomer 1 | Homochiral, absolute and realtive stereochemistry unknown | N-(1-(4-(6-fluoroquinolin-4-yl)cyclohexyl)propyl)biphenyl-4-carboxamide | | 1.83 | 466.9 |
| Example 260 Isomer 2 | Homochiral, absolute and realtive stereochemistry unknown | N-(1-(4-(6-fluoroquinolin-4-yl)cylcohexyl)propyl)biphenyl-4-carboxamide | | 1.93 | 467.1 |
| Example 261 Isomer 3 | Homochiral, absolute and realtive stereochemistry unknown | N-(1-(4-(6-fluoroquinolin-4-yl)cyclohexyl)propyl)biphenyl-4-carboxamide | | 1.90 | 467.1 |
| Example 262 Isomer 4 | Homochiral, absolute and realtive stereochemistry unknown | N-(1-(4-(6-fluoroquinolin-4-yl)cyclohexyl)propyl)biphenyl-4-carboxamide | | 1.85 | 467.4 |
| Example 263 | Diastereomer mixture | N-(1-(4-(6-fluoroquinolin-4-yl)cyclohexyl)propyl)-6-methoxynicotinamide | | 1.35-1.39 | 422.3 |

*unless otherwise noted

Biological Examples

Assessment of Inhibitor Activity in HeLa Cell-Based Indoleamine 2,3-Dioxygenase (IDO) Assay HeLa (ATCC® CCL-2) cells were obtained from the ATCC® and cultured in Dulbecco's Modified Eagle Medium supplemented with 4.5 g/L glucose, 4.5 g/L L-glutamine and 4.5 g/L sodium pyruvate (#10-013-CV, Corning), 2 mM L-alanyl-L-glutamine dipeptide (#35050-061, Gibco), 100 U/mL penicillin, 100 μg/mL streptomycin (#SV30010, HyClone) and 10% fetal bovine serum (#SH30071.03 HyClone). Cells were maintained in a humidified incubator at 37° C. in 5% $CO_2$.

IDO activity was assessed as a function of kynurenine production as follows: HeLa cells were seeded in a 96-well culture plate at a density of 5,000 cells/well and allowed to equilibrate overnight. After 24 hours, the media was aspirated and replaced with media containing IFNγ (#285-IF/CF, R&D Systems) at a final concentration of 25 ng/mL. A serial dilution of each test compound was added to the cells in a total volume of 200 μL of culture medium. After a further 48 hour incubation, 170 μL of supernatant was transferred from each well to a fresh 96-well plate. 12.1 μL of 6.1N trichloroacetic acid (#T0699, Sigma-Aldrich) was added to each well and mixed, followed by incubation at 65° C. for 20 minutes to hydrolyze N-formylkynurenine, the product of indoleamine 2,3-dioxygenase, to kynurenine. The reaction mixture was then centrifuged for 10 mins at 500×g to sediment the precipitate. 100 μL of the supernatant was transferred from each well to a fresh 96-well plate. 100 μl of 2% (w/v) p-dimethylaminobenzaldehyde (#15647-7, Sigma-Aldrich) in acetic acid (#A6283, Sigma-Aldrich) was added to each well mixed and incubated at room temperature for 20 mins. Kynurenine concentrations were determined by measuring absorbance at 480 nm and calibrating against an L-kynurenine (#K8625, Sigma-Aldrich) standard curve using a SPECTRAMAX® M2e microplate reader (Molecular Devices). The percentage activity at each inhibitor concentration was determined and $IC_{50}$ values assessed using nonlinear regression.

Activity for compounds described herein is provided in FIG. 1, wherein potency levels are provided as follows: (Potency: IDO $IC_{50}$: A<0.1 μM; B<1 μM; C<10 μM)

Evaluation of Biological Activity

Exemplary compounds were tested for inhibition of IDO activity. Experimental procedures and results are provided below.

HEK293 cells were transfected with a pCDNA-based mammalian expression vector harboring human IDO1 cDNA (NM 002164.2) by electroporation. They were cultured in medium (DMEM with 10% FBS) containing 1 mg/ml G418 for two weeks. Clones of HEK293 cells that stably expressed human IDO1 protein were selected and expanded for IDO inhibition assay.

The human IDO1/HEK293 cells were seeded at 10,000 cells per 50 μL per well with RPMI/phenol red free media contains 10% FBS in a 384-well black wall clear bottom tissue culture plate (Matrix Technologies LLC) 100 nL of certain concentration of compound was then added to each well using ECHO liquid handling systems. The cells were incubated for 20 hours in 37° C. incubator with 5% $CO_2$.

The compound treatments were stopped by adding trichloroacetic acid (Sigma-Aldrich) to a final concentration at 0.2%. The cell plate was further incubated at 50° C. for 30 minute. The equal volume supernatant (20 μL) and 0.2% (w/v) Ehrlich reagent (4-dimethylaminobenzaldehyde, Sigma-Aldrich) in glacial acetic acid were mixed in a new clear bottom 384-well plate. This plate was then incubated at room temperature for 30 minute. The absorbance at 490 nm was measured on Envision plate reader.

Compound $IC_{50}$ values were calculated using the counts of 500 nM of a reference standard treatment as one hundred percent inhibition, and counts of no compound but DMSO treatment as zero percent inhibition.

Activity for compounds described herein is provided in FIG. 1, wherein potency levels are provided as follows: (Potency: IDO $IC_{50}$: A<0.05 μM; B<0.25 μM; C<2 μM)

Results of the IDO assays are shown in the table below.

| HEK Human IDO-1 | |
|---|---|
| Example No. | Bio Activity A < 0.05, b < 0.250, c < 2.0 |
| 40 | C |
| 41 | B |
| 42 | C |
| 43 | C |
| 44 | A |
| 45 | C |
| 46 | C |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 59 | A |
| 60 | A |
| 61 | A |
| 66 | A |
| 67 | A |
| 68 | A |
| 69 | A |
| 70 | A |
| 71 | A |
| 72 | C |
| 75 | B |
| 76 | C |
| 77 | B |
| 78 | C |
| 79 | A |
| 80 | C |
| 81 | C |
| 84 | C |
| 86 | B |
| 87 | B |
| 88 | C |
| 89 | B |
| 90 | C |
| 91 | B |
| 92 | C |
| 93 | C |
| 97 | B |
| 119 | A |
| 120 | A |
| 121 | B |
| 122 | B |
| 123 | B |
| 124 | A |
| 125 | B |
| 130 | B |
| 131 | B |
| 139 | C |
| 140 | ? |

-continued

| HEK Human IDO-1 | |
| --- | --- |
| Example No. | Bio Activity A < 0.05, b < 0.250, c < 2.0 |
| 144 | C |
| 145 | C |
| 146 | C |
| 147 | C |
| 148 | C |
| 149 | B |
| 157a | B |
| 157b | A |
| 157c | C |
| 157d | C |
| 157e | C |
| 158a | A |
| 158b | A |
| 158c | A |
| 158d | A |
| 158e | C |
| 159a | A |
| 159b | B |
| 159c | A |
| 159d | A |
| 159e | C |
| 160a | A |
| 160b | C |
| 160c | C |
| 160d | B |
| 160e | A |
| 161a | C |
| 161b | A |
| 161c | B |
| 161e | C |
| 163 | A |
| 164a | B |
| 164b | A |
| 164c | A |
| 164d | A |
| 165a | C |
| 165b | A |
| 165c | A |
| 165d | A |
| 176 | A |
| 178 | B |
| 194 | A |
| 195 | A |
| 196 | A |
| 197 | B |
| 198 | A |
| 199 | C |
| 200 | B |
| 201 | B |
| 202 | A |
| 203a | C |
| 203b | B |
| 203c | A |
| 203d | A |
| 207 | A |
| 208 | B |
| 209 | B |
| 210 | B |
| 211 | B |
| 212 | C |
| 213 | A |
| 214 | B |
| 215 | C |
| 216 | B |
| 217 | C |
| 218 | C |
| 219 | B |
| 220 | B |
| 221 | A |
| 222 | C |
| 223 | A |
| 224 | B |
| 225 | Nt |
| 226 | C |

-continued

| HEK Human IDO-1 | |
| --- | --- |
| Example No. | Bio Activity A < 0.05, b < 0.250, c < 2.0 |
| 227 | C |
| 228 | C |
| 229 | Nt |
| 230 | A |
| 231a | B |
| 231b | C |
| 231c | C |
| 231d | C |
| 231e | A |
| 232 | B |
| 233 | A |
| 234 | A |
| 235 | A |
| 236 | A |
| 237 | C |
| 238 | A |
| 239 | A |
| 240 | C |
| 241 | A |
| 242 | B |
| 243 | A |
| 244 | A |
| 245 | A |
| 246 | B |
| 247 | A |
| 248 | A |
| 249 | A |
| 250 | A |
| 251 | B |
| 252 | A |
| 253 | A |
| 254 | A |
| 255 | A |
| 256 | A |
| 257 | Nt |
| 258 | A |
| 259 | |
| 260 | |
| 261 | |
| 262 | |
| 263 | |

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A compound of the formula (I):

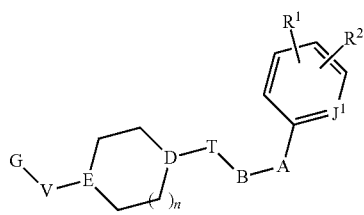

or a pharmaceutically acceptable salt, hydrate or solvate thereof, wherein,
the subscript n is 1;
A is —C(O)—;
B is —NH—;
T is —CR$^3$R$^4$—;
D is C(R$^5$);
E is C(R$^6$);
V is a bond;
G is an optionally substituted quinolinyl;
J$^1$ is CH or C(R$^2$), when R$^2$ is attached to the ring vertex identified as J$^1$;
R$^1$ and R$^2$ are independently hydrogen, halogen, optionally substituted C$_1$-C$_4$ haloalkyl, optionally substituted C$_3$-C$_6$ cycloalkyl, optionally substituted 3- to 6-membered cycloheteroalkyl, optionally substituted phenyl, optionally substituted heteroaryl, optionally substituted C$_1$-C$_4$ alkyl, optionally substituted C$_1$-C$_4$ alkoxy, CN, SO$_2$NH$_2$, NHSO$_2$CH$_3$, NHSO$_2$CF$_3$, OCF$_3$, SO$_2$CH$_3$, SO$_2$CF$_3$, or CONH$_2$, and when R$^1$ and R$^2$ are on adjacent vertices of a phenyl ring they may be joined together to form a 5- or 6-membered cycloheteroalkyl ring having one or two ring vertices independently selected from O, N and S, wherein said cycloheteroalkyl ring is optionally substituted with from one to three members selected from fluoro and C$_1$-C$_3$ alkyl;
R$^3$ and R$^4$ are independently hydrogen, optionally substituted C$_1$-C$_6$ alkyl, optionally substituted C$_1$-C$_6$ haloalkyl, fluorine, OH, CN, CO$_2$H, C(O)NH$_2$, N(R$^{5a}$)$_2$, optionally substituted —O—C$_1$-C$_6$ alkyl, —(CR$^5$R$^5$)$_m$—OH, —(CR$^5$R$^5$)$_m$—CO$_2$H, —(CR$^5$R$^5$)$_m$—C(O)NH$_2$, —(CR$^5$R$^5$)$_m$—C(O)NHR$^{5a}$, —(CR$^5$R$^5$)$_m$—N(R$^{5a}$)$_2$, —NH(CR$^5$R$^5$)$_m$CO$_2$H or —NH(CR$^5$R$^5$)$_m$—C(O)NH$_2$;
each R$^5$ is independently H, F, OH, optionally substituted C$_1$-C$_6$ alkyl or optionally substituted —O—C$_1$-C$_6$ alkyl;
each R$^{5a}$ is independently H, or optionally substituted C$_1$-C$_6$ alkyl;
R$^6$ is H, OH, F, optionally substituted C$_1$-C$_6$ alkyl, optionally substituted —O—C$_1$-C$_6$ alkyl, or —N(R$^{5a}$)$_2$;
and each m is independently 1, 2, or 3.

2. The compound of claim 1, of the formula:

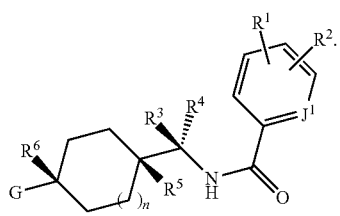

3. The compound of claim 1, of the formula:

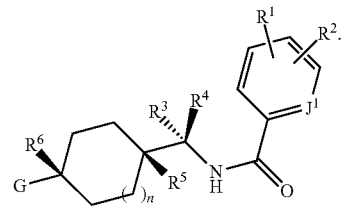

4. The compound of claim 1, of the formula:

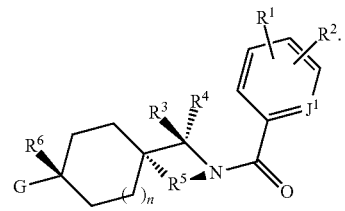

5. The compound of claim 1, of the formula:

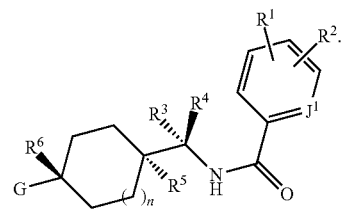

6. The compound of claim 1 that is:
4-Chloro-N—((R)-1-((1s,4S)-4-(6-fluoroquinolin-4-yl)cyclohexyl)ethyl)benzamide;
N—((R)-1-((1s,4S)-4-(6-fluoroquinolin-4-yl)cyclohexyl)ethyl)benzamide;
N—((R)-1-((1s,4S)-4-(6-fluoroquinolin-4-yl)cyclohexyl)ethyl)-2-methylbenzamide;
N—((R)-1-((1s,4S)-4-(6-fluoroquinolin-4-yl)cyclohexyl)ethyl)-3-methylbenzamide;
N—((R)-1-((1s,4S)-4-(6-fluoroquinolin-4-yl)cyclohexyl)ethyl)-4-methylbenzamide;
N—((R)-1-((1s,4S)-4-(6-fluoroquinolin-4-yl)cyclohexyl)ethyl)-2-methoxybenzamide;
N—((R)-1-((1s,4S)-4-(6-fluoroquinolin-4-yl)cyclohexyl)ethyl)-3-methoxybenzamide;
2-fluoro-N—((R)-1-((1s,4S)-4-(6-fluoroquinolin-4-yl)cyclohexyl)ethyl)benzamide;
3-fluoro-N—((R)-1-((1s,4S)-4-(6-fluoroquinolin-4-yl)cyclohexyl)ethyl)benzamide;
2-chloro-N—((R)-1-((1s,4S)-4-(6-fluoroquinolin-4-yl)cyclohexyl)ethyl)benzamide;
3-chloro-N—((R)-1-((1s,4S)-4-(6-fluoroquinolin-4-yl)cyclohexyl)ethyl)benzamide;
3,4-dichloro-N—((R)-1-((1s,4S)-4-(6-fluoroquinolin-4-yl)cyclohexyl)ethyl)benzamide;
4-fluoro-N—((R)-1-((1s,4S)-4-(6-fluoroquinolin-4-yl)cyclohexyl)ethyl)benzamide;
N—((R)-1-((1s,4S)-4-(6-fluoroquinolin-4-yl)cyclohexyl)ethyl)-[1,1'-biphenyl]-3-carboxamide;

3,5-dichloro-N—((R)-1-((1s,4S)-4-(6-fluoroquinolin-4-yl)cyclohexyl)ethyl)benzamide;
N—((R)-1-((1s,4S)-4-(6-fluoroquinolin-4-yl)cyclohexyl)ethyl)-4-methoxybenzamide;
N—((R)-1-((1s,4S)-4-(6-fluoroquinolin-4-yl)cyclohexyl)ethyl)-[1,1'-biphenyl]-2-carboxamide;
N—((R)-1-((1s,4S)-4-(6-fluoroquinolin-4-yl)cyclohexyl)ethyl)-[1,1'-biphenyl]-4-carboxamide;
4-Chloro-N—((R)-1-(cis-4-(6-fluoroquinolin-4-yl)cyclohexyl)propyl)benzamide;
4-Chloro-N—((S)-1-(cis-4-(6-fluoroquinolin-4-yl)cyclohexyl)propyl)benzamide;
4-Chloro-N—((R)-1-(trans-4-(6-fluoroquinolin-4-yl)cyclohexyl)propyl)benzamide;
4-Chloro-N—((S)-1-(trans-4-(6-fluoroquinolin-4-yl)cyclohexyl)propyl)benzamide;
4-Cyano-N—((R)-1-(cis-4-(6-fluoroquinolin-4-yl)cyclohexyl)propyl)benzamide;
4-Cyano-N—((S)-1-(cis-4-(6-fluoroquinolin-4-yl)cyclohexyl)propyl)benzamide;
4-Cyano-N—((R)-1-(trans-4-(6-fluoroquinolin-4-yl)cyclohexyl)propyl)benzamide;
4-Cyano-N—((S)-1-(trans-4-(6-fluoroquinolin-4-yl)cyclohexyl)propyl)benzamide;
4-cyano-N—((R)-1-(cis-4-(6-fluoroquinolin-4-yl)cyclohexyl)ethyl)benzamide;
5-(3-fluoro-4-methoxyphenyl)-N—((R)-1-(cis-4-(6-fluoroquinolin-4-yl)cyclohexyl)ethyl)picolinamide;
(R)-1-(cis-4-(6-fluoroquinolin-4-yl)cyclohexyl)-N-methylethanamine;
N—((R)-1-(cis-4-(6-fluoroquinolin-4-yl)cyclohexyl)ethyl)-4-(1H-pyrrol-1-yl)benzamide;
N—((R)-1-(cis-4-(6-fluoroquinolin-4-yl)cyclohexyl)ethyl)-4-(1H-imidazol-1-yl)benzamide;
4-chloro-N—((R)-1-((1s,4S)-4-(6-fluoroquinolin-4-yl)cyclohexyl)but-3-en-1-yl)benzamide;
N—((R)-1-((1s,4S)-4-(6-fluoroquinolin-4-yl)cyclohexyl)but-3-en-1-yl)-[1,1'-biphenyl]-4-carboxamide
N-1-((1 S,4S)-4-(quinolin-3-yl)cyclohexyl)propyl)-[1,1'-biphenyl]-4-carboxamide;
N-(1-((1R,4R)-4-(quinolin-3-yl)cyclohexyl)propyl)-[1,1'-biphenyl]-4-carboxamide;
N—((R)-1-((1s,4S)-4-(quinolin-3-yl)cyclohexyl)propyl)-[1,1'-biphenyl]-4-carboxamide;
N—((S)-1-((1s,4R)-4-(quinolin-3-yl)cyclohexyl)propyl)-[1,1'-biphenyl]-4-carboxamide;
N—((R)-1-((1r,4R)-4-(quinolin-3-yl)cyclohexyl)propyl)-[1,1'-biphenyl]-4-carboxamide;
N—((S)-1-((1r,4S)-4-(quinolin-3-yl)cyclohexyl)propyl)-[1,1'-biphenyl]-4-carboxamide;
4-chloro-N—((R)-1-(cis-4-(quinolin-3-yl)cyclohexyl)propyl)benzamide;
4-chloro-N—((S)-1-(cis-4-(quinolin-3-yl)cyclohexyl)propyl)benzamide;
4-chloro-N—((R)-1-(trans-4-(quinolin-3-yl)cyclohexyl)propyl)benzamide;
4-chloro-N—((S)-1-(trans-4-(quinolin-3-yl)cyclohexyl)propyl)benzamide;
N-(1-((1s,4s)-4-(6-(trifluoromethyl)quinolin-4-yl)cyclohexyl)propyl)biphenyl-4-carboxamide;
N—((R)-1-((1s,4S)-4-(6-fluoroquinolin-4-yl)cyclohexyl)ethyl)-4-(5-methyl-1,3,4-oxadiazol-2-yl)benzamide;
N—((R)-1-((1s,4S)-4-(6-fluoroquinolin-4-yl)cyclohexyl)ethyl)-4-(pyrazin-2-yl)benzamide;
N—((R)-1-((1s,4S)-4-(6-fluoroquinolin-4-yl)cyclohexyl)ethyl)-4-(pyrimidin-5-yl)benzamide;
N—((R)-1-((1s,4S)-4-(6-fluoroquinolin-4-yl)cyclohexyl)ethyl)-4-(1-methyl-1H-imidazol-4-yl)benzamide;
N—((R)-1-((1s,4S)-4-(6-fluoroquinolin-4-yl)cyclohexyl)ethyl)-4-(2-methoxypyrimidin-4-yl)benzamide;
N—((R)-1-((1s,4S)-4-(6-fluoroquinolin-4-yl)cyclohexyl)ethyl)-4-(6-methylsulfonyl)pyridin-3-yl)benzamide;
N—((R)-1-((1s,4S)-4-(6-fluoroquinolin-4-yl)cyclohexyl)ethyl)-4-(2-methylthiazol-5-yl)benzamide;
N—((R)-1-((1s,4S)-4-(6-fluoroquinolin-4-yl)cyclohexyl)ethyl)-4-(5-methoxypyridin-2-yl)benzamide;
4-(2-cyanopyrimidin-5-yl)-N—((R)-1-((1s,4S)-4-(6-fluoroquinolin-4-yl)cyclohexyl)ethyl)benzamide;
N—((R)-1-((1s,4S)-4-(6-fluoroquinolin-4-yl)cyclohexyl)ethyl)-4-(2-methoxythiazol-4-yl)benzamide;
N—((R)-1-((1s,4S)-4-(6-fluoroquinolin-4-yl)cyclohexyl)ethyl)-4'-(2-hydroxypropan-2-yl)biphenyl-4-carboxamide;
N—((R)-1-((1s,4S)-4-(6-fluoroquinolin-4-yl)cyclohexyl)ethyl)-4-(thiazol-4-yl)benzamide;
N—((R)-1-((1s,4S)-4-(6-fluoroquinolin-4-yl)cyclohexyl)ethyl)-4-(1,3,4-oxadiazol-2-yl)benzamide;
N—((R)-1-((1s,4S)-4-(6-fluoroquinolin-4-yl)cyclohexyl)ethyl)-4-(6-methoxypyridin-3-yl)benzamide;
N—((R)-1-((1s,4S)-4-(6-fluoroquinolin-4-yl)cyclohexyl)ethyl)-4-morpholinobenzamide;
4-cyclopropyl-N—((R)-1((1s,4S)-4-(6-fluoroquinolin-4-yl)cyclohexyl)ethyl)benzamide;
N—((R)-1-((1s,4S)-4-(6-fluoroquinolin-4-yl)cyclohexyl)ethyl)-4-(1-methylcyclopropyl)benzamide;
N—((R)-1-((1s,4S)-4-(6-fluoroquinolin-4-yl)cyclohexyl)ethyl)-4-(trifluoromethyl)benzamide;
N—((R)-1-((1s,4S)-4-(6-fluoroquinolin-4-yl)cyclohexyl)ethyl)-4-(oxazol-5-yl)benzamide;
N—((R)-1-((1s,4S)-4-(6-fluoroquinolin-4-yl)cyclohexyl)ethyl)-4-(1-methyl-1H-1,2,4-triazol-5-yl)benzamide;
N—((R)-1-((1s,4S)-4-(6-fluoroquinolin-4-yl)cyclohexyl)ethyl)-4-(5-methylthiazol-2-yl)benzamide;
4-(5-cyanothiazol-2-yl)-N—((R)-1-((1s,4S)-4-(6-fluoroquinolin-4-yl)cyclohexyl)ethyl)benzamide;
4-chloro-N-(1-((1s,4s)-4-(6-(trifluoromethyl)quinolin-4-yl)cyclohexyl)propyl)benzamide;
4-(1H-pyrrol-1-yl)-N-(1-((1s,4S)-4-(6-(trifluoromethyl)quinolin-4-yl)cyclohexyl)propyl)benzamide;
N-(1-(4-(6-fluoroquinolin-4-yl)cyclohexyl)propyl)-4-(thiazol-2-yl)benzamide; or
N-(1-(4-(6-fluoroquinolin-4-yl)cyclohexyl)propyl)biphenyl-4-carboxamide;
or a pharmaceutically acceptable salt thereof.

7. A pharmaceutical composition comprising a compound of claim 1, and a pharmaceutically acceptable excipient.

8. A combination comprising a compound of claim 1 and at least one additional therapeutic agent.

9. The combination of claim 8, wherein the at least one additional therapeutic agent is a chemotherapeutic agent, an immune- and/or inflammation-modulating agent, an anti-hypercholesterolemia agent, or an anti-infective agent.

10. The combination of claim 8, wherein the at least one additional therapeutic agent is an immune checkpoint inhibitor.

11. The combination of claim 10, wherein said immune checkpoint inhibitor is selected from the group consisting of ipilimumab, nivolumab and pembrolizumab.

12. The compound of claim 1, wherein G is unsubstituted.

13. The compound of claim 1, wherein G is substituted.

14. The compound of claim 13, wherein the G is substituted with halogen.

15. The compound of claim 1, wherein $R^5$ is H or $C_1$-$C_6$alkyl.

16. The compound of claim 1, wherein $R^5$ is H.

17. The compound of claim 1, wherein $R^6$ is H, OH, F, $C_1$-$C_6$ alkyl, —O—$C_1$-$C_6$ alkyl, or —N($R^{5a}$)$_2$.

18. The compound of claim 1, wherein $R^6$ is H or $C_1$-$C_6$ alkyl.

19. The compound of claim 1, wherein $R^6$ is H.

20. The compound of claim 1, wherein $R^3$ and $R^4$ are independently hydrogen or optionally substituted $C_1$-$C_6$ alkyl.

21. The compound of claim 1, wherein $R^3$ and $R^4$ are independently hydrogen or $C_1$-$C_6$ alkyl.

22. The compound of claim 1 that is:
- 4-Chloro-N—((R)-1-((1s,4S)-4-(6-fluoroquinolin-4-yl)cyclohexyl)ethyl)benzamide;
- N—((R)-1-((1s,4S)-4-(6-fluoroquinolin-4-yl)cyclohexyl)ethyl)benzamide;
- N—((R)-1-((1s,4S)-4-(6-fluoroquinolin-4-yl)cyclohexyl)ethyl)-2-methylbenzamide;
- N—((R)-1-((1s,4S)-4-(6-fluoroquinolin-4-yl)cyclohexyl)ethyl)-3-methylbenzamide;
- N—((R)-1-((1s,4S)-4-(6-fluoroquinolin-4-yl)cyclohexyl)ethyl)-4-methylbenzamide;
- N—((R)-1-((1s,4S)-4-(6-fluoroquinolin-4-yl)cyclohexyl)ethyl)-2-methoxybenzamide;
- N—((R)-1-((1s,4S)-4-(6-fluoroquinolin-4-yl)cyclohexyl)ethyl)-3-methoxybenzamide;
- 2-fluoro-N—((R)-1-((1s,4S)-4-(6-fluoroquinolin-4-yl)cyclohexyl)ethyl)benzamide;
- 3-fluoro-N—((R)-1-((1s,4S)-4-(6-fluoroquinolin-4-yl)cyclohexyl)ethyl)benzamide;
- 2-chloro-N—((R)-1-((1s,4S)-4-(6-fluoroquinolin-4-yl)cyclohexyl)ethyl)benzamide;
- 3-chloro-N—((R)-1-((1s,4S)-4-(6-fluoroquinolin-4-yl)cyclohexyl)ethyl)benzamide;
- 3,4-dichloro-N—((R)-1-((1s,4S)-4-(6-fluoroquinolin-4-yl)cyclohexyl)ethyl)benzamide;
- 4-fluoro-N—((R)-1-((1s,4S)-4-(6-fluoroquinolin-4-yl)cyclohexyl)ethyl)benzamide;
- N—((R)-1-((1s,4S)-4-(6-fluoroquinolin-4-yl)cyclohexyl)ethyl)-[1,1'-biphenyl]-3-carboxamide;
- 3,5-dichloro-N—((R)-1-((1s,4S)-4-(6-fluoroquinolin-4-yl)cyclohexyl)ethyl)benzamide;
- N—((R)-1-((1s,4S)-4-(6-fluoroquinolin-4-yl)cyclohexyl)ethyl)-4-methoxybenzamide;
- N—((R)-1-((1s,4S)-4-(6-fluoroquinolin-4-yl)cyclohexyl)ethyl)-[1,1'-biphenyl]-2-carboxamide;
- N—((R)-1-((1s,4S)-4-(6-fluoroquinolin-4-yl)cyclohexyl)ethyl)-[1,1'-biphenyl]-4-carboxamide;
- 4-cyano-N—((R)-1-(cis-4-(6-fluoroquinolin-4-yl)cyclohexyl)ethyl)benzamide;
- 5-(3-fluoro-4-methoxyphenyl)-N—((R)-1-(cis-4-(6-fluoroquinolin-4-yl)cyclohexyl)ethyl)picolinamide;
- (R)-1-(cis-4-(6-fluoroquinolin-4-yl)cyclohexyl)-N-methylethanamine;
- N—((R)-1-(cis-4-(6-fluoroquinolin-4-yl)cyclohexyl)ethyl)-4-(1H-pyrrol-1-yl)benzamide;
- N—((R)-1-(cis-4-(6-fluoroquinolin-4-yl)cyclohexyl)ethyl)-4-(1H-imidazol-1-yl)benzamide;
- N—((R)-1-((1s,4S)-4-(6-fluoroquinolin-4-yl)cyclohexyl)ethyl)-4-(5-methyl-1,3,4-oxadiazol-2-yl)benzamide;
- N—((R)-1-((1s,4S)-4-(6-fluoroquinolin-4-yl)cyclohexyl)ethyl)-4-(pyrazin-2-yl)benzamide;
- N—((R)-1-((1s,4S)-4-(6-fluoroquinolin-4-yl)cyclohexyl)ethyl)-4-(pyrimidin-5-yl)benzamide;
- N—((R)-1-((1s,4S)-4-(6-fluoroquinolin-4-yl)cyclohexyl)ethyl)-4-(1-methyl-1H-imidazol-4-yl)benzamide;
- N—((R)-1-((1s,4S)-4-(6-fluoroquinolin-4-yl)cyclohexyl)ethyl)-4-(2-methoxypyrimidin-4-yl)benzamide;
- N—((R)-1-((1s,4S)-4-(6-fluoroquinolin-4-yl)cyclohexyl)ethyl)-4-(6-methylsulfonyl)pyridin-3-yl)benzamide;
- N—((R)-1-((1s,4S)-4-(6-fluoroquinolin-4-yl)cyclohexyl)ethyl)-4-(2-methylthiazol-5-yl)benzamide;
- N—((R)-1-((1s,4S)-4-(6-fluoroquinolin-4-yl)cyclohexyl)ethyl)-4-(5-methoxypyridin-2-yl)benzamide;
- 4-(2-cyanopyrimidin-5-yl)-N—((R)-1-((1s,4S)-4-(6-fluoroquinolin-4-yl)cyclohexyl)ethyl)benzamide;
- N—((R)-1-((1s,4S)-4-(6-fluoroquinolin-4-yl)cyclohexyl)ethyl)-4-(2-methoxythiazol-4-yl)benzamide;
- N—((R)-1-((1s,4S)-4-(6-fluoroquinolin-4-yl)cyclohexyl)ethyl)-4'-(2-hydroxypropan-2-yl)biphenyl-4-carboxamide;
- N—((R)-1-((1s,4S)-4-(6-fluoroquinolin-4-yl)cyclohexyl)ethyl)-4-(thiazol-4-yl)benzamide;
- N—((R)-1-((1s,4S)-4-(6-fluoroquinolin-4-yl)cyclohexyl)ethyl)-4-(1,3,4-oxadiazol-2-yl)benzamide;
- N—((R)-1-((1s,4S)-4-(6-fluoroquinolin-4-yl)cyclohexyl)ethyl)-4-(6-methoxypyridin-3-yl)benzamide;
- N—((R)-1-((1s,4S)-4-(6-fluoroquinolin-4-yl)cyclohexyl)ethyl)-4-morpholinobenzamide;
- 4-cyclopropyl-N—((R)-1-((1s,4S)-4-(6-fluoroquinolin-4-yl)cyclohexyl)ethyl)benzamide;
- N—((R)-1-((1s,4S)-4-(6-fluoroquinolin-4-yl)cyclohexyl)ethyl)-4-(1-methylcyclopropyl)benzamide;
- N—((R)-1-((1s,4S)-4-(6-fluoroquinolin-4-yl)cyclohexyl)ethyl)-4-(trifluoromethyl)benzamide;
- N—((R)-1-((1s,4S)-4-(6-fluoroquinolin-4-yl)cyclohexyl)ethyl)-4-(oxazol-5-yl)benzamide;
- N—((R)-1-((1s,4S)-4-(6-fluoroquinolin-4-yl)cyclohexyl)ethyl)-4-(1-methyl-1H-1,2,4-triazol-5-yl)benzamide;
- N—((R)-1-((1s,4S)-4-(6-fluoroquinolin-4-yl)cyclohexyl)ethyl)-4-(5-methylthiazol-2-yl)benzamide; or
- 4-(5-cyanothiazol-2-yl)-N—((R)-1-((1s,4S)-4-(6-fluoroquinolin-4-yl)cyclohexyl)ethyl)benzamide;
or a pharmaceutically acceptable salt thereof.

23. The compound of claim 1 that is 4-Chloro-N—((R)-1-((1s,4S)-4-(6-fluoroquinolin-4-yl)cyclohexyl)ethyl)benzamide or a pharmaceutically acceptable salt thereof.

24. The compound of claim 1 that is N—((R)-1-((1s,4S)-4-(6-fluoroquinolin-4-yl)cyclohexyl)ethyl)-4-methylbenzamide or a pharmaceutically acceptable salt thereof.

25. The compound of claim 1 that is 4-fluoro-N—((R)-1-((1s,4S)-4-(6-fluoroquinolin-4-yl)cyclohexyl)ethyl)benzamide or a pharmaceutically acceptable salt thereof.

26. The compound of claim 1 that is N—((R)-1-((1s,4S)-4-(6-fluoroquinolin-4-yl)cyclohexyl)ethyl)-4-methoxybenzamide or a pharmaceutically acceptable salt thereof.

27. The compound of claim 1 that is N—((R)-1-((1s,4S)-4-(6-fluoroquinolin-4-yl)cyclohexyl)ethyl)-[1,1'-biphenyl]-4-carboxamide or a pharmaceutically acceptable salt thereof.

28. The compound of claim 1 that is 4-cyano-N—((R)-1-(cis-4-(6-fluoroquinolin-4-yl)cyclohexyl)ethyl)benzamide or a pharmaceutically acceptable salt thereof.

29. The compound of claim 1 that is (R)-1-(cis-4-(6-fluoroquinolin-4-yl)cyclohexyl)-N-methylethanamine or a pharmaceutically acceptable salt thereof.

30. The compound of claim 1 that is N—((R)-1-(cis-4-(6-fluoroquinolin-4-yl)cyclohexyl)ethyl)-4-(1H-pyrrol-1-yl)benzamide or a pharmaceutically acceptable salt thereof.

31. The compound of claim 1 that is N—((R)-1-(cis-4-(6-fluoroquinolin-4-yl)cyclohexyl)ethyl)-4-(1H-imidazol-1-yl)benzamide or a pharmaceutically acceptable salt thereof.

32. The compound of claim 1 that is N—((R)-1-((1s,4S)-4-(6-fluoroquinolin-4-yl)cyclohexyl)ethyl)-4-(5-methyl-1,3,4-oxadiazol-2-yl)benzamide or a pharmaceutically acceptable salt thereof.

33. The compound of claim 1 that is N—((R)-1-((1s,4S)-4-(6-fluoroquinolin-4-yl)cyclohexyl)ethyl)-4-(thiazol-4-yl)benzamide or a pharmaceutically acceptable salt thereof.

34. The compound of claim 1 that is N—((R)-1-((1s,4S)-4-(6-fluoroquinolin-4-yl)cyclohexyl)ethyl)-4-(1,3,4-oxadiazol-2-yl)benzamide or a pharmaceutically acceptable salt thereof.

* * * * *

UNITED STATES PATENT AND TRADEMARK OFFICE
CERTIFICATE OF CORRECTION

PATENT NO.       : 9,598,422 B2
APPLICATION NO.  : 14/933879
DATED            : March 21, 2017
INVENTOR(S)      : Hilary Beck et al.

Page 1 of 1

It is certified that error appears in the above-identified patent and that said Letters Patent is hereby corrected as shown below:

In the Claims

Claim 6, Column 205, Line 39, after "carboxamide" insert -- ; --.

Claim 6, Column 205, Line 40, delete "N-1-" and insert -- N-(1- --, therefor.

Claim 6, Column 205, Line 40, delete "((1 S,4S)" and insert -- ((1S,4S) --, therefor.

Signed and Sealed this
Tenth Day of October, 2017

Joseph Matal
*Performing the Functions and Duties of the*
*Under Secretary of Commerce for Intellectual Property and*
*Director of the United States Patent and Trademark Office*